US009108970B2

(12) United States Patent
Arikawa et al.

(10) Patent No.: US 9,108,970 B2
(45) Date of Patent: Aug. 18, 2015

(54) FUSED HETEROAROMATIC PYRROLIDINONES

(71) Applicant: Takeda Pharmaceutical Company Limited, Osaka (JP)

(72) Inventors: Yasuyoshi Arikawa, Osaka (JP); Benjamin Jones, Cardiff-by-the-Sea, CA (US); Betty Lam, San Diego, CA (US); Christopher Smith, San Diego, CA (US); Masashi Takahashi, Osaka (JP); Qing Dong, San Diego, CA (US); Victoria Feher, San Diego, CA (US); Zhe Nie, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 96 days.

(21) Appl. No.: 13/886,032

(22) Filed: May 2, 2013

(65) Prior Publication Data

US 2013/0245031 A1 Sep. 19, 2013

Related U.S. Application Data

(62) Division of application No. 12/972,333, filed on Dec. 17, 2010, now Pat. No. 8,440,689.

(60) Provisional application No. 61/386,964, filed on Sep. 27, 2010, provisional application No. 61/289,969, filed on Dec. 23, 2009.

(51) Int. Cl.
| | |
|---|---|
| *C07D 471/04* | (2006.01) |
| *A61K 31/437* | (2006.01) |
| *A61P 11/06* | (2006.01) |
| *A61P 35/00* | (2006.01) |
| *A61P 17/06* | (2006.01) |
| *A61P 29/00* | (2006.01) |
| *A61P 11/08* | (2006.01) |
| *A61P 37/02* | (2006.01) |
| *A61K 31/527* | (2006.01) |
| *A61K 45/06* | (2006.01) |
| *C07D 487/10* | (2006.01) |
| *C07D 519/00* | (2006.01) |
| *C07D 487/04* | (2006.01) |
| *A61K 31/519* | (2006.01) |

(52) U.S. Cl.
CPC ............ *C07D 487/04* (2013.01); *A61K 31/437* (2013.01); *A61K 31/519* (2013.01); *A61K 31/527* (2013.01); *A61K 45/06* (2013.01); *C07D 471/04* (2013.01); *C07D 487/10* (2013.01); *C07D 519/00* (2013.01)

(58) Field of Classification Search
CPC .............. C07D 471/04; A61K 31/519
USPC .......................................... 546/113; 514/300
See application file for complete search history.

(56) References Cited

U.S. PATENT DOCUMENTS

| 5,238,950 | A | 8/1993 | Clader et al. |
|---|---|---|---|
| 6,432,963 | B1 | 8/2002 | Hisamichi et al. |
| 7,105,667 | B2 | 9/2006 | Pitts et al. |
| 7,320,992 | B2 | 1/2008 | Tegley et al. |
| 7,745,641 | B2 | 6/2010 | Murakata et al. |
| 8,440,689 | B2 | 5/2013 | Arikawa et al. |
| 2003/0092908 | A1 | 5/2003 | Pitts et al. |
| 2003/0187261 | A1 | 10/2003 | Havlicek et al. |
| 2003/0191143 | A1 | 10/2003 | Pitts et al. |

(Continued)

FOREIGN PATENT DOCUMENTS

| CA | 2731926 | 2/2010 |
|---|---|---|
| CA | 2732087 | 2/2010 |

(Continued)

OTHER PUBLICATIONS

Hisamichi, et al. "Synthentic studies on novel Syk inhibitors. Part 1: Synthesis and structure-activity relationships of pyrimidine-5-carboxamide derivatives," Bioorganic & Medicinal Chemistry 13 (2005) 4936-4951.

Hirabayashi, et al. "A novel Syk family kinase inhibitor: Design, synthesis, and structure-activity relationship of 1,2,4-triazolo[4,3-c]pyrimidine and 1,2,4-triazolo[1,5-c]pyrimidine derivatives," Bioorganic & Medicinal Chemistry 16 (2008) 7347-7357.

Hirabayashi, et al. "Structure-activity relationship studies of imidazo[1,2-c]pyrimidine derivatives as potent and orally effective Syk family kinases inhibitors," Bioorganic & Medicinal Chemistry 16 (2008) 9247-9260.

(Continued)

*Primary Examiner* — Susanna Moore
(74) *Attorney, Agent, or Firm* — Matthew J. Russo

(57) ABSTRACT

Disclosed are compounds of Formula 1,

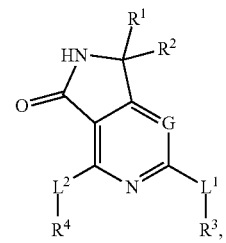

and pharmaceutically acceptable salts thereof, wherein G, $L^1$, $L^2$, $R^1$, $R^2$, $R^3$, and $R^4$ are defined in the specification. This disclosure also relates to materials and methods for preparing compounds of Formula 1, pharmaceutical compositions containing them, and their use for treating disorders, diseases, and conditions involving the immune system and inflammation, including rheumatoid arthritis, hematological malignancies, epithelial cancers (i.e., carcinomas), and other disorders, diseases, and conditions for which inhibition of SYK is indicated.

31 Claims, No Drawings

(56) References Cited

U.S. PATENT DOCUMENTS

| | | |
|---|---|---|
| 2006/0116516 A1 | 6/2006 | Pitts et al. |
| 2010/0152159 A1 | 6/2010 | Mitchell et al. |
| 2010/0298557 A1 | 11/2010 | Yagi et al. |
| 2012/0027834 A1 | 2/2012 | Andre et al. |
| 2013/0116260 A1 | 5/2013 | Arikawa et al. |
| 2014/0206680 A1 | 7/2014 | Adams et al. |

FOREIGN PATENT DOCUMENTS

| | | |
|---|---|---|
| EP | 0540334 | 5/1993 |
| EP | 1184376 | 3/2002 |
| EP | 1293213 | 3/2003 |
| EP | 1244668 | 4/2006 |
| EP | 1880993 | 1/2008 |
| EP | 2108642 | 10/2009 |
| JP | 63107966 | 5/1988 |
| JP | 2009067729 | 4/2009 |
| WO | 99/32479 | 7/1999 |
| WO | 01/09124 | 2/2001 |
| WO | 0109134 | 2/2001 |
| WO | 0143731 | 6/2001 |
| WO | 0149688 | 7/2001 |
| WO | 0183485 | 11/2001 |
| WO | 02087513 | 11/2002 |
| WO | 03000688 | 1/2003 |
| WO | 03009852 | 2/2003 |
| WO | 03057695 | 7/2003 |
| WO | 03063794 | 8/2003 |
| WO | 2004016597 | 2/2004 |
| WO | 2004037814 | 5/2004 |
| WO | 2004041810 | 5/2004 |
| WO | 2004087053 | 10/2004 |
| WO | 2004087698 | 10/2004 |
| WO | 2004087699 | 10/2004 |
| WO | 2005012294 | 2/2005 |
| WO | 2005021532 | 3/2005 |
| WO | 2005039564 | 5/2005 |
| WO | 2005056524 | 6/2005 |
| WO | 2006028833 | 3/2006 |
| WO | 2006062981 | 6/2006 |
| WO | 2006068770 | 6/2006 |
| WO | 2006108107 | 10/2006 |
| WO | 2006129100 | 12/2006 |
| WO | 2007002781 | 1/2007 |
| WO | 2007023382 | 3/2007 |
| WO | 2007025043 | 3/2007 |
| WO | 2007053844 | 5/2007 |
| WO | 2007070872 | 6/2007 |
| WO | 2007084557 | 7/2007 |
| WO | 2008033798 | 3/2008 |
| WO | 2008051493 | 5/2008 |
| WO | 2008057402 | 5/2008 |
| WO | 2008064274 | 5/2008 |
| WO | 2008118332 | 10/2008 |
| WO | 2008151184 | 12/2008 |
| WO | 2009026107 | 2/2009 |
| WO | 2009062118 | 5/2009 |
| WO | 2009080638 | 7/2009 |
| WO | 2009/105675 | 8/2009 |
| WO | 2009102468 | 8/2009 |
| WO | 2009/123967 | 10/2009 |
| WO | 2009/136995 | 12/2009 |
| WO | 2009/145856 | 12/2009 |
| WO | 2009/150230 | 12/2009 |
| WO | 2010/027500 | 3/2010 |
| WO | 2010/068258 | 6/2010 |
| WO | 2010/146133 | 12/2010 |
| WO | 2011/075515 | 6/2011 |
| WO | 2011/075517 | 6/2011 |
| WO | 2011/075560 | 6/2011 |
| WO | 2011/134971 | 11/2011 |

OTHER PUBLICATIONS

Hirabayashi et al., "Structure-activity relationship studies of 5-benzylaminoimidazo[1,2-c] pyrimidine-8-carboxamide derivatives as potent, highly selective ZAP-70 kinase inhibitors," Bioorganic & Medicinal Chemistry 17 (2009) 284-294.

Xie, et al., "Pharmacophore modeling study based on known Spleen tyrosine kinase inhibitors together with virtual screening for identifying novel inhibitors," Bioorganic & Medicinal Chemistry Letters 19 (2009) 1944-1949.

Cywin, et al., "Discovery and SAR of Novel [1,6]Naphthyridines as Potent Inhibitors of Spleen Tyrosine Kinase (SYK)," Bioorganic & Medicinal Chemistry Letters 13 (2003) 1415-1418.

Moore, et al., "An analysis of the diaminopyrimidine patent estates describing spleen tyrosine kinase inhibitors by Rigel and Portola," Export Opinion on Therapeutic Patents (2010) 20(12) 1703-17022.

Yamamoto, et al., "The Orally Available Spleen Tyrosine Kinase Inhibitor 2-[7-(3,4-Dimethoxyphenyl)-imidazo[1,2-c] pyrimidin-5-ylamino]-nicotinamide Dihydrochloride (BAY 61-3606) Blocks Antigen-Induced Airway Inflammation in Rodents," The Journal of Pharmacology and Experimental Therapeutics, vol. 306, No. 3 (2003) 1174-1181.

Braselmann, et al., "R406, an Orally Available Spleen Tyrosine Kinase Inhibitor Blocks Fc Receptor Signaling and Reduces Immune Complex-Mediated Inflammation," The Journal of Pharmacology and Experimental Therapeutics, vol. 319, No. 3 (2006) 998-1008.

Lai, et al., "Potent Small Molecule Inhibitors of Spleen Tyrosine Kinase (Syk)," Bioorganic & Medicinal Chemistry Letters 13 (2003) 3111-3114.

Farmer, et al., "Discovery and SAR of novel 4-thiazolyl-2-phenylaminopyrimidines as potent inhibitors of spleen tyrosine kinase (SYK)," Bioorganic & Medicinal Chemistry Letters 18 (2008) 6231-6235.

Liddle, et al., "Discovery of GSK143, a highly potent, selective and orally efficacious spleen tyrosine kinase inhibitor," Bioorganic & Medicinal Chemistry Letters 21 (2011) 6188-6194.

Bajpai, Malini "Fostamatinib, a Syk inhibitor prodrug for the treatment of inflammatory diseases," IDrugs 2009 12 (3):174-185.

Ruzza, et al., "Therapeutic prospect of Syk inhibitors," Export Opinion on Therapeutic Patents (2009) 19(10) 1361-1376.

U.S. Appl. No. 12/972,333 Office Action mailed Oct. 12, 2012.

U.S. Appl. No. 12/972,333 Notice of Allowance mailed Jan. 22, 2013.

U.S. Appl. No. 13/518,806 Office Action mailed May 29, 2014.

U.S. Appl. No. 13/518,806 Notice of Allowance mailed Oct. 29, 2014.

U.S. Appl. No. 14/128,576 Office Action mailed Nov. 3, 2014.

FUSED HETEROAROMATIC PYRROLIDINONES

RELATED APPLICATIONS

This application is a divisional of U.S. Ser. No. 12/972,333, filed Dec. 17, 2010, now U.S. Pat. No. 8,440,689, claims the benefit of U.S. Provisional Application No. 61/289,969, filed Dec. 23, 2009, and U.S. Provisional Application No. 61/386,964, filed Sep. 27, 2010, which are herein incorporated by reference.

FIELD OF THE INVENTION

This invention relates to fused heteroaromatic pyrrolidinone compounds, to pharmaceutical compositions containing them, and to the use of the compounds for treating disorders and conditions involving the immune system and inflammation, including rheumatoid arthritis. The heteroaromatic pyrrolidinones are inhibitors of spleen tyrosine kinase.

BACKGROUND OF THE INVENTION

Spleen tyrosine kinase (SYK) is a 72 kDa non-receptor cytoplasmic tyrosine kinase. SYK has a primary amino acid sequence similar to that of zeta-associated protein-70 (ZAP-70) and is involved in receptor-mediated signal transduction. The N-terminal domain of SYK contains two Src-homology 2 (SH2) domains, which bind to diphosphorylated immunoreceptor tyrosine-based activation motifs (ITAMs) found in the cytoplasmic signaling domains of many immunoreceptor complexes. The C-terminus contains the catalytic domain, and includes several catalytic loop autophosphorylation sites that are responsible for receptor-induced SYK activation and subsequent downstream signal propagation. SYK is expressed in many cell types involved in adaptive and innate immunity, including lymphocytes (B cells, T cells, and NK cells), granulocytes (basophils, neutrophils, and eosinophils), monocytes, macrophages, dendritic cells, and mast cells. SYK is expressed in other cell types, including airway epithelium and fibroblasts in the upper respiratory system. See, e.g., Martin Turner et al., *Immunology Today* (2000) 21(3): 148-54; and Michael P. Sanderson et al., *Inflammation & Allergy-Drug Targets* (2009) 8:87-95.

SYK's role in ITAM-dependent signaling and its expression in many cell types suggest that compounds which inhibit SYK activity may be useful for treating disorders involving the immune system and inflammation. Such disorders include Type I hypersensitivity reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); and inflammation of the lung (chronic obstructive pulmonary disease). See, e.g., Brian R. Wong et al., *Expert Opin. Investig. Drugs* (2004) 13(7):743-62; Sanderson et al. (2009); Jane Denyer & Vipul Patel, *Drug News Perspective* (2009) 22(3): 146-50; Esteban S. Masuda & Jochen Schmitz, *Pulmonary Pharmacology & Therapeutics* (2008) 21:461-67; Malini Bajpai et al., *Expert Opin. Investig. Drugs* (2008) 17(5):641-59; and Anna Podolanczuk et al., *Blood* (2009) 113:3154-60. Other disorders include hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma); as well as epithelial cancers, such as lung cancer, pancreatic cancer, and colon cancer. See, e.g., Cynthia K. Hahn et al., *Cancer Cell* (2009) 16:281-294; D. H. Chu et al., *Immunol. Rev.* (1998) 165:167-180; A. L. Feldman et al., *Leukemia* (2008) 22:1139-43; A. Rinaldi et al., *Br. J. Haematol.* (2006) 132: 303-16; B. Streubel et al., *Leukemia* (2006) 20:313-18; Maike Buchner et al., *Cancer Research* (2009) 69(13):5424-32; A. D. Baudot et al., *Oncogene* (2009) 28:3261-73; and Anurag Singh et al., *Cancer Cell* (2009) 15:489-500.

Various SYK inhibitors have been described in published patent applications. See, e.g., EP 1184376 A1; WO 01/83485 A1; WO 03/057695 A1; WO 2006/129100 A1; WO 01/09134 A1; WO 03/063794 A1; WO 2005/012294 A1; WO 2004/087699 A2; WO 2009/026107 A1; WO2009136995 A2; and WO2009/145856 A1.

SUMMARY OF THE INVENTION

This invention provides fused heteroaromatic pyrrolidinone derivatives, including 6,7-dihydro-5H-pyrrolo[3,4-d]pyrimidin-5-ones, 1H-pyrrolo[3,4-c]pyridin-3(2H)-ones, and pharmaceutically acceptable complexes, salts, solvates, and hydrates thereof. This invention also provides pharmaceutical compositions containing the heteroaromatic pyrrolidinone derivatives, and uses of the heteroaromatic pyrrolidinone derivatives to treat disorders and conditions involving the immune system and inflammation, including rheumatoid arthritis.

One aspect of the invention provides compounds of Formula 1:

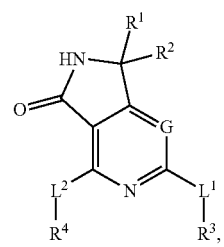

or pharmaceutically acceptable salts thereof, wherein:
G is selected from N and C($R^5$);
$L^1$ and $L^2$ are each independently selected from —NH— and a bond;
$R^1$ and $R^2$ are each independently selected from hydrogen, halo, $C_{1-3}$ alkyl, and $C_{1-3}$ haloalkyl, or $R^1$ and $R^2$, together with the atom to which they are attached, form a $C_{3-6}$ cycloalkyl;
$R^3$ is selected from $C_{2-6}$ alkyl, $C_{3-8}$ cycloalkyl, $C_{2-5}$ heterocyclyl, and $C_{1-9}$ heteroaryl, each optionally substituted with from one to five substituents independently selected from halo, oxo, —$NO_2$, —CN, $R^6$, and $R^7$;
$R^4$ is selected from $C_{3-8}$ cycloalkyl, $C_{2-5}$ heterocyclyl, $C_{6-14}$ aryl, and $C_{1-9}$ heteroaryl, each optionally substituted with from one to five substituents independently selected from halo, oxo, —CN, $R^6$, and $R^7$;
$R^5$ is selected from hydrogen, halo, —CN, $C_{1-4}$ alkyl, $C_{2-4}$ alkenyl, $C_{2-4}$ alkynyl, $C_{2-5}$ heterocyclyl, $C_{1-5}$ heteroaryl, and $R^{10}$, wherein the alkyl, alkenyl, alkynyl moieties are each optionally substituted with from one to five substituents independently selected from halo, —CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with from one to four substituents independently selected from halo, —$NO_2$, —CN, $C_{1-4}$ alkyl, $C_{2-4}$ alkenyl, $C_{2-4}$ alkynyl, $C_{1-4}$ haloalkyl, and $R^{10}$;

each R⁶ is independently selected from —OR⁸, —N(R⁸)R⁹, —NR⁸C(O)R⁹, —C(O)R⁸, —C(O)OR⁸, —C(O)N(R⁸)R⁹, —C(O)N(R⁸)OR⁹, —C(O)N(R⁸)S(O)₂R⁹, —N(R⁸)S(O)₂R⁹, —S(O)ₙR⁸, and —S(O)₂N(R⁸)R⁹;

each R⁷ is independently selected from C₁₋₆ alkyl, C₂₋₆ alkenyl, C₂₋₆ alkynyl, C₃₋₆ cycloalkyl-(CH₂)ₘ—, C₆₋₁₄ aryl-(CH₂)ₘ—, C₂₋₅ heterocyclyl-(CH₂)ₘ—, and C₁₋₉ heteroaryl-(CH₂)ₘ—, each optionally substituted with from one to five substituents independently selected from halo, oxo, —NO₂, —CN, C₁₋₆ alkyl, C₁₋₆ haloalkyl, and R¹⁰;

each R⁸ and R⁹ is independently selected from hydrogen or from C₁₋₆ alkyl, C₂₋₆ alkenyl, C₂₋₆ alkynyl, C₃₋₆ cycloalkyl-(CH₂)ₘ—, C₆₋₁₄ aryl-(CH₂)ₘ—, C₂₋₅ heterocyclyl-(CH₂)ₘ—, and C₁₋₉ heteroaryl-(CH₂)ₘ—, each optionally substituted with from one to five substituents independently selected from halo, oxo, —NO₂, —CN, C₁₋₆ alkyl, C₁₋₆ haloalkyl, and R¹⁰;

each R¹⁰ is independently selected from —OR¹¹, —N(R¹¹)R¹², —N(R¹¹)C(O)R¹², —C(O)R¹¹, —C(O)OR¹¹, —C(O)N(R¹¹)R¹², —C(O)N(R¹¹)OR¹², —C(O)N(R¹¹)S(O)₂R¹², —NR¹¹S(O)₂R¹², —S(O)ₙR¹¹, and —S(O)₂N(R¹¹)R¹²;

each R¹¹ and R¹² is independently selected from hydrogen and C₁₋₆ alkyl;

each n is independently selected from 0, 1 and 2; and each m is independently selected from 0, 1, 2, 3, and 4;

wherein each of the aforementioned heteroaryl moieties has one to four heteroatoms independently selected from N, O, and S, and each of the aforementioned heterocyclyl moieties is saturated or partially unsaturated and has one or two heteroatoms independently selected from N, O, and S.

Another aspect of the invention provides a compound which is selected from the following group of compounds and their pharmaceutically acceptable salts:

2-((1R,2S)-2-Aminocyclohexylamino)-4-(m-tolylamino)-6,7-dihydro-5H-pyrrolo[3,4-d]pyrimidin-5-one;

2-((1R,2S)-2-Aminocyclohexylamino)-4-(3-fluorophenylamino)-6,7-dihydro-5H-pyrrolo[3,4-d]pyrimidin-5-one;

2-((1R,2S)-2-Aminocyclohexylamino)-4-(3-chlorophenylamino)-6,7-dihydro-5H-pyrrolo[3,4-d]pyrimidin-5-one;

4-(1H-Indazol-6-ylamino)-2-((1R,2S)-2-aminocyclohexylamino)-6,7-dihydro-5H-pyrrolo[3,4-d]pyrimidin-5-one;

2-((1R,2S)-2-aminocyclohexylamino)-4-(3-(trifluoromethyl)phenylamino)-6,7-dihydro-5H-pyrrolo[3,4-d]pyrimidin-5-one;

cis-2-(2-aminocyclohexylamino)-4-(3-(trifluoromethyl)phenylamino)-6,7-dihydro-5H-pyrrolo[3,4-d]pyrimidin-5-one;

2-(1-Methyl-1H-pyrazol-4-yl)-4-(m-tolylamino)-6,7-dihydro-5H-pyrrolo[3,4-d]pyrimidin-5-one;

2-(4-Ethylpiperazin-1-yl)-4-(m-tolylamino)-6,7-dihydro-5H-pyrrolo[3,4-d]pyrimidin-5-one;

2-(Cyclohexylamino)-4-(m-tolylamino)-6,7-dihydro-5H-pyrrolo[3,4-d]pyrimidin-5-one;

cis-2-(2-Hydroxycyclohexylamino)-4-(m-tolylamino)-6,7-dihydro-5H-pyrrolo[3,4-d]pyrimidin-5-one;

2-(3-Aminopiperidin-1-yl)-4-(m-tolylamino)-6,7-dihydro-5H-pyrrolo[3,4-d]pyrimidin-5-one;

6-((1R,2S)-2-Aminocyclohexylamino)-4-(m-tolylamino)-1H-pyrrolo[3,4-c]pyridin-3(2H)-one;

2-((1R,2S)-2-Aminocyclohexylamino)-4-(1-methyl-1H-pyrazol-4-yl)-6,7-dihydro-5H-pyrrolo[3,4-d]pyrimidin-5-one;

2-((1R,2S)-2-Aminocyclohexylamino)-4-(1-isobutyl-1H-pyrazol-4-yl)-6,7-dihydro-5H-pyrrolo[3,4-d]pyrimidin-5-one;

2-((1R,2S)-2-Aminocyclohexylamino)-4-phenyl-6,7-dihydro-5H-pyrrolo[3,4-d]pyrimidin-5-one;

2-((1R,2S)-2-Aminocyclohexylamino)-4-(benzo[b]thiophen-3-yl)-6,7-dihydro-5H-pyrrolo[3,4-d]pyrimidin-5-one;

2-((1R,2S)-2-Aminocyclohexylamino)-4-(1-ethyl-1H-pyrazol-4-yl)-6,7-dihydro-5H-pyrrolo[3,4-d]pyrimidin-5-one;

2-((1R,2S)-2-Aminocyclohexylamino)-4-(1-benzyl-1H-pyrazol-4-yl)-6,7-dihydro-5H-pyrrolo[3,4-d]pyrimidin-5-one;

2-((1R,2S)-2-Aminocyclohexylamino)-4-(imidazo[1,2-a]pyridin-3-yl)-6,7-dihydro-5H-pyrrolo[3,4-d]pyrimidin-5-one;

2-((1R,2S)-2-Aminocyclohexylamino)-4-(1-propyl-1H-pyrazol-4-yl)-6,7-dihydro-5H-pyrrolo[3,4-d]pyrimidin-5-one;

2-((1R,2S)-2-Aminocyclohexylamino)-4-(1-(2-methoxyethyl)-1H-pyrazol-4-yl)-6,7-dihydro-5H-pyrrolo[3,4-d]pyrimidin-5-one;

4-(1H-Indazol-6-ylamino)-6-((1R,2S)-2-aminocyclohexylamino)-1H-pyrrolo[3,4-c]pyridin-3(2H)-one;

6-((1R,2S)-2-Aminocyclohexylamino)-4-(4-fluoro-3-methylphenylamino)-1H-pyrrolo[3,4-c]pyridin-3(2H)-one;

6-((1R,2S)-2-Aminocyclohexylamino)-7-fluoro-4-(m-tolylamino)-1H-pyrrolo[3,4-c]pyridin-3(2H)-one;

6-((1R,2S)-2-Aminocyclohexylamino)-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(1-methyl-1H-pyrazol-4-yl)-1H-pyrrolo[3,4-c]pyridin-3(2H)-one;

6-((1R,2S)-2-Aminocyclohexylamino)-7-chloro-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(pyrazolo[1,5-a]pyridin-3-yl)-1H-pyrrolo[3,4-c]pyridin-3(2H)-one;

2-(2-(Aminomethyl)piperidin-1-yl)-4-(m-tolylamino)-6,7-dihydro-5H-pyrrolo[3,4-d]pyrimidin-5-one;

6-((1R,2S)-2-Aminocyclohexylamino)-4-(3-(methylsulfonyl)phenylamino)-1H-pyrrolo[3,4-c]pyridin-3(2H)-one;

6-((1R,2S)-2-Aminocyclopentylamino)-4-(3-(methylsulfonyl)phenylamino)-1H-pyrrolo[3,4-c]pyridin-3(2H)-one;

(R)-4-Methyl-2-(4-(3-(methylsulfonyl)phenylamino)-3-oxo-2,3-dihydro-1H-pyrrolo[3,4-c]pyridin-6-ylamino)pentanamide;

(R)-4-Methyl-2-(4-(1-methyl-1H-pyrazol-4-yl)-3-oxo-2,3-dihydro-1H-pyrrolo[3,4-c]pyridin-6-ylamino)pentanamide;

2-((1R,2S)-2-(Dimethylamino)cyclohexylamino)-4-(m-tolylamino)-6,7-dihydro-5H-pyrrolo[3,4-d]pyrimidin-5-one;

2-((1R,2S)-2-(Methylamino)cyclohexylamino)-4-(m-tolylamino)-6,7-dihydro-5H-pyrrolo[3,4-d]pyrimidin-5-one;

2'-((1R,2S)-2-Aminocyclohexylamino)-4'-(m-tolylamino)spiro[cyclopropane-1,7'-pyrrolo[3,4-d]pyrimidin]-5'(6'H)-one;

2-(2-Aminoethylamino)-4-(m-tolylamino)-6,7-dihydro-5H-pyrrolo[3,4-d]pyrimidin-5-one;

2-(2-Amino-2-methylpropylamino)-4-(m-tolylamino)-6,7-dihydro-5H-pyrrolo[3,4-d]pyrimidin-5-one;

2-(5-Oxo-4-(m-tolylamino)-6,7-dihydro-5H-pyrrolo[3,4-d]pyrimidin-2-ylamino)acetamide;

2-((2-Aminoethyl)(methyl)amino)-4-(m-tolylamino)-6,7-dihydro-5H-pyrrolo[3,4-d]pyrimidin-5-one;

2-(Pyrrolidin-2-ylmethylamino)-4-(m-tolylamino)-6,7-dihydro-5H-pyrrolo[3,4-d]pyrimidin-5-one;
2-(3-Aminopyrrolidin-1-yl)-4-(m-tolylamino)-6,7-dihydro-5H-pyrrolo[3,4-d]pyrimidin-5-one;
2-((1R,2S)-2-Aminocyclohexylamino)-4-(1,5-dimethyl-1H-pyrazol-4-yl)-6,7-dihydro-5H-pyrrolo[3,4-d]pyrimidin-5-one;
2-((1R,2S)-2-Aminocyclohexylamino)-4-(1H-indol-2-yl)-6,7-dihydro-5H-pyrrolo[3,4-d]pyrimidin-5-one;
2-((1R,2S)-2-Aminocyclohexylamino)-4-(1H-pyrazol-5-yl)-6,7-dihydro-5H-pyrrolo[3,4-d]pyrimidin-5-one;
2-(3-Aminopropyl)-4-(m-tolylamino)-6,7-dihydro-5H-pyrrolo[3,4-d]pyrimidin-5-one;
6-((1R,2S)-2-Aminocyclohexylamino)-4-(benzofuran-3-yl)-7-fluoro-1H-pyrrolo[3,4-c]pyridin-3(2H)-one;
6-((1R,2S)-2-aminocyclohexylamino)-7-fluoro-4-(imidazo[1,2-a]pyridin-3-yl)-1H-pyrrolo[3,4-c]pyridin-3(2H)-one;
6-((1R,2S)-2-aminocyclohexylamino)-4-(benzo[b]thiophen-3-yl)-7-fluoro-1H-pyrrolo[3,4-c]pyridin-3(2H)-one;
6-((1S,2R)-2-Aminocyclohexylamino)-7-fluoro-4-(1-methyl-1H-pyrazol-4-yl)-1H-pyrrolo[3,4-c]pyridin-3(2H)-one;
(R)-6-(2-Amino-3-ethoxypropylamino)-4-(m-tolylamino)-1H-pyrrolo[3,4-c]pyridin-3(2H)-one;
(R)-6-(2-Amino-3-ethoxypropylamino)-7-fluoro-4-(m-tolylamino)-1H-pyrrolo[3,4-c]pyridin-3(2H)-one;
6-(2-Amino-3,3,3-trifluoropropylamino)-4-(m-tolylamino)-1H-pyrrolo[3,4-c]pyridin-3(2H)-one;
(R)-4-Methyl-2-(3-oxo-4-(m-tolylamino)-2,3-dihydro-1H-pyrrolo[3,4-c]pyridin-6-ylamino)pentanamide;
6-(cis-4-Aminotetrahydrofuran-3-ylamino)-4-(m-tolylamino)-1H-pyrrolo[3,4-c]pyridin-3(2H)-one;
6-((1R,2S)-2-Aminocyclohexylamino)-4-(1-ethyl-1H-pyrazol-4-yl)-1H-pyrrolo[3,4-c]pyridin-3(2H)-one;
6-((1R,2S)-2-Aminocyclohexylamino)-4-(1-ethyl-1H-pyrazol-4-yl)-7-fluoro-1H-pyrrolo[3,4-c]pyridin-3(2H)-one;
6-((1R,2S)-2-Aminocyclohexylamino)-4-(1-cyclopropyl-1H-pyrazol-4-yl)-1H-pyrrolo[3,4-c]pyridin-3(2H)-one;
6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one;
6-((1R,2S)-2-Aminocyclohexylamino)-4-(1-cyclopropyl-1H-pyrazol-4-yl)-7-fluoro-1H-pyrrolo[3,4-c]pyridin-3(2H)-one;
cis-6-(2-Aminocyclohexylamino)-7-fluoro-4-(1-methyl-1H-pyrazol-4-yl)-1H-pyrrolo[3,4-c]pyridin-3(2H)-one;
6-((3R,4R)-3-Aminotetrahydro-2H-pyran-4-ylamino)-7-fluoro-4-(1-methyl-1H-pyrazol-4-yl)-1H-pyrrolo[3,4-c]pyridin-3(2H)-one;
6-(cis-2-Amino-4,4-difluorocyclopentylamino)-7-fluoro-4-(1-methyl-1H-pyrazol-4-yl)-1H-pyrrolo[3,4-c]pyridin-3(2H)-one;
6-(cis-2-Amino-3,3-difluorocyclohexylamino)-7-fluoro-4-(1-methyl-1H-pyrazol-4-yl)-1H-pyrrolo[3,4-c]pyridin-3(2H)-one;
6-(cis-2-Amino-3,3-difluorocyclohexylamino)-4-(1-(difluoromethyl)-1H-pyrazol-4-yl)-7-fluoro-1H-pyrrolo[3,4-c]pyridin-3(2H)-one;
6-(cis-2-amino-3,3-difluorocyclohexylamino)-4-(1-cyclopropyl-1H-pyrazol-4-yl)-7-fluoro-1H-pyrrolo[3,4-c]pyridin-3(2H)-one;
(R)-2-(7-Fluoro-4-(1-methyl-1H-pyrazol-4-yl)-3-oxo-2,3-dihydro-1H-pyrrolo[3,4-c]pyridin-6-ylamino)-4-methylpentanamide;
(R)-2-(4-(1-(Difluoromethyl)-1H-pyrazol-4-yl)-7-fluoro-3-oxo-2,3-dihydro-1H-pyrrolo[3,4-c]pyridin-6-ylamino)-4-methylpentanamide;
(R)-2-(4-(1-Cyclopropyl-1H-pyrazol-4-yl)-7-fluoro-3-oxo-2,3-dihydro-1H-pyrrolo[3,4-c]pyridin-6-ylamino)-4-methylpentanamide;
(R)-2-(4-(Benzofuran-3-yl)-7-fluoro-3-oxo-2,3-dihydro-1H-pyrrolo[3,4-c]pyridin-6-ylamino)-4-methylpentanamide;
(R)-2-(7-Fluoro-3-oxo-4-(pyrazolo[1,5-a]pyridin-3-yl)-2,3-dihydro-1H-pyrrolo[3,4-c]pyridin-6-ylamino)-4-methylpentanamide;
6-((1R,2S)-2-Aminocyclohexylamino)-7-chloro-4-(m-tolylamino)-1H-pyrrolo[3,4-c]pyridin-3(2H)-one;
6-((1R,2S)-2-Aminocyclohexylamino)-3-oxo-4-(m-tolylamino)-2,3-dihydro-1H-pyrrolo[3,4-c]pyridine-7-carbonitrile;
(R)-6-(2-Amino-3-methoxypropylamino)-4-(m-tolylamino)-1H-pyrrolo[3,4-c]pyridin-3(2H)-one;
(R)-6-(2-Amino-3-methoxypropylamino)-3-oxo-4-(m-tolylamino)-2,3-dihydro-1H-pyrrolo[3,4-c]pyridine-7-carbonitrile;
(R)-6-(2-Amino-3-methoxypropylamino)-7-fluoro-4-(m-tolylamino)-1H-pyrrolo[3,4-c]pyridin-3(2H)-one;
7-Acryloyl-6-((1R,2S)-2-aminocyclohexylamino)-4-(m-tolylamino)-1H-pyrrolo[3,4-c]pyridin-3(2H)-one;
6-((1R,2S)-2-Aminocyclohexylamino)-7-iodo-4-(m-tolylamino)-1H-pyrrolo[3,4-c]pyridin-3(2H)-one;
6-((1R,2S)-2-Aminocyclohexylamino)-7-(1H-pyrazol-4-yl)-4-(m-tolylamino)-1H-pyrrolo[3,4-c]pyridin-3(2H)-one;
6-(cis-2-Amino-3,3-difluorocyclohexylamino)-4-(m-tolylamino)-1H-pyrrolo[3,4-c]pyridin-3(2H)-one;
6-((1R,2S)-2-Aminocyclohexylamino)-7-(1-methyl-1H-pyrazol-5-yl)-4-(m-tolylamino)-1H-pyrrolo[3,4-c]pyridin-3(2H)-one;
6-((3R,4R)-3-Aminotetrahydro-2H-pyran-4-ylamino)-4-(m-tolylamino)-1H-pyrrolo[3,4-c]pyridin-3(2H)-one;
6-((3R,4R)-4-Aminotetrahydro-2H-pyran-3-ylamino)-4-(m-tolylamino)-1H-pyrrolo[3,4-c]pyridin-3(2H)-one;
tert-Butyl (1S,2R)-2-(3-oxo-7-phenyl-4-(m-tolylamino)-2,3-dihydro-1H-pyrrolo[3,4-c]pyridin-6-ylamino)cyclohexylcarbamate;
6-((1R,2S)-2-Aminocyclohexylamino)-7-methyl-4-(m-tolylamino)-1H-pyrrolo[3,4-c]pyridin-3(2H)-one;
6-((3R,4R)-3-Aminotetrahydro-2H-pyran-4-ylamino)-7-fluoro-4-(m-tolylamino)-1H-pyrrolo[3,4-c]pyridin-3(2H)-one;
6-((1R,2S)-2-Aminocyclohexylamino)-7-methyl-4-(1-methyl-1H-pyrazol-4-yl)-1H-pyrrolo[3,4-c]pyridin-3(2H)-one;
(R)-6-(2-Amino-3-methoxypropylamino)-4-(1-methyl-1H-pyrazol-4-yl)-1H-pyrrolo[3,4-c]pyridin-3(2H)-one;
6-((3R,4R)-3-Aminotetrahydro-2H-pyran-4-ylamino)-7-fluoro-4-(pyrazolo[1,5-a]pyridin-3-yl)-1H-pyrrolo[3,4-c]pyridin-3(2H)-one;
6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one;
6-((3R,4R)-3-Aminotetrahydro-2H-pyran-4-ylamino)-4-(benzofuran-3-yl)-7-fluoro-1H-pyrrolo[3,4-c]pyridin-3(2H)-one;
(S)-6-(3-Aminopyrrolidin-1-yl)-7-fluoro-4-(1-methyl-1H-pyrazol-4-yl)-1H-pyrrolo[3,4-c]pyridin-3(2H)-one;
(S)-6-(3-Aminopiperidin-1-yl)-7-fluoro-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(1-isopropyl-1H-pyrazol-4-yl)-1H-pyrrolo[3,4-c]pyridin-3(2H)-one;

7-Fluoro-4,6-bis(1-methyl-1H-pyrazol-4-yl)-1H-pyrrolo[3,4-c]pyridin-3(2H)-one;

6-((1R,2S)-2-Aminocyclohexylamino)-7-bromo-4-(1-methyl-1H-pyrazol-4-yl)-1H-pyrrolo[3,4-c]pyridin-3(2H)-one;

2-((1R,2S)-2-Aminocyclohexylamino)-4-(1-(4-fluorophenyl)-1H-pyrazol-4-yl)-6,7-dihydro-5H-pyrrolo[3,4-d]pyrimidin-5-one;

(R)-6-(2-Amino-3-methoxypropylamino)-7-fluoro-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(thiophen-3-yl)-1H-pyrrolo[3,4-c]pyridin-3(2H)-one;

6-((3R,4R)-3-Aminotetrahydro-2H-pyran-4-ylamino)-7-fluoro-4-(4-methylthiophen-2-yl)-1H-pyrrolo[3,4-c]pyridin-3(2H)-one;

6-((1R,2S)-2-Aminocyclohexylamino)-7-fluoro-4-(4-methylthiophen-2-yl)-1H-pyrrolo[3,4-c]pyridin-3(2H)-one;

6-((1R,2S)-2-Aminocyclohexylamino)-7-fluoro-4-(thiophen-3-yl)-1H-pyrrolo[3,4-c]pyridin-3(2H)-one;

(R)-2-(7-Fluoro-4-(1-methyl-1H-pyrazol-4-yl)-3-oxo-2,3-dihydro-1H-pyrrolo[3,4-c]pyridin-6-ylamino)-N,4-dimethylpentanamide;

6-((1R,2S)-2-Aminocyclohexylamino)-7-fluoro-4-(5-methylthiophen-2-yl)-1H-pyrrolo[3,4-c]pyridin-3(2H)-one;

(R)-2-(7-Fluoro-4-(4-methylthiophen-2-yl)-3-oxo-2,3-dihydro-1H-pyrrolo[3,4-c]pyridin-6-ylamino)-4-methylpentanamide;

(R)-2-(7-Fluoro-3-oxo-4-(thiophen-3-yl)-2,3-dihydro-1H-pyrrolo[3,4-c]pyridin-6-ylamino)-4-methylpentanamide;

(R)-2-(7-Fluoro-4-(5-methylthiophen-2-yl)-3-oxo-2,3-dihydro-1H-pyrrolo[3,4-c]pyridin-6-ylamino)-4-methylpentanamide;

6-((1R,2S)-2-Aminocyclohexylamino)-4-(2-aminothiazol-5-yl)-7-fluoro-1H-pyrrolo[3,4-c]pyridin-3(2H)-one;

(R)-2-(7-Fluoro-4-(furan-2-yl)-3-oxo-2,3-dihydro-1H-pyrrolo[3,4-c]pyridin-6-ylamino)-4-methylpentanamide;

(R)-2-(7-Fluoro-4-(furan-3-yl)-3-oxo-2,3-dihydro-1H-pyrrolo[3,4-c]pyridin-6-ylamino)-4-methylpentanamide;

(R)-2-(7-Fluoro-4-(5-methylfuran-2-yl)-3-oxo-2,3-dihydro-1H-pyrrolo[3,4-c]pyridin-6-ylamino)-4-methylpentanamide;

(R)-2-(4-(5-Cyanothiophen-2-yl)-7-fluoro-3-oxo-2,3-dihydro-1H-pyrrolo[3,4-c]pyridin-6-ylamino)-4-methylpentanamide;

(R)-2-(4-(4-Cyanothiophen-2-yl)-7-fluoro-3-oxo-2,3-dihydro-1H-pyrrolo[3,4-c]pyridin-6-ylamino)-4-methylpentanamide;

(R)-2-(7-Fluoro-3-oxo-4-(thiazol-5-yl)-2,3-dihydro-1H-pyrrolo[3,4-c]pyridin-6-ylamino)-4-methylpentanamide;

(R)-2-(7-Fluoro-4-(isothiazol-5-yl)-3-oxo-2,3-dihydro-1H-pyrrolo[3,4-c]pyridin-6-ylamino)-4-methylpentanamide;

6-((1R,2S)-2-Aminocyclohexylamino)-7-fluoro-1,1-dimethyl-4-(1-methyl-1H-pyrazol-4-yl)-1H-pyrrolo[3,4-c]pyridin-3(2H)-one; ((1R,2S)-2-Aminocyclohexylamino)-7-fluoro-4-(1-methyl-1H-pyrazol-3-yl)-1H-pyrrolo[3,4-c]pyridin-3(2H)-one;

6-((1R,2S)-2-Aminocyclohexylamino)-7-fluoro-4-(2-methylthiazol-5-yl)-1H-pyrrolo[3,4-c]pyridin-3(2H)-one;

6-((3R,4R)-3-Aminotetrahydro-2H-pyran-4-ylamino)-7-fluoro-4-(5-methylthiophen-2-yl)-1H-pyrrolo[3,4-c]pyridin-3(2H)-one;

6-((1R,2S)-2-Aminocyclohexylamino)-7-fluoro-1-methyl-4-(1-methyl-1H-pyrazol-4-yl)-1H-pyrrolo[3,4-c]pyridin-3(2H)-one;

(R)-2-(7-Fluoro-3-oxo-4-(thiophen-2-yl)-2,3-dihydro-1H-pyrrolo[3,4-c]pyridin-6-ylamino)-4-methylpentanamide;

6-((3R,4R)-3-Aminotetrahydro-2H-pyran-4-ylamino)-7-fluoro-4-(thiophen-2-yl)-1H-pyrrolo[3,4-c]pyridin-3(2H)-one;

6-((3R,4R)-3-Aminotetrahydro-2H-pyran-4-ylamino)-7-fluoro-4-(thiazol-5-yl)-1H-pyrrolo[3,4-c]pyridin-3(2H)-one;

6-((1R,2S)-2-Aminocyclohexylamino)-7-fluoro-4-(thiophen-2-yl)-1H-pyrrolo[3,4-c]pyridin-3(2H)-one;

6-((3R,4R)-3-Aminotetrahydro-2H-pyran-4-ylamino)-7-fluoro-4-(4-(trifluoromethyl)-1H-imidazol-1-yl)-1H-pyrrolo[3,4-c]pyridin-3(2H)-one;

6-((1R,2S)-2-Aminocyclohexylamino)-7-fluoro-4-(4-methyl-1H-imidazol-1-yl)-1H-pyrrolo[3,4-c]pyridin-3(2H)-one;

6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one;

6-((3R,4R)-3-Aminotetrahydro-2H-pyran-4-ylamino)-7-fluoro-4-(2-methylthiazol-5-yl)-1H-pyrrolo[3,4-c]pyridin-3(2H)-one;

(R)-2-(7-Fluoro-4-(2-methylthiazol-5-yl)-3-oxo-2,3-dihydro-1H-pyrrolo[3,4-c]pyridin-6-ylamino)-4-methylpentanamide;

6-((3R,4R)-3-Aminotetrahydro-2H-pyran-4-ylamino)-4-(5-chlorothiophen-2-yl)-7-fluoro-1H-pyrrolo[3,4-c]pyridin-3(2H)-one;

6-((3R,4R)-3-Aminotetrahydro-2H-pyran-4-ylamino)-4-(1-cyclopropyl-1H-pyrazol-4-yl)-7-fluoro-1H-pyrrolo[3,4-c]pyridin-3(2H)-one; and a stereoisomer of any of the aforementioned compounds and their pharmaceutically acceptable salts.

A further aspect of the invention provides a pharmaceutical composition which includes: a compound of Formula 1, as defined above, or a pharmaceutically acceptable salt thereof, or a compound selected from the group of compounds defined in the preceding paragraph, or a pharmaceutically acceptable salt thereof and a pharmaceutically acceptable excipient.

An additional aspect of the invention provides a use as a medicament of a compound of Formula 1, as defined above, or a pharmaceutically acceptable salt thereof, or a compound selected from the group of compounds defined above, or a pharmaceutically acceptable salt thereof.

Another aspect of the invention provides a use of a compound of Formula 1, as defined above, or pharmaceutically acceptable salt thereof, or a compound selected from the group of compounds defined above, or a pharmaceutically acceptable salt thereof, for the manufacture of a medicament for the treatment of a disease or condition for which a SYK inhibitor is indicated.

A further aspect of the invention provides a method of treating a disease or condition in a subject for which a SYK inhibitor is indicated, the method comprising administering to the subject an effective amount of a compound of Formula 1, as defined above, or a compound selected from the group of compounds defined above, or a pharmaceutically acceptable salt thereof.

An additional aspect of the invention provides a method of treating a disease or condition in a subject, the method comprising administering to the subject an effective amount of a compound of Formula 1, as defined above, or a pharmaceutically acceptable salt thereof, or a compound selected from the group of compounds defined above, or a pharmaceutically acceptable salt thereof, wherein the disease or condition is selected from allergic rhinitis, allergic asthma, atopic dermatitis, rheumatoid arthritis, multiple sclerosis, systemic lupus erythematosus, psoriasis, immune thrombocytopenic purpura, inflammatory bowel disease, chronic obstructive pulmonary disease, and thrombosis.

Another aspect of the invention provides a method of treating a disease or condition in a subject, the method comprising administering to the subject an effective amount of a compound of Formula 1, as defined above, or pharmaceutically acceptable salt thereof, or a compound selected from the group of compounds defined above, or a pharmaceutically acceptable salt thereof, wherein the disease or condition is selected from a hematological malignancy and an epithelial cancer.

A further aspect of the invention provides a combination of an effective amount of a compound of Formula 1, as defined above, or pharmaceutically acceptable salt thereof, or a compound selected from the group of compounds defined above, or a pharmaceutically acceptable salt thereof, and at least one additional pharmacologically active agent.

DETAILED DESCRIPTION OF THE INVENTION

Unless indicated otherwise, this disclosure uses definitions given below.

"Substituted," when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alk-1-yl" refers to an alkyl group, as defined above, which is attached to a parent group or substrate through a carbon atom located at the 1 position of the alkyl group.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalk-1-yl" refers to a cycloalkyl group, as defined above, which is attached to a parent group or substrate through a carbon atom located at the 1 position of the cycloalkyl group.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached to a parent group or to a substrate at any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-5}$ heterocyclyl refers to a heterocyclyl group having 2 to 5 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound. Examples of monocyclic heterocyclyl groups include oxiranyl, thiaranyl, aziridinyl (e.g., aziridin-1-yl and aziridin-2-yl), oxetanyl, thiatanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

"Heteroaryl" refers to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating," as defined immediately above.

"Drug," "drug substance," "active pharmaceutical ingredient," and the like, refer to a compound (e.g., compounds of Formula 1 and compounds specifically named above) that may be used for treating a subject in need of treatment.

"Therapeutically effective amount" of a drug refers to the quantity of the drug that may be used for treating a subject and may depend on the weight and age of the subject and the route of administration, among other things.

"Excipient" refers to any substance that may influence the bioavailability of a drug, but is otherwise pharmacologically inactive.

"Pharmaceutical composition" refers to the combination of one or more drug substances and one or more excipients.

"Drug product," "pharmaceutical dosage form," "dosage form," "final dosage form" and the like, refer to a pharmaceutical composition that is administered to a subject in need of treatment and generally may be in the form of tablets, capsules, sachets containing powder or granules, liquid solutions or suspensions, patches, films, and the like.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); BSA (bovine serum albumin); Cbz (carbobenzyloxy); dba (dibenzylideneacetone); DCC (1,3-dicyclohexylcarbodiimide); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); EDA ethoxylated dodecyl alcohol, Brj®35); EDCI (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethyl-amine); EtOAc (ethyl acetate); EtOH (ethanol); FAM (5-carboxyfluorescein); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); LDA (lithium diisopropylamide); LiHMDS (lithium bis(trimethylsilyl) amide); mCPBA (m-chloroperoxybenzoic acid); Me (methyl); MeOH (methanol); MTBE (methyl tert-butyl ether); MOI (multiplicity of infection); mp (melting point); NaOt-Bu (sodium tertiary butoxide); NBS (N-bromosuccinimide); NCS(N-chlorosuccinimide); NIS (N-iodosuccinimide); PE (petroleum ether); Ph (phenyl); pIC$_{50}$ (-log$_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); SYK (spleen tyrosine kinase); TCEP (tris(2-carboxyethyl)phosphine); TFA (trifluoroacetic acid); TFAA (2,2,2-trifluoroacetic anhydride); THF (tetrahydrofuran); and Tris buffer (2-amino-2-hydroxymethyl-propane-1,3-diol buffer).

This disclosure concerns compounds of Formula 1, which includes compounds specifically named above, and their pharmaceutically acceptable complexes, salts, solvates and hydrates. This disclosure also concerns materials and methods for preparing compounds of Formula 1, pharmaceutical compositions containing them, and their use for treating disorders, diseases, and conditions involving the immune system and inflammation, including rheumatoid arthritis, hematological malignancies, epithelial cancers (i.e., carcinomas), and other disorders, diseases, and conditions for which inhibition of SYK is indicated.

Compounds of Formula 1 include those in which $L^1$ is a bond and $L^2$ is —NH—; $L^1$ is —NH— and $L^2$ is a bond; $L^1$ and $L^2$ are both bonds; or $L^1$ and $L^2$ are both —NH—.

Compounds of Formula 1 also include those in which $R^1$ is hydrogen and $R^2$ is $C_{1-3}$ alkyl, in particular, methyl or ethyl; $R^1$ and $R^2$ are both $C_{1-3}$ alkyl groups, in particular methyl; $R^1$ and $R^2$, together with the carbon atom to which they are attached, form a cyclopropyl group; or $R^1$ and $R^2$ are both hydrogen atoms.

Compounds of Formula 1 include those in which $L^1$ is —NH— and $L^2$ is —NH— or a bond; G is N; $R^1$ and $R^2$ are both hydrogen; and $R^3$ is a 2-amino-$C_{3-8}$ cycloalk-1-yl, or more particularly 2-amino-cyclohex-1-yl, optionally substituted with from one to four substituents independently selected from halo, oxo, —NO$_2$, —CN, $R^6$, and $R^7$.

Compounds of Formula 1 also include those in which $L^1$ is —NH— and $L^2$ is —NH— or a bond; G is N; $R^1$ and $R^2$ are both hydrogen; and $R^3$ is a 2-amino-$C_{2-6}$ alk-1-yl, or more particularly 2-aminoethan-1-yl or 2-amino-2-oxoethan-1-yl, optionally substituted with from one to five, from one to four or from one to two substituents, respectively, independently selected from halo, oxo, —NO$_2$, —CN, $R^6$, and $R^7$.

Compounds of Formula 1 further include those in which $L^1$ is —NH— and $L^2$ is —NH— or a bond; G is N; $R^1$ and $R^2$ are both hydrogen; and $R^3$ is a $C_{2-5}$ heterocyclyl, or more particularly an amino-$C_{2-5}$ heterocyclyl such as 3-aminotetrahydro-2H-pyran-4-yl, optionally substituted with from one to five or from one to four substituents, respectively, independently selected from halo, oxo, —NO$_2$, —CN, $R^6$, and $R^7$, wherein the heterocyclyl moiety has 5 or 6 ring atoms.

Compounds of Formula 1 include those in which $L^1$ is —NH— and $L^2$ is —NH— or a bond; G is N; $R^1$ and $R^2$ are both hydrogen; and $R^4$ is a $C_{6-14}$ aryl, or more particularly phenyl, optionally substituted with from one to five substituents independently selected from halo, oxo, —CN, $R^6$, and $R^7$.

Compounds of Formula 1 also include those in which $L^1$ is —NH— and $L^2$ is —NH— or a bond; G is N; $R^1$ and $R^2$ are both hydrogen; and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 also include those in which $L^1$ is —NH— and $L^2$ is —NH— or a bond; G is N; $R^1$ and $R^2$ are both hydrogen; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 further include those in which $L^1$ is —NH— and $L^2$ is —NH— or a bond; G is N; $R^1$ and $R^2$ are both hydrogen; and $R^4$ is a pyrazole moiety (e.g., pyrazol-4-yl) optionally substituted with from one to three substituents independently selected from halo, —CN, $R^6$, and $R^7$.

Compounds of Formula 1 include those in which $L^1$ is —NH— and $L^2$ is —NH— or a bond; G is C($R^5$); $R^1$ and $R^2$ are both hydrogen; and $R^5$ is a $C_{1-5}$ heteroaryl optionally substituted with from one to four substituents independently selected from halo, —NO$_2$, —CN, $C_{1-4}$ alkyl, $C_{2-4}$ alkenyl, $C_{2-4}$ alkynyl, $C_{1-4}$ haloalkyl, and $R^{10}$.

Compounds of Formula 1 also include those in which $L^1$ is —NH— and $L^2$ is —NH— or a bond; G is $C(R^5)$; $R^1$ and $R^2$ are both hydrogen; and $R^5$ is hydrogen or halo, or more particularly, chloro or fluoro.

Compounds of Formula 1 include those in which $L^1$ is —NH— and $L^2$ is —NH— or a bond; G is $C(R^5)$; $R^1$ and $R^2$ are both hydrogen; and $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$.

Compounds of Formula 1 also include those in which $L^1$ is —NH— and $L^2$ is —NH— or a bond; G is $C(R^5)$; $R^1$ and $R^2$ are both hydrogen; and $R^3$ is a 2-amino-$C_{2-6}$ alk-1-yl, or more particularly 2-aminoethan-1-yl or 2-amino-2-oxoethan-1-yl, optionally substituted with from one to five, from one to four or from one to two substituents, respectively, independently selected from halo, oxo, —$NO_2$, —CN, $R^6$, and $R^7$.

Compounds of Formula 1 further include those in which $L^1$ is —NH— and $L^2$ is —NH— or a bond; G is $C(R^5)$; $R^1$ and $R^2$ are both hydrogen; and $R^3$ is a $C_{2-5}$ heterocyclyl, or more particularly an amino-$C_{2-5}$ heterocyclyl such as 3-aminotetrahydro-2H-pyran-4-yl, optionally substituted with from one to five or from one to four substituents, respectively, independently selected from halo, oxo, —$NO_2$, —CN, $R^6$, and $R^7$, wherein the heterocyclyl moiety has 5 or 6 ring atoms.

Compounds of Formula 1 include those in which $L^1$ is —NH— and $L^2$ is —NH— or a bond; G is $C(R^5)$; $R^1$ and $R^2$ are both hydrogen; and $R^4$ is a $C_{6-14}$ aryl, or more particularly phenyl, optionally substituted with from one to five substituents independently selected from halo, oxo, —CN, $R^6$, and $R^7$.

Compounds of Formula 1 also include those in which $L^1$ is —NH— and $L^2$ is —NH— or a bond; G is $C(R^5)$; $R^1$ and $R^2$ are both hydrogen, and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 also include those in which $L^1$ is —NH— and $L^2$ is —NH— or a bond; G is $C(R^5)$; $R^1$ and $R^2$ are both hydrogen; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 further include those in which $L^1$ is —NH— and $L^2$ is —NH— or a bond; G is $C(R^5)$; $R^1$ and $R^2$ are both hydrogen; and $R^4$ is pyrazole moiety (e.g., pyrazol-4-yl) optionally substituted with from one to three substituents independently selected from halo, —CN, $R^6$, and $R^7$.

Compounds of Formula 1 include those in which $L^1$ is —NH— and $L^2$ is —NH— or a bond; G is N; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{6-14}$ aryl, or more particularly phenyl, optionally substituted with from one to five substituents independently selected from halo, oxo, —CN, $R^6$, and $R^7$.

Compounds of Formula 1 also include those in which $L^1$ is —NH— and $L^2$ is —NH— or a bond; G is N; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 include those in which $L^1$ is —NH— and $L^2$ is —NH— or a bond; G is N; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 further include those in which $L^1$ is —NH— and $L^2$ is —NH— or a bond; G is N; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a pyrazole moiety (e.g., pyrazol-4-yl) optionally substituted with from one to three substituents independently selected from halo, —CN, $R^6$, and $R^7$.

Compounds of Formula 1 include those in which $L^1$ is —NH— and $L^2$ is —NH— or a bond; G is $C(R^5)$; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{6-14}$ aryl, or more particularly phenyl, optionally substituted with from one to five substituents independently selected from halo, oxo, —CN, $R^6$, and $R^7$.

Compounds of Formula 1 also include those in which $L^1$ is —NH— and $L^2$ is —NH— or a bond; G is $C(R^5)$; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 include those in which $L^1$ is —NH— and $L^2$ is —NH— or a bond; G is $C(R^5)$; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 further include those in which $L^1$ is —NH— and $L^2$ is —NH— or a bond; G is $C(R^5)$; $R^1$ and $R^2$ are both hydrogen; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a pyrazole moiety (e.g., pyrazol-4-yl) optionally substituted with from one to three substituents independently selected from halo, —CN, $R^6$, and $R^7$.

Compounds of Formula 1 include any of the aforementioned embodiments in which $L^1$ is —NH— and $L^2$ is a bond.

Thus, compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^3$ is a 2-amino-$C_{2-6}$ alk-1-yl, or more particularly 2-aminoethan-1-yl or 2-amino-2-oxoethan-1-yl, optionally substituted with from one to five, from one to four or from two to two substituents, respectively, independently selected from halo, oxo, —$NO_2$, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^3$ is a $C_{2-5}$ heterocyclyl, or more particularly an amino-$C_{2-5}$ heterocyclyl such as 3-aminotetrahydro-2H-pyran-4-yl, optionally substituted with from one to five or from one to four substituents, respectively, independently selected from halo, oxo, —$NO_2$, —CN, $R^6$, and $R^7$, wherein the heterocyclyl moiety has 5 or 6 ring atoms.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^4$ is a $C_{6-14}$ aryl, or more particularly phenyl, optionally substituted with from one to five substituents independently selected from halo, oxo, —CN, $R^6$, and $R^7$.

Compounds of Formula 1 also include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; and $R^4$ is a pyrazole moiety (e.g., pyrazol-4-yl) optionally substituted with from one to three substituents independently selected from halo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{6-14}$ aryl, or more particularly phenyl, optionally substituted with from one to five substituents independently selected from halo, oxo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a $C_{1-9}$ heteroaryl, or more particularly a monocyclic $C_{2-4}$ heteroaryl, optionally substituted with from one to five or from one to four substituents, respectively, independently selected from halo, oxo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a monocyclic $C_{2-4}$ heteroaryl selected from pyrrolyl, furanyl, thiopheneyl, pyrazolyl, imidazolyl, isoxazolyl, oxazolyl, isothiazoly, and thiazolyl, or more particularly from thiopheneyl, pyrazolyl, isothiazoly, and thiazolyl, each optionally substituted with from one to three substituents independently selected from halo, —CN, $R^6$, and $R^7$.

Compounds of Formula 1 include those in which $L^1$ is —NH—; $L^2$ is a bond; G is $C(R^5)$; $R^1$ and $R^2$ are both hydrogen; $R^5$ is hydrogen or halo, or more particularly, chloro or fluoro; $R^3$ is a 2-amino-$C_{3-8}$ cycloalk-1-yl, or more particularly 2-amino-cyclohex-1-yl, optionally substituted with from one to four substituents independently selected from halo, oxo, —$NO_2$, —CN, $R^6$, and $R^7$; and $R^4$ is a pyrazole moiety (e.g., pyrazol-4-yl) optionally substituted with from one to three substituents independently selected from halo, —CN, $R^6$, and $R^7$.

Compounds of Formula 1 also include any of the above embodiments in which one or more of the $R^3$, $R^4$, $R^5$, $R^7$, $R^8$, and $R^9$ substituents have no optional substituents.

All references to compounds, including compounds of Formula 1 and compounds named in the specification, generally include all complexes, salts, solvates, hydrates, and liquid crystals of the compounds. Likewise, all references to compounds include all complexes, solvates, hydrates, and liquid crystals of the salts of the compounds.

Compounds of Formula 1, which include compounds specifically named above, may form pharmaceutically acceptable complexes, salts, solvates and hydrates. These salts include acid addition salts (including di-acids) and base salts. Pharmaceutically acceptable acid addition salts include nontoxic salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include nontoxic salts derived from bases, including metal cations, such as an alkali or alkaline earth metal cation, as well as amines. Examples of suitable metal cations include sodium ($Na^+$), potassium ($K^+$), magnesium ($Mg^{2+}$), calcium ($Ca^{2+}$), zinc ($Zn^{2+}$), and aluminum ($Al^{3+}$). Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+$($CH_3$)$_3$). See, e.g., N. H. Hartshorne and A. Stuart, Crystals and the Polarizing Microscope (4th ed, 1970).

All references to compounds, including compounds of Formula 1 and compounds named in the specification, generally include all polymorphs and crystal habits, prodrugs, metabolites, stereoisomers, and tautomers thereof, as well as all isotopically-labeled compounds thereof.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Certain compounds described herein may have stereoisomers. These compounds may exist as single enantiomers (enantiopure compounds) or mixtures of enantiomers (enriched and racemic samples), which depending on the relative excess of one enantiomer over another in a sample, may exhibit optical activity. Such stereoisomers, which are non-superimposable mirror images, possess a stereogenic axis or one or more stereogenic centers (i.e., chirality). Other compounds may be stereoisomers that are not mirror images. Such stereoisomers, which are known as diastereoisomers, may be chiral or achiral (contain no stereogenic centers).

They include molecules containing an alkenyl or cyclic group, so that cis/trans (or Z/E) stereoisomers are possible, or molecules containing two or more stereogenic centers, in which inversion of a single stereogenic center generates a corresponding diastereoisomer. Unless stated or otherwise clear (e.g., through use of stereobonds, stereocenter descriptors, etc.) the scope of the invention and disclosure generally includes the reference compound and its stereoisomers, whether they are each pure (e.g., enantiopure) or mixtures (e.g., enantiomerically enriched or racemic).

Geometrical (cis/trans) isomers may be separated by conventional techniques such as chromatography and fractional crystallization.

Individual enantiomers of compounds may be prepared via chiral synthesis from a suitable optically pure precursor or isolated via resolution of the racemate (or the racemate of a salt or derivative) using, for example, chiral HPLC. Alternatively, the racemate (or a racemic precursor) may be reacted with a suitable enantiomerically pure compound (e.g., acid or base) to yield a pair of diastereoisomers, each composed of a single enantiomer, which are separated via, say, fractional recrystallization or chromatography. The desired enantiomer is subsequently regenerated from the appropriate diastereoisomer. Often, the desired enantiomer may be further enriched by recrystallization in a suitable solvent (e.g., ACN) when it is it available in sufficient quantity (e.g., typically not much less than about 85% ee, and in some cases, not much less than about 90% ee). For a further discussion of techniques for separating stereoisomers, see E. L. Eliel and S. H. Wilen, *Stereochemistry of Organic Compounds* (1994).

"Tautomers" refer to structural isomers that are interconvertible via a low energy barrier. Tautomeric isomerism (tautomerism) may take the form of proton tautomerism in which the compound contains, for example, an imino, keto, or oxime group, or valence tautomerism in which the compound contains an aromatic moiety.

Compounds described herein also include all pharmaceutically acceptable isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^{2}H$ and $^{3}H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^{2}H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^{3}H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^3$, $R^4$, $R^5$, $R^7$, $R^8$, $R^9$, $L^1$ and $L^2$) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^3$ that is a moiety having a potentially reactive amine. In such cases, $R^3$ would include the moiety with or without, say, a Boc or Cbz group attached to the amine.

Scheme 1 illustrates a method for preparing compound 1-5. Starting material 1-0 (e.g., methyl 6-methyl-2,4-dioxo-1,2,3,4-tetrahydropyrimidine-5-carboxylate) is chlorinated at elevated temperature (e.g., 95-105° C.) using phosphoryl trichloride as a reactive solvent, in the presence of a catalytic amount of N,N-dimethyl aniline to give a methylpyrimidine carboxylate 1-1. The 2-chloro and 4-chloro groups of intermediate 1-1 are subsequently displaced via treatment with an appropriately-substituted amine. As depicted in Scheme 1, the 2-chloro group is reacted with $R^4$—$NH_2$ (e.g. substituted aniline) in a polar aprotic organic solvent (e.g., ACN or THF) and in the presence of a hindered base such as $Et_3N$ or DIPEA (2 eq) to give intermediate 1-2. The reaction may be carried out at elevated temperatures (e.g. 90° C. or reflux conditions). In a similar manner, the 4-chloro group is displaced with $R^3$—$NH_2$ to give intermediate 1-3. The second displacement is carried out at elevated temperatures (e.g., 90° C. or reflux conditions) in a polar aprotic organic solvent (e.g., DMA or DMF) in the presence of a hindered base (e.g., $Et_3N$ or DIPEA).

Scheme 1 shows two methods for cyclizing intermediate 1-3. In one method, intermediate 1-3 is oxidized with $SeO_2$ (2-4 eq) in an organic solvent, such as 1,4-dioxane, under reflux conditions (e.g., about 100° C.) to give a ketone (or aldehyde) intermediate (not shown). Subsequent reaction with 2,4-dimethoxybenzylamine in the presence of a mild reducing agent, such as sodium cyanoborohydride (1.5 eq) or sodium triacetoxy-borohydride in MeOH, gives via reductive amination, an amino intermediate which cyclizes to 1-4, either immediately or upon heating to about 50° C. The dimethoxybenzyl group can be removed by treating intermediate 1-4 with an acid (e.g., TFA) at about 60° C., which gives the desired compound 1-5. In a second method, intermediate 1-3 is treated with a bromination reagent such as NBS in the presence of an initiator (e.g., dibenzoyl peroxide or AIBN) in $CCl_4$. Refluxing the reaction mixture gives intermediate 1-6, which is treated with a source of ammonia (e.g., ammonium hydroxide) in THF to give 1-5.

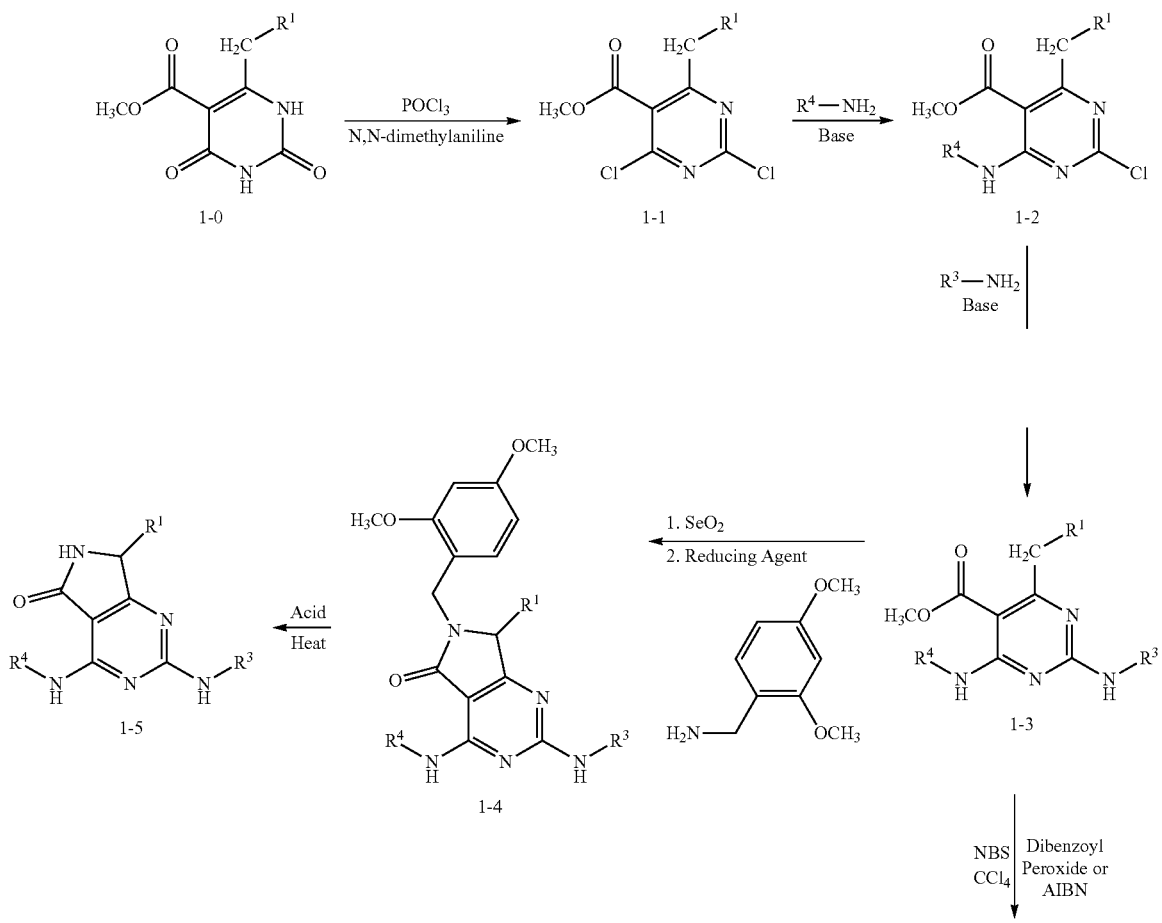

Scheme 1

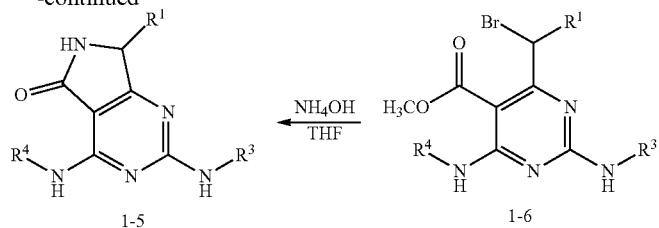
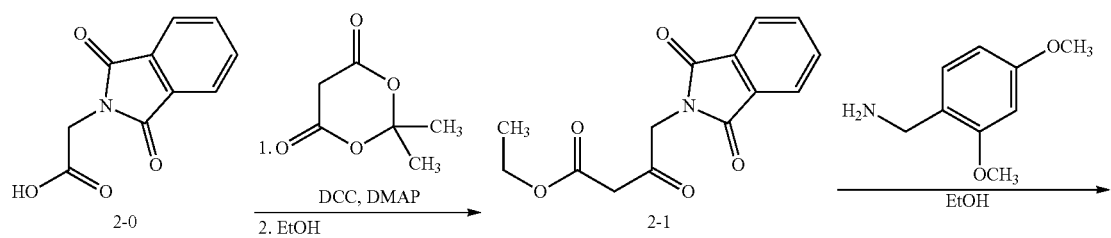
Scheme 2
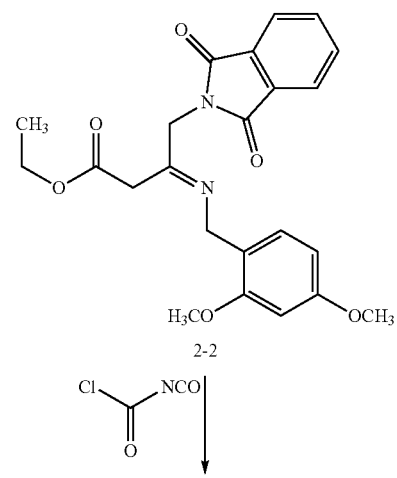
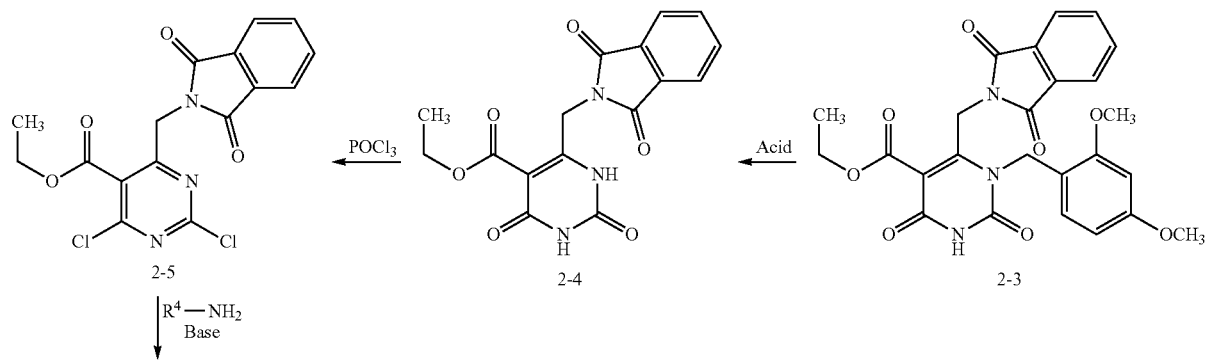

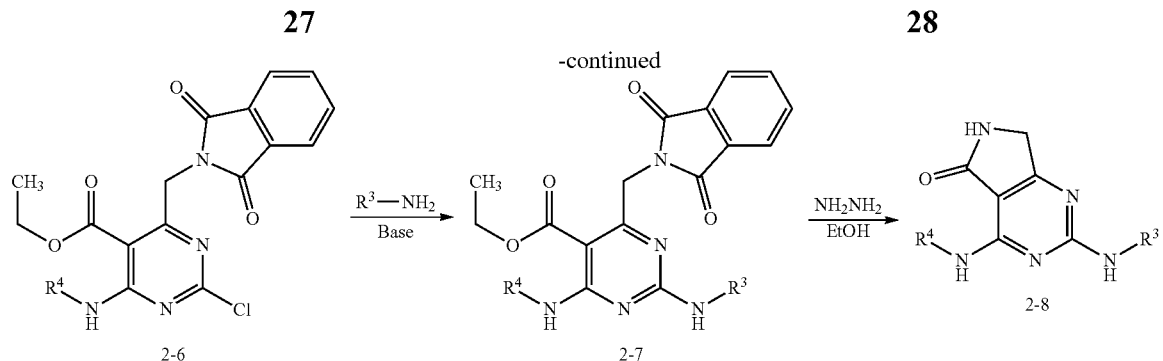

Scheme 2 provides a method for preparing compound 2-8. Starting material 2-0 (2-(1,3-dioxoisoindolin-2-yl)acetic acid) is reacted with 2,2-dimethyl-1,3-dioxane-4,6-dione (1-1.5 eq) and 4-dimethylaminopyridine (1-1.5 eq) in the presence of DCC (1-1.5 eq) and an organic solvent such as dichloromethane to give intermediate 2-1. Subsequent treatment of 2-1 with 2,4-dimethoxybenzylamine (1 eq) in EtOH at about 50° C. gives an imine 2-2, which is isolated, re-dissolved in an organic solvent (e.g., THF) and treated with an activated carbonylisocyanate (e.g., carbonisocyanatidic chloride, 1 eq) at about 80° C. to give intermediate 2-3. Treating 2-3 with an acid (e.g., TFA at RT to 60° C.) removes the dimethoxybenzyl group to give intermediate 2-4, which is subsequently reacted with a chlorinating agent (e.g., POCl₃) under refluxing conditions (e.g., about 100° C.) to give intermediate 2-5. Stepwise displacement of the two chloro groups with appropriately-substituted amines (R⁴—NH₂ and R³—NH₂) gives intermediates 2-6 and 2-7. Treatment of intermediate 2-7 with hydrazine hydrate (4-5 eq) in EtOH with heating (e.g., at about 65° C.) gives compound 2-8.

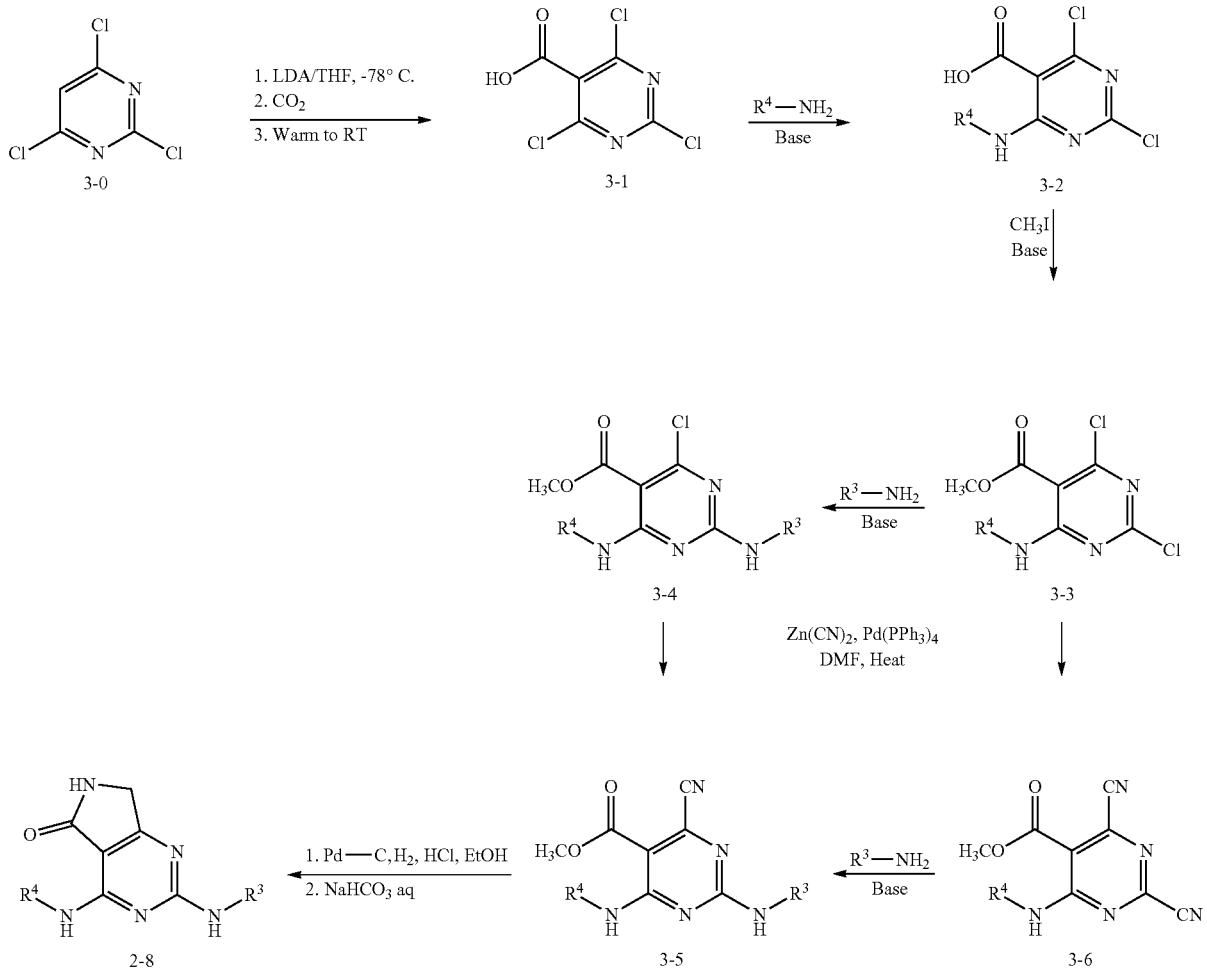

Scheme 3 provides another method for preparing compound 2-8. Starting material 3-0 (2,4,6-trichloropyrimidine) is treated with a strong base such as LDA (made freshly from diisopropyl amine and n-BuLi or purchased) at −78° C. in dry THF, followed by quenching with dry ice. Warming the mixture to RT and stirring gives intermediate 3-1. Displacement of a chloro group via treatment with an appropriately-substituted amine ($R^4$—$NH_2$, 1 eq) in the presence of a hindered base (e.g., $Et_3N$ or DIPEA, 2 eq) and a polar aprotic organic solvent (e.g., DMF) gives intermediate 3-2. Subsequent treatment of 3-2 with MeI (1-1.5 eq) and a base (e.g. sodium bicarbonate, 1.5-3 eq) yields an ester 3-3, which may proceed to compound 2-8 through two different routes. In one route, intermediate 3-3 undergoes treatment with an appropriately-substituted amine ($R^3$—$NH_2$, 1-1.1 eq) in the presence of a hindered base (e.g., DIPEA) and a polar aprotic organic solvent (e.g., THF) to give intermediate 3-4 and an isomer. Following isolation, intermediate 3-4 is reacted with zinc cyanide (0.5-1 eq) and a catalytic amount (10%) of tetrakis (triphenylphosphine) palladium(0) in DMF at about 90° C. to give nitrile 3-5. Reduction of the nitrile group to an amine via hydrogenation using Pd on carbon (5-10%) in EtOH and a catalytic amount of HCl gives, upon treatment with sodium bicarbonate, 2-8.

In an alternative route, intermediate 3-3 is first converted to nitrile 3-6 via palladium-catalyzed cyanation by heating a mixture of 3-3, zinc cyanide (0.5-1 eq), tetrakis(triphenyl phosphine)palladium(0) (0.1 eq), and a polar aprotic solvent (e.g., DMF) in a microwave oven at about 120° C. for about 1 hour. Following isolation, intermediate 3-6 is converted at RT to 3-5 via reaction with an appropriately-substituted amine ($R^3$—$NH_2$, 1-1.5 eq) in a polar aprotic solvent (e.g., DMF) and in the presence of a hindered base (e.g., DIPEA). As described above, reduction of the nitrile group of 3-5 and subsequent cyclization gives compound 2-8.

Scheme 4 shows a method for preparing compound 4-6. Lithiation of starting material 4-0 (2,6-di-halo-3-iodopyridine) via directed ortho-lithiation by LDA in THF at −78° C., followed by quenching with dry ice, gives 4-1, which is subsequently esterified at RT using MeI and a base (e.g., potassium carbonate). As in Scheme 3, the iodo group of intermediate 4-2 is converted to a nitrile group via palladium-catalyzed cyanation to give 4-3. Stepwise displacement of the two chloro groups with appropriately-substituted amines ($R^4$—$NH_2$ and $R^3$—$NH_2$) gives intermediates 4-4 and 4-5. As in the ring-closure step depicted in Scheme 3, hydrogenation followed by cyclization gives compound 4-6.

Scheme 4

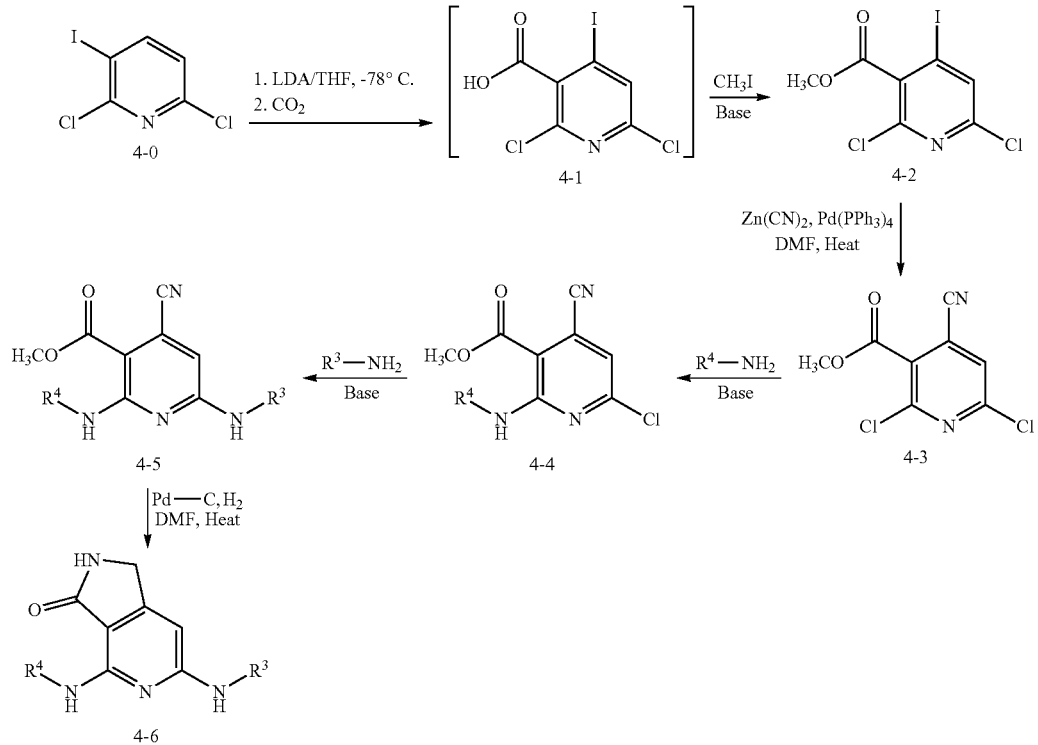

Scheme 5 depicts a method for preparing compound 5-4. Starting material 1-1 (methyl 2,4-dichloro-6-methylpyrimidine-5-carboxylate) is reacted with an aromatic boronic acid or borate (e.g., $R^4$—$B(OR^{13})_2$, where $R^4$ is $C_{6-14}$ aryl or $C_{1-9}$ heteroaryl, and e.g., each $R^{13}$ is H or $C_{1-4}$ alkyl) in the presence of a palladium catalyst (e.g., $Pd(PPh_3)_4$, $(PPh_3)_2PdCl_2$, etc.), a base (e.g., KF or $Na_2CO_3$), and an organic solvent (e.g., dioxane, DMF, etc.). The Suzuki-type coupling is carried out at elevated temperature (e.g., about 90° C.) and gives intermediate 5-1. Displacement of the chloro group with an appropriately-substituted amine ($R^3$—$NH_2$) gives intermediate 5-2. As in Scheme 1, the methyl group on pyrimidine is oxidized with $SeO_2$ (2-4 eq) in an organic solvent (e.g., 1,4-dioxane) under reflux conditions to give an aldehyde intermediate, which is subsequently reacted with 2,4-dimethoxy-benzylamine in the presence of a mild reducing agent (e.g., about 1.5 eq of $NaCNBH_3$ or $NaBH(OAc)_3$) in MeOH, to give, via reductive amination, an amino intermediate which cyclizes to 5-3, either immediately or upon heating to about 50° C. Treating intermediate 5-3 with an acid (e.g., TFA) at about 60° C. gives compound 5-4.

lamine in the presence of a mild reducing agent (e.g., about 1.5 eq of $NaCNBH_3$ or $NaBH(OAc)_3$) in MeOH, to give intermediate 6-2. Treating 6-2 with an acid (e.g., TFA) at about 60° C. yields compound 6-3.

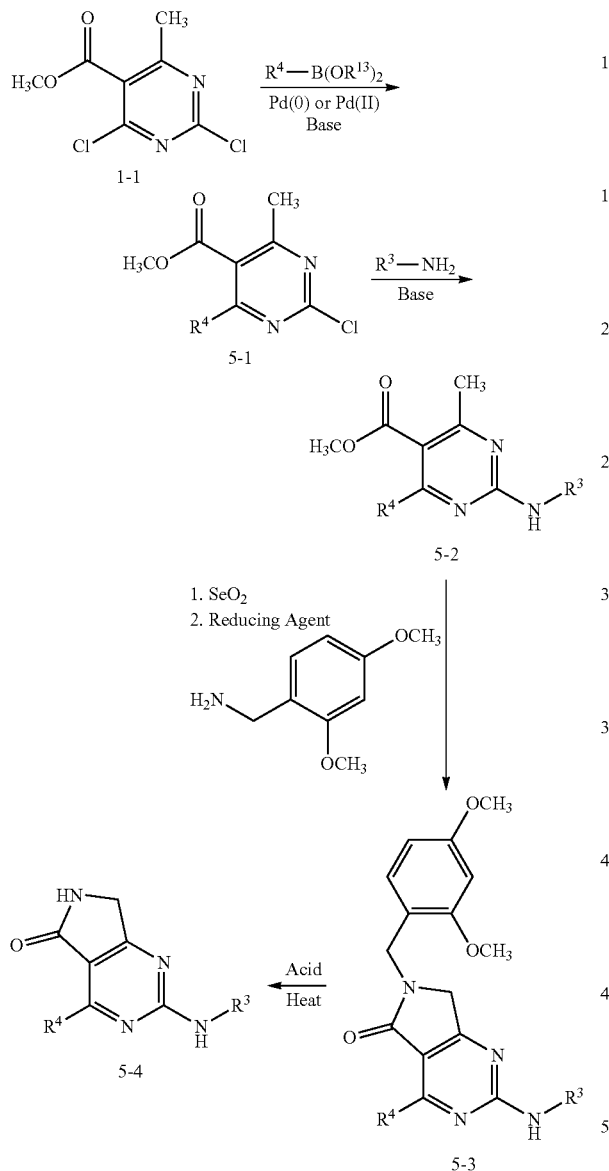

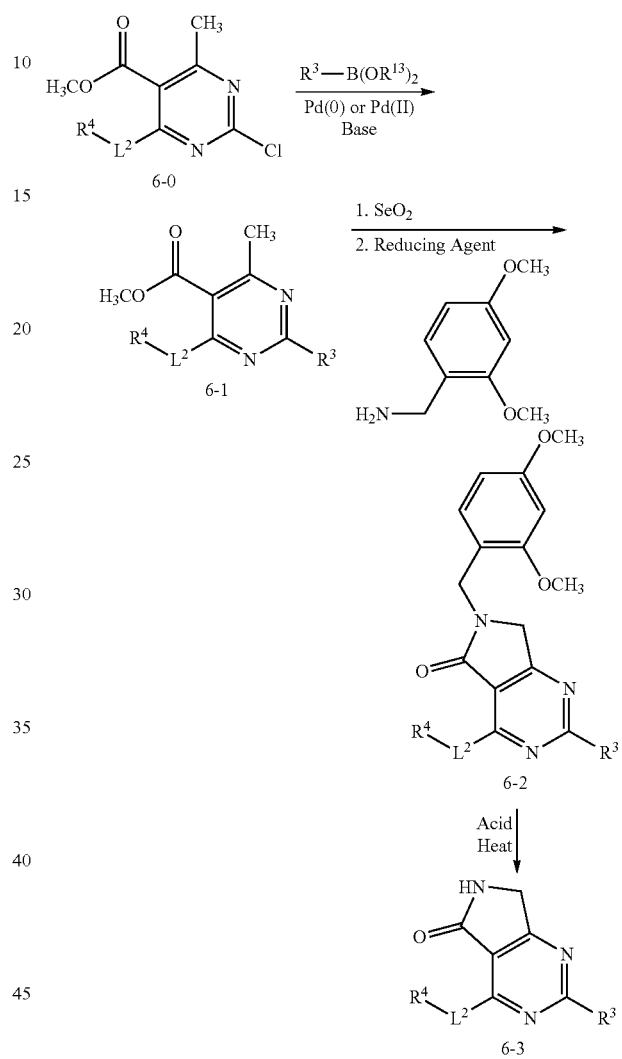

Scheme 6 depicts a method for preparing compound 6-3. Starting material 6-0, which may be prepared from methyl 2,4-dichloro-6-methylpyrimidine-5-carboxylate using the methods described above, is reacted with an aromatic boronic acid or borate (e.g., $R^3$—$B(OR^{13})_2$, where $R^3$ is $C_{6-14}$ aryl or $C_{1-9}$ heteroaryl and e.g., $R^{13}$ is H or $C_{1-4}$ alkyl) in the presence of a palladium catalyst (e.g., $Pd(PPh_3)_4$, $(PPh_3)_2PdCl_2$, etc.), a base (e.g., KF or $Na_2CO_3$), and an organic solvent (e.g., dioxane, DMF, DME, etc.). The Suzuki-type coupling is carried out at elevated temperature (e.g., about 90° C.) and gives intermediate 6-1. The methyl group on pyrimidine is oxidized with $SeO_2$ (2-4 eq) in an organic solvent (e.g., 1,4-dioxane) under reflux conditions to give an aldehyde intermediate, which is subsequently reacted with 2,4-dimethoxybenzy- Scheme 7 illustrates methods for preparing compounds 7-2, 7-3, 7-4, 7-5, and 7-6. Starting material 7-0, which may be prepared using the methods described above, may be reacted with NBS or NIS to give halo-pyridine intermediate 7-1 ($Y^1$ is Br or I). As in Scheme 3, the halo group of 7-1 may be converted to a nitrile group via palladium-catalyzed cyanation to give 7-2. Compound 7-2 is subsequently reacted with a Grignard reagent ($R^7$—MgBr) to give an imine intermediate (not shown), which upon acid hydrolysis, yields compound 7-3. Alternatively, halo-pyridine intermediate 7-1 may be reacted with $NHR^8R^9$ in the presence of a palladium (II) catalyst (e.g., $PdCl_2(dppf)$), a stoichiometric amount of base (e.g., NaOt-Bu), and an organic solvent (e.g., dioxane, toluene, etc.), at elevated temperature (e.g., about 100° C.). The Buchwald-Hartwig coupling gives heteroaryl amine 7-4. In addition, 7-1 may be reacted with a terminal alkyne (HC≡$R^{13}$, e.g., $R^{13}$ is H or $C_{1-4}$ alkyl) in the presence of a palladium(II) catalyst (e.g., $(PPh_3)_2PdCl_2$), a copper(I) cocatalyst (e.g., CuI), and an amine base (e.g. Et₃N), at RT. Following the Sonogashira coupling, reduction of the alkyne moiety yields compound 7-5 with $R^5$ being, e.g., $C_{1-5}$ alkyl. Compound 7-1 may be reacted with an aromatic boronic acid or borate (e.g., $R^5$—B(OR$^{13}$)₂, where $R^5$ is $C_{1-9}$ heteroaryl and e.g., $R^{13}$ is H or $C_{1-4}$ alkyl) in the presence of a palladium catalyst (e.g., Pd(PPh₃)₄, (PPh₃)₂PdCl₂, etc.), a base (e.g., KF or Na₂CO₃), and an organic solvent (e.g., dioxane, DMF, etc.). The Suzuki-type coupling is carried out at elevated temperature (e.g., about 90° C.) and gives compound 7-5 with $R^5$ being $C_{1-9}$ heteroaryl.

Scheme 8 shows an alternative method for preparing compound 4-6. Starting material 8-0 (2-chloro-3-iodopyridine) undergoes ortho-directed lithiation via treatment with LDA in THF at −78° C. Quenching with dry ice gives 8-1, which is subsequently esterified at RT using iodomethane and a base (e.g., potassium carbonate). As in Scheme 4, the iodo group of intermediate 8-2 is converted to a nitrile group via palladium-catalyzed cyanation or through treatment with cyanocopper or zinc cyanide in a suitable solvent (e.g., DMF, DMA, etc.) at elevated temperature. The $R^4$ substituent is installed on 8-3 using a Suzuki reaction, which gives intermediate 8-4. N-oxi-

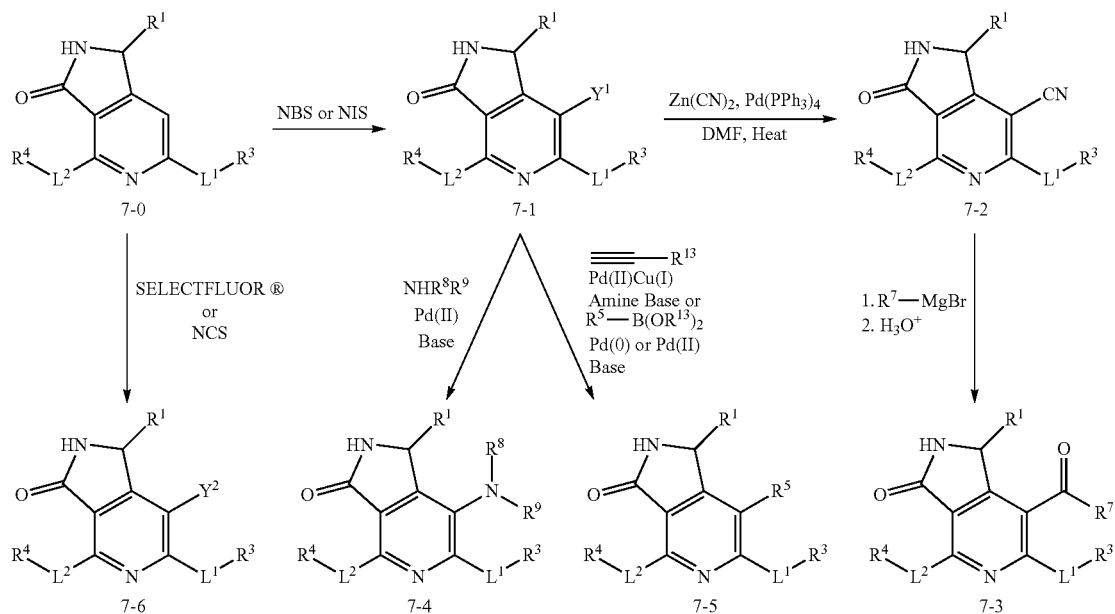

Scheme 7

As shown in Scheme 7, compound 7-0 may alternatively be treated with a fluorinating agent, such as SELECTFLUOR® (1-(chloromethyl)-4-fluoro-1,4-diazoniabicyclo[2.2.2]octane ditetrafluoroborate), in an organic solvent (e.g., DCM) or a mixture of organic solvents (e.g., DCM and MeOH), to give a fluoro-pyridine derivative 7-6 ($Y^2$ is F). Similarly, 7-0 may be treated with a chlorinating agent, such as NCS, in an aprotic solvent (e.g., DCM) to give a chloro-pyridine derivative 7-6 ($Y^2$ is Cl).

dation of the pyridine moiety via treatment with hydrogen peroxide/urea complex gives an activated intermediate 8-5, which is chlorinated through reaction with phosphorus oxychloride at an elevated temperature (e.g., 90-100° C.). Displacement of the chloro group on 8-6 via reaction with an appropriately-substituted amine ($R^3$—NH₂) gives intermediate 8-7. Subsequent reduction through palladium-catalyzed hydrogenation and cyclization gives compound 4-6.

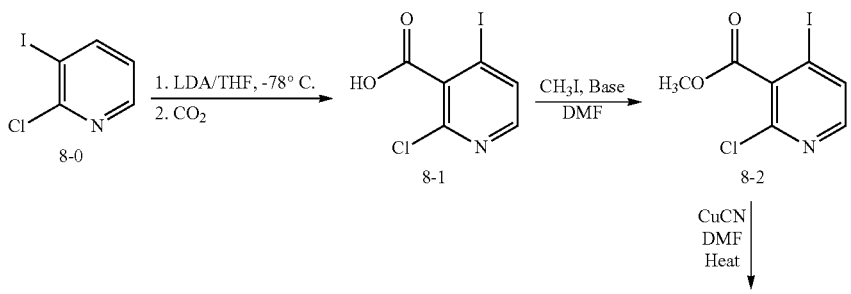

Scheme 8

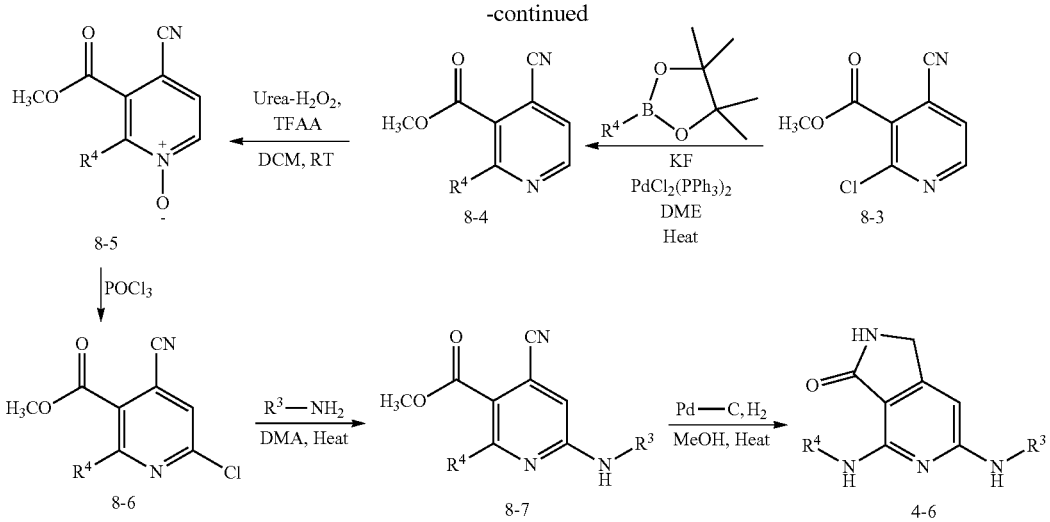

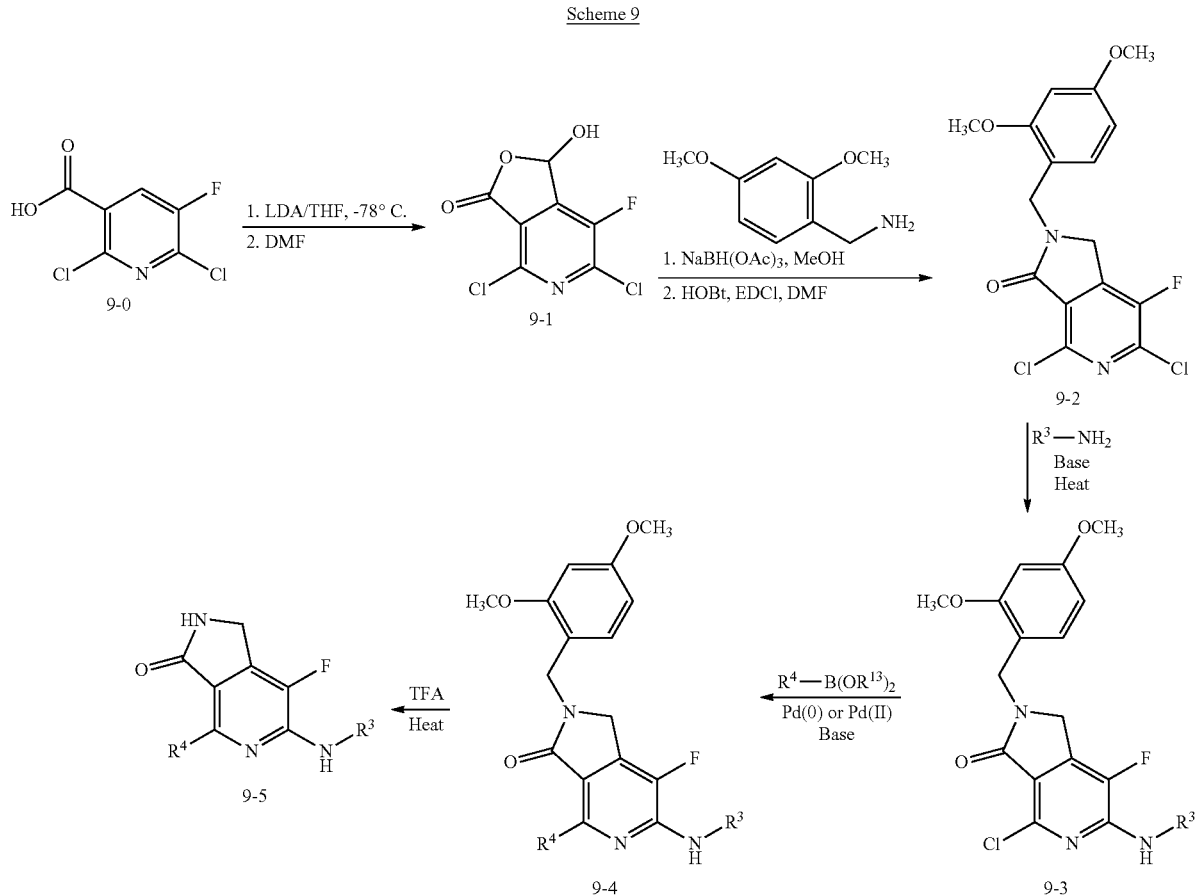

Scheme 9

Scheme 9 depicts the synthesis of compound 9-5. Starting material 9-0 (2,6-dichloro-5-fluoronicotinic acid) is lithiated via treatment with LDA in THF at −78° C. Quenching with DMF gives an aldehyde intermediate 9-1, which undergoes reductive amination through reaction with an amine (e.g., 2,4-dimethoxyphenyl)methanamine) and reducing agent (e.g., NaBH(OAc)$_3$). The resulting amino acid (not shown) is cyclized via amide coupling, which employs a suitable coupling agent (e.g., EDCI, DCC, etc.), catalyst (HOBt, DMAP, etc.), and solvent (e.g., DMF, DMSO, ACN, THF, DCM, etc.). As in previous schemes, displacement of the chloro group of compound 9-2 with an appropriate amine ($R^3$—$NH_2$) gives intermediate 9-3, which is subsequently reacted with an aromatic boronic acid or borate (e.g., $R^4$—$B(OR^{13})_2$ in the presence of a palladium catalyst (e.g., Pd(PPh₃)₄, (PPh₃)₂PdCl₂, etc.), base (e.g., KF or Na₂CO₃), and organic solvent (e.g., dioxane, DMF, etc.) at elevated temperature (e.g., about 90° C.) to give 9-4. Following the Suzuki coupling, treatment of 9-4 with TFA at elevated temperature (e.g., 40-60° C.) generates 9-5.

aldehyde) intermediate (not shown), which is reacted with 2,4-dimethoxybenzylamine in the presence of a reducing agent to give, via reductive amination, an amino acid intermediate which cyclizes to 10-2. The methylthio group is converted to methylsulfonyl using mCPBA (m-chloroper-

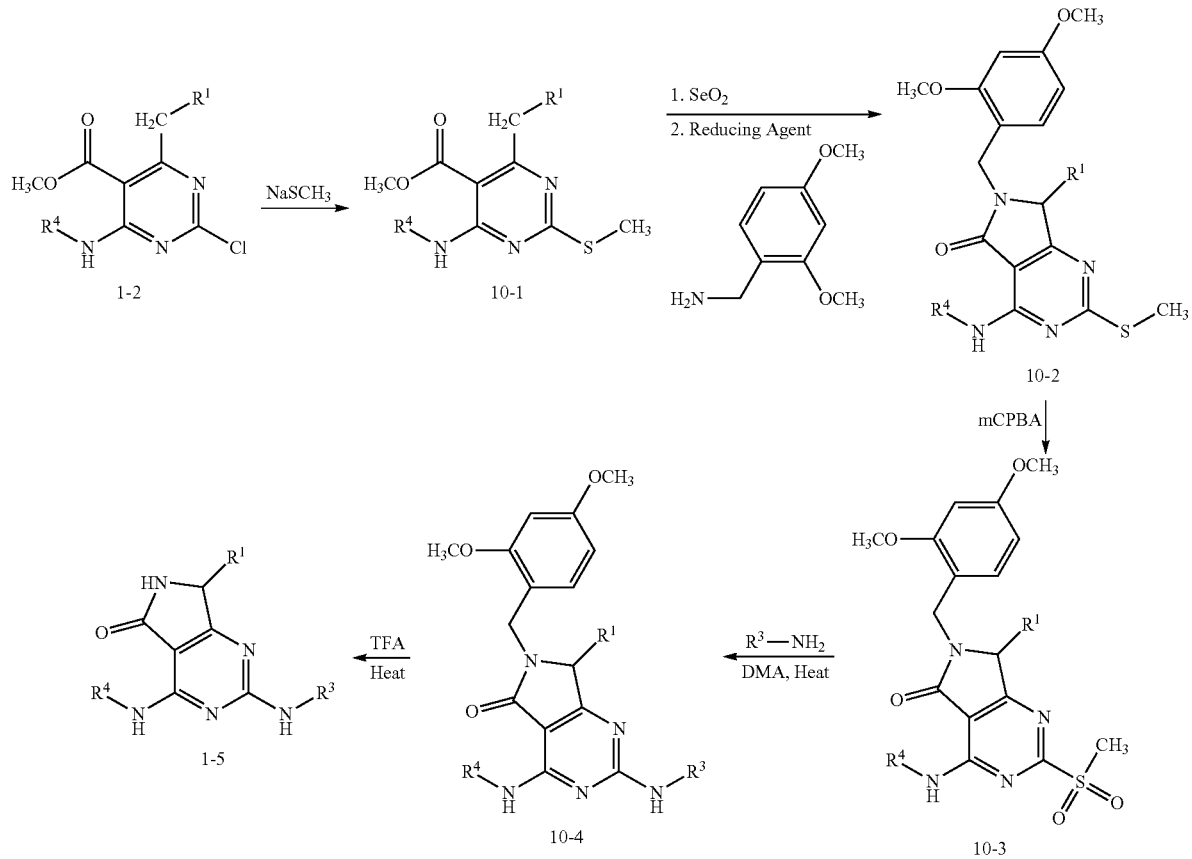

Scheme 10

Scheme 10 shows another method for preparing compound 1-5. The chloro group of compound 1-2 is first displaced with sodium methanethiolate to give 10-1. As in Scheme 1, intermediate 10-1 is oxidized with SeO₂ to give a ketone (or oxybenzoic acid), which is displaced with an appropriate amine (R³—NH₂) to give intermediate 10-4. Treatment of 10-4 with an acid (e.g., TFA) at elevated temperature (e.g., 40-60° C.) gives compound 1-5.

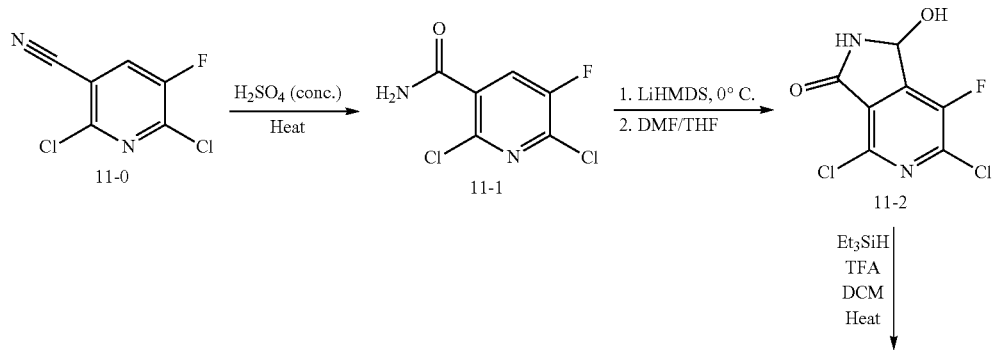

Scheme 11

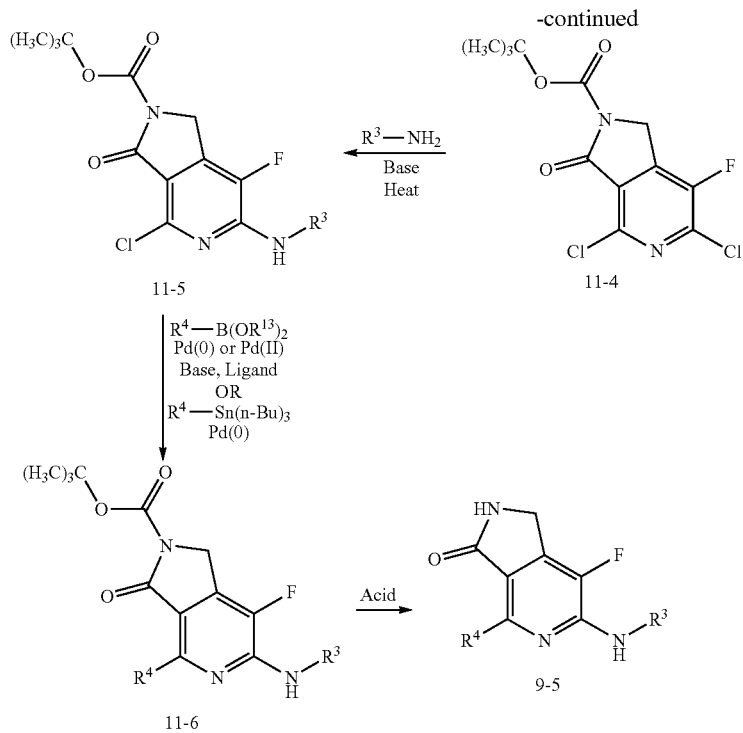

Scheme 11 depicts an alternate synthesis of compound 9-5. Starting material 11-0 (2,6-dichloro-5-fluoronicotinonitrile) is hydrolyzed by treatment with concentrated sulfuric acid at elevated temperature (e.g., about 65° C.) to give amide 11-1, which is lithiated via treatment with LiHMDS at about 0° C. or reaction with LDA in THF at −78° C. Quenching with DMF gives aldehyde intermediate 11-2, which is reduced to lactam 11-3 by treatment with a reducing agent (e.g., triethyl silane) and an acid (e.g., TFA) in an organic solvent (e.g., DCM). Following installation of a Boc protecting group on lactam 11-3, displacement of a chloro group on compound 11-4 via reaction with an appropriate amine ($R^3$—$NH_2$) gives intermediate 11-5. The intermediate is subsequently reacted with an aromatic boronic acid or borate (e.g., $R^4$—$B(OR^{13})_2$ in the presence of a palladium catalyst (e.g., $Pd(PPh_3)_4$, $(PPh_3)_2PdCl_2$, $Pd_2(dba)_3$, etc.), an optional ligand (e.g., 2-(dicyclohexylphosphino)biphenyl), a base (e.g., KF or $Na_2CO_3$), and an organic solvent (e.g., dioxane, DMF, etc.) to give compound 11-6. The Suzuki reaction is carried out at elevated temperature (e.g., 90-160° C.), either by conventional heating or via microwave irradiation. Alternatively, compound 11-5 may be reacted with an aromatic tin reagent (e.g., $R^4$—$Sn(n-Bu)_3$) in the presence of a palladium catalyst (e.g., $Pd(PPh_3)_4$) and an organic solvent (e.g., toluene) at elevated temperature (e.g., about 100° C.). Following the Suzuki or Stille coupling, treatment of 11-6 with an acid (e.g., TFA or HCl) at RT or above (e.g., about 20-60° C.) generates 9-5.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), Remington: The Science and Practice of Pharmacy (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include antioxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic) acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat disorders, diseases, and conditions for which inhibition of SYK is indicated. Such disorders, diseases, and conditions generally relate to any unhealthy or abnormal state in a subject for which the inhibition of SYK provides a therapeutic benefit. More particularly, such disorders, diseases, and conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease) and thrombosis. The compounds of Formula 1 may also be used to treat disorders, diseases, and conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of Formula 1 may also be used to treat autoimmune disorders in addition to those listed above. Such disorders, diseases, and conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, compounds of Formula 1 may be used to treat inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemic inflammatory response syndrome.

The compounds of Formula 1 may also be used to treat specific diseases that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Bechet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more disorders, diseases or conditions for which SYK is indicated, including disorders, diseases, and conditions involving the immune system, inflammation, and abnormal cell growth. For example, compounds of Formula 1, which include compounds specifically named above, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflamatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying anti-rheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restenosis, the compounds of Formula 1 may be combined with one or more cardiovascular agents such as calcium channel blockers, statins, fibrates, beta-blockers, ACE inhibitors, and platelet aggregation inhibitors.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and *streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g, thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include *bacillus* Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha ($TGF_\alpha$), $TGF_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hetaptocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogensis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity: SYK Inhibition

The ability of compounds to inhibit SYK activity may be assessed using a variety of methods, including in vitro and in vivo assays. The following in vitro assay measures a test compound's ability to inhibit SYK-mediated phosphorylation of a FAM-labeled SYK-specific substrate (5FAM-KKKKEEIYFFFG-NH$_2$).

SYK protein is prepared from cDNA encoding human spleen tyrosine kinase and is expressed in insect cells using a baculovirus expression vector. The cDNA (IMAGE: 3542895) is purchased from Open Biosystems. The SYK kinase domain (residues 356-635) is amplified via PCR and cloned into plasmid pFastBac1 (Invitrogen) at BamHI/XbaI sites. Recombinant plasmid encoding Met-Ala-Lys-SYK (356-635)-HHHHHH is sequenced and transformed into *E. coli* DH10Bac strain. The recombinant bacmid DNA is isolated and transfected into Sf9 insect cells. Recombinant virus is harvested 72 h after transfection. High titer viral stock is prepared by infecting Sf9 cells at a multiplicity of infection (MOI) of approximately 0.01. A suspension of Sf9 cells (10 L) is infected with recombinant virus (MOI=5) and is incubated in a Wave Bioreactor (GE-Healthcare) for 48 h. The cells are harvested and stored at −80° C.

To purify the expressed protein, the frozen Sf9 cells (10 L) are broken into small (<1 cm) particles and suspended in a lysis buffer (300 mL) containing 20 mM Tris (pH 7.6), 0.25 mM TCEP, 100 mM NaCl, 5% glycerol and a protease inhibitor. The suspension is stirred at RT until completely thawed, lysed an additional 2-4 min on a rotary blade homogenizer, and then centrifuged at 4200 g for 1 h. Following centrifugation, the supernatant is poured through cheese cloth and combined with a nickel chelating resin (Probond Resin™, Invitrogen) which is pre-equilibrated in a wash buffer containing 10 mM Tris (pH 7.6), 0.25 mM TCEP, 300 mM NaCl, 5% glycerol, and 20 mM imidazole. The mixture is agitated for 3 h in a cold room and then centrifuged at 900 g for 10 min. The resin is dispersed in wash buffer (50 mL), centrifuged for 10 min at 900 g, re-dispersed in a small amount of wash buffer (5 mL), and then pour into a disposable Poly-Prep chromatography column, through which wash buffer is passed by gravity until no protein is observed in coomassie buffer (about 120 mL of wash buffer). An elution buffer (30 mL) containing 10 mM HEPES (pH 7.4), 150 mM NaCl, 10% glycerol, 5 mM DTT, and 400 mM imidazole is used to elute the SYK protein from the resin. The eluate is concentrated (5 mL) and further purified on a Superdex 200 column (1.2 mL/min for 160 min, 10 mM HEPES (pH 7.4), 10 mM NaCl, 10 mM MgCl, 0.1 mM EDTA, and 0.25 mM TCEP). The chromatographed fractions are run on SDS-PAGE and the requisite fractions are pooled and concentrated. Final delivery buffer is 10 mM HEPES (pH 7.4), 10 mM Methione, 150 mM NaCl, 10% glycerol, 5 mM DTT.

SYK inhibition is determined using a black 384 well plate format in buffer containing 50 mM HEPES, 10 mM NaCl, 10 mM MgCl$_2$, 0.2 mM EDTA, 0.01% EDA (Brij®35), 1 mM DTT, and 0.1 mg/ml BSA at pH 7.3. Each test compound is prepared in DMSO using 2-fold serial dilutions for 11 data points, which are added to the buffer so that each dilution contains 3% DMSO. To each well is added 2 μL of 3 μM 5FAM-KKKKEEIYFFFG-NH$_2$ (in buffer), 2 μL of diluted test compound (3% DMSO in buffer), and 2 μL of 2.4 nM SYK and 45 μM ATP (in buffer). The reaction mixture is incubated at RT for 60 min, and quenched by adding 50 mM Hepes, 30 mM EDTA, 0.1% Triton X-100 (pH 7.3). To quantify the fluorescent-labeled substrate and product following reaction, the test plate is loaded on a Caliper LC-3000, which measures percent of conversion by microfluidic-based separation. Corresponding IC$_{50}$ values are calculated by non-linear curve fitting of the compound concentrations and percent of inhibition to the standard IC$_{50}$ equation and reported as pIC$_{50}$, i.e., −log(IC$_{50}$), where IC$_{50}$ is molar concentration.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), spt (septet) and br (broad). The mass spectra (m/z) were recorded using either electrospray ionization (ESI) or atmospheric pressure chemical ionization (APCI). The following abbreviations are used for common solvents: CDCl$_3$ (deuterochloroform), DMSO-d$_6$ (deuterodimethylsulfoxide), CD$_3$OD (deuteromethanol), and THF-d$_8$ (deuterotetrahydrofuran). "Ammonia" refers to a concentrated solution of ammonia in water possessing a specific gravity of 0.88.

Where indicated, products of certain preparations and examples are purified by mass-triggered HPLC (e.g., Pump: Waters™ 2525; MS: ZQ™; Software: MassLynx™), flash chromatography or preparative thin layer chromatography (TLC). Preparative HPLC is carried out using either acidic or basic conditions. Acid conditions are typically gradients in Solvent A (water with 0.05% TFA) and Solvent B (acetonitrile with 0.035% TFA); basic conditions are typically gradients in Solvent A (10 mM NH$_4$HCO$_3$ in water) and Solvent B (10 mM NH$_4$HCO$_3$ in 20/80 (v/v) water/acetonitrile). The mentioned preparative HPLC conditions use acidic conditions unless indicated as basic. Preparative TLC is typically carried out on silica gel 60 F$_{254}$ plates. After isolation by chromatography, the solvent is removed and the product is obtained by drying in a centrifugal evaporator (e.g., GeneVac™), rotary evaporator, evacuated flask, lyophilizer, etc. Reactions in an inert (e.g., nitrogen) or reactive (e.g., H$_2$) atmosphere are typically carried out at a pressure of about 1 atmosphere (14.7 psi) or greater.

Preparation 1

Methyl 2,4-dichloro-6-methylpyrimidine-5-carboxylate

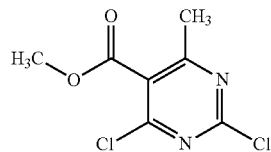

To a suspension of methyl 6-methyl-2,4-dioxo-1,2,3,4-tetrahydropyrimidine-5-carboxylate (1 g, 5.43 mmol) in POCl$_3$ (10 mL) was added 10 drops of N,N-dimethylaniline. The reaction mixture was heated at 105° C. for 6 h until it became a clear solution. It was then cooled, concentrated under reduced pressure, poured over ice, and extracted with EtOAc. The organic extract was washed with water and brine, dried and concentrated under reduced pressure to give the title compound as greenish-yellow solid (940 mg, 78%). [M+H] calc'd for $C_7H_6Cl_2N_2O_2$, 222; found, 221, 223.

Preparation 2

Methyl 2-chloro-4-methyl-6-(m-tolylamino)pyrimidine-5-carboxylate

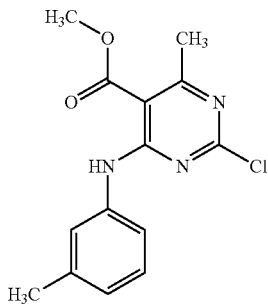 [SMILES: COC(=O)c1c(C)nc(Cl)nc1Nc1cccc(C)c1]

A mixture of methyl 2,4-dichloro-6-methylpyrimidine-5-carboxylate (940 mg, 4.25 mmol), m-toluidine (0.461 mL, 4.25 mmol) and N-ethyldiisopropylamine (1.481 mL, 8.51 mmol) in $CH_3CN$ (30 mL) was heated under reflux for 3 h. The mixture was diluted with EtOAc, and was washed with brine and water. The organic extract was dried and concentrated under reduced pressure to give the title compound as a light yellow solid (1.2 g, 97%). [M+H] calc'd for $C_{14}H_{14}N_3ClO_2$, 292; found, 292.

Example 1

2-((1R,2S)-2-Aminocyclohexylamino)-4-(m-tolylamino)-6,7-dihydro-5H-pyrrolo[3,4-d]pyrimidin-5-one

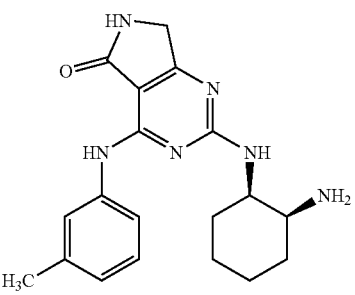 [SMILES: Cc1cccc(Nc2nc(N[C@@H]3CCCC[C@@H]3N)nc3c2C(=O)NC3)c1]

A. Methyl 2-((1R,2S)-2-(tert-butoxycarbonylamino)cyclohexylamino)-4-methyl-6-(m-tolylamino)pyrimidine-5-carboxylate

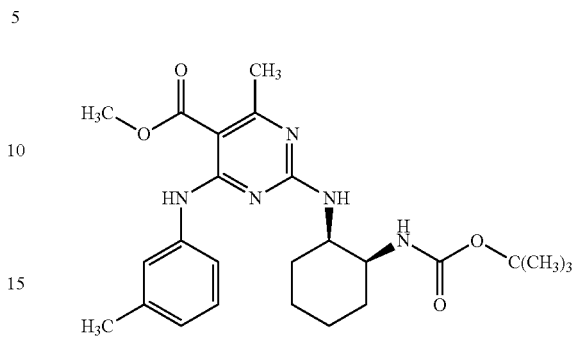

A solution of methyl 2-chloro-4-methyl-6-(m-tolylamino)pyrimidine-5-carboxylate (1.2 g, 4.11 mmol), tert-butyl (1S,2R)-2-aminocyclohexylcarbamate (0.882 g, 4.11 mmol) and triethylamine (1.720 mL, 12.34 mmol) in DMA (10 mL) was heated at 90° C. for 4 h. The solution was then diluted with EtOAc, washed with brine and water. The organic extract was dried and concentrated under reduced pressure to give a light yellow residue; white crystals were formed upon triturating with ACN (5 mL). The resultant solid was filtered, washed with ACN, and dried to give the title compound as white solid (1.2 g, 62%). [M+H] calc'd for $C_{25}H_{35}N_5O_4$, 470; found, 470.

B. tert-Butyl (1S,2R)-2-(6-(2,4-dimethoxybenzyl)-5-oxo-4-(m-tolylamino)-6,7-dihydro-5H-pyrrolo[3,4-d]pyrimidin-2-ylamino)cyclohexylcarbamate

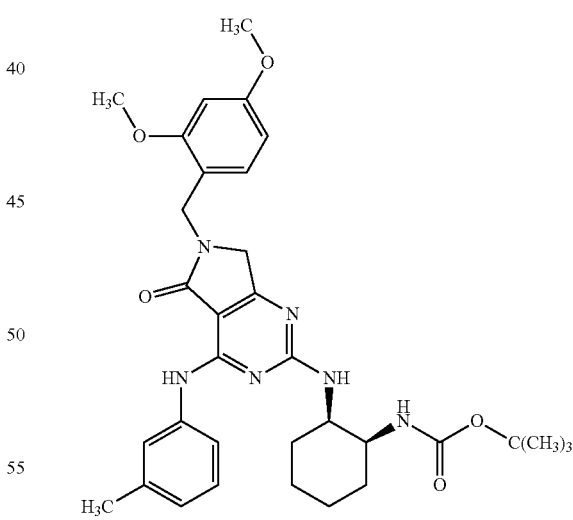

A mixture of methyl 2-((1R,2S)-2-(tert-butoxycarbonylamino)cyclohexylamino)-4-methyl-6-(m-tolylamino)pyrimidine-5-carboxylate (500 mg, 1.065 mmol) and selenium dioxide (236 mg, 2.130 mmol) in dioxane (10 mL) was heated at 100° C. for 24 h. The solution was subsequently cooled and filtered. The filtrate was concentrated under reduced pressure and dried to give a brown foam (534 mg; dihydroxyl form was observed via mass spectroscopy), which was used directly in the next step without further purification. A mixture of the unpurified intermediate (534 mg, 1.065 mmol) and (2,4-dimethoxyphenyl)methanamine (0.160 mL, 1.065 mmol) in MeOH (10 mL) was stirred at RT for 10 min, after which sodium cyanoborohydride (100 mg, 1.597 mmol) was added, and the reaction mixture was stirred at RT for 20 h. The reaction mixture was warmed to 50° C. and stirred for an additional 2 h to complete the reaction. The mixture was cooled to RT and the solid filtered and washed with MeOH to give the title compound as a pinkish solid (237 mg, 37%). [M+H] calc'd for $C_{33}H_{42}N_6O_5$, 603; found, 603.

C. 2-((1R,2S)-2-Aminocyclohexylamino)-4-(m-tolylamino)-6,7-dihydro-5H-pyrrolo[3,4-d]pyrimidin-5-one A mixture of crude tert-butyl (1S,2R)-2-(6-(2,4-dimethoxybenzyl)-5-oxo-4-(m-tolylamino)-6,7-dihydro-5H-pyrrolo[3,4-d]pyrimidin-2-ylamino)cyclohexylcarbamate (235 mg, 0.390 mmol) in TFA (5 mL) was stirred at 60° C. for 2 h and was then purified by reverse phase preparative HPLC. The fractions were collected, concentrated under reduced pressure, diluted in EtOAc, and basified with an aqueous saturated solution of $NaHCO_3$. The organic extract was dried and concentrated under reduced pressure to give the title compound as a white solid (60 mg, 44%). $^1$H NMR (400 MHz, DMSO-$d_6$) δ ppm 1.33-1.60 (m, 10 H), 2.32 (s, 3 H), 3.16 (m, 2 H), 3.92 (br s, 1 H), 4.14 (s, 2 H), 6.88 (d, J=7.07 Hz, 1 H), 7.13 (br s, 1 H), 7.22 (t, J=7.45 Hz, 1 H), 7.34-7.55 (m, 1 H), 7.70 (br s, 1 H), 8.01 (br s, 1 H), 8.58 (br s, 1 H). [M+H] calc'd for $C_{19}H_{24}N_6O$, 353; found, 353.

Example 2

2-((1R,2S)-2-Aminocyclohexylamino)-4-(3-fluorophenylamino)-6,7-dihydro-5H-pyrrolo[3,4-d]pyrimidin-5-one

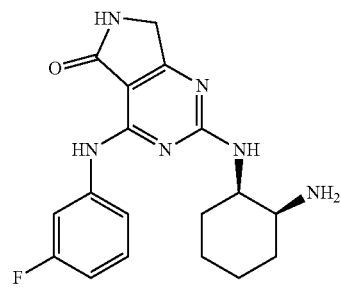 [SMILES: N[C@H]1CCCC[C@H]1Nc1nc2c(c(Nc3cccc(F)c3)n1)C(=O)NC2]

The title compound was prepared in a manner similar to EXAMPLE 1 by reacting methyl 2,4-dichloro-6-methylpyrimidine-5-carboxylate with 3-fluoroaniline instead of m-toluidine. The final product was purified via reverse phase preparative HPLC. Lyophilization gave a TFA salt of the title compound as a white solid. $^1$H NMR (400 MHz, DMSO-$d_6$) δ ppm 1.29-1.56 (m, 2 H), 1.56-1.73 (m, 4 H), 1.77-1.85 (br s, 2 H), 4.22 (br s, 4 H), 6.90 (br s, 1 H), 7.25-7.44 (m, 2 H), 7.48 (br s, 1 H), 7.77 (br s, 3 H), 8.20 (d, J=13.64 Hz, 1 H), 8.83 (d, J=14.40 Hz, 1H). [M+H] calc'd for $C_{18}H_{21}FN_6O$, 357; found, 357.

Example 3

2-((1R,2S)-2-Aminocyclohexylamino)-4-(3-chlorophenylamino)-6,7-dihydro-5H-pyrrolo[3,4-d]pyrimidin-5-one

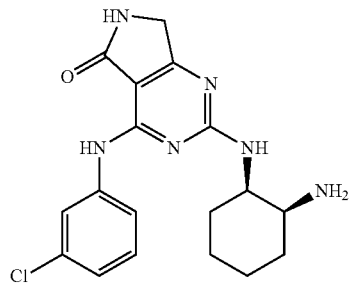 [SMILES: N[C@H]1CCCC[C@H]1Nc1nc2c(c(Nc3cccc(Cl)c3)n1)C(=O)NC2]

The title compound was prepared in a manner similar to EXAMPLE 1 by reacting methyl 2,4-dichloro-6-methylpyrimidine-5-carboxylate with 3-chloroaniline instead of m-toluidine. The final product was purified via reverse phase preparative HPLC. Lyophilization gave a TFA salt of the title compound as a white solid. $^1$H NMR (400 MHz, DMSO-$d_6$) δ ppm 1.43 (br s, 2 H), 1.67-1.96 (m, 6 H), 4.20 (br s, 3 H), 7.13 (d, J=7.33 Hz, 1 H), 7.36 (t, J=8.08 Hz, 1 H), 7.48 (br s, 1 H), 7.75 (br s, 2 H), 8.16 (br s, 1 H), 8.82 (br s, 1 H). [M+H] calc'd for $C_{18}H_{21}ClN_6O$, 373; found, 373.

Example 4

4-(1H-Indazol-6-ylamino)-2-((1R,2S)-2-aminocyclohexylamino)-6,7-dihydro-5H-pyrrolo[3,4-d]pyrimidin-5-one

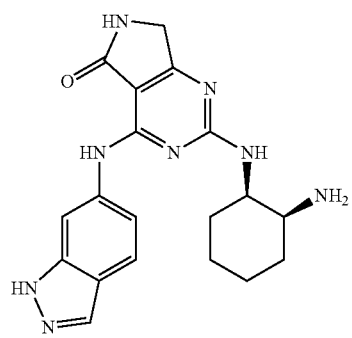 [SMILES: N[C@H]1CCCC[C@H]1Nc1nc2c(c(Nc3ccc4cn[nH]c4c3)n1)C(=O)NC2]

The title compound was prepared in a manner similar to EXAMPLE 1 by reacting methyl 2,4-dichloro-6-methylpyrimidine-5-carboxylate with 1H-indazol-6-amine instead of m-toluidine. The final product was purified via reverse phase preparative HPLC. Lyophilization gave a TFA salt of the title compound as a white solid. $^1$H NMR (400 MHz, DMSO-$d_6$) δ ppm 1.43-1.92 (br s, 8 H), 2.33 (s, 1 H), 3.57 (m, 1 H), 4.21 (br s, 2 H), 6.94 (s, 1 H), 7.07 (s, 1 H), 7.14-7.31 (m, 1 H), 7.43

(m, 1 H), 7.71 (d, J=8.59 Hz, 2 H), 8.01 (s, 1 H), 8.14 (br s, 1 H), 8.84 (s, 1 H), 12.99 (br s, 1 H). [M+H] calc'd for $C_{19}H_{22}N_8O$, 379; found, 379.

Example 5

2-((1R,2S)-2-Aminocyclohexylamino)-4-(3-(trifluoromethyl)phenylamino)-6,7-dihydro-5H-pyrrolo[3,4-d]pyrimidin-5-one

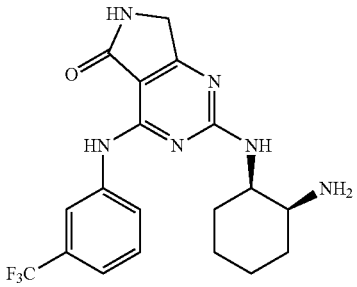 [SMILES: N[C@H]1CCCC[C@H]1Nc1nc2c(c(Nc3cccc(C(F)(F)F)c3)n1)C(=O)NC2]

A. Methyl 4-(bromomethyl)-2-((1R,2S)-2-(tert-butoxycarbonylamino)cyclohexyl-amino)-6-(3-(trifluoromethyl)phenylamino)pyrimidine-5-carboxylate

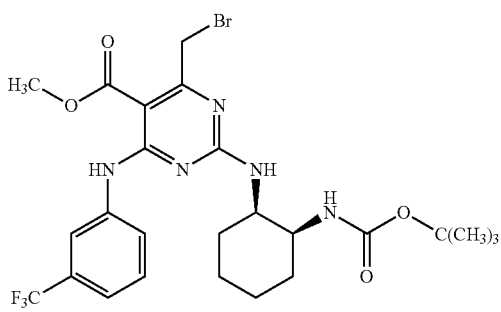 [SMILES: COC(=O)c1c(CBr)nc(N[C@@H]2CCCC[C@@H]2NC(=O)OC(C)(C)C)nc1Nc1cccc(C(F)(F)F)c1]

Methyl 2-((1R,2S)-2-(tert-butoxycarbonylamino)cyclohexylamino)-4-methyl-6-(3-(trifluoromethyl)phenylamino)pyrimidine-5-carboxylate (104 mg, 0.199 mmol), which was prepared in a manner similar to methyl 2-((1R,2S)-2-(tert-butoxycarbonylamino)cyclohexyl-amino)-4-methyl-6-(m-tolylamino)pyrimidine-5-carboxylate in step B of EXAMPLE 1 using 3-(trifluoromethyl)aniline in place of m-toluidine in step A of the example, was combined with 1-bromopyrrolidine-2,5-dione (53.0 mg, 0.298 mmol) and benzoic peroxyanhydride (48.1 mg, 0.199 mmol) in $CCl_4$ (10 mL), and the resulting mixture was stirred at 70° C. for 18 h. The reaction was stopped. The mixture was concentrated under reduced pressure, separated between water and EtOAc. The organic extract was dried and concentrated under reduced pressure to give the title compound, which was used in the next step without further purification. [M+H] calc'd for $C_{25}H_{31}BrN_5O_4$, 603; found, 604.

B. 2-((1R,2S)-2-Aminocyclohexylamino)-4-(3-(trifluoromethyl)phenylamino)-6,7-dihydro-5H-pyrrolo[3,4-d]pyrimidin-5-one

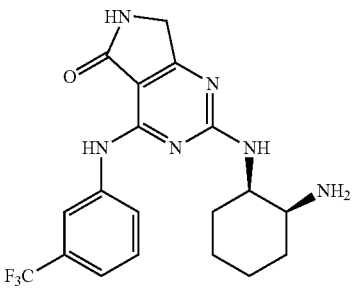 [SMILES: N[C@H]1CCCC[C@H]1Nc1nc2c(c(Nc3cccc(C(F)(F)F)c3)n1)C(=O)NC2]

A mixture of methyl 4-(bromomethyl)-2-((1R,2S)-2-(tert-butoxycarbonyl-amino)cyclohexylamino)-6-(3-(trifluoromethyl)phenylamino)pyrimidine-5-carboxylate (120 mg, 0.199 mmol) in THF was treated with ammonium hydroxide. The reaction mixture was stirred at RT overnight, and subsequently worked up and purified by reverse phase preparative HPLC. The fractions were collected and concentrated under reduced pressure to give a residue, which was treated with TFA/DCM. The final product was purified again by preparative HPLC. Lyophilization gave a TFA salt of the title compound as a white solid (2.6 mg, 3%). [M+H] calc'd for $C_{19}H_{21}F_3N_6O$, 407; found, 407.

Example 6 cis-2-(2-Aminocyclohexylamino)-4-(3-(trifluoromethyl)phenylamino)-6,7-dihydro-5H-pyrrolo[3,4-d]pyrimidin-5-one

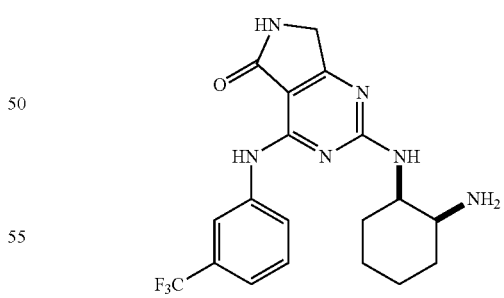

The title compound was prepared in a manner similar to EXAMPLE 5 using methyl cis-2-(2-(tert-butoxycarbonylamino)cyclohexylamino)-4-methyl-6-(3-(trifluoromethyl)phenylamino)pyrimidine-5-carboxylate in place of methyl 2-((1R,2S)-2-(tert-butoxycarbonylamino)cyclohexylamino)-4-methyl-6-(3-(trifluoromethyl)phenylamino)pyrimidine-5-carboxylate. The final product was purified via reverse phase preparative HPLC. Lyophilization gave a TFA

Example 7

2-(1-Methyl-1H-pyrazol-4-yl)-4-(m-tolylamino)-6,7-dihydro-5H-pyrrolo[3,4-d]pyrimidin-5-one

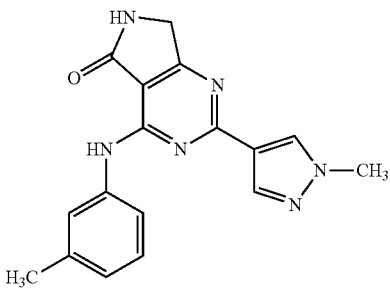

A TFA salt of the title compound was prepared in a manner similar to EXAMPLE 1 using 1-methyl-4-(4,4,5,5-tetramethyl-1,3,2-dioxaborolan-2-yl)-1H-pyrazole in place of tert-butyl (1S,2R)-2-aminocyclohexylcarbamate. $^1$H NMR (500 MHz, DMSO-$d_6$) δ ppm 2.37 (s, 3 H), 3.93 (s, 3 H), 4.39 (s, 2 H), 6.95 (d, J=7.32 Hz, 1 H), 7.32 (t, J=7.81 Hz, 1 H), 7.62 (s, 1 H), 7.77 (d, J=8.30 Hz, 1 H), 8.03 (s, 1 H), 8.37 (s, 1 H), 8.65 (s, 1 H), 8.82 (s, 1 H). [M+H] calc'd for $C_{17}H_{16}N_6O$, 321; found, 321.

Preparation 3

Ethyl 2,4-dichloro-6-((1,3-dioxoisoindolin-2-yl)methyl)pyrimidine-5-carboxylate

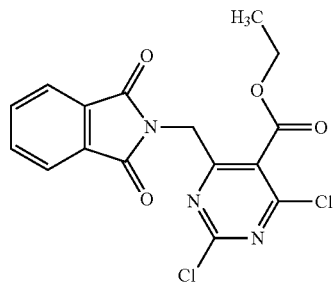 [SMILES: CCOC(=O)c1c(Cl)nc(Cl)nc1CN1C(=O)c2ccccc2C1=O]

A. Ethyl 4-(1,3-dioxo-1,3-dihydro-2H-isoindol-2-yl)-3-oxobutanoate

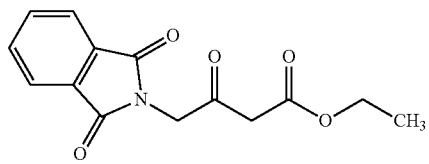 [SMILES: CCOC(=O)CC(=O)CN1C(=O)c2ccccc2C1=O]

To a solution of 2-(1,3-dioxoisoindolin-2-yl)acetic acid (3.01 g, 14.67 mmol), 2,2-dimethyl-1,3-dioxane-4,6-dione (2.23 g, 15.47 mmol) and 4-dimethylaminopyridine (2.73 g, 22.35 mmol) in dichloromethane (150 mL) was added a solution of DCC (3.36 g, 16.28 mmol) in DCM (50 mL) at 0° C. The mixture was stirred at RT for 16 h. The insoluble materials were filtered off, and the filtrate was washed with 5% NaHSO$_4$ aqueous solution. The organic phase was dried over anhydrous Na$_2$SO$_4$, filtered and the filtrate was concentrated under reduced pressure. The residue was treated with EtOH (200 mL) and the resulting mixture was stirred at 70° C. for 4 h and then concentrated under reduced pressure. Water was added to the residue and the mixture was extracted with EtOAc. The organic layers were washed with water and brine, dried over anhydrous MgSO$_4$, and filtered. The filtrate was concentrated under reduced pressure and the residue was washed with IPE to give the title compound as a colorless solid (3.43 g, 85%). $^1$H NMR (400 MHz, CDCl$_3$) δ ppm 1.31 (t, J=6.8 Hz, 3H), 3.58 (s, 2H), 4.24 (q, J=6.8 Hz, 2H), 4.67 (s, 2H), 7.73-7.78 (m, 2H), 7.86-7.91 (m, 2H).

B. Ethyl 1-(2,4-dimethoxybenzyl)-6-((1,3-dioxoisoindolin-2-yl)methyl)-2,4-dioxo-1,2,3,4-tetrahydropyrimidine-5-carboxylate

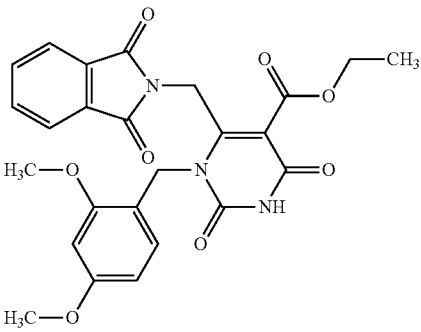 [SMILES: CCOC(=O)c1c(CN2C(=O)c3ccccc3C2=O)n(Cc2ccc(OC)cc2OC)c(=O)[nH]c1=O]

A mixture of ethyl 4-(1,3-dioxo-1,3-dihydro-2H-isoindol-2-yl)-3-oxobutanoate (249.8 mg, 0.908 mmol) and (2,4-dimethoxyphenyl)methanamine (152 mg, 0.908 mmol) in EtOH (4 mL) was stirred at 50° C. for 16 h. The obtained solid was isolated by filtration to give a colorless solid (51.7 mg). To a suspension of the solid in THF (4 mL) was added carbonisocyanatidic chloride (96 mg, 0.908 mmol) and the mixture was stirred at 80° C. for 1 h. After cooling to RT, water (10 mL) was added and the mixture was extracted with EtOAc. The organic layers were washed with brine, dried over anhydrous Na$_2$SO$_4$, and filtered. The filtrate was concentrated under reduced pressure and the residue was purified by column chromatography (SiO$_2$, hexane/EtOAc=1/1) to give the title compound (56.2 mg, 13%). $^1$H NMR (400 MHz, CDCl$_3$) δ ppm 1.28 (t, J=7.2 Hz, 3H), 3.63 (s, 3H), 3.81 (s, 3H), 4.22 (q, J=7.2 Hz, 2H), 4.95 (s, 2H), 5.12 (s, 2H), 6.18 (dd, J=8.4, 6.4 Hz, 1H), 6.23 (d, J=6.4 Hz, 1H), 6.75 (d, J=8.4 Hz, 1H), 7.63-7.72 (m, 4H), 8.23 (br s, 1H).

C. Ethyl 6-((1,3-dioxoisoindolin-2-yl)methyl)-2,4-dioxo-1,2,3,4-tetrahydropyrimidine-5-carboxylate

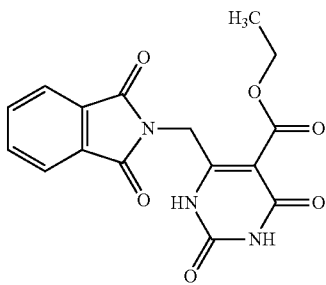 [SMILES: CCOC(=O)c1c(CN2C(=O)c3ccccc3C2=O)[nH]c(=O)[nH]c1=O]

To trifluoroacetic acid (2 mL, 26.0 mmol) was added ethyl 1-(2,4-dimethoxybenzyl)-6-((1,3-dioxoisoindolin-2-yl)methyl)-2,4-dioxo-1,2,3,4-tetrahydropyrimidine-5-carboxylate (198.9 mg, 0.403 mmol) at 0° C. The mixture was stirred at 0° C. for 1 h, then at RT for 6 h. The mixture was concentrated under reduced pressure, and the residue was washed with IPE (5 mL) to give the title compound (183.3 mg). $^1$H NMR (400 MHz, CDCl$_3$) δ ppm 1.42 (t, J=7.2 Hz, 3H), 4.45 (q, J=7.2 Hz, 2H), 4.98 (s, 2H), 7.78-7.81 (m, 2H), 7.91-7.93 (m, 2H), 8.19 (br s, 1H), 8.96 (br s, 1H).

D. Ethyl 2,4-dichloro-6-((1,3-dioxoisoindolin-2-yl)methyl)pyrimidine-5-carboxylate A mixture of ethyl 6-((1,3-dioxoisoindolin-2-yl)methyl)-2,4-dioxo-1,2,3,4-tetrahydropyrimidine-5-carboxylate (96.1 mg, 0.280 mmol) and phosphorus oxychloride (1 mL, 10.92 mmol) was stirred at 100° C. for 12 h and allowed to cool. The mixture was concentrated under reduced pressure to remove excess POCl$_3$. The residue was treated with saturated aq NaHCO$_3$ and extracted with EtOAc. The organic phase was washed with saturated aqueous NaHCO$_3$, water, and brine, was dried over anhydrous Na$_2$SO$_4$, and then filtered through SiO$_2$. The filtrate was concentrated under reduced pressure and the residue was purified by column chromatography (SiO$_2$, hexanes/EtOAc=4/1) to give the title compound (46.0 mg, 43%). $^1$H NMR (400 MHz, CDCl$_3$) δ ppm 1.42 (t, J=7.2 Hz, 3H), 4.45 (q, J=7.2 Hz, 2H), 5.05 (s, 2H), 7.76-7.80 (m, 2H), 7.89-7.93 (m, 2H).

Example 8

2-((1R,2S)-2-Aminocyclohexylamino)-4-(m-tolyamino)-6,7-dihydro-5H-pyrrolo[3,4-d]pyrimidin-5-one (free base)

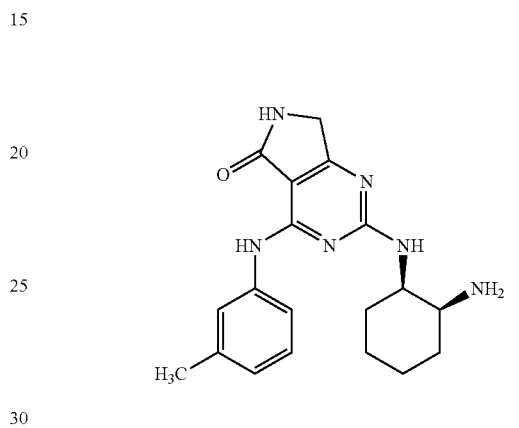

A. Ethyl 2-chloro-4-((1,3-dioxoisoindolin-2-yl)methyl)-6-(m-tolylamino)pyrimidine-5-carboxylate

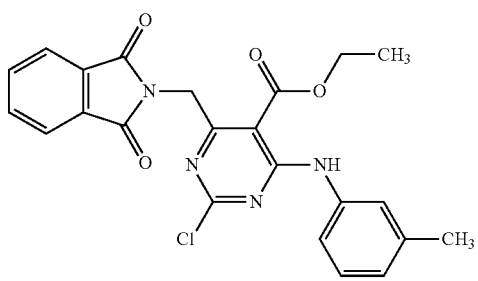 [SMILES: CCOC(=O)c1c(CN2C(=O)c3ccccc3C2=O)nc(Cl)nc1Nc1cccc(C)c1]

To a solution of ethyl 2,4-dichloro-6-((1,3-dioxoisoindolin-2-yl)methyl)pyrimidine-5-carboxylate (45.3 mg, 0.119 mmol) in MeCN (1 mL) was added m-toluidine (0.020 mL, 0.187 mmol) and N,N-diisopropylethylamine (0.037 mL, 0.212 mmol). The mixture was stirred at RT for 12 h. Saturated aq NaHCO$_3$ was added to the mixture, which was subsequently extracted with EtOAc. The organic layers were washed again with saturated aq NaHCO$_3$, water, and brine, were dried over anhydrous Na$_2$SO$_4$, and then filtered through SiO$_2$. The filtrate was concentrated under reduced pressure and the residue was washed with IPE to give the title compound as a pale brown solid (37.1 mg, 69%). $^1$H NMR (400 MHz, CDCl$_3$) δ ppm 1.50 (t, J=7.2 Hz, 3H), 2.36 (s, 3H), 4.52 (q, J=7.2 Hz, 2H), 5.20 (s, 2H), 6.97-6.98 (m, 1H), 7.23-7.27

(m, 1H), 7.33 (br s, 1H), 7.45-7.47 (m, 1H), 7.73-7.78 (m, 2H), 7.89-7.94 (m, 2H), 10.67 (br s, 1H).

B. Ethyl 2-((1R,2S)-2-(tert-butoxycarbonylamino) cyclohexylamino)-4-((1,3-dioxoisoindolin-2-yl)methyl)-6-(m-tolylamino)pyrimidine-5-carboxylate

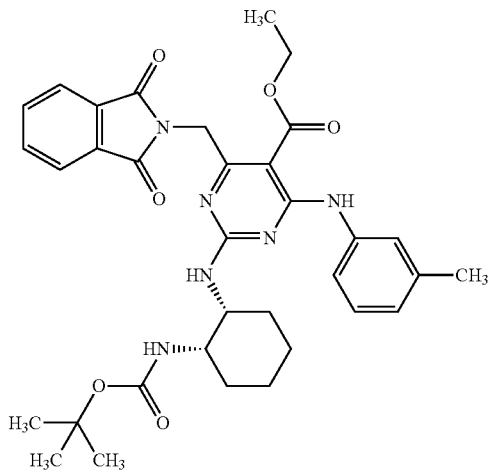 [SMILES: CCOC(=O)c1c(CN2C(=O)c3ccccc3C2=O)nc(N[C@@H]2CCCC[C@@H]2NC(=O)OC(C)(C)C)nc1Nc1cccc(C)c1]

A mixture of ethyl 2-chloro-4-((1,3-dioxoisoindolin-2-yl)methyl)-6-(m-tolylamino)pyrimidine-5-carboxylate (96.3 mg, 0.214 mmol), tert-butyl (1S,2R)-2-aminocyclohexylcarbamate (58.14 mg, 0.271 mmol) and Et$_3$N (0.030 mL, 0.214 mmol) in DMA (2 mL) was stirred at 80° C. for 3 h. Saturated aq NaHCO$_3$ was added to the mixture, which was extracted with EtOAc. The combined organic layers were washed with aqueous NaHCO$_3$, water, and brine, were dried over anhydrous Na$_2$SO$_4$, and then filtered through SiO$_2$. The filtrate was concentrated under reduced pressure and the residue was purified by column chromatography (SiO$_2$, hexanes/EtOAc=3/1) to give the title compound as a yellow oil (123.8 mg, 92%). $^1$H NMR (400 MHz, CDCl$_3$) δ ppm 1.12-1.71 (m, 20H), 2.33 (s, 3H), 3.39-3.57 (m, 1H), 3.84-3.99 (m, 1H), 4.42 (q, J=7.2 Hz, 2H), 4.55-4.79 (m, 1H), 5.16 (s, 2H), 5.41 (br s, 1H), 6.87-6.89 (m, 1H), 7.16-7.49 (m, 3H), 7.74-7.75 (m, 2H), 7.90-7.91 (m, 2H), 10.68-10.81 (m, 1H). [M+H] calc'd for C$_{34}$H$_{41}$N$_6$O$_6$, 629; found, 629.

C. tert-Butyl (1S,2R)-2-(5-oxo-4-(m-tolylamino)-6,7-dihydro-5H-pyrrolo[3,4-d]pyrimidin-2-ylamino)cyclohexylcarbamate

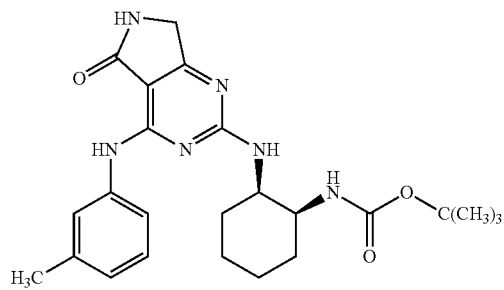 [SMILES: Cc1cccc(Nc2nc(N[C@@H]3CCCC[C@@H]3NC(=O)OC(C)(C)C)nc3c2C(=O)NC3)c1]

A mixture of ethyl 2-((1R,2S)-2-(tert-butoxycarbonylamino)cyclohexylamino)-4-((1,3-dioxoisoindolin-2-yl)methyl)-6-(m-tolylamino)pyrimidine-5-carboxylate (109 mg, 0.174 mmol) and hydrazine hydrate (36.5 mg, 0.729 mmol) in EtOH (2 mL) was stirred at 65° C. for 12 h. After cooling, the mixture was concentrated under reduced pressure and the residue was treated with water and extracted with EtOAc. The combined organic layers were washed with aqueous NaHCO$_3$, water, and brine, were filtered through SiO$_2$, and the filtrate was concentrated under reduced pressure. The residue was recrystallized from EtOAc/hexanes and filtered to give the title compound (34.8 mg). The filtrate was concentrated and triturated with IPE to give a second batch (20.3 mg) of the title compound (total 65.1 mg, 83%). $^1$H NMR (400 MHz, DMSO-d$_6$) δ ppm 1.24-1.79 (m, 17H), 2.32 (s, 3H), 3.84 (br s, 1H), 4.06 (br s, 1H), 4.14 (s, 2H), 6.55-6.70 (m, 1H), 6.87-7.04 (m, 2H), 7.20-7.24 (m, 1H), 7.40-7.48 (m, 1H), 7.68-7.80 (m, 1H), 8.01-8.06 (m, 1H), 8.56-8.59 (m, 1H). [M+H] calc'd for C$_{24}$H$_{33}$N$_6$O$_3$, 453; found, 453.

D. 2-((1R,2S)-2-Aminocyclohexylamino)-4-(m-tolylamino)-6,7-dihydro-5H-pyrrolo[3,4-d]pyrimidin-5-one To a solution of tert-butyl (1S,2R)-2-(5-oxo-4-(m-tolylamino)-6,7-dihydro-5H-pyrrolo[3,4-d]pyrimidin-2-ylamino)cyclohexylcarbamate (50.4 mg, 0.111 mmol) in HOAc (2 mL) was added hydrochloric acid (0.5 mL, 16.46 mmol). The mixture was stirred at RT for 30 min and then concentrated under reduced pressure. The residue was treated with saturated aq NaHCO$_3$ and extracted with EtOAc. The organic layers were washed with saturated aq NaHCO$_3$, water, and brine, were dried over anhydrous Na$_2$SO$_4$, and then filtered. The filtrate was concentrated under reduced pressure and the residue was purified by column chromatography (SiO$_2$, EtOAc/MeOH=20/1) to give the title compound as a white powder (11.3 mg, 29%). $^1$H NMR (400 MHz, CDCl$_3$) δ ppm 1.48-1.80 (m, 10H), 2.37 (s, 3H), 3.24 (br s, 1H), 4.07 (br s, 1H), 4.20 (s, 2H), 5.55 (br s, 1H), 5.89 (br s, 1H), 6.89-6.91 (m, 1H), 7.22-7.24 (m, 1H), 7.53-7.63 (m, 2H), 8.49 (br s, 1H). [M+H] calc'd for C$_{19}$H$_{25}$N$_6$O, 353; found, 353.

Preparation 4

Methyl 2,4-dichloro-6-(m-tolylamino)pyrimidine-5-carboxylate

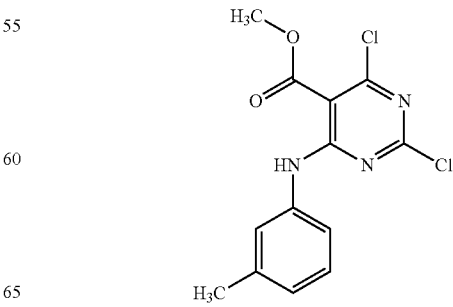

A. 2,4,6-Trichloropyrimidine-5-carboxylic acid

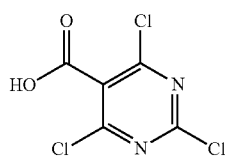 [SMILES: O=C(O)c1c(Cl)nc(Cl)nc1Cl]

To a solution of diisopropylamine (23.42 mL, 164 mmol) in THF (200 mL) was slowly added butyllithium (100 mL, 160 mmol) at −78° C. The mixture was stirred at −78° C. for 15 min. To this mixture was slowly added a solution of 2,4,6-trichloropyrimidine (20.06 g, 109 mmol) in THF (50 mL) at −78° C. The mixture was stirred for 1 h. Dry ice was added and the mixture was stirred at RT for 1 h. To the mixture was added 1N HCl, which was subsequently extracted with EtOAc. The organic layers were basified with aqueous NaHCO$_3$, and washed with EtOAc. The aqueous layer was then acidified with 1N HCl, and extracted with EtOAc. The organic layers were washed with 1N HCl, water, and brine, were dried over anhydrous MgSO$_4$, and then filtered. The filtrate was concentrated under reduced pressure. The residue was washed with hexane to give the desired product as a pale brown solid (12.28 g, 49%). $^1$H NMR (500 MHz, CDCl$_3$) δ ppm 7.65 (br s, 1H).

B. 2,4-Dichloro-6-(m-tolylamino)pyrimidine-5-carboxylic acid

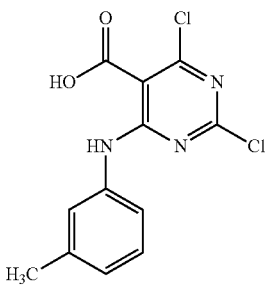 [SMILES: Cc1cccc(Nc2nc(Cl)nc(Cl)c2C(=O)O)c1]

To a solution of 2,4,6-trichloropyrimidine-5-carboxylic acid (5.69 g, 25.02 mmol) in DMF (60 mL) was added Et$_3$N (8 mL, 57.4 mmol) and m-toluidine (3.2 mL, 29.5 mmol) at 0° C. The mixture was stirred at RT for 12 h. To the mixture was added 1N HCl. The mixture was extracted with EtOAc. The organic layers were basified with saturated aq NaHCO$_3$ and the aqueous layers were washed with EtOAc. The washed aqueous layer was acidified with 1N HCl and extracted with EtOAc. The combined organic layers were washed with 1N HCl, water, and brine, were dried over anhydrous Na$_2$SO$_4$, and then filtered. The filtrate was concentrated under reduced pressure, triturated with hexane, and filtered to give a first batch of the title compound (4.36 g). The filtrate was concentrated, triturated with hexane, and filtered to give a second batch (0.36 g) of the title compound (total 4.72 g, 63%). $^1$H NMR (500 MHz, DMSO-d$_6$) δ ppm 2.30 (s, 3H), 7.00-7.02 (m, 1H), 7.25-7.28 (m, 2H), 7.33-7.35 (m, 1H), 10.13 (s, 1H), 1H not detected. [M+H] calc'd for C$_{12}$H$_{10}$Cl$_2$N$_3$O$_2$, 298; found, 298.

C. Methyl 2,4-dichloro-6-(m-tolylamino)pyrimidine-5-carboxylate

To a solution of 2,4-dichloro-6-(m-tolylamino)pyrimidine-5-carboxylic acid (7.67 g, 25.7 mmol) in DMF (80 mL) was added NaHCO$_3$ (3.30 g, 39.3 mmol) and iodomethane (1.605 mL, 25.7 mmol) at 0° C. The mixture was stirred at RT for 14 h, after which saturated aq NaHCO$_3$ was added. The mixture was extracted with EtOAc. The organic layers were washed with aqueous NaHOC$_3$, water, and brine, were dried over anhydrous Na$_2$SO$_4$, and then filtered through SiO$_2$. The filtrate was concentrated under reduced pressure. The residue was triturated with isopropyl ether and filtered to give a first batch (5.28 g) of the title compound. The filtrate was concentrated, triturated with IPE, and filtered to give a second batch (0.66 g) of the title compound as a yellow solid (total 5.94 g, 74%). $^1$H NMR (500 MHz, CDCl$_3$) δ ppm 2.38 (s, 3H), 4.00 (s, 3H), 7.02-7.03 (m, 1H), 7.27-7.33 (m, 2H), 7.44-7.46 (m, 1H), 10.30 (br s, 1H). [M+H] calc'd for C$_{13}$H$_{12}$Cl$_2$N$_3$O$_2$, 312; found, 312.

Example 9

2-(4-Ethylpiperazin-1-yl)-4-(m-tolylamino)-6,7-dihydro-5H-pyrrolo[3,4-d]pyrimidin-5-one

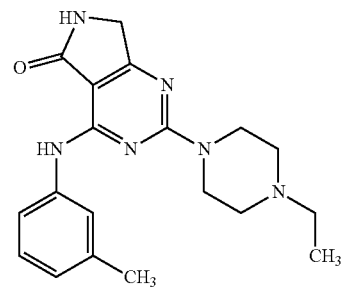 [SMILES: CCN1CCN(c2nc3c(c(Nc4cccc(C)c4)n2)C(=O)NC3)CC1]

A. Methyl 4-chloro-2-(4-ethylpiperazin-1-yl)-6-(m-tolylamino)pyrimidine-5-carboxylate

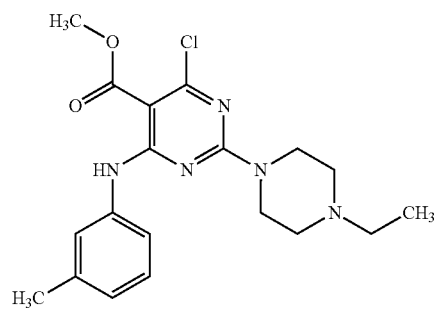 [SMILES: CCN1CCN(c2nc(Cl)c(C(=O)OC)c(Nc3cccc(C)c3)n2)CC1]

A mixture of methyl 2,4-dichloro-6-(m-tolylamino)pyrimidine-5-carboxylate (502.6 mg, 1.610 mmol), N-ethyldiisopropylamine (0.3 mL, 1.718 mmol) and N-ethylpiperazine (0.21 mL, 1.653 mmol) in THF (8 mL) was stirred at RT for 12 h. Saturated aq NaHCO$_3$ was added and the resulting mixture was extracted with EtOAc. The organic layers were washed with saturated aq NaHCO$_3$, water, and brine, were dried over anhydrous Na$_2$SO$_4$, and then filtered through SiO$_2$.

The filtrate was concentrated under reduced pressure and the residue was purified by column chromatography (SiO$_2$, hexanes/EtOAc=4/1) to give the title compound (152.6 mg, 24%). $^1$H NMR (500 MHz, CDCl$_3$) δ ppm 1.12 (t, J=6.5 Hz, 3H), 2.35 (s, 3H), 2.48 (br s, 6H), 3.82-3.97 (m, 7H), 6.92-6.93 (m, 1H), 7.21-7.22 (m, 1H), 7.37-7.42 (m, 2H), 10.45 (s, 1H). [M+H] calc'd for C$_{19}$H$_{25}$ClN$_5$O$_2$, 390; found, 390.

B. Methyl 4-cyano-2-(4-ethylpiperazin-1-yl)-6-(m-tolylamino)pyrimidine-5-carboxylate

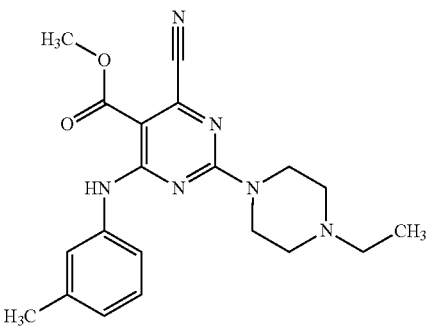 [SMILES: CCN1CCN(c2nc(C#N)c(C(=O)OC)c(Nc3cccc(C)c3)n2)CC1]

A mixture of methyl 4-chloro-2-(4-ethylpiperazin-1-yl)-6-(m-tolylamino)pyrimidine-5-carboxylate (152.6 mg, 0.391 mmol), tetrakis(triphenylphosphine)palladium (40.8 mg, 0.035 mmol) and zinc(II) cyanide (25.2 mg, 0.215 mmol) in DMF (3 mL) was stirred at 90° C. for 3 h. Water was added and the resulting mixture was extracted with EtOAc. The organic layers were washed with aq NaHCO$_3$, water, and brine, were dried over anhydrous Na$_2$SO$_4$, and then filtered through SiO$_2$. The filtrate was concentrated under reduced pressure and the residue was purified by column chromatography (SiO$_2$ hexanes/EtOAc=5/1) to give the title compound as a yellow oil (51.1 mg, 34%). $^1$H NMR (500 MHz, CDCl$_3$) δ ppm 1.12 (t, J=7.5 Hz, 3H), 2.35 (s, 3H), 2.44-2.49 (m, 6H), 3.81-3.98 (m, 7H), 6.95-6.96 (m, 1H), 7.23-7.26 (m, 1H), 7.37-7.47 (m, 2H), 10.46 (s, 1H). [M+H] calc'd for C$_{20}$H$_{25}$N$_6$O$_2$, 381; found, 381.

C. 2-(4-Ethylpiperazin-1-yl)-4-(m-tolylamino)-6,7-dihydro-5H-pyrrolo[3,4-d]pyrimidin-5-one A mixture of methyl 4-cyano-2-(4-ethylpiperazin-1-yl)-6-(m-tolylamino)pyrimidine-5-carboxylate (49.8 mg, 0.131 mmol) and palladium on carbon (10.1 mg) in EtOH (3 mL) and 1N HCl (3 mL) was stirred at RT for 2 h under a hydrogen atmosphere. The insoluble materials were filtered off, and the filtrate was concentrated under reduced pressure. The residue was treated with saturated aq NaHCO$_3$ and EtOAc for 3 h. The mixture was extracted with EtOAc. The organic layers were washed with aq NaHCO$_3$, water, and brine, were dried over anhydrous Na$_2$SO$_4$, and then filtered. The filtrate was concentrated under reduced pressure and the residue was purified by column chromatography twice (SiO$_2$, EtOAc then DM1020 EtOAc/MeOH=20/1) to give the title compound as a white solid (19.8 mg, 43%). $^1$H NMR (500 MHz, CDCl$_3$) δ ppm 1.19 (br s, 3H), 2.36 (s, 3H), 2.5 (br s, 6H), 4.08 (br s, 4H), 4.23 (s, 2H), 5.50 (s, 1H), 6.91-6.92 (m, 1H), 7.22-7.26 (m, 1H), 7.49-7.54 (m, 2H), 8.44 (s, 1H). [M+H] calc'd for C$_{19}$H$_{25}$N$_6$O, 353; found, 353.

Example 10

2-(Cyclohexylamino)-4-(m-tolylamino)-6,7-dihydro-5H-pyrrolo[3,4-d]pyrimidin-5-one

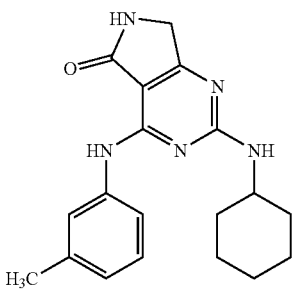 [SMILES: Cc1cccc(Nc2nc(NC3CCCCC3)nc3c2C(=O)NC3)c1]

A. Methyl 2,4-dicyano-6-(m-tolylamino)pyrimidine-5-carboxylate

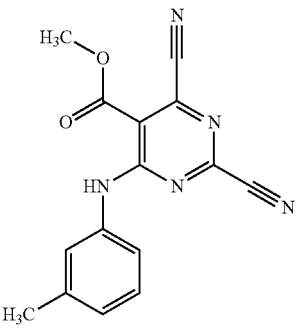 [SMILES: COC(=O)c1c(C#N)nc(C#N)nc1Nc1cccc(C)c1]

A mixture of methyl 2,4-dichloro-6-(m-tolylamino)pyrimidine-5-carboxylate (500.5 mg, 1.603 mmol), zinc(II) cyanide (100.7 mg, 0.857 mmol) and tetrakis(triphenylphosphine)palladium (187.3 mg, 0.162 mmol) in DMF (5 mL) was stirred at 120° C. for 1 h in a microwave oven. After cooling, saturated aq NaHCO$_3$ was added and the mixture was extracted with EtOAc. The organic layers were washed with aq NaHCO$_3$, water, and brine, were dried over anhydrous Na$_2$SO$_4$, and then filtered through SiO$_2$. The filtrate was concentrated under reduced pressure and the residue was purified by column chromatography (SiO$_2$, hexanes/EtOAc=4/1) to afford a yellow solid (182.5 mg), which was washed with IPE to give the title compound (117.5 mg). $^1$H NMR (500 MHz, CDCl$_3$) δ ppm 2.41 (s, 3H), 4.12 (s, 3H), 7.10-7.12 (m, 1H), 7.31-7.35 (m, 2H), 7.42-7.43 (m, 1H), 10.65 (br s, 1H). [M+H] calc'd for $C_{15}H_{12}N_5O_2$, 294; found, 294.

B. Methyl 4-cyano-2-(cyclohexylamino)-6-(m-tolylamino)pyrimidine-5-carboxylate

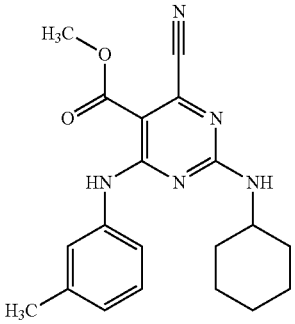 [SMILES: COC(=O)c1c(C#N)nc(NC2CCCCC2)nc1Nc1cccc(C)c1]

A mixture of methyl 2,4-dicyano-6-(m-tolylamino)pyrimidine-5-carboxylate (102.3 mg, 0.349 mmol), N,N-diisopropylethylamine (0.075 mL, 0.429 mmol) and cyclohexylamine (0.05 mL, 0.437 mmol) in DMF (2 mL) was stirred at RT for 14 h. Saturated aq NaHCO$_3$ was added and the mixture was extracted with EtOAc. The organic layers were washed with aq NaHCO$_3$, water, and brine, and were filtered through SiO$_2$. The filtrate was concentrated under reduced pressure and the residue was purified by column chromatography (SiO$_2$, hexanes/EtOAc=4/1) to give the title compound as a yellow oil (114.7 mg, 90%). $^1$H NMR (500 MHz, CDCl$_3$) δ ppm 1.19-1.45 (m, 5H), 1.64-1.67 (m, 1H), 1.73-1.80 (m, 2H), 2.00-2.05 (m, 2H), 2.38 (s, 3H), 3.75-3.82 (m, 1H), 3.98 (s, 3H), 5.57-5.58 (br d, J=7.9 Hz, 1H), 6.97-6.98 (m, 1H), 7.27-7.29 (m, 1H), 7.46-7.51 (m, 2H), 10.62 (br s, 1H). [M+H] calc'd for $C_{20}H_{24}N_5O_2$, 366; found, 366.

C. 2-(Cyclohexylamino)-4-(m-tolylamino)-6,7-dihydro-5H-pyrrolo[3,4-d]pyrimidin-5-one A mixture of methyl 4-cyano-2-(cyclohexylamino)-6-(m-tolylamino)pyrimidine-5-carboxylate (112.6 mg, 0.308 mmol) and palladium on carbon (26.4 mg, 0.248 mmol) in MeOH (2 mL) and HCl (1N, 2 mL) was stirred at RT for 4 h under a hydrogen atmosphere. Saturated aq NaHCO$_3$ was added and the mixture was stirred for 12 h. The mixture was filtered and the filtrate was concentrated under reduced pressure. The residue was extracted with EtOAc. The organic layers were washed with aq NaHCO$_3$, water, and brine, were dried over anhydrous Na$_2$SO$_4$, and then filtered through SiO$_2$. The filtrate was concentrated under reduced pressure and the residue was purified by column chromatography (SiO$_2$, EtOAc) to give a white solid (72.2 mg, 69%). The white solid was recrystallized from EtOH gave the title compound (35.2 mg). $^1$H NMR (500 MHz, DMSO-d$_6$) δ ppm 1.14-1.17 (m, 1H), 1.24-1.34 (m, 4H), 1.62-1.63 (m, 1H), 1.73-1.78 (m, 2H), 1.89-1.97 (m, 2H), 2.33 (s, 3H), 3.74-3.83 (m, 1H), 4.12-4.17 (m, 2H), 6.86-6.88 (m, 1H), 7.20-7.23 (m, 1H), 7.42-7.52 (m, 2H), 7.76 (s, 1H), 8.00-8.05 (m, 1H), 8.53-8.57 (m, 1H). [M+H] calc'd for $C_{19}H_{24}N_5O$, 338; found, 338.

Example 11 cis-2-(2-Hydroxycyclohexylamino)-4-(m-tolylamino)-6,7-dihydro-5H-pyrrolo[3,4-d]pyrimidin-5-one

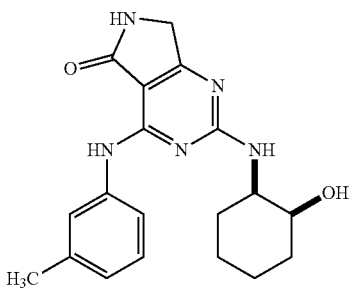

The above compound was prepared in a manner similar to EXAMPLE 10 using cis-2-aminocyclohexanol in place of cyclohexylamine. $^1$H NMR (500 MHz, DMSO-d$_6$) δ ppm 1.31-1.37 (m, 2H), 1.46-1.78 (m, 6H), 2.32 (s, 3H), 3.82-3.96 (m, 2H), 4.13-4.17 (m, 2H), 4.66-4.71 (m, 1H), 6.86-6.92 (m, 2H), 7.20-7.23 (m, 1H), 7.46-7.50 (m, 1H), 7.71-7.77 (m, 1H), 8.03-8.08 (m, 1H), 8.58-8.59 (m, 1H). [M+H] calc'd for $C_{19}H_{24}N_5O_2$, 354; found, 354.

Example 12

2-(3-Aminopiperidin-1-yl)-4-(m-tolylamino)-6,7-dihydro-5H-pyrrolo[3,4-d]pyrimidin-5-one

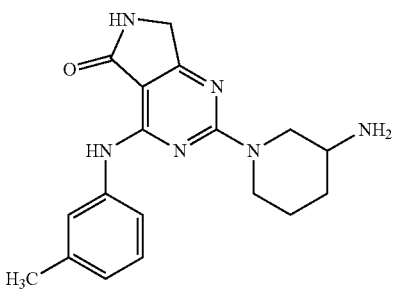 [SMILES: Cc1cccc(Nc2nc(N3CCCC(N)C3)nc3c2C(=O)NC3)c1]

The above compound was prepared in a manner similar to EXAMPLE 10 using tert-butyl piperidin-3-ylcarbamate in place of cyclohexylamine. Following cyclization, tert-butyl 1-(5-oxo-4-(m-tolylamino)-6,7-dihydro-5H-pyrrolo[3,4-d]pyrimidin-2-yl)piperidin-3-ylcarbamate (20.00 mg, 0.046 mmol) was treated with 4M HCl in dioxane (2 mL, 8.00 mmol) at RT for 5 h to deprotect the Boc group. The mixture was subsequently basified with 2N NaOH, extracted with EtOAc, washed with brine, dried over MgSO$_4$, and evaporated. The residue was purified by recrystallization (EtOH-Hexane) to give the title compound as white solid (10 mg, 64.8% yield). $^1$H NMR (500 MHz, DMSO-d$_6$) δ ppm 0.99-2.03 (m, 4 H), 2.30 (s, 3 H), 2.57-3.07 (m, 3 H), 4.16 (s, 2 H), 4.26-4.86 (m, 2 H), 6.88 (d, J=5.6 Hz, 1 H), 7.23 (s, 1 H), 7.42-7.55 (m, 1 H), 7.59 (s, 1 H), 8.08 (s, 1 H), 8.55 (s, 1 H). [M+H] calc'd for $C_{18}H_{22}N_6O$, 339; found, 339.

Preparation 5

Methyl 2,6-dichloro-4-cyanonicotinate

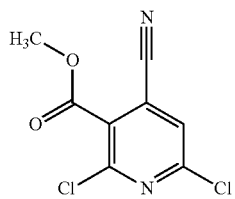

A. Methyl 2,6-dichloro-4-iodonicotinate

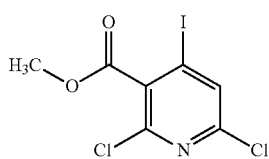

A solution of n-butyllithium in hexane (1.6M, 120 mL, 192 mmol) was added dropwise to a solution of diisopropylamine (31.2 mL, 219 mmol) in THF (200 mL) at −78° C. and the mixture was stirred for 30 min. A solution of 2,6-dichloro-3-iodopyridine (50.0 g, 183 mmol) in THF (100 mL) was added dropwise to the reaction mixture at −78° C. and the resulting mixture was stirred at −78° C. for 2 h. After adding dry ice to the reaction mixture, the mixture was warmed to RT and stirred overnight. The resulting mixture was quenched with $H_2O$ and the organic phase was washed with $H_2O$. The combined aqueous phase was acidified with HCl and extracted with $CHCl_3$ (3×). The organic phases were combined, washed with brine, dried over $MgSO_4$, and evaporated. After the residue was dissolved into DMF (500 mL), $K_2CO_3$ (39.2 g, 284 mmol) and $CH_3I$ (17.73 mL, 284 mmol) were added. The reaction mixture was stirred at RT for 3 h. To the resulting mixture was added 1N HCl and $Et_2O$. The aqueous phase was extracted with $Et_2O$ and the combined organic layers were washed with $H_2O$ and brine, dried over $MgSO_4$ and evaporated. The residue was purified by chromatography on $SiO_2$ to give the title compound as a white solid (7.24 g, 11%). $^1H$ NMR (500 MHz, $CDCl_3$) δ ppm 3.99 (s, 3 H), 7.77 (s, 1H). [M+H] calc'd for $C_7H_4Cl_1NO_2$, 332; found, 332.

B. Methyl 2,6-dichloro-4-cyanonicotinate

A mixture of tetrakis(triphenylphosphine)palladium (34.8 mg, 0.03 mmol), methyl 2,6-dichloro-4-iodonicotinate (100 mg, 0.301 mmol) and dicyanozinc (38.9 mg, 0.331 mmol) in DMF (2 mL) was stirred at 100° C. overnight under $N_2$ atmosphere. To the resulting mixture were added $H_2O$ and EtOAc. The aqueous phase was extracted with EtOAc, and the combined organic layers were washed with $H_2O$ and brine, dried over $MgSO_4$ and evaporated. The residue was purified by chromatography on $SiO_2$ to give the title compound as a white solid (28 mg, 40%). $^1H$ NMR (500 MHz, DMSO-$d_6$) δ ppm 3.99 (s, 3 H), 8.44 (s, 1H).

Preparation 6

Methyl 6-chloro-4-cyano-2-(m-tolylamino)nicotinate

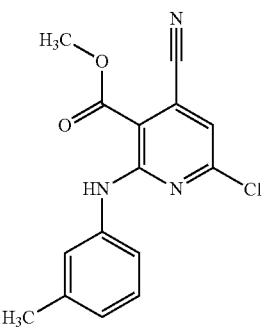 [SMILES: COC(=O)c1c(C#N)cc(Cl)nc1Nc1cccc(C)c1]

A solution of methyl 2,6-dichloro-4-cyanonicotinate (455 mg, 1.97 mmol), triethylamine (0.549 mL, 3.94 mmol) and m-toluidine (0.32 mL, 2.95 mmol) in THF (10 mL) was stirred at RT for 3 days. Water was added to the resulting mixture, and the aqueous phase was extracted with EtOAc. The organic phases were combined, washed with $H_2O$ and brine, dried over $MgSO_4$, and evaporated. The residue was purified by chromatography on $SiO_2$ to give the title compound as a yellow solid (198 mg, 33.3%). $^1H$ NMR (500 MHz, $CDCl_3$) δ ppm 2.40 (s, 3 H), 3.99 (s, 3H), 6.92 (s, 1H), 7.05-7.14 (m, 4H), 7.33 (t, J=7.81 Hz, 1H).

Preparation 7 tert-Butyl (1S,2R)-2-(3-oxo-4-(m-tolylamino)-2,3-dihydro-1H-pyrrolo[3,4-c]pyridin-6-ylamino)cyclohexylcarbamate

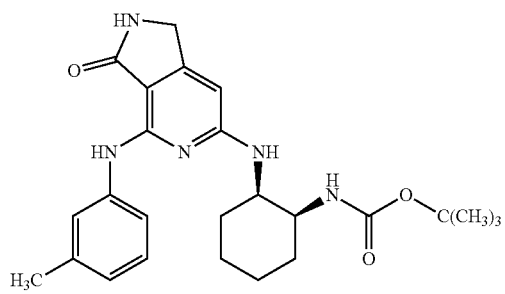 [SMILES: Cc1cccc(Nc2nc(N[C@@H]3CCCC[C@@H]3NC(=O)OC(C)(C)C)cc3c2C(=O)NC3)c1]

A. Methyl 6-((1R,2S)-2-(tert-butoxycarbonylamino)cyclohexylamino)-4-cyano-2-(m-tolylamino)nicotinate

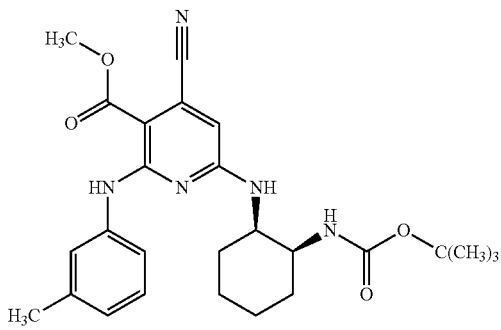 [SMILES: COC(=O)c1c(C#N)cc(N[C@@H]2CCCC[C@@H]2NC(=O)OC(C)(C)C)nc1Nc1cccc(C)c1]

A solution of methyl 6-chloro-4-cyano-2-(m-tolylamino)nicotinate (198 mg, 0.656 mmol), tert-butyl (1S,2R)-2-aminocyclohexylcarbamate (562 mg, 2.62 mmol) and Et$_3$N (0.402 mL, 2.89 mmol) was stirred at reflux overnight. To the resulting mixture were added H$_2$O and EtOAc. The aqueous phase was extracted with EtOAc. The organic layers were combined, washed with brine, dried over MgSO$_4$, and evaporated. The residue was triturated with EtOAc. The resulting solid was filtered, rinsed with EtOAc, and dried to give the title compound as a yellow solid (250 mg, 79%). $^1$H NMR (500 MHz, CDCl$_3$) δ ppm 1.23-1.77 (m, 17 H), 2.34 (s, 3 H), 3.94 (br s, 3 H), 3.98 (br s, 1H), 4.80 (s, 1H), 6.15 (s, 1 H), 6.91 (d, J=5.37 Hz, 1 H), 7.21 (t, J=7.81 Hz, 1H), 7.29 (s, 1H), 7.47-7.55 (m, 1 H), 10.64 (br s, 1 H).

B. tert-Butyl (1S,2R)-2-(3-oxo-4-(m-tolylamino)-2,3-dihydro-1H-pyrrolo[3,4-c]pyridin-6-ylamino)cyclohexylcarbamate Methyl 6-((1R,2S)-2-(tert-butoxycarbonylamino)cyclohexylamino)-4-cyano-2-(m-tolylamino)nicotinate (100 mg, 0.209 mmol) was dissolved into DMF (5 mL). To the solution was added palladium on carbon (22.19 mg, 0.209 mmol) and the resulting mixture was stirred at 80° C. overnight under H$_2$ atmosphere. The mixture was filtered, the filtrate was evaporated, and the residue was diluted with H$_2$O and EtOAc. The aqueous phase was extracted with EtOAc. The organic phases were combined, washed with H$_2$O and brine, dried over MgSO$_4$, and evaporated. The residue was purified by recrystallization (EtOH-Hexane) to give the title compound as a white solid (70 mg, 74.3%). $^1$H NMR (500 MHz, CDCl$_3$) δ ppm 1.03-2.10 (m, 17 H), 2.34 (s, 3 H), 3.81-4.29 (m, 4 H), 5.03 (s, 1 H), 5.32 (s, 1 H), 5.81 (s, 1 H), 6.20 (s, 1 H), 6.81 (s, 1 H), 7.18 (s, 1 H), 7.49 (s, 1 H), 7.64 (s, 1 H), 8.77 (s, 1 H). [M+H] calc'd for C$_{25}$H$_{33}$N$_5$O$_3$, 452; found, 452.

Example 13

6-((1R,2S)-2-Aminocyclohexylamino)-4-(m-tolylamino)-1H-pyrrolo[3,4-c]pyridin-3(2H)-one

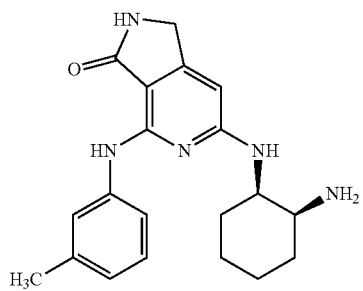

A mixture of tert-butyl (1S,2R)-2-(3-oxo-4-(m-tolylamino)-2,3-dihydro-1H-pyrrolo[3,4-c]pyridin-6-ylamino)cyclohexylcarbamate (50.0 mg, 0.111 mmol) and 4N HCl in dioxane (2 mL, 8.00 mmol) was stirred at RT for 2 h. The reaction mixture was concentrated under reduced pressure, the residue was purified by reverse phase preparative HPLC. The fractions were collected, concentrated, diluted with EtOAc, and basified with saturated aq NaHCO$_3$ solution. The organic extract was dried and evaporated to give the title compound as a white solid (10 mg, 25.7%). $^1$H NMR (500 MHz, CDCl$_3$) δ ppm 1.19-1.77 (m, 8 H), 2.29 (s, 3 H), 3.20 (br s, 1 H), 3.99 (br s, 1 H), 4.19 (s, 2 H), 6.06 (s, 1 H), 6.75 (d, J=7.32 Hz, 2H), 7.14 (t, J=7.81 Hz, 1 H), 7.48 (d, J=7.32 Hz, 1 H), 7.60 (s, 1 H), 7.90 (s, 1 H), 8.87 (s, 1 H). [M+H] calc'd for C$_{20}$H$_{25}$N$_5$O, 352; found, 352.

Example 14

2-((1R,2S)-2-Aminocyclohexylamino)-4-(1-methyl-1H-pyrazol-4-yl)-6,7-dihydro-5H-pyrrolo[3,4-d]pyrimidin-5-one

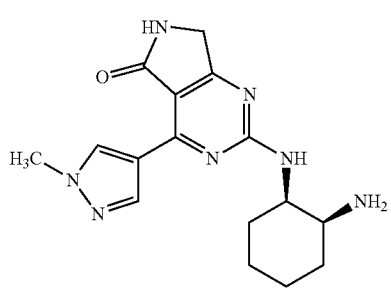 [SMILES: Cn1cc(-c2nc(N[C@@H]3CCCC[C@@H]3N)nc3c2C(=O)NC3)cn1]

A. Methyl 2-chloro-4-methyl-6-(1-methyl-1H-pyrazol-4-yl)pyrimidine-5-carboxylate

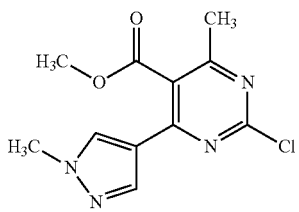 [SMILES: COC(=O)c1c(C)nc(Cl)nc1-c1cnn(C)c1]

A mixture of methyl 2,4-dichloro-6-methylpyrimidine-5-carboxylate (0.79 g, 3.57 mmol), 1-methyl-4-(4,4,5,5-tetramethyl-1,3,2-dioxaborolan-2-yl)-1H-pyrazole (0.595 g, 2.86 mmol) and bis(triphenylphosphine)palladium chloride (0.050 g, 0.071 mmol) in dioxane (5 mL) was stirred at RT for 10 min, after which potassium fluoride (1.038 g, 17.87 mmol) was added. The mixture was stirred under a nitrogen atmosphere and heated at 90° C. for 12 h. The reaction mixture was filtered through a bed of Celite 545, rinsed with DCM and a small amount of MeOH. Following solvent removal, the residue was dispersed in DMSO/MeOH (1/1) and purified via reverse phase preparative HPLC to give the title compound (237 mg, 25%). [M+H] calc'd for $C_{11}H_{11}ClN_4O_2$, 267; found, 267.

B. Methyl 2-((1R,2S)-2-(tert-butoxycarbonylamino)cyclohexylamino)-4-methyl-6-(1-methyl-1H-pyrazol-4-yl)pyrimidine-5-carboxylate

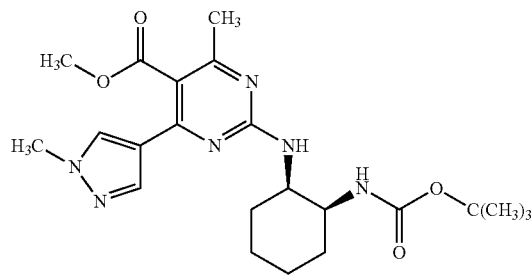 [SMILES: COC(=O)c1c(C)nc(N[C@@H]2CCCC[C@@H]2NC(=O)OC(C)(C)C)nc1-c1cnn(C)c1]

To a mixture of methyl 2-chloro-4-methyl-6-(1-methyl-1H-pyrazol-4-yl)pyrimidine-5-carboxylate (0.227 g, 0.851 mmol) and tert-butyl (1S,2R)-2-aminocyclohexylcarbamate (0.182 g, 0.851 mmol) in DMA (3 mL) was added Et$_3$N (0.356 mL, 2.55 mmol). The reaction mixture was heated at 90° C. for 4 h. The reaction mixture was cooled to RT and poured onto ice. The solid was filtered and dried under high vacuum to yield the title compound as an off-white foam (170 mg). [M+H] calc'd for $C_{22}H_{32}N_6O_4$, 445; found, 445.

C. Methyl 2-((1R,2S)-2-(tert-butoxycarbonylamino)cyclohexylamino)-4-formyl-6-(1-methyl-1H-pyrazol-4-yl)pyrimidine-5-carboxylate

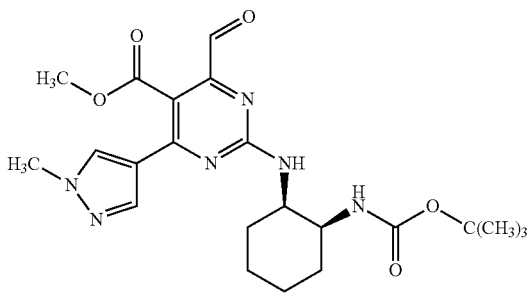 [SMILES: COC(=O)c1c(C=O)nc(N[C@@H]2CCCC[C@@H]2NC(=O)OC(C)(C)C)nc1-c1cnn(C)c1]

To a 25 mL round bottom flask was added methyl 2-((1R,2S)-2-(tert-butoxycarbonylamino)cyclohexylamino)-4-methyl-6-(1-methyl-1H-pyrazol-4-yl)pyrimidine-5-carboxylate (0.17 g, 0.382 mmol), selenium dioxide (0.085 g, 0.765 mmol) and dioxane. The reaction mixture was heated at 100° C. overnight, cooled to RT, and filtered through a bed of Celite 545, which was rinsed with MeOH. The solvent was removed to give the title compound as yellowish-brown foam, which was used in the next step without further purification (245 mg).

D. tert-Butyl (1S,2R)-2-(6-(2,4-dimethoxybenzyl)-4-(1-methyl-1H-pyrazol-4-yl)-5-oxo-6,7-dihydro-5H-pyrrolo[3,4-d]pyrimidin-2-ylamino)cyclohexylcarbamate

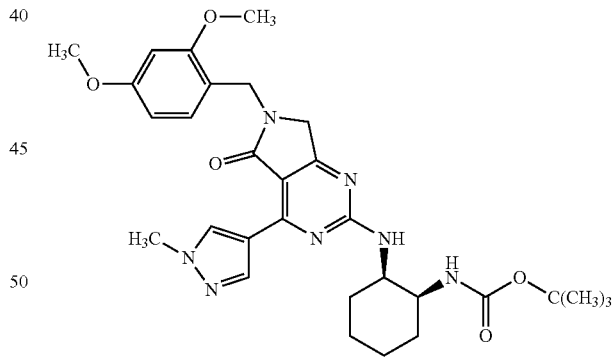

Methyl 2-((1R,2S)-2-(tert-butoxycarbonylamino)cyclohexylamino)-4-formyl-6-(1-methyl-1H-pyrazol-4-yl)pyrimidine-5-carboxylate (0.175 g, 0.382 mmol) was dissolved in DCM (2 mL) and MeOH (1 mL). To this mixture was added (2,4-dimethoxyphenyl)methanamine (0.057 mL, 0.382 mmol) and sodium acetate (0.094 g, 1.145 mmol). The mixture was stirred in a capped 20 mL vial for 1 h, after which sodium cyanoborohydride (0.060 g, 0.954 mmol) was added. The reaction mixture was stirred at RT overnight. After the solvent was removed under reduced pressure, the residue was dissolved in DMSO/MeOH (1/1) solution. An off-white solid precipitate was initially formed, which was isolated by vacuum filtration, rinsed with MeOH, and air dried to give a first batch of the title compound (6.7 mg). The mother liquor was purified via preparative HPLC. The fractions were concentrated under reduced pressure until an off-white solid precipitate was formed, which was collected by vacuum filtration and air dried to give a second batch (46 mg) of the title compound (total 62.5 mg, 28%). [M+H] calc'd for $C_{30}H_{39}N_7O_5$, 578; found, 578.

E. 2-((1R,2S)-2-Aminocyclohexylamino)-4-(1-methyl-1H-pyrazol-4-yl)-6,7-dihydro-5H-pyrrolo[3,4-d]pyrimidin-5-one tert-Butyl (1S,2R)-2-(6-(2,4-dimethoxybenzyl)-4-(1-methyl-1H-pyrazol-4-yl)-5-oxo-6,7-dihydro-5H-pyrrolo[3,4-d]pyrimidin-2-ylamino)cyclohexylcarbamate (0.0625 g, 0.108 mmol) was dissolved in TFA (2 mL) and heated at 70° C. for 1 h. The solvent was removed under reduced pressure and the resulting residue was dispersed in DMSO/MeOH (1/1) solution. A pale purple precipitate was formed and was separated by filtration. The filtrate, which contained the product, was purified via reverse phase preparative HPLC. Lyophilized fractions gave a TFA salt of the title compound as a white solid (21 mg, 59%). $^1$H NMR (500 MHz, DMSO-d$_6$) δ ppm 1.28-1.52 (m, 2 H) 1.51-1.94 (m, 6 H) 3.93 (s, 3 H) 4.14-4.30 (m, 2 H) 4.29-4.58 (m, 1 H) 7.51 (d, J=6.83 Hz, 1 H) 7.71 (br s, 2 H) 8.29 (s, 1 H) 8.34-8.69 (m, 1 H) 9.11 (d, J=17.09 Hz, 1 H). [M+H] calc'd for $C_{16}H_{21}N_7O$, 328; found, 328.

Example 15

2-((1R,2S)-2-Aminocyclohexylamino)-4-(1-isobutyl-1H-pyrazol-4-yl)-6,7-dihydro-5H-pyrrolo[3,4-d]pyrimidin-5-one A TFA salt of the title compound was prepared in a manner similar to EXAMPLE 14 using 1-isobutyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (500 MHz, CD$_3$OD) δ ppm 0.92 (d, J=1.00 Hz, 6 H), 0.87-1.00 (m, 6 H), 1.45-1.70 (m, 2 H), 1.46-1.70 (m, 2 H), 1.70-2.00 (m, 6 H), 2.22 (spt, J=13.70 Hz, 1 H), 3.64 (br s, 1 H), 4.02 (d, J=6.83 Hz, 2 H), 4.30 (s, 2 H), 4.63 (d, J=3.91 Hz, 1 H), 8.54 (s, 1 H), 9.12 (br s, 1 H). [M+H] calc'd for $C_{19}H_{27}N_7O$, 370; found, 370.

Example 16

2-((1R,2S)-2-Aminocyclohexylamino)-4-phenyl-6,7-dihydro-5H-pyrrolo[3,4-d]pyrimidin-5-one

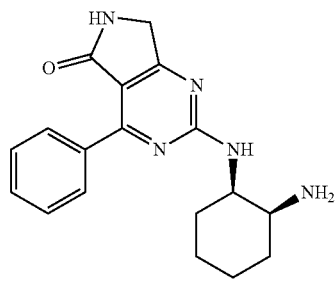 [SMILES: N[C@H]1CCCC[C@H]1Nc1nc2c(c(-c3ccccc3)n1)C(=O)NC2]

The title compound was prepared in a manner similar to EXAMPLE 14 using phenylboronic acid in place of 1-methyl-4-(4,4,5,5-tetramethyl-1,3,2-dioxaborolan-2-yl)-1H-pyrazole. The final product was purified via reverse phase preparative HPLC. The fractions were collected, concentrated, neutralized with saturated aq NaHCO$_3$, and extracted into EtOAc. The organic phase was dried over anhydrous Na$_2$SO$_4$ and the solvent removed in vacuo to give the title compound as an off-white film. $^1$H NMR (400 MHz, CD$_3$OD) δ ppm 1.40-1.95 (m, 8 H), 3.27 (br s, 1 H), 4.18-4.54 (m, 3 H), 7.35-7.59 (m, 3 H), 8.12 (br s, 2 H). [M+H] calc'd for $C_{18}H_{21}N_5O$, 324; found, 324.

Example 17

2-((1R,2S)-2-Aminocyclohexylamino)-4-(benzo[b]thiophen-3-yl)-6,7-dihydro-5H-pyrrolo[3,4-d]pyrimidin-5-one

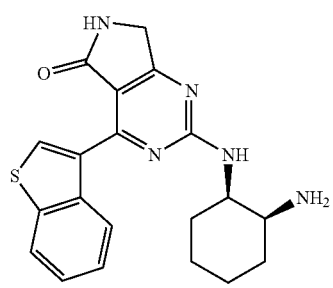 [SMILES: N[C@H]1CCCC[C@H]1Nc1nc2c(c(-c3csc4ccccc34)n1)C(=O)NC2]

A TFA salt of the title compound was prepared in a manner similar to EXAMPLE 14 using benzo[b]thiophen-3-ylboronic acid in place of 1-methyl-4-(4,4,5,5-tetramethyl-1,3,2-dioxaborolan-2-yl)-1H-pyrazole. $^1$H NMR (400 MHz, CD$_3$OD) δ ppm 1.44-2.02 (m, 8 H), 3.53-3.84 (m, 1 H), 4.25-4.43 (m, 2 H), 4.54-4.72 (m, 1 H), 7.32-7.55 (m, 2 H), 7.84-8.03 (m, 1 H), 8.40-8.88 (m, 1 H), 8.86-9.10 (m, 1 H). [M+H] calc'd for $C_{20}H_{21}N_5OS$, 380; found, 380.

Example 18

2-((1R,2S)-2-Aminocyclohexylamino)-4-(1-ethyl-1H-pyrazol-4-yl)-6,7-dihydro-5H-pyrrolo[3,4-d]pyrimidin-5-one

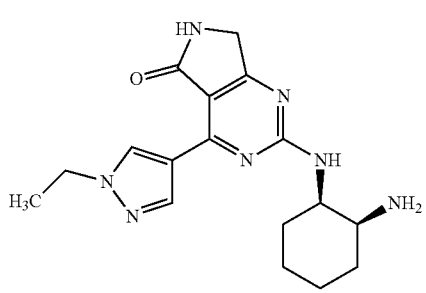 [SMILES: CCn1cc(-c2nc(N[C@@H]3CCCC[C@@H]3N)nc3c2C(=O)NC3)cn1]

A TFA salt of the title compound was prepared in a manner similar to EXAMPLE 14 using 1-ethyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (400 MHz, CD$_3$OD) δ ppm 1.47-1.55 (m, 3 H), 1.54-1.99 (m, 8 H), 3.64 (br s, 1 H), 4.26 (q, J=7.32 Hz, 2 H), 4.30 (s, 2 H), 4.63 (br s, 1 H), 8.54 (br s, 1 H), 9.14 (s, 1 H). [M+H] calc'd for $C_{17}H_{23}N_7O$, 342; found, 342.

Example 19

2-((1R,2S)-2-Aminocyclohexylamino)-4-(1-benzyl-1H-pyrazol-4-yl)-6,7-dihydro-5H-pyrrolo[3,4-d]pyrimidin-5-one

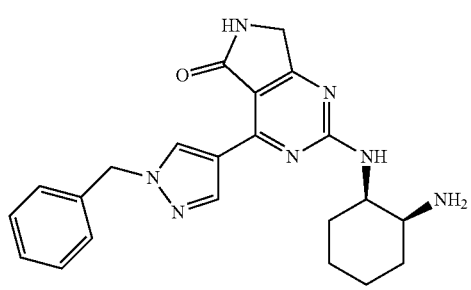 [SMILES: N[C@H]1CCCC[C@H]1Nc1nc2c(c(-c3cnn(Cc4ccccc4)c3)n1)C(=O)NC2]

A TFA salt of the title compound was prepared in a manner similar to EXAMPLE 14 using 1-benzyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (400 MHz, CD$_3$OD) δ ppm 1.45-1.69 (m, 2 H), 1.69-2.00 (m, 6 H), 3.63 (br s, 1 H), 4.29 (s, 2 H), 4.61 (br s, 1 H), 5.40 (s, 2 H), 7.22-7.41 (m, 5 H), 8.58 (s, 1 H), 9.16 (br s, 1 H). [M+H] calc'd for $C_{22}H_{25}N_7O$, 404; found, 404.

Example 20

2-((1R,2S)-2-Aminocyclohexylamino)-4-(imidazo[1,2-a]pyridin-3-yl)-6,7-dihydro-5H-pyrrolo[3,4-d]pyrimidin-5-one

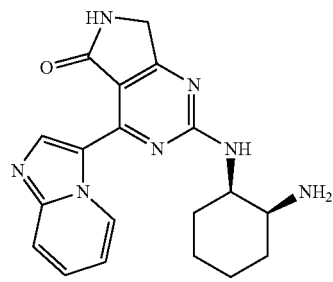 [SMILES: N[C@H]1CCCC[C@H]1Nc1nc2c(c(-c3cnc4ccccn34)n1)C(=O)NC2]

A TFA salt of the title compound was prepared in a manner similar to EXAMPLE 14 using imidazo[1,2-a]pyridin-3-ylboronic acid in place of 1-methyl-4-(4,4,5,5-tetramethyl-1,3,2-dioxaborolan-2-yl)-1H-pyrazole. $^1$H NMR (500 MHz, CD$_3$OD) δ ppm 1.47-1.73 (m, 2 H), 1.74-2.03 (m, 6 H), 3.68 (br s, 1 H), 4.27-4.54 (m, 2 H), 4.58-4.75 (m, 1 H), 7.52-7.79 (m, 1 H), 8.00-8.12 (m, 1 H), 8.14 (t, J=7.57 Hz, 1 H), 10.23 (br s, 1 H), 10.81 (d, J=5.86 Hz, 1 H). [M+H] calc'd for $C_{19}H_{21}N_7O$, 364; found, 364.

Example 21

2-((1R,2S)-2-Aminocyclohexylamino)-4-(1-propyl-1H-pyrazol-4-yl)-6,7-dihydro-5H-pyrrolo[3,4-d]pyrimidin-5-one

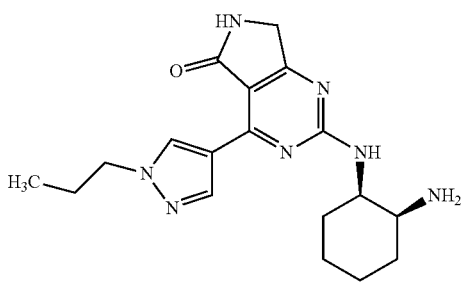 [SMILES: CCCn1cc(-c2nc(N[C@@H]3CCCC[C@@H]3N)nc3c2C(=O)NC3)cn1]

A TFA salt of the title compound was prepared in a manner similar to EXAMPLE 14 using 1-propyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (500 MHz, CD$_3$OD) δ ppm 0.92 (t, J=1.00 Hz, 3 H), 1.43-1.70 (m, 2 H), 1.69-2.14 (m, 8 H), 3.62

(br s, 1 H), 4.18 (t, J=6.83 Hz, 2 H), 4.24-4.41 (m, 2 H), 4.63 (br s, 1 H), 8.56 (br s, 1 H), 9.13 (br s, 1 H). [M+H] calc'd for $C_{18}H_{25}N_7O$, 356; found, 356.

Example 22

2-((1R,2S)-2-Aminocyclohexylamino)-4-(1-(2-methoxyethyl)-1H-pyrazol-4-yl)-6,7-dihydro-5H-pyrrolo[3,4-d]pyrimidin-5-one

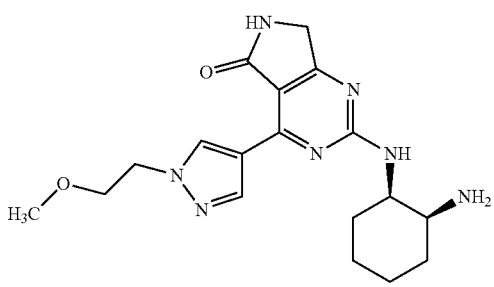 [SMILES: COCCn1cc(-c2nc(N[C@@H]3CCCC[C@@H]3N)nc3c2C(=O)NC3)cn1]

A TFA salt of the title compound was prepared in a manner similar to EXAMPLE 14 using 1-(2-methoxyethyl)-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (500 MHz, CD$_3$OD) δ ppm 1.45-1.70 (m, 2 H), 1.70-2.05 (m, 6 H), 3.33-3.35 (m, 3 H), 3.63 (br s, 1 H), 3.73-3.90 (m, 2 H), 4.30 (s, 2 H), 4.33-4.47 (m, 2 H), 4.63 (br s, 1 H), 8.58 (br s, 1 H), 9.13 (br s, 1 H). [M+H] calc'd for $C_{18}H_{25}N_7O_2$, 372; found, 372.

Example 23

4-(1H-Indazol-6-ylamino)-6-((1R,2S)-2-aminocyclohexylamino)-1H-pyrrolo[3,4-c]pyridin-3(2H)-one

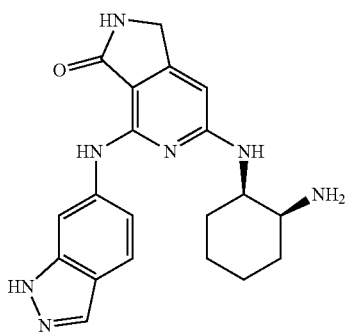 [SMILES: N[C@H]1CCCC[C@H]1Nc1cc2c(c(Nc3ccc4cn[nH]c4c3)n1)C(=O)NC2]

A. Methyl 2-(1H-indazol-6-ylamino)-6-chloro-4-cyanonicotinate

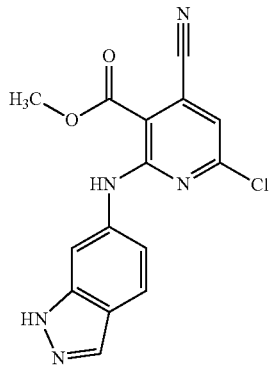 [SMILES: COC(=O)c1c(C#N)cc(Cl)nc1Nc1ccc2cn[nH]c2c1]

A mixture of methyl 2,6-dichloro-4-cyanonicotinate (250 mg, 1.082 mmol), 1H-indazol-6-amine (173 mg, 1.299 mmol) and Et$_3$N (0.226 mL, 1.623 mmol) in THF (10 mL) was stirred at 80° C. overnight. Water and EtOAc were added to the mixture. The organic phase was washed with H$_2$O and brine, dried over MgSO$_4$, and evaporated. The residue was purified by chromatography on SiO$_2$(Hexane/EtOAc=5/1) to give the title compound as a yellow solid (120 mg, 38.5%).

B. Methyl 2-(1H-indazol-6-ylamino)-6-((1R,2S)-2-(tert-butoxycarbonylamino)cyclohexylamino)-4-cyanonicotinate

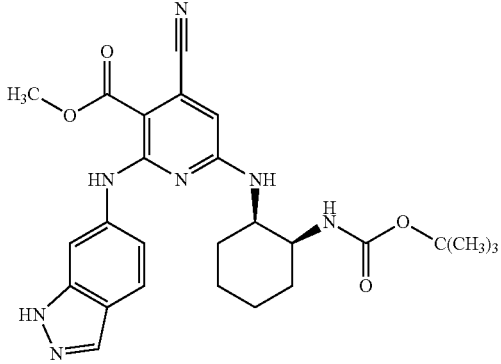 [SMILES: COC(=O)c1c(C#N)cc(N[C@@H]2CCCC[C@@H]2NC(=O)OC(C)(C)C)nc1Nc1ccc2cn[nH]c2c1]

A solution of methyl 2-(1H-indazol-6-ylamino)-6-chloro-4-cyanonicotinate (115 mg, 0.351 mmol), tert-butyl (1S,2R)-2-aminocyclohexylcarbamate (90 mg, 0.421 mmol) and Et$_3$N (0.073 mL, 0.526 mmol) in THF (1 mL) was stirred at reflux overnight. Water and EtOAc were added to the mixture. The aqueous phase was extracted with EtOAc. The organic phases were combined, washed with H$_2$O and brine, dried over MgSO$_4$, and evaporated. The residue was rinsed with EtOAc to give the title compound as yellow solid (110 mg, 62.0%). $^1$H NMR (500 MHz, CDCl$_3$) δ ppm 1.00-1.86 (m, 17 H), 3.84 (s, 3 H), 3.91 (br s, 1 H), 4.12 (br s, 1 H), 6.51 (s, 1 H), 6.63

(d, J=8.79 Hz, 1 H), 7.13 (d, J=8.30 Hz, 1 H), 7.97 (s, 1 H), 8.03 (br s, 1 H), 10.71 (br s, 1 H), 12.87 (br s, 1 H).

C. Methyl 2-(1H-indazol-6-ylamino)-6-((1R,2S)-2-aminocyclohexylamino)-4-cyanonicotinate

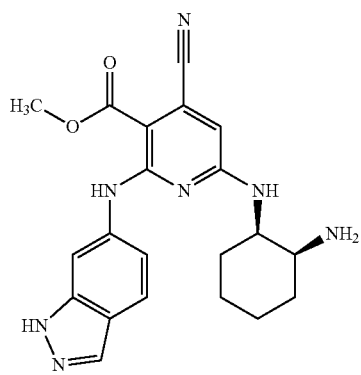 [SMILES: COC(=O)c1c(C#N)cc(N[C@@H]2CCCC[C@@H]2N)nc1Nc1ccc2cn[nH]c2c1]

A solution of methyl 2-(1H-indazol-6-ylamino)-6-((1R,2S)-2-(tert-butoxycarbonylamino)cyclohexylamino)-4-cyanonicotinate (110 mg, 0.218 mmol) and TFA (2 mL, 26.9 mmol) in DCM (1 mL) was stirred at room temperature for 3 h. Following reaction, the mixture was concentrated in vacuo to give the title compound, which was used in the next step without further purification.

D. 4-(1H-Indazol-6-ylamino)-6-((1R,2S)-2-aminocyclohexylamino)-1H-pyrrolo[3,4-c]pyridin-3(2H)-one To a solution of methyl 2-(1H-indazol-6-ylamino)-6-((1R,2S)-2-aminocyclohexylamino)-4-cyanonicotinate (88 mg, 218 mmol) in MeOH (2 mL) was added palladium on carbon, and the resulting mixture was stirred at room temperature overnight under H$_2$ atmosphere. The mixture was subsequently filtered to remove the catalyst and the filtrate was evaporated. The residue was diluted with saturated aq NaHCO$_3$ and MeOH, and the mixture was stirred at RT for 30 min. The resulting suspension was filtered and the precipitate was washed with EtOAc and dried to give the title compound as a white solid (15 mg, 18.2%). $^1$H NMR (500 MHz, DMSO-d$_6$) δ ppm 1.22-1.74 (m, 8 H), 3.13 (br s, 1H), 3.94-4.07 (m, 1 H), 4.21 (s, 2 H), 6.02-6.14 (m, 1 H), 6.70 (br s, 1 H), 7.13 (d, J=8.30 Hz, 1 H), 7.63 (d, J=8.30 Hz, 1 H), 7.94 (d, J=2.93 Hz, 2 H), 8.23 (s, 1 H), 9.08 (s, 1 H), 12.84 (br s, 1 H). [M+H] calc'd for C$_{20}$H$_{23}$N$_7$O, 378; found, 378.

Example 24

6-((1R,2S)-2-Aminocyclohexylamino)-4-(4-fluoro-3-methylphenylamino)-1H-pyrrolo[3,4-c]pyridin-3(2H)-one

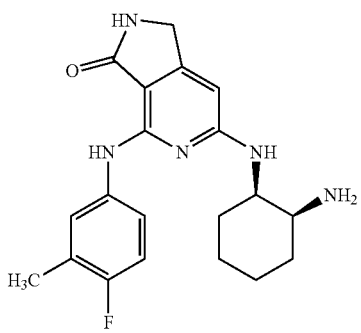 [SMILES: Cc1cc(Nc2nc(N[C@@H]3CCCC[C@@H]3N)cc3c2C(=O)NC3)ccc1F]

A. Methyl 6-chloro-4-cyano-2-(4-fluoro-3-methylphenylamino)nicotinate

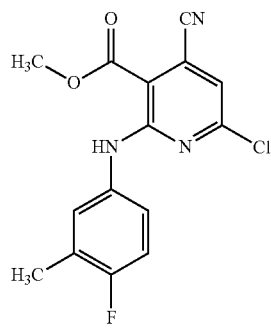 [SMILES: COC(=O)c1c(C#N)cc(Cl)nc1Nc1ccc(F)c(C)c1]

A solution of methyl 2,6-dichloro-4-cyanonicotinate (500 mg, 2.164 mmol), 4-fluoro-3-methylaniline (325 mg, 2.60 mmol) and Et$_3$N (0.452 mL, 3.25 mmol) in ACN (5 mL) was stirred at 50° C. for 24 h. Water and EtOAc were added to the mixture and the aqueous phase was extracted with EtOAc. The organic phases were combined, washed with H$_2$O and brine, dried over MgSO$_4$, and evaporated. The residue was purified by chromatography on SiO$_2$ to give the title compound, which contains some starting material and was used without further purification (390 mg). [M+H] calc'd for C$_{15}$H$_{11}$ClFN$_3$O$_2$, 320; found, 320.

B. Methyl 6-((1R,2S)-2-(tert-butoxycarbonylamino)cyclohexylamino)-4-cyano-2-(4-fluoro-3-methylphenylamino)nicotinate

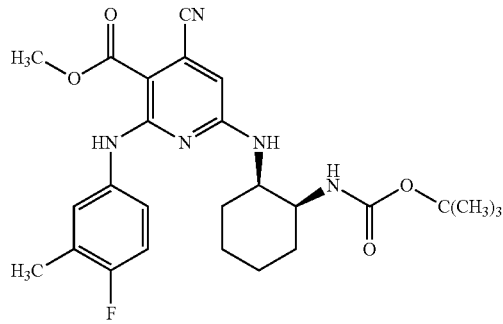 [SMILES: COC(=O)c1c(C#N)cc(N[C@@H]2CCCC[C@@H]2NC(=O)OC(C)(C)C)nc1Nc1ccc(F)c(C)c1]

A mixture of methyl 6-chloro-4-cyano-2-(4-fluoro-3-methylphenylamino)nicotinate (390 mg, 1.220 mmol), Et$_3$N (0.204 mL, 1.464 mmol) and tert-butyl (1S,2R)-2-aminocyclohexylcarbamate (392 mg, 1.830 mmol) in THF (5 mL) was stirred at 80° C. overnight. Water and EtOAc were subsequently added to the mixture and the aqueous phase was extracted with EtOAc. The organic phases were combined, washed with H$_2$O and brine, dried over MgSO$_4$, and evaporated. The residue was diluted with EtOAc and filtered to give the title compound as a yellow solid (75 mg, 12.36%). $^1$H NMR (500 MHz, DMSO-d$_6$) δ ppm 1.03-1.71 (m, 17 H), 2.22 (d, J=0.98 Hz, 3 H), 3.80-3.82 (m, 3 H), 3.83 (br s, 1 H), 4.01-4.09 (m, 1 H), 6.48 (s, 1 H), 6.62 (d, J=7.81 Hz, 1 H), 7.06 (t, J=9.03, 1 H), 7.39 (d, J=4.39 Hz, 1 H), 7.50-7.68 (m, 1 H), 10.41 (br s, 1 H).

C. tert-Butyl (1S,2R)-2-(4-(4-fluoro-3-methylphenylamino)-3-oxo-2,3-dihydro-1H-pyrrolo[3,4-c]pyridin-6-ylamino)cyclohexylcarbamate

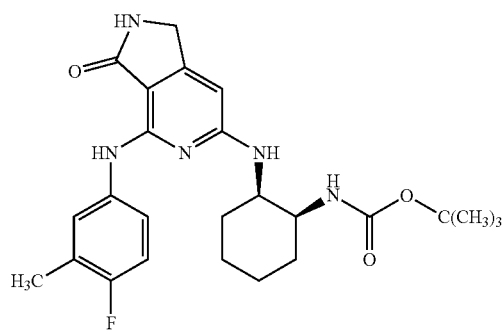 [SMILES: Cc1cc(Nc2nc(N[C@@H]3CCCC[C@@H]3NC(=O)OC(C)(C)C)cc3c2C(=O)NC3)ccc1F]

A mixture of methyl 6-((1R,2S)-2-(tert-butoxycarbonylamino)cyclohexylamino)-4-cyano-2-(4-fluoro-3-methylphenylamino)nicotinate (75 mg, 0.151 mmol) and platinum oxide (34.2 mg, 0.151 mmol) in DCM (2 mL) and HOAc (0.5 mL) was stirred at RT under H$_2$ atmosphere. The mixture was subsequently filtered through Celite. The filtrate was concentrated and the residue was purified by preparative HPLC to give the title compound (50 mg, 70.6%). [M+H] calc'd for C$_{25}$H$_{32}$FN$_5$O$_3$, 470; found, 470.

D. 6-((1R,2S)-2-Aminocyclohexylamino)-4-(4-fluoro-3-methylphenylamino)-1H-pyrrolo[3,4-c]pyridin-3(2H)-one A solution of tert-butyl (1S,2R)-2-(4-(4-fluoro-3-methylphenylamino)-3-oxo-2,3-dihydro-1H-pyrrolo[3,4-c]pyridin-6-ylamino)cyclohexylcarbamate (50.0 mg, 0.106 mmol) and TFA (1 mL, 12.98 mmol) in DCM (0.5 mL) was stirred at RT for 1 hr. The resulting mixture was concentrated and the residue was purified by preparative HPLC to give the title compound as a white solid (1 mg, 2.54%). $^1$H NMR (500 MHz, CD$_3$OD) δ ppm 1.14-1.95 (m, 8 H), 2.28 (s, 3 H), 3.73 (br s, 1 H), 4.30 (s, 2H), 4.38 (s, 1 H), 6.17 (s, 1 H), 7.00 (t, J=9.03 Hz, 1 H), 7.41-7.54 (m, 2 H).

Example 25

6-((1R,2S)-2-Aminocyclohexylamino)-7-fluoro-4-(m-tolylamino)-1H-pyrrolo[3,4-c]pyridin-3(2H)-one

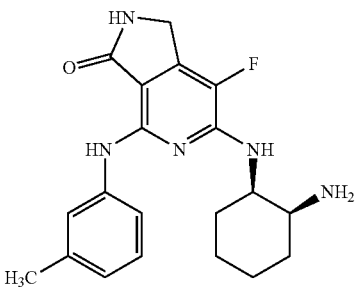

A. tert-Butyl (1S,2R)-2-(7-fluoro-3-oxo-4-(m-tolylamino)-2,3-dihydro-1H-pyrrolo[3,4-c]pyridin-6-ylamino)cyclohexylcarbamate

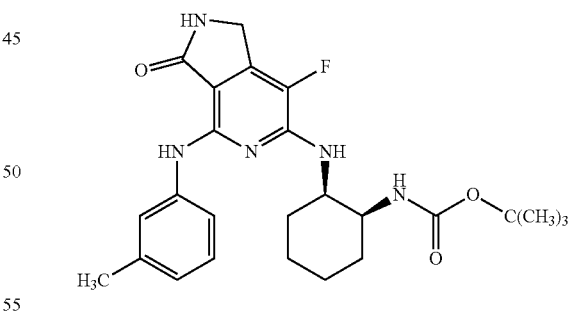

A solution of tert-butyl (1S,2R)-2-(3-oxo-4-(m-tolylamino)-2,3-dihydro-1H-pyrrolo[3,4-c]pyridin-6-ylamino)cyclohexylcarbamate (94 mg, 0.208 mmol) and SELECTFLUOR® (73.7 mg, 0.208 mmol) was stirred at 0° C. for 5 h and at RT for 1 h. The mixture was filtered and the filtrate was purified by preparative HPLC. The fractions were collected and concentrated. The residue was washed with saturated aq NaHCO$_3$ solution, extracted with EtOAc, washed with brine, dried over MgSO$_4$, and evaporated to give the title compound as yellow solid (45 mg, 46.0%). [M+H] calc'd for C$_{25}$H$_{32}$FN$_5$O$_3$, 470; found, 470.

B. 6-((1R,2S)-2-Aminocyclohexylamino)-7-fluoro-4-(m-tolylamino)-1H-pyrrolo[3,4-c]pyridin-3(2H)-one A solution of tert-butyl (1S,2R)-2-(7-fluoro-3-oxo-4-(m-tolylamino)-2,3-dihydro-1H-pyrrolo[3,4-c]pyridin-6-ylamino)cyclohexylcarbamate (40.0 mg, 0.085 mmol) and TFA (2 mL, 26.0 mmol) in DCM (1 mL) was stirred at RT for 1 h. The mixture was concentrated and the resulting residue was purified by preparative HPLC to give the title compound as a white solid (20 mg, 63.5%). $^1$H NMR (500 MHz, DMSO-$d_6$) δ ppm 1.36-1.97 (m, 8 H), 2.30 (s, 3 H), 3.70 (br s, 1 H), 4.27 (br s, 1 H), 4.33-4.46 (m, 2 H), 6.73 (d, J=6.35 Hz, 1 H), 6.79 (d, J=7.32 Hz, 1 H), 7.17 (t, J=7.57 Hz, 1 H), 7.43 (d, J=7.81 Hz, 1 H), 7.46 (s, 1 H), 7.76 (br s, 2 H), 8.29 (s, 1 H), 8.79 (s, 1 H). [M+H] calc'd for $C_{20}H_{24}FN_5O$, 370; found, 370.

Preparation 8

Methyl 2-chloro-4-cyanonicotinate

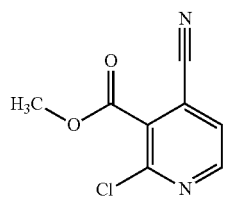

A. Methyl 2-chloro-4-iodonicotinate

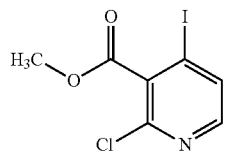

Butyllithium in hexane solution (1.6 M, 13.70 mL, 21.93 mmol) was added drop wise to a solution of diisopropylamine (3.57 mL, 25.06 mmol) in THF (100 mL) at −78° C. and the mixture was stirred for 30 min. A solution of 2-chloro-3-iodopyridine (5.00 g, 20.88 mmol) in THF (50 mL) was added drop wise to the reaction mixture at −78° C. and the resulting mixture was stirred at −78° C. for 2 h. Dry ice was added to the reaction mixture, which was warmed to room temperature and stirred overnight. The resulting mixture was quenched with $H_2O$ and the organic phase was washed with $H_2O$. The combined aqueous phase was acidified with concentrated HCl and extracted with EtOAc. The organic phases were combined, washed with brine, dried over $MgSO_4$, and evaporated to yield crude 2-chloro-4-iodonicotinic acid, which was combined with potassium carbonate (5.77 g, 41.8 mmol) and iodomethane (1.567 mL, 25.06 mmol) in DMF (70 mL). The mixture was stirred at room temperature for 1 h, which was followed by the addition of $Et_2O$ and $H_2O$. The organic phase was washed with $H_2O$ and brine, dried over $MgSO_4$, and evaporated. The residue was purified by chromatography on $SiO_2$ to give the title compound as a white solid (3.23 g, 52.0%). $^1$H NMR (500 MHz, CDCl$_3$) δ ppm 4.01 (s, 3 H), 7.68-7.76 (m, 1 H), 7.97-8.11 (m, 1 H). [M+H] calc'd for $C_7H_5ClINO_2$, 298; found, 298.

B. Methyl 2-chloro-4-cyanonicotinate

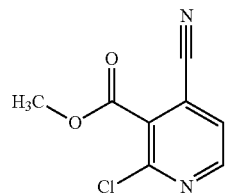

A solution of methyl 2-chloro-4-iodonicotinate (3.20 g, 10.76 mmol) and cyanocopper (0.963 g, 10.76 mmol) in DMA (40 mL) was stirred at 140° C. overnight. Following reaction, the mixture was filtered through Celite and the filtrate was diluted with $H_2O$ and EtOAc. The aqueous phase was extracted with EtOAc. The organic phases were combined, washed with $H_2O$ and brine, dried over $MgSO_4$, and evaporated. The residue was purified by chromatography on $SiO_2$ (Hexane/EtOAc=10/1) to give the title compound as a white solid (730 mg, 34.5%). $^1$H NMR (500 MHz, CDCl$_3$) δ ppm 4.07 (s, 3 H), 7.57 (d, J=5.37 Hz, 1 H), 8.66 (d, J=4.88 Hz, 1 H).

Preparation 9

Methyl 6-chloro-4-cyano-2-(1-methyl-1H-pyrazol-4-yl)nicotinate

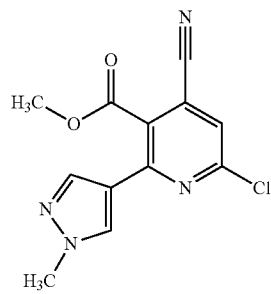 [SMILES: COC(=O)c1c(C#N)cc(Cl)nc1-c1cnn(C)c1]

A. Methyl 4-cyano-2-(1-methyl-1H-pyrazol-4-yl)nicotinate

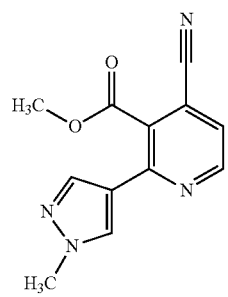 [SMILES: COC(=O)c1c(C#N)ccnc1-c1cnn(C)c1]

A mixture of methyl 2-chloro-4-cyanonicotinate (730 mg, 3.71 mmol), 1-methyl-4-(4,4,5,5-tetramethyl-1,3,2-dioxaborolan-2-yl)-1H-pyrazole (927 mg, 4.46 mmol), trans-dichlorobis(triphenylphosphine)palladium (261 mg, 0.371 mmol) and potassium fluoride (2697 mg, 14.85 mmol) in DME (15 mL) was stirred at 120° C. for 1 h under microwave irradiation. The mixture was filtered through Celite, and the filtrate was diluted with $H_2O$ and EtOAc. The organic phase was washed with $H_2O$ and brine, dried over $MgSO_4$, and evaporated. The residue was purified by chromatography on $SiO_2$ to give the title compound as a pale yellow solid (470 mg, 52.3%). $^1H$ NMR (500 MHz, $CDCl_3$) δ ppm 3.97 (s, 3 H), 4.03 (s, 3 H), 7.41 (d, J=4.88 Hz, 1 H), 7.82 (s, 1 H), 7.91 (s, 1 H), 8.79 (d, J=4.88 Hz, 1 H). [M+H] calc'd for $C_{12}H_{10}N_4O_2$, 243; found, 243.

B. Methyl 6-chloro-4-cyano-2-(1-methyl-1H-pyrazol-4-yl)nicotinate

To a mixture of methyl 4-cyano-2-(1-methyl-1H-pyrazol-4-yl)nicotinate (470 mg, 1.940 mmol) in DCM (10 mL) was added urea-hydrogen peroxide compound (1/1, 913 mg, 9.70 mmol), and 2,2,2-trifluoroacetic anhydride (1.370 mL, 9.70 mmol) at 0° C. The mixture was stirred at room temperature for 4 h. More urea-hydrogen peroxide compound (1/1, 400 mg) was added and the mixture was stirred at RT for an additional 3 h after which was added saturated aq $NaHCO_3$ solution and $CHCl_3$. The aqueous phase was extracted with $CHCl_3$ (3×), and the combined organic layers were washed with brine, dried over $MgSO_4$, and evaporated to obtain crude 4-cyano-3-(methoxycarbonyl)-2-(1-methyl-1H-pyrazol-4-yl)pyridine 1-oxide, which was combined with phosphorus oxychloride (2 mL, 21.46 mmol). The resulting mixture was stirred at 80° C. for 5 h and then concentrated to a residue, which was neutralized with 2N NaOH. The organic phase was washed with brine, dried over $MgSO_4$, and evaporated. The residue was purified by chromatography on $SiO_2$(Hexane/EtOAc=1/1) to give the title compound as a white solid (155 mg, 41.3%). $^1H$ NMR (500 MHz, $CDCl_3$) δ ppm 3.96 (s, 3 H), 4.03 (s, 3 H), 7.41 (s, 1 H), 7.81 (s, 1 H), 7.94 (s, 1 H). [M+H] calc'd for $C_{12}H_9ClN_4O_2$, 277; found, 277.

Preparation 10 tert-Butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate

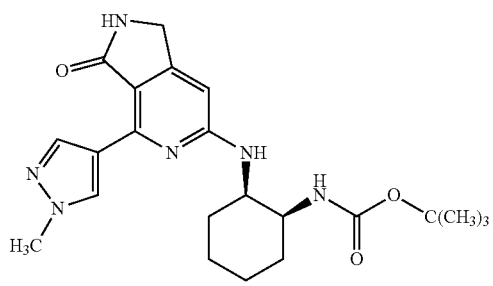 [SMILES: Cn1cc(-c2nc(N[C@@H]3CCCC[C@@H]3NC(=O)OC(C)(C)C)cc3c2C(=O)NC3)cn1]

A. Methyl 6-((1R,2S)-2-(tert-butoxycarbonylamino)cyclohexylamino)-4-cyano-2-(1-methyl-1H-pyrazol-4-yl)nicotinate

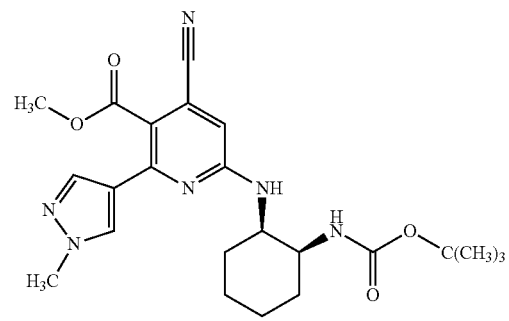 [SMILES: COC(=O)c1c(C#N)cc(N[C@@H]2CCCC[C@@H]2NC(=O)OC(C)(C)C)nc1-c1cnn(C)c1]

A mixture of methyl 6-chloro-4-cyano-2-(1-methyl-1H-pyrazol-4-yl)nicotinate (155 mg, 0.560 mmol) and tert-butyl (1S,2R)-2-aminocyclohexylcarbamate (144 mg, 0.672 mmol) in DMA (2 mL) was stirred at 150° C. for 1 h under microwave irradiation. To the resulting mixture were added $H_2O$ and EtOAc. The organic phase was washed with $H_2O$ (3×) and brine, dried over $MgSO_4$, and evaporated. The residue was purified by chromatography on $SiO_2$ to give the title compound as a yellow oil (100 mg, 39.3%). $^1H$ NMR (500 MHz, $CDCl_3$) δ ppm 1.34-1.95 (m, 17 H), 3.92 (s, 3 H), 3.93 (s, 3 H), 4.87 (br s, 1 H), 5.66 (br s, 1 H), 6.52 (s, 1 H), 7.78-7.83 (m, 2 H). [M+H] calc'd for $C_{23}H_{30}N_6O_4$, 455; found, 455.

B. tert-Butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate A solution of methyl 6-((1R,2S)-2-(tert-butoxycarbonylamino)cyclohexylamino)-4-cyano-2-(1-methyl-1H-pyrazol-4-yl)nicotinate (110 mg, 0.242 mmol) and palladium on carbon (2.58 mg, 0.024 mmol) in MeOH (5 mL) and HOAc (1 mL) was stirred at RT overnight under $H_2$ atmosphere. After reaction, the mixture was filtered through Celite, the filtrate was evaporated, and the residue was diluted with MeOH and sat aq $NaHCO_3$. The mixture was stirred at RT for 30 min and extracted with EtOAc. The organic phase was washed with brine, dried over $MgSO_4$, and evaporated. The residue was purified by chromatography on $SiO_2$ and preparative HPLC to give the title compound (60 mg, 58.1%). $^1H$ NMR (500 MHz, $CDCl_3$) δ ppm 1.26-1.87 (m, 17 H), 3.91 (s, 3 H), 4.25

(br s, 2 H), 5.16-5.49 (m 2 H), 6.23 (br s, 1 H), 6.75 (br s, 1 H), 8.18-8.44 (m, 1 H), 8.76-9.05 (m, 1 H).

Example 26

6-((1R,2S)-2-Aminocyclohexylamino)-4-(1-methyl-1H-pyrazol-4-yl)-1H-pyrrolo[3,4-c]pyridin-3(2H)-one

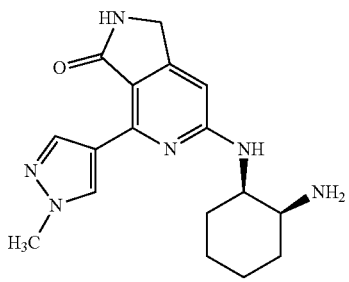 [SMILES: Cn1cc(-c2nc(N[C@@H]3CCCC[C@@H]3N)cc3c2C(=O)NC3)cn1]

A mixture of tert-butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate (94 mg, 0.22 mmol) and TFA (1 mL, 12.98 mmol) in DCM (1 mL) was stirred at RT for 2 h. The mixture was subsequently concentrated. The residue was purified by preparative HPLC (01-25; 5.45 min) and basified to give the title compound as a yellow solid (10 mg, 14%). $^1$H NMR (500 MHz, DMSO-$d_6$) δ ppm 122-1.61 (m, 8 H), 3.63 (s, 3 H), 4.19 (s, 2 H), 6.46 (br s, 1 H), 7.98 (s, 1 H), 8.29 (s, 1 H), 8.85 (s, 1 H). [M+H] calc'd for $C_{17}H_{22}N_6O$, 327; found, 327.

Preparation 11

(3R,4R)-Tetrahydro-2H-pyran-3,4-diamine

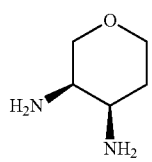

A. (3R,4S)-Tetrahydro-2H-pyran-3,4-diyl diacetate

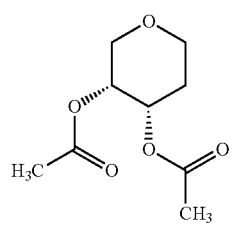

A mixture of (3R,4S)-3,4-dihydro-2H-pyran-3,4-diyl diacetate (8 g, 40 mmol) and Pd/C (10%, 5.0 g) in MeOH was stirred at RT for 12 h under H$_2$ atmosphere (50 psi). After filtration, the residue was concentrated to give the title compound, which was used without further purification (7.5 g). $^1$H NMR (400 MHz, CDCl$_3$) δ ppm 2.06 (s, 6 H), 3.95-4.03 (m, 2 H), 4.84 (t, J=4.0 Hz, 1 H), 5.15-5.20 (m, 1 H), 5.43 (t, J=4.0 Hz, 1 H), 6.49 (d, J=4.0 Hz, 1 H).

B. (3R,4S)-Tetrahydro-2H-pyran-3,4-diol

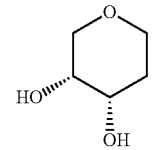

(3R,4S)-Tetrahydro-2H-pyran-3,4-diyl diacetate (7.5 g, 0.4 mmol) and sodium methylate (8.64 g, 0.16 mol) in MeOH was stirred overnight at RT. The reaction mixture was subsequently quenched with 6 N HCl in an ice bath. The mixture was concentrated to dryness. The residue was treated with EtOAc (500 mL) and vigorously stirred at 45° C. for 30 min. After filtration, the filtrate was concentrated to give the title compound, which was used without further purification (4.4 g). $^1$H NMR (400 MHz, CDCl$_3$) δ ppm 1.79-1.84 (m, 1 H), 2.00 (s, 6 H), 3.56-3.67 (m, 2 H), 3.88-3.97 (m, 2 H), 5.09-5.14 (m, 2 H).

C. (3R,4R)-3,4-Diazidotetrahydro-2H-pyran

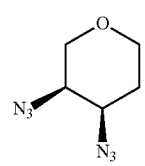 [SMILES: [N-]=[N+]=N[C@H]1COCC[C@H]1N=[N+]=[N-]]

(3R,4S)-Tetrahydro-2H-pyran-3,4-diol (5.0 g, 42.4 mmol) was dissolved in DCM (50 mL). To the mixture was added pyridine (2.5 eq), and in an ice bath, trifluoromethane-sulfonic anhydride (21.5 g, 94.3 mmol). The reaction was complete in 15 min. To the mixture was added DMF (50 mL) and hexamethylphosphoramide (1 mL), followed by sodium azide (25.0 g, 385.0 mmol). The reaction mixture was stirred at 50° C. for 3 h. DCM was removed under reduced pressure. Water was added and the mixture was extracted with EtOAc (3×30 mL). The organic layer was washed with water, dried over Na$_2$SO$_4$, and concentrated to give the title compound, which was used without further purification (1.88 g). $^1$H NMR (400 MHz, CDCl$_3$) δ ppm 1.85-1.90 (m, 1 H), 2.05-2.09 (m, 1 H), 3.54-3.60 (m, 1 H), 3.65-3.72 (m, 1 H), 3.81-3.89 (m, 1 H), 3.91-3.95 (m, 1 H).

D. (3R,4R)-Tetrahydro-2H-pyran-3,4-diamine

A mixture of (3R,4R)-3,4-diazidotetrahydro-2H-pyran (1.0 g, 5.9 mmol), di-tert-butyl pyrocarbonate (2.8 g, 12.9 mmol) and Pd/C (10%, 1.0 g) in MeOH was stirred at RT for 12 h under H$_2$ atmosphere (50 psi). After filtration, the residue was concentrated and purified by column chromatography eluting with EtOAc and petroleum ether (EtOAc/PE=1/3) to give the intermediate di-tert-butyl N,N-((3R,4R)-tetrahydro-2H-pyran-3,4-diyl)-biscarbamate (1.2 g). The intermediate was dissolved in 1 M HCl-EtOAc and stirred at RT overnight to give the title compound (400 mg, 58%). $^1$H NMR (400

MHz, CDCl$_3$) δ ppm 1.93-1.97 (m, 1 H), 2.12-2.22 (m, 1 H), 3.60-3.66 (m, 1 H), 3.76-3.79 (m, 2 H), 3.86-3.92 (m, 1 H), 4.04-4.15 (m, 1 H). [M+H] calc'd for C$_5$H$_{12}$N$_2$O, 117; found, 117.

Example 27

6-((3R,4R)-3-Aminotetrahydro-2H-pyran-4-ylamino)-4-(1-methyl-1H-pyrazol-4-yl)-1H-pyrrolo[3,4-c]pyridin-3(2H)-one

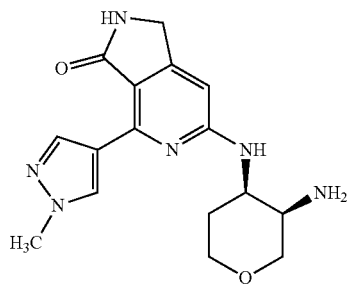 [SMILES: Cn1cc(-c2nc(N[C@@H]3CCOC[C@@H]3N)cc3c2C(=O)NC3)cn1]

A TFA salt of the title compound was prepared in a manner similar to EXAMPLE 26 using (3R,4R)-tetrahydro-2H-pyran-3,4-diamine in place of tert-butyl (1S,2R)-2-aminocyclohexylcarbamate. The desired stereoisomer was isolated using preparative HPLC. $^1$H NMR (500 MHz, DMSO-d$_6$) δ ppm 3.52 (m, 2 H), 3.78-4.01 (m & s, 10 H), 4.21-4.42 (m & s, 3 H), 6.50 (s, 1 H), 7.91 (br s, 2 H), 8.29-8.39 (m, 1 H), 8.88-8.96 (m, 1 H). [M+H] calc'd for C$_{16}$H$_{20}$N$_6$O$_2$, 329; found, 329.

Example 28

6-((1R,2S)-2-Aminocyclohexylamino)-7-fluoro-4-(1-methyl-1H-pyrazol-4-yl)-1H-pyrrolo[3,4-c]pyridin-3(2H)-one

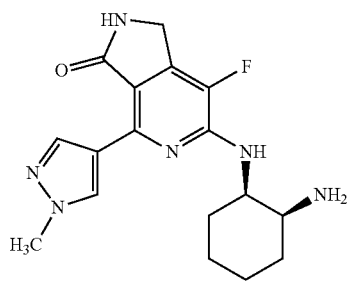 [SMILES: Cn1cc(-c2nc(N[C@@H]3CCCC[C@@H]3N)c(F)c3c2C(=O)NC3)cn1]

A. tert-Butyl (1S,2R)-2-(7-fluoro-4-(1-methyl-1H-pyrazol-4-yl)-3-oxo-2,3-dihydro-1H-pyrrolo[3,4-c]pyridin-6-ylamino)cyclohexylcarbamate

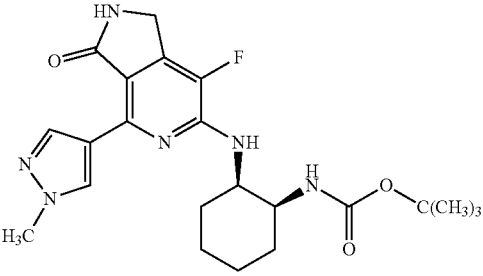 [SMILES: Cn1cc(-c2nc(N[C@@H]3CCCC[C@@H]3NC(=O)OC(C)(C)C)c(F)c3c2C(=O)NC3)cn1]

A solution of tert-butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate (150 mg, 0.352 mmol) and SELECTFLUOR® (150 mg, 0.422 mmol) in DCM (1 mL) and MeOH (1 mL) was stirred at RT overnight. Water was subsequently added and the mixture was extracted with CHCl$_3$ (3×). The organic phases were combined, washed with brine, dried over MgSO$_4$, and evaporated. The residue was purified by preparative HPLC to give the title compound (15 mg, 9.60%). [M+H] calc'd for C$_{22}$H$_{29}$FN$_6$O$_3$, 445; found, 445.

B. 6-((1R,2S)-2-Aminocyclohexylamino)-7-fluoro-4-(1-methyl-1H-pyrazol-4-yl)-1H-pyrrolo[3,4-c]pyridin-3(2H)-one A solution of tert-butyl (1S,2R)-2-(7-fluoro-4-(1-methyl-1H-pyrazol-4-yl)-3-oxo-2,3-dihydro-1H-pyrrolo[3,4-c]pyridin-6-ylamino)cyclohexylcarbamate (15 mg, 0.034 mmol) and TFA (0.5 mL, 6.49 mmol) in DCM (0.5 mL) was stirred at RT for 30 min. The reaction mixture was concentrated and the resulting residue was purified by preparative HPLC to give a TFA salt of the title compound (7 mg, 60.2%). $^1$H NMR (500 MHz, DMSO-d$_6$) δ ppm 1.37-2.01 (m, 8 H), 3.67 (br s, 1 H), 3.89 (s, 3 H), 4.32-4.43 (m, 2 H), 4.45 (br s, 1 H), 6.77 (d, J=6.35 Hz, 1 H), 7.93 (br s, 3 H), 8.30 (s, 1 H), 8.36 (s, 1 H), 8.84 (s, 1 H). [M+H] calc'd for C$_{17}$H$_{21}$FN$_6$O, 345; found, 345.

Example 29

6-((1R,2S)-2-Aminocyclohexylamino)-7-chloro-4-(1-methyl-1H-pyrazol-4-yl)-1H-pyrrolo[3,4-c]pyridin-3(2H)-one

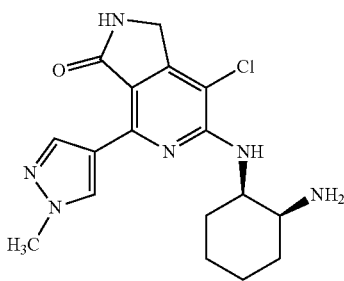

A. tert-Butyl (1S,2R)-2-(7-chloro-4-(1-methyl-1H-pyrazol-4-yl)-3-oxo-2,3-dihydro-1H-pyrrolo[3,4-c]pyridin-6-ylamino)cyclohexylcarbamate

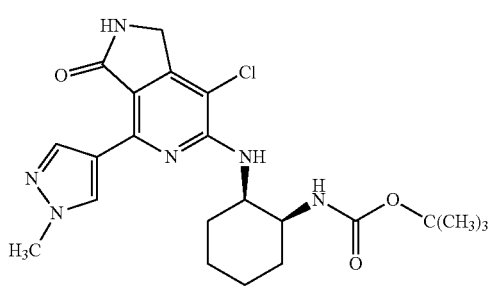 [SMILES: Cn1cc(-c2nc(N[C@@H]3CCCC[C@@H]3NC(=O)OC(C)(C)C)c(Cl)c3c2C(=O)NC3)cn1]

A solution of tert-butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate (30 mg, 0.070 mmol) and N-chlorosuccinimide (9.86 mg, 0.074 mmol) in DCM (1 mL) was stirred at RT overnight. Additional N-chlorosuccinimide (1 eq) was added and the mixture was stirred at RT for 3 h. Water and CHCl$_3$ were added to the mixture and the organic phase was washed with brine, dried over MgSO$_4$, and evaporated. The residue was purified by preparative HPLC to give the title compound (20 mg, 61.7%). $^1$H NMR (500 MHz, CDCl$_3$) δ ppm 1.18-2.09 (m, 17 H), 4.02 (s, 3 H), 4.28-4.45 (m, 2 H), 5.80 (br s, 1 H), 8.39 (br s, 1 H), 9.03 (br s, 1 H). [M+H] calc'd for C$_{22}$H$_{29}$ClN$_6$O$_3$, 461; found, 461.

B. 6-((1R,2S)-2-Aminocyclohexylamino)-7-chloro-4-(1-methyl-1H-pyrazol-4-yl)-1H-pyrrolo[3,4-c]pyridin-3(2H)-one A solution of tert-butyl (1S,2R)-2-(7-chloro-4-(1-methyl-1H-pyrazol-4-yl)-3-oxo-2,3-dihydro-1H-pyrrolo[3,4-c]pyridin-6-ylamino)cyclohexylcarbamate (10.00 mg, 0.022 mmol) in HCl (0.5 mL, 16.46 mmol) and HOAc (1 mL) was stirred at RT for 30 min. The reaction mixture was concentrated and the resulting residue was washed with IPE to give the HCl salt of the title compound (5 mg, 63.9%). $^1$H NMR (500 MHz, DMSO-d$_6$) δ ppm 1.48-1.97 (m, 8 H), 3.72-3.78 (m, 1 H), 3.96 (br s, 3 H), 4.35 (d, J=4.88 Hz, 2 H), 4.57 (br s, 1 H), 6.29 (d, J=6.83 Hz, 1 H), 7.93 (br s, 2 H), 8.40-8.45 (m, 1 H), 8.49 (s, 1 H), 8.98 (s, 1 H). [M+H] calc'd for C$_{17}$H$_{21}$ClN$_6$O, 361; found, 361.

Preparation 12

4,6-Dichloro-2-(2,4-dimethoxybenzyl)-7-fluoro-1H-pyrrolo[3,4-c]pyridin-3(2H)-one

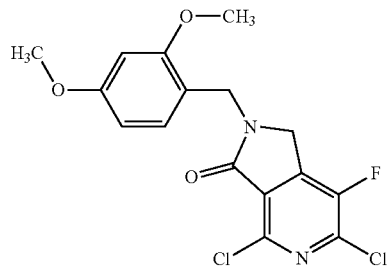 [SMILES: COc1ccc(CN2Cc3c(F)c(Cl)nc(Cl)c3C2=O)c(OC)c1]

A. 4,6-Dichloro-7-fluoro-1-hydroxyfuro[3,4-c]pyridin-3(1H)-one

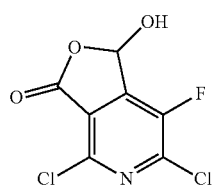 [SMILES: O=C1OC(O)c2c(F)c(Cl)nc(Cl)c21]

To a butyllithium-hexane solution (100 mL, 160 mmol) in THF (200 mL) was slowly added diisopropylamine (27.4 mL, 192 mmol) in THF (15 mL) at −78° C. The mixture was stirred at the same temperature for 15 min. A solution of 2,6-dichloro-5-fluoronicotinic acid (14.98 g, 71.4 mmol) in THF (15 mL) was added and the mixture was stirred for 2 h. Next, DMF (29.3 mL, 378 mmol) was added and the mixture was stirred for 1 h. Hydrochloric acid (1N, 400 mL) was added and the mixture was subsequently extracted with EtOAc (2×300 mL). The organic phase was basified with saturated aq NaHCO$_3$ solution and the aqueous phase was separated. The aqueous phase was re-acidified with 1N HCl (300 mL) and extracted with EtOAc (2×300 mL). The organic phase was washed with H$_2$O (200 mL) and brine (200 mL), dried over MgSO$_4$, and evaporated. The residue was washed with Hexane/EtOAc (1/8) to give the title compound as a white solid (11.5 g, 67.7%). $^1$H NMR (500 MHz, DMSO-d$_6$) δ ppm 6.85 (br s, 1 H), 8.82 (br s, 1 H).

B. 4,6-Dichloro-2-(2,4-dimethoxybenzyl)-7-fluoro-1H-pyrrolo[3,4-c]pyridin-3(2H)-one A mixture of 4,6-dichloro-7-fluoro-1-hydroxyfuro[3,4-c]pyridin-3(1H)-one (25.8 g, 108 mmol) and (2,4-dimethoxyphenyl)methanamine (34.2 mL, 228 mmol) in MeOH (400 mL) was stirred at RT for 2 h. Sodium triacetoxyhydroborate (22.98 g, 108 mmol) was added to the mixture, which was stirred at RT for 2 h. Next, HCl (2N, 120 mL) was added and the resulting solid (17.3 g) was isolated by filtration. A mixture of the solid, N1-((ethylimino)methylene)-N3,N3-dimethylpropane-1,3-diamine hydrochloride (10.35 g, 54 mmol)

and 1H-benzo[d][1,2,3]triazol-1-ol hydrate (8.27 g, 54 mmol) in DMF (200 mL) was stirred at room temperature for 2 h. Next, water was added and the mixture was extracted with EtOAc (2×300 mL). The organic phases were combined, washed with saturated aq NaHCO$_3$ solution (300 mL), H$_2$O (300 mL), and brine (300 mL), dried over anhydrous Na$_2$SO$_4$, and filtered. The filtrate was concentrated under reduced pressure and the residue was washed with EtOAc to give the title compound as a pale yellow solid (6.7 g, 16.7%). [M+H] calc'd for C$_{16}$H$_{13}$Cl$_2$FN$_2$O$_3$, 371; found, 371.

Preparation 13 tert-Butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate

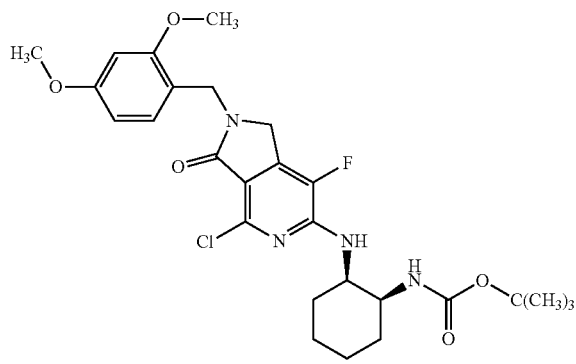 [SMILES: COc1ccc(CN2Cc3c(F)c(N[C@@H]4CCCC[C@@H]4NC(=O)OC(C)(C)C)nc(Cl)c3C2=O)c(OC)c1]

A mixture of 4,6-dichloro-2-(2,4-dimethoxybenzyl)-7-fluoro-1H-pyrrolo[3,4-c]pyridin-3(2H)-one (4.8 g, 12.93 mmol) and tert-butyl (1S,2R)-2-aminocyclohexylcarbamate (4.16 g, 19.40 mmol) and diisopropylethylamine (3.39 mL, 19.40 mmol) in ACN (20 mL) was stirred at 100° C. for 3 days. Water and EtOAc were added and the aqueous phase was extracted with EtOAc. The organic phases were combined, washed with brine, dried over MgSO$_4$, and evaporated. The residue was purified by chromatography on SiO$_2$ (Hexane/EtOAc=1/1) to give the title compound as a brown amorphous solid (3.31 g, 46.6%). $^1$H NMR (500 MHz, CDCl$_3$) δ ppm 1.35-2.02 (m, 17 H), 3.80 (s, 3 H), 3.84 (s, 3 H), 4.01 (br s, 1 H), 4.20 (s, 2H), 4.23 (br s, 1 H), 4.66 (s, 2 H), 4.91 (br s, 1 H), 6.40-6.52 (m, 2 H), 7.20-7.28 (m, 1 H). [M+H] calc'd for C$_{27}$H$_{34}$ClFN$_4$O$_5$, 549; found, 549.

Example 30

6-((1R,2S)-2-Aminocyclohexylamino)-7-fluoro-4-(1-methyl-1H-pyrazol-4-yl)-1H-pyrrolo[3,4-c]pyridin-3(2H)-one (HCl salt)

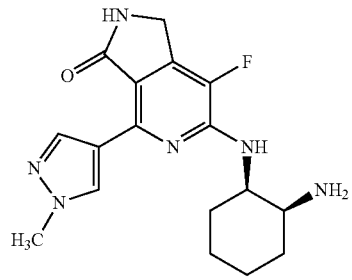 [SMILES: Cn1cc(-c2nc(N[C@@H]3CCCC[C@@H]3N)c(F)c3c2C(=O)NC3)cn1]

A. tert-Butyl (1S,2R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate

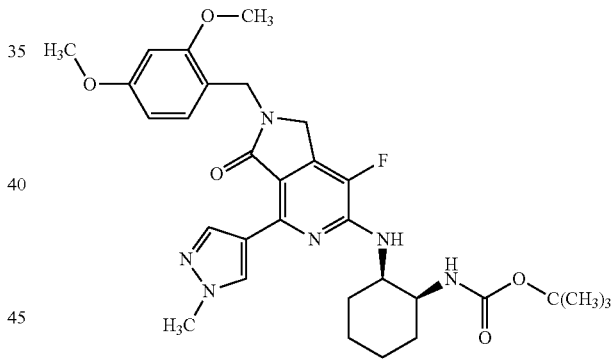

A mixture of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (200 mg, 0.364 mmol), sodium carbonate (77 mg, 0.729 mmol), 1-methyl-4-(4,4,5,5-tetramethyl-1,3,2-dioxaborolan-2-yl)-1H-pyrazole (91 mg, 0.437 mmol) and bis(triphenylphosphine)palladium chloride (25.6 mg, 0.036 mmol) in DME (2 mL) and H$_2$O (0.667 mL) was stirred at 85° C. for 2 h. To the resulting mixture was added EtOAc. The aqueous phase was extracted with EtOAc. The organic phases were combined, washed with brine, dried over MgSO$_4$, and evaporated. The residue was purified by chromatography on SiO$_2$(Hexane/EtOAc=2/3) to give the title compound as a yellow oil (88 mg, 40.6%). $^1$H NMR (500 MHz, CDCl$_3$) δ ppm 1.28-2.01 (m, 17 H), 3.80 (d, J=2.93 Hz, 3 H), 3.85 (s, 3 H), 3.91-4.01 (m, 4 H), 4.23 (br s, 2 H), 4.41 (br s, 1 H), 4.68 (d, J=1.95 Hz, 2 H), 5.36 (br s, 1 H), 6.36-6.54 (m, 2 H), 7.15-7.21 (m, 1 H), 8.26 (br s, 1 H), 9.02 (br s, 1 H). [M+H] calc'd for C$_{31}$H$_{39}$FN$_6$O$_5$, 595; found, 595.

B. 6-((1R,2S)-2-Aminocyclohexylamino)-7-fluoro-4-(1-methyl-1H-pyrazol-4-yl)-1H-pyrrolo[3,4-c]pyridin-3(2H)-one A solution of tert-butyl (1S,2R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate (2.4 g, 4.04 mmol) and TFA (5 mL, 64.9 mmol) was stirred at 80° C. for 30 min. The resulting suspension was diluted with EtOAc (5 mL) and filtered. The filtrate was evaporated in vacuo. The residue was diluted with $H_2O$ (300 mL) and EtOAc (100 mL) and filtered. The precipitate was washed with EtOAc and dried to give the title compound as a TFA salt (900 mg). The filtrate was extracted with EtOAc (200 mL). The aqueous phase was neutralized with saturated aq $NaHCO_3$ solution and extracted with EtOAc (2×400 mL) and THF (2×200 mL). The organic phases were combined, dried over $MgSO_4$, and evaporated. The residue was washed with EtOAc to give a first crop (400 mg) of the title compound as the free base. The TFA salt obtained above was diluted with saturated aq $NaHCO_3$ solution (20 mL) and stirred at RT overnight. The resulting suspension was filtered and the solids were washed with EtOAc to give a second crop (700 mg) of the title compound as the free base (1.1 g, 79%).

C. 6-((1R,2S)-2-Aminocyclohexylamino)-7-fluoro-4-(1-methyl-1H-pyrazol-4-yl)-1H-pyrrolo[3,4-c]pyridin-3(2H)-one (HCl salt)

To a solution of 6-((1R,2S)-2-aminocyclohexylamino)-7-fluoro-4-(1-methyl-1H-pyrazol-4-yl)-1H-pyrrolo[3,4-c]pyridin-3(2H)-one (2.300 g, 6.68 mmol) in THF (300 mL) was added 1N HCl in EtOAc (20 mL, 20.0 mmol) dropwise and the mixture was stirred at room temperature for 30 min. The resulting suspension was filtered and the precipitate was collected and washed with EtOAc (10 mL) to afford crude HCl salt of the title compound (2.55 g). The crude compound was recrystallized from EtOH (60 mL) and $H_2O$ (16 mL) to give the HCl salt of the title compound as a white solid (1.5 g, 59.0%). $^1$H NMR (500 MHz, DMSO-$d_6$) δ ppm 1.34-1.99 (m, 8 H), 3.67 (br s, 3 H), 3.89 (br s, 3 H), 4.32-4.43 (m, 2 H), 4.45 (br s, 1 H), 6.76 (d, J=5.86 Hz, 1 H), 7.88 (br s, 3 H), 8.29 (d, J=4.88 Hz, 1 H), 8.36 (s, 1 H), 8.84 (s, 1 H). [M+H] calc'd for $C_{17}H_{21}FN_6O$, 345; found, 345.

Example 31

6-((1R,2S)-2-Aminocyclohexylamino)-7-fluoro-4-(pyrazolo[1,5-a]pyridin-3-yl)-1H-pyrrolo[3,4-c]pyridin-3(2H)-one

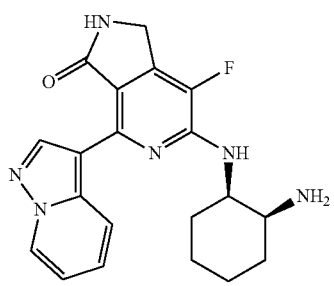 [SMILES: N[C@H]1CCCC[C@H]1Nc1nc(-c2cnn3ccccc23)c2c(c1F)CNC2=O]

A. tert-butyl (1S,2R)-2-(2-(2,4-dimethoxybenzyl)-7-fluoro-3-oxo-4-(pyrazolo[1,5-a]pyridin-3-yl)-2,3-dihydro-1H-pyrrolo[3,4-c]pyridin-6-ylamino)cyclohexylcarbamate

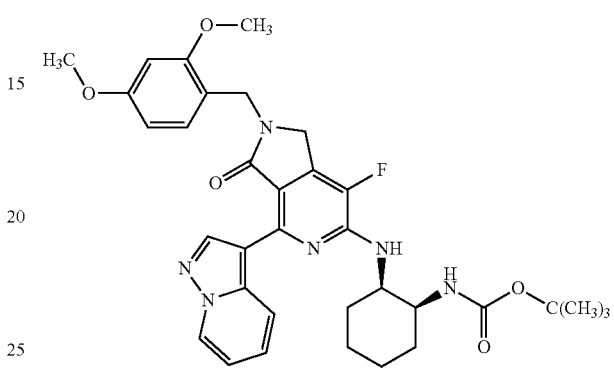

A mixture of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (100 mg, 0.182 mmol), 3-(4,4,5,5-tetramethyl-1,3,2-dioxaborolan-2-yl)pyrazolo[1,5-a]pyridine (53.4 mg, 0.219 mmol), sodium carbonate (48.3 mg, 0.455 mmol) and tetrakis(triphenylphosphine)palladium (21.05 mg, 0.018 mmol) in DME (1 mL) and $H_2O$ (0.333 mL) was stirred at 85° C. for 3 h. Following reaction, the mixture was filtered and the filtrate was diluted with EtOAc and $H_2O$. The aqueous phase was extracted with EtOAc. The organic phases were combined, washed with brine, dried over $MgSO_4$, and evaporated. The residue was purified by chromatography on $SiO_2$ to give the title compound (53 mg, 46.1%). $^1$H NMR (500 MHz, CDCl$_3$) δ ppm 1.17-2.03 (m, 17 H), 3.74-3.81 (m, 3 H), 3.84-3.89 (m, 3 H), 4.04 (br s, 1 H), 4.26 (br s, 2 H), 4.46 (br s, 1 H), 4.71 (br s, 2 H), 6.36-6.55 (m, 2 H), 6.83 (d, J=5.86 Hz, 1 H), 7.18-7.31 (m, 2 H), 8.42 (br s, 1 H), 8.47-8.57 (m, 1 H), 9.42 (br s, 1 H).

B. 6-((1R,2S)-2-Aminocyclohexylamino)-7-fluoro-4-(pyrazolo[1,5-a]pyridin-3-yl)-1H-pyrrolo[3,4-c]pyridin-3(2H)-one A mixture of tert-butyl (1S,2R)-2-(2-(2,4-dimethoxybenzyl)-7-fluoro-3-oxo-4-(pyrazolo[1,5-a]pyridin-3-yl)-2,3-dihydro-1H-pyrrolo[3,4-c]pyridin-6-ylamino)cyclohexylcarbamate (52 mg, 0.082 mmol) and TFA (1 mL, 12.98 mmol) was stirred at 65° C. for 30 min. The mixture was concentrated and the residue was purified by preparative HPLC to give the title compound as a white solid (15 mg, 47.8%). $^1$H NMR (500 MHz, DMSO-$d_6$) δ ppm 1.21-2.07 (m, 8 H), 3.31 (br s, 1 H), 4.18-4.26 (m, 1 H), 4.46 (br s, 2 H), 6.61 (br s, 1 H), 7.09 (d, J=6.35 Hz, 1 H), 7.49 (d, J=7.32, 1 H), 8.36 (br s, 1 H), 8.59 (d, J=7.81 Hz, 1 H), 8.83 (d, J=6.83 Hz, 1 H), 9.56 (br s, 1 H). [M+H] calc'd for $C_{20}H_{21}FN_6O$, 381; found, 381.

Example 32

2-(2-(Aminomethyl)piperidin-1-yl)-4-(m-tolylamino)-6,7-dihydro-5H-pyrrolo[3,4-d]pyrimidin-5-one

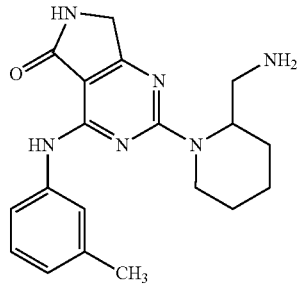 [SMILES: Cc1cccc(Nc2nc(N3CCCCC3CN)nc3c2C(=O)NC3)c1]

A. Methyl 2-(2-((tert-butoxycarbonylamino)methyl) piperidin-1-yl)-4-chloro-6-(m-tolylamino)pyrimidine-5-carboxylate

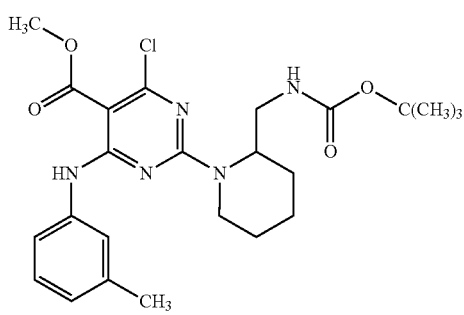 [SMILES: COC(=O)c1c(Cl)nc(N2CCCCC2CNC(=O)OC(C)(C)C)nc1Nc1cccc(C)c1]

A mixture of methyl 2,4-dichloro-6-(m-tolylamino)pyrimidine-5-carboxylate (600.6 mg, 1.924 mmol), tert-butyl piperidin-2-ylmethylcarbamate (500.9 mg, 2.337 mmol) and N-ethyl-N-isopropylpropan-2-amine (0.4 mL, 2.296 mmol) in DMF (10 mL) was stirred at 0° C. for 3 h. Water (50 mL) was added to the mixture, which was extracted with EtOAc (2×40 mL). The organic layers were washed with saturated aq NaHCO₃ (20 mL), water (20 mL) and brine (20 mL), were dried over anhydrous Na₂SO₄, and then filtered (DM1020). The filtrate was concentrated under reduced pressure and the residue was purified by column chromatography (SiO₂, hexanes/EtOAc=4/1) to give the title compound as a clear oil (310.5 mg). ¹H NMR (500 MHz, CDCl₃) δ ppm 1.34-1.74 (m, 15H), 2.35-2.37 (m, 3H), 3.03-3.21 (m, 2H), 3.60-3.71 (m, 1H), 3.90 (s, 3H), 4.43-5.04 (m, 3H), 6.94-6.98 (m, 1H), 7.23-7.46 (m, 3H), 10.13-10.43 (m, 1H). [M+H] calc'd for $C_{24}H_{33}ClN_5O_4$, 490; found, 490.

B. Methyl 2-(2-((tert-butoxycarbonylamino)methyl) piperidin-1-yl)-4-cyano-6-(m-tolylamino)pyrimidine-5-carboxylate

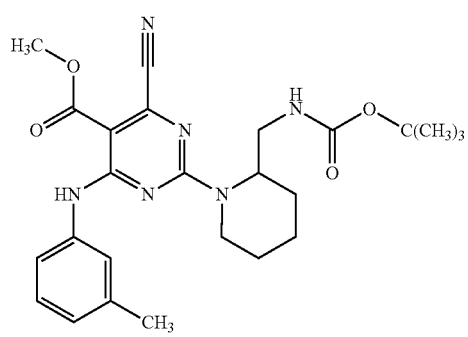 [SMILES: COC(=O)c1c(C#N)nc(N2CCCCC2CNC(=O)OC(C)(C)C)nc1Nc1cccc(C)c1]

A mixture of methyl 2-(2-((tert-butoxycarbonylamino)methyl)piperidin-1-yl)-4-chloro-6-(m-tolylamino)pyrimidine-5-carboxylate (399.7 mg, 0.816 mmol), tetrakis(triphenylphosphine)palladium(0) (96.3 mg, 0.083 mmol), and zinc cyanide (53.2 mg, 0.453 mmol) in DMF (5 mL) was stirred at 120° C. for 1 h under microwave irradiation. Water (50 mL) was added and the mixture was extracted with EtOAc (2×100 mL). The organic layers were washed with saturated aq NaHCO₃ (50 mL), water (50 mL), and brine (50 mL), were dried over anhydrous Na₂SO₄, and then filtered (DM1020). The filtrate was concentrated under reduced pressure and was purified by column chromatography (SiO₂, hexanes/EtOAc=4/1) to give the title compound as a colorless oil (315.0 mg, 80%). ¹H NMR (500 MHz, CDCl₃) δ ppm 1.34-1.77 (m, 15H), 2.36-2.39 (m, 3H), 3.00-3.21 (m, 2H), 3.49-3.69 (m, 1H), 3.97 (s, 3H), 4.49-5.10 (m, 3H), 6.96-7.02 (m, 1H), 7.24-7.41 (m, 3H), 10.14-10.45 (m, 1H). [M+H] calc'd for $C_{25}H_{33}N_6O_4$, 481; found, 481.

C. tert-Butyl (1-(5-oxo-4-(m-tolylamino)-6,7-dihydro-5H-pyrrolo[3,4-d]pyrimidin-2-yl)piperidin-2-yl) methylcarbamate

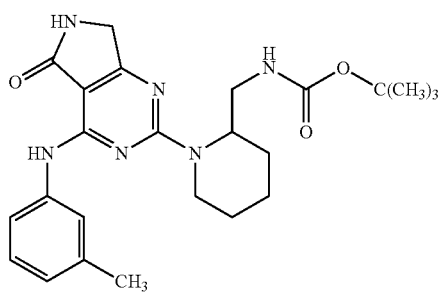 [SMILES: Cc1cccc(Nc2nc(N3CCCCC3CNC(=O)OC(C)(C)C)nc3c2C(=O)NC3)c1]

A mixture of methyl 2-(2-((tert-butoxycarbonylamino)methyl)piperidin-1-yl)-4-cyano-6-(m-tolylamino)pyrimidine-5-carboxylate (310.1 mg, 0.645 mmol), palladium on carbon (72.4 mg, 0.680 mmol) in EtOH (8 mL), and 1N HCl (4 mL) was stirred at RT for 16 h. The mixture was filtered to remove the catalyst. The filtrate was treated with saturated aq NaHCO$_3$ (20 mL) for 3 h. The mixture was concentrated under reduced pressure and the residue was extracted with EtOAc (2×40 mL). The organic layers were washed with saturated aq NaHCO$_3$ (20 mL), water (20 mL), and brine (20 mL), were dried over anhydrous Na$_2$SO$_4$, and then filtered through SiO$_2$. The filtrate was concentrated under reduced pressure to give the title compound as a colorless solid (213.4 mg, 73%). $^1$H-NMR (DMSO-d$_6$) δ ppm 1.28 (s, 9H), 1.35 (br s, 1H), 1.49-1.56 (m, 2H), 1.67-1.69 (m, 3H), 2.31 (s, 3H), 3.06 (br s, 1H), 3.24 (br s, 2H), 4.16 (s, 2H), 4.67 (br s, 1H), 5.08 (br s, 1H), 6.77 (br s, 1H), 6.87 (d, 1H, J=7.0 Hz), 7.23-7.25 (m, 1H), 7.53 (br s, 2h), 8.07 (s, 1H), 8.55 (s, 1H). [M+H] calc'd for C$_{24}$H$_{33}$N$_6$O$_3$, 453; found, 453.5.

D. 2-(2-(Aminomethyl)piperidin-1-yl)-4-(m-tolylamino)-6,7-dihydro-5H-pyrrolo[3,4-d]pyrimidin-5-one To a solution of tert-butyl (1-(5-oxo-4-(m-tolylamino)-6,7-dihydro-5H-pyrrolo[3,4-d]pyrimidin-2-yl)piperidin-2-yl)methylcarbamate (207.1 mg, 0.458 mmol) in HOAc (3 mL) was added HCl (1 mL, 32.9 mmol). The mixture was stirred at RT for 1 h and then concentrated under reduced pressure. The residue was treated with saturated aq NaHCO$_3$ (50 mL) and was extracted with EtOAc-THF (1/1, 2×40 mL). The organic layers were washed with saturated aq NaHCO3 (20 mL), water (20 mL), and brine (20 mL), were dried over anhydrous Na$_2$SO$_4$, and then filtered. The filtrate was concentrated under reduced pressure and the residue was washed with EtOH to give the title compound as a pale yellow solid (27.4 mg, 17%). $^1$H-NMR (DMSO-d$_6$) δ ppm 1.32-1.70 (m, 7H), 1.89-1.92 (m, 1H), 2.31 (s, 3H), 2.74-2.87 (m, 1H), 2.81-2.85 (m, 1H), 2.94 (br s, 1H), 4.17 (s, 2H), 4.68-4.79 (m, 2H), 6.88 (d, 1H, J=7.5 Hz), 7.22-7.25 (m, 1H), 7.49-7.50 (m, 1H), 7.60 (s, 1H), 8.06 (s, 1H), 8.58 (s, 1H). [M+H] calc'd for C$_{19}$H$_{25}$N$_6$O, 353; found, 353.5.

Preparation 14

Methyl 6-chloro-4-cyano-2-(3-(methylsulfonyl)phenylamino)nicotinate

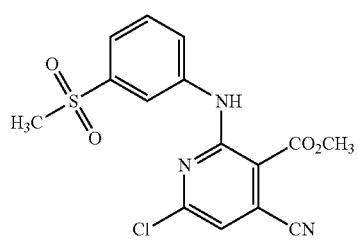 [SMILES: COC(=O)c1c(C#N)cc(Cl)nc1Nc1cccc(S(C)(=O)=O)c1]

A. Methyl 6-chloro-4-cyano-2-(3-(methylthio)phenylamino)nicotinate

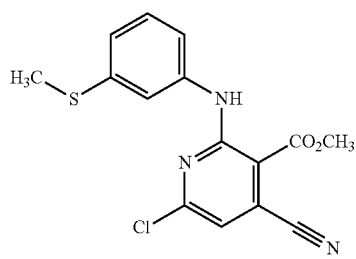 [SMILES: COC(=O)c1c(C#N)cc(Cl)nc1Nc1cccc(SC)c1]

A mixture of methyl 2,6-dichloro-4-cyanonicotinate (340.8 mg, 1.475 mmol), DIPEA (0.3 mL, 1.718 mmol) and 3-(methylthio)aniline (234.8 mg, 1.687 mmol) in CH$_3$CN (5 mL) was stirred at 60° C. for 2 days. After the mixture was cooled, saturated aq NaHCO$_3$ (30 mL) was added and the mixture was extracted with EtOAc (2×30 mL). The organic layers were washed with saturated aq NaHCO$_3$ (20 mL), water (20 mL) and brine (20 mL), were dried over anhydrous Na$_2$SO$_4$, and then filtered through SiO$_2$. The filtrate was concentrated under reduced pressure and the residue was washed with IPE and filtered to give the title compound as a yellow solid (157.8 mg). The filtrate was purified by column chromatography (SiO$_2$, hexanes/EtOAc=8/1) to give another crop (135.5 mg) of the title compound as a yellow oil of (total 293 mg, 60%). $^1$H-NMR (CDCl$_3$) δ ppm 2.52 (s, 3H), 4.05 (s, 3H), 7.00 (s, 1H), 7.03-7.05 (m, 1H), 7.25-7.32 (m, 2H), 7.66-7.67 (m, 1H), 10.51 (br s, 1H). [M+H] calc'd for C$_{15}$H$_{13}$ClN$_3$O$_2$S, 334; found, 334.

B. Methyl 6-chloro-4-cyano-2-(3-(methylsulfonyl)phenylamino)nicotinate

To a solution of methyl 6-chloro-4-cyano-2-(3-(methylthio)phenylamino)nicotinate (291.1 mg, 0.872 mmol) in DMF (10 mL) was added m-chloroperoxybenzoic acid (538.9 mg, 2.405 mmol) at 0° C. The mixture was stirred at RT for 16 h. Aqueous Na$_2$S$_2$O$_3$ (30 mL) was added and the mixture was extracted with EtOAc (2×30 mL). The organic layers were washed with saturated aq NaHCO$_3$ (20 mL), water (20 mL) and brine (20 mL), were dried over anhydrous Na$_2$SO$_4$, and then filtered (DM1020). The filtrate was concentrated under reduced pressure and the residue was washed with IPE to give the title compound as a yellow solid (158.2 mg, 50%). $^1$H-NMR (CDCl$_3$) δ ppm 3.11 (s, 3H), 4.07 (s, 3H), 7.10 (s, 1H), 7.57-7.60 (m, 1H), 7.70-7.72 (m, 1H), 7.91-7.93 (m, 1H), 8.25-8.26 (m, 1H), 10.73 (s, 1H).

Example 33

6-((1R,2S)-2-Aminocyclohexylamino)-4-(3-(methylsulfonyl)phenylamino)-1H-pyrrolo[3,4-c]pyridin-3(2H)-one

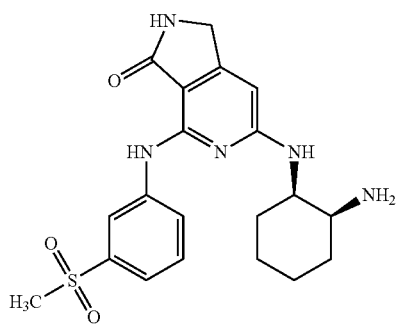 [SMILES: CS(=O)(=O)c1cccc(Nc2nc(N[C@@H]3CCCC[C@@H]3N)cc3c2C(=O)NC3)c1]

A. Methyl 6-((1R,2S)-2-(tert-butoxycarbonylamino)cyclohexylamino)-4-cyano-2-(3-(methylsulfonyl)phenylamino)nicotinate

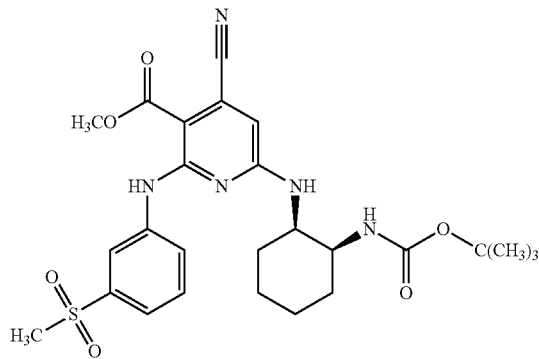 [SMILES: COC(=O)c1c(C#N)cc(N[C@@H]2CCCC[C@@H]2NC(=O)OC(C)(C)C)nc1Nc1cccc(S(C)(=O)=O)c1]

A mixture of methyl 6-chloro-4-cyano-2-(3-(methylsulfonyl)phenylamino)nicotinate (162.8 mg, 0.445 mmol), tert-butyl (1S,2R)-2-aminocyclohexylcarbamate (111.6 mg, 0.521 mmol) and Et₃N (0.1 mL, 0.717 mmol) in THF (6 mL) and DMF (6.00 mL) was stirred at 60° C. for 12 h. After the mixture was cooled, saturated aq NaHCO₃ (30 mL) was added and the mixture was extracted with EtOAc (2×30 mL). The organic layers were washed with saturated aq NaHCO₃ (15 mL), water (15 mL) and brine (15 mL), were dried over anhydrous Na₂SO₄, and filtered through SiO₂. The filtrate was concentrated under reduced pressure and the residue was washed with IPE to give the title compound as a yellow solid (182.2 mg, 75%). ¹H-NMR (CDCl₃) δ ppm 1.42-1.67 (m, 15H), 1.84-1.91 (m, 2H), 3.07 (s, 3H), 3.95-3.97 (m, 4H), 4.16-4.17 (m, 1H), 4.77 (s, 1H), 6.24 (s, 1H), 7.48-7.51 (m, 1H), 7.58-7.61 (m, 1H), 7.77-7.78 (m, 1H), 8.41 (s, 1H), 10.99 (s, 1H), 1H not detected.

B. Methyl 6-((1R,2S)-2-aminocyclohexylamino)-4-cyano-2-(3-(methylsulfonyl)phenylamino)nicotinate

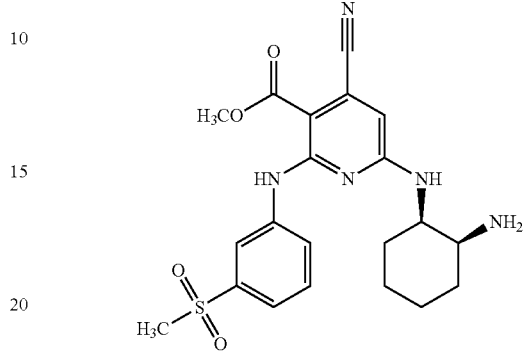

To a solution of methyl 6-((1R,2S)-2-(tert-butoxycarbonylamino)cyclohexylamino)-4-cyano-2-(3-(methylsulfonyl)phenylamino)nicotinate (178.3 mg, 0.328 mmol) in HOAc (4 mL) was added HCl (4 mL, 132 mmol). The mixture was stirred at RT for 4 h and then concentrated under reduced pressure. Water (15 mL) and 1M HCl (15 mL) were added to the concentrate and the aqueous layer was washed with EtOAc (10 mL). The washed aqueous layer was basified with saturated aqueous NaHCO₃ (50 mL) and extracted with EtOAc (2×30 mL). The organic layers were combined, washed with saturated aq NaHCO₃ (20 mL), water (20 mL) and brine (20 mL), dried over anhydrous Na₂SO₄, and filtered. The filtrate was concentrated under reduced pressure to give the title compound as a brown solid (123.2 mg, 85%). ¹H-NMR (CDCl₃) δ ppm 1.45-16.4 (m, 6H), 1.77-1.79 (m, 4H), 3.06 (s, 3H), 3.17-3.18 (m, 1H), 3.94 (s, 3H), 4.10-4.14 (m, 1H), 6.03-6.05 (m, 1H), 6.29 (s, 1H), 7.48-7.51 (m, 1H), 7.58-7.60 (m, 1H), 7.71-7.72 (m, 1H), 8.53 (s, 1H), 11.01 (s, 1H).

C. 6-((1R,2S)-2-Aminocyclohexylamino)-4-(3-(methylsulfonyl)phenylamino)-1H-pyrrolo[3,4-c]pyridin-3(2H)-one A mixture of methyl 6-((1R,2S)-2-aminocyclohexylamino)-4-cyano-2-(3-(methylsulfonyl)phenylamino)nicotinate (117.3 mg, 0.264 mmol) and palladium on carbon (23.6 mg, 0.222 mmol) in MeOH (4 mL) and 1N HCl (4 mL) was stirred at RT for 16 h under a hydrogen atmosphere. The mixture was filtered to remove the catalyst and the filtrate was treated with saturated aq NaHCO₃ (20 mL) and stirred at RT for 20 h. The mixture was concentrated under reduced pressure and the residue was extracted with EtOAc/THF (2/1, 2×30 mL). The organic layers were washed with saturated aq NaHCO₃ (15 mL), water (15 mL) and brine (15 mL), were dried over anhydrous Na₂SO₄, and then filtered. The filtrate was concentrated under reduced pressure and the residue was purified by column chromatography (DM1020, EtOAc/MeOH=20/1) to give the desired product (37.2 mg, 34%). The product was recrystallized from EtOH to give the title compound as a colorless solid (13.2 mg, 12%). ¹H-NMR (DMSO-d₆) δ ppm 1.31-1.41 (m, 4H), 1.55-1.68 (m, 6H), 3.05 (s, 1H), 3.21 (s, 3H), 4.08 (s, 1H), 4.23 (s, 2H), 6.17 (s, 1H), 6.78-6.79

(m, 1H), 7.46-7.47 (m, 1H), 7.53-7.56 (m, 1H), 7.96-7.99 (m, 2H), 8.49 (s, 1H), 9.18 (s, 1H).

Example 34

6-((1R,2S)-2-Aminocyclopentylamino)-4-(3-(methylsulfonyl)phenylamino)-1H-pyrrolo[3,4-c]pyridin-3(2H)-one (HCl salt)

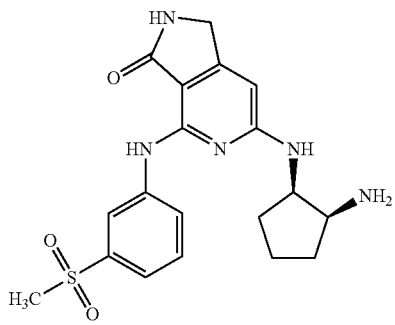 [SMILES: CS(=O)(=O)c1cccc(Nc2nc(N[C@@H]3CCC[C@@H]3N)cc3c2C(=O)NC3)c1]

A. Methyl 6-((1R,2S)-2-(tert-butoxycarbonylamino)cyclopentylamino)-4-cyano-2-(3-(methylsulfonyl)phenylamino)nicotinate

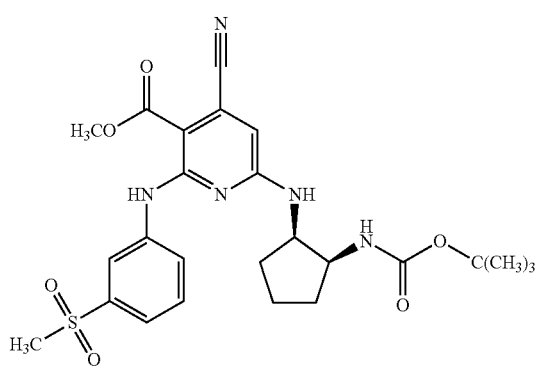 [SMILES: COC(=O)c1c(C#N)cc(N[C@@H]2CCC[C@@H]2NC(=O)OC(C)(C)C)nc1Nc1cccc(S(C)(=O)=O)c1]

A mixture of methyl 6-chloro-4-cyano-2-(3-(methylsulfonyl)phenylamino)nicotinate (165.0 mg, 0.451 mmol), Et₃N (0.15 mL, 1.076 mmol), and tert-butyl (1S,2R)-2-aminocyclopentylcarbamate (142.0 mg, 0.709 mmol) in DMF (6 mL) was stirred at 60° C. for 12 h. Saturated aq NaHCO₃ (20 mL) was added to the mixture, which was subsequently extracted with EtOAc (2×30 mL). The organic layers were washed with saturated aq NaHCO₃ (20 mL), water (20 mL) and brine (20 mL), were dried over anhydrous Na₂SO₄, and filtered (DM1020). The filtrate was concentrated under reduced pressure. The residue was purified by column chromatography (SiO₂, hexanes/EtOAc=1/1) and then triturated with IPE to provide the title compound (147 mg).

B. tert-Butyl (1S,2R)-2-(4-(3-(methylsulfonyl)phenylamino)-3-oxo-2,3-dihydro-1H-pyrrolo[3,4-c]pyridin-6-ylamino)cyclopentylcarbamate

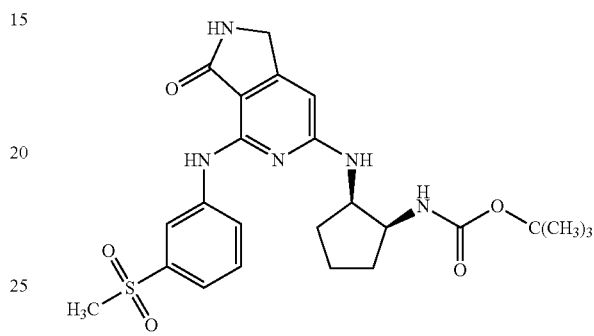

A mixture of methyl 6-((1R,2S)-2-(tert-butoxycarbonylamino)cyclopentylamino)-4-cyano-2-(3-(methylsulfonyl)phenylamino)nicotinate (141.1 mg, 0.266 mmol) and palladium hydroxide on carbon (43.2 mg, 0.308 mmol) in MeOH (10 mL) and HOAc (10 mL) was stirred at RT for 12 h under a hydrogen atmosphere. The mixture was filtered to remove the catalyst and the filtrate was concentrated under reduced pressure. The residue was treated with saturated aq NaHCO₃ (20 mL) and MeOH (20 mL). The mixture was stirred at RT for 6 h and then concentrated under reduced pressure. The residue was treated with saturated aq NaHCO₃ (30 mL) and extracted with EtOAc (2×50 mL). The organic layers were washed with saturated aq NaHCO₃ (20 mL), water (20 mL) and brine (20 mL), were dried over anhydrous Na₂SO₄, and filtered. The filtrate was concentrated under reduced pressure and the residue was purified by column chromatography (DM1020, EtOAc) to give the desired product (46.5 mg). The product was washed with IPE/EtOAc to give the title compound as a pale brown solid (34.7 mg, 26%).

C. 6-((1R,2S)-2-Aminocyclopentylamino)-4-(3-(methylsulfonyl)phenylamino)-1H-pyrrolo[3,4-c]pyridin-3(2H)-one (HCl salt)

A mixture of tert-butyl (1S,2R)-2-(4-(3-(methylsulfonyl)phenylamino)-3-oxo-2,3-dihydro-1H-pyrrolo[3,4-c]pyridin-6-ylamino)cyclopentylcarbamate (16.5 mg, 0.329 mmol) and HCl (1 mL, 32.9 mmol) in HOAc (2 mL) was stirred at RT for 3 h. The mixture was concentrated under reduced pressure and the residue was recrystallized from EtOH—H₂O to give the title compound (9.6 mg, 67%). ¹H-NMR (DMSO-d₆) δ ppm 1.63-1.79 (m, 4H), 20.3-2.06 (m, 1H), 2.19-2.20 (m, 1H), 3.32 (s, 3H), 3.74 (br s, 1H), 4.23-4.28 (m, 2H), 4.45 (br s, 1H), 6.22 (s, 1H), 7.34-7.35 (m, 1H), 7.51-7.58 (m, 3H), 7.73 (br s, 3H), 8.13 (s, 1H), 8.82 (s, 1H), 9.26 (s, 1H).

Example 35

(R)-4-Methyl-2-(4-(3-(methylsulfonyl)phenylamino)-3-oxo-2,3-dihydro-1H-pyrrolo[3,4-c]pyridin-6-ylamino)pentanamide

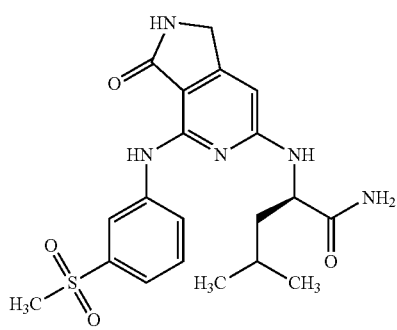 [SMILES: CC(C)C[C@@H](Nc1cc2c(c(Nc3cccc(S(C)(=O)=O)c3)n1)C(=O)NC2)C(N)=O]

A. (R)-Methyl 6-(1-amino-4-methyl-1-oxopentan-2-ylamino)-4-cyano-2-(3-(methylsulfonyl)phenylamino)nicotinate

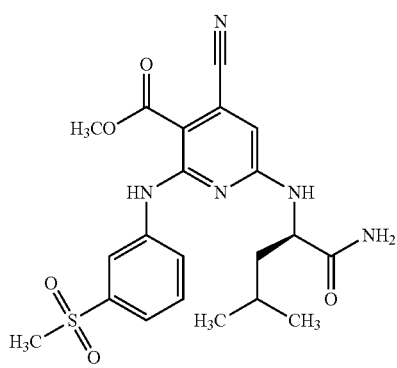 [SMILES: COC(=O)c1c(C#N)cc(N[C@H](CC(C)C)C(N)=O)nc1Nc1cccc(S(C)(=O)=O)c1]

A mixture of methyl 6-chloro-4-cyano-2-(3-(methylsulfonyl)phenylamino)nicotinate (120.7 mg, 0.330 mmol), (R)-2-amino-4-methylpentanamide (67.1 mg, 0.515 mmol), and $Et_3N$ (0.1 mL, 0.717 mmol) in DMF (4 mL) was stirred at 60° C. for 14 h. Saturated aq $NaHCO_3$ (20 mL) was added to the mixture, which was subsequently extracted with EtOAc (2×30 mL). The organic layers were washed with saturated aq $NaHCO_3$ (20 mL), water (20 mL) and brine (20 mL), were dried over anhydrous $Na_2SO_4$, and filtered (DM1020). The filtrate was concentrated under reduced pressure. The residue was purified by column chromatography ($SiO_2$, hexanes/EtOAc=1/2) and then triturated with IPE to give the title compound (76 mg, 50%).

B. (R)-4-Methyl-2-(4-(3-(methylsulfonyl)phenylamino)-3-oxo-2,3-dihydro-1H-pyrrolo[3,4-c]pyridin-6-ylamino)pentanamide A mixture of (R)-methyl 6-(1-amino-4-methyl-1-oxopentan-2-ylamino)-4-cyano-2-(3-(methylsulfonyl)phenylamino)nicotinate (73.2 mg, 0.159 mmol) and palladium hydroxide on carbon (23.2 mg, 0.165 mmol) in MeOH (6 mL) and HOAc (3 mL) was stirred at RT for 12 h under a hydrogen atmosphere. The mixture was filtered to remove the catalyst and the filtrate was concentrated under reduced pressure. The residue was treated with saturated aq $NaHCO_3$ (20 mL) and MeOH (20 mL). The resulting mixture was stirred at RT for 16 h and then concentrated under reduced pressure. The residue was treated with saturated aq $NaHCO_3$ (30 mL) and extracted with EtOAc (2×50 mL). The organic layers were washed with saturated aq $NaHCO_3$ (20 mL), water (20 mL) and brine (20 mL), were dried over anhydrous $Na_2SO_4$, and filtered. The filtrate was concentrated under reduced pressure and the residue was recrystallized from EtOH to give the title compound as a white solid (18.8 mg, 27%). $^1$H-NMR (DMSO-$d_6$) δ ppm 0.87-0.94 (m, 6H), 1.54-1.63 (m, 2H), 1.76 (br s, 1H), 3.32 (s, 3H), 4.24 (s, 2H), 4.50 (br s, 1H), 6.17 (s, 1H), 7.00-7.04 (m, 2H), 7.22 (br s, 1H), 7.47-7.57 (m, 2H), 8.01 (br s, 1H), 8.06 (s, 1H), 8.45 (br s, 1H), 9.23 (s, 1H). [M+H] calc'd for $C_{20}H_{26}N_5O_4S$, 432; found, 432.5.

Example 36

(R)-4-Methyl-2-(4-(1-methyl-1H-pyrazol-4-yl)-3-oxo-2,3-dihydro-1H-pyrrolo[3,4-c]pyridin-6-ylamino)pentanamide

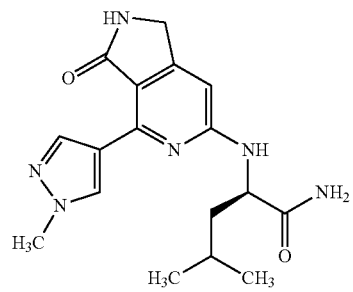 [SMILES: CC(C)C[C@@H](Nc1cc2c(c(-c3cnn(C)c3)n1)C(=O)NC2)C(N)=O]

A. (R)-Methyl 6-(1-amino-4-methyl-1-oxopentan-2-ylamino)-4-cyano-2-(1-methyl-1H-pyrazol-4-yl)nicotinate

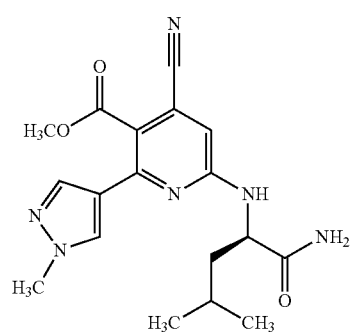 [SMILES: COC(=O)c1c(C#N)cc(N[C@H](CC(C)C)C(N)=O)nc1-c1cnn(C)c1]

A mixture of methyl 6-chloro-4-cyano-2-(1-methyl-1H-pyrazol-4-yl)nicotinate (82.9 mg, 0.300 mmol) and (R)-2-amino-4-methylpentanamide (39.0 mg, 0.300 mmol) in DMA (2 mL) was stirred at 150° C. for 12 h. Water was subsequently added and the mixture was extracted with EtOAc. The organic layers were washed with saturated aq NaHCO₃, water, and brine, were dried over anhydrous Na₂SO₄, and filtered. The filtrate was concentrated under reduced pressure. The residue was purified by column chromatography (SiO₂, EtOAc) to give the title compound as a yellow oil (11.7 mg, 11%).

B. (R)-4-Methyl-2-(4-(1-methyl-1H-pyrazol-4-yl)-3-oxo-2,3-dihydro-1H-pyrrolo[3,4-c]pyridin-6-ylamino)pentanamide A mixture of (R)-methyl 6-(1-amino-4-methyl-1-oxopentan-2-ylamino)-4-cyano-2-(1-methyl-1H-pyrazol-4-yl)nicotinate (20.3 mg, 0.055 mmol) and palladium hydroxide (10 mg, 0.094 mmol) in MeOH (2 mL) and HOAc (2 mL) was stirred at RT for 3 h under a hydrogen atmosphere. The mixture was filtered to remove the catalyst and the filtrate was concentrated under reduced pressure. The residue was treated with saturated aq NaHCO₃ (20 mL) and EtOAc (20 mL) for 12 h. The mixture was extracted with EtOAc (2×20 mL). The organic layers were washed with saturated aq NaHCO₃ (20 mL), water (20 mL) and brine (20 mL), were dried over anhydrous Na₂SO₄, and filtered. The filtrate was concentrated under reduced pressure and the residue was purified by column chromatography (DM1020, EtOAc/MeOH=15/1-10/1) to give the title compound as a white solid (10.2 mg, 54%). $^1$H-NMR (DMSO-d₆) δ ppm 0.88-0.95 (m, 6H), 1.52-1.60 (m, 2H), 1.73-1.76 (m, 1H), 3.88 (s, 3H), 4.21 (s, 2H), 4.48 (br s, 1H), 6.43 (s, 1H), 6.90 (s, 1H), 7.03 (br s, 1H), 7.42 (s, 1H), 8.01 (s, 1H), 8.41 (s, 1H), 8.92 (s, 1H). [M+H] calc'd for C₁₇H₂₃N₆O₂, 343; found, 343.

Example 37

2-((1R,2S)-2-(Dimethylamino)cyclohexylamino)-4-(m-tolylamino)-6,7-dihydro-5H-pyrrolo[3,4-d]pyrimidin-5-one

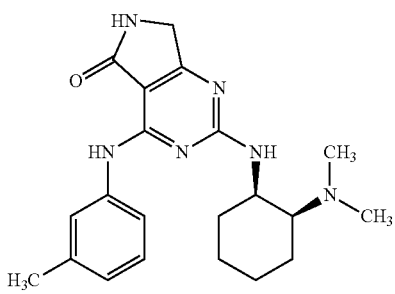

A solution of 2-((1R,2S)-2-aminocyclohexylamino)-4-(m-tolylamino)-6,7-dihydro-5H-pyrrolo[3,4-d]pyrimidin-5-one (10 mg, 0.028 mmol), paraformaldehyde (0.852 mg, 0.028 mmol) in MeOH (2 mL) was stirred at RT for 10 min. Sodium cyanotrihydroborate (1.783 mg, 0.028 mmol) was added and the reaction mixture was stirred at RT overnight. The mixture was purified by reverse phase preparative HPLC to give the TFA salt of the title compound (5 mg, 46%). $^1$H NMR (400 MHz, DMSO-d₆) δ ppm 1.44-1.57 (m, 4 H), 1.85 (br s, 4 H), 2.32 (s, 3 H), 2.64-2.87 (2s, 6 H), 4.20 (d, J=4.55 Hz, 2 H), 6.91 (d, J=7.07 Hz, 1 H), 7.00 (s, 1 H), 7.13 (s, 1 H), 7.17-7.34 (m, 2 H), 8.19 (br s, 1 H), 8.68 (br s, 1 H). [M+H] calc'd for C₂₁H₂₈N₆O, 381; found, 381.

Example 38

2-((1R,2S)-2-(Methylamino)cyclohexylamino)-4-(m-tolylamino)-6,7-dihydro-5H-pyrrolo[3,4-d]pyrimidin-5-one

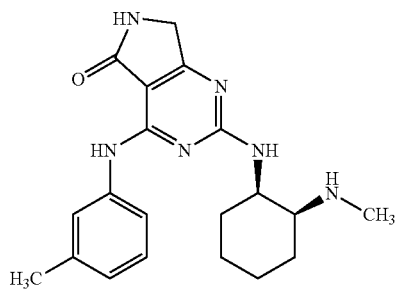

A solution of 2-((1R,2S)-2-Aminocyclohexylamino)-4-(m-tolylamino)-6,7-dihydro-5H-pyrrolo[3,4-d]pyrimidin-5-one (17.7 mg, 0.050 mmol), paraformaldehyde (1.508 mg, 0.050 mmol) in MeOH (2 mL) was stirred at RT for 10 min. Sodium cyanotrihydroborate (3.16 mg, 0.050 mmol) was added and the reaction mixture was stirred at RT for 4 h. The reaction was stopped and the mixture was purified by reverse phase preparative HPLC to give the TFA salt of the title compound (5 mg, 27%). $^1$H NMR (400 MHz, DMSO-d₆) δ ppm 1.35-1.79 (m, 8 H), 2.32 (s, 3 H), 4.20 (br s, 2 H), 6.52 (br s, 2 H), 6.91 (d, J=7.33 Hz, 1 H), 7.24 (t, J=7.71 Hz, 2 H), 8.03 (br s, 1 H), 8.16 (br s, 2 H), 8.40 (br s, 1 H), 8.66 (br s, 1 H). [M+H] calc'd for C₂₀H₂₆N₆O, 367; found, 367.

Example 39

2'-((1R,2S)-2-Aminocyclohexylamino)-4'-(m-tolylamino)spiro[cyclopropane-1,7'-pyrrolo[3,4-d]pyrimidin]-5'(6'H)-one

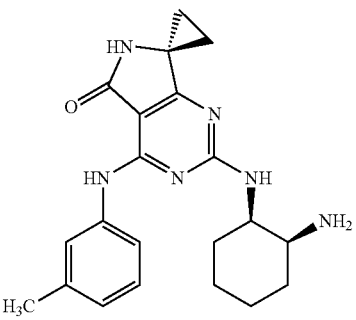

A. tert-Butyl (1S,2R)-2-(5'-oxo-4'-(m-tolylamino)-5', 6'-dihydrospiro[cyclopropane-1,7'-pyrrolo[3,4-d]pyrimidine]-2'-ylamino)cyclohexylcarbamate

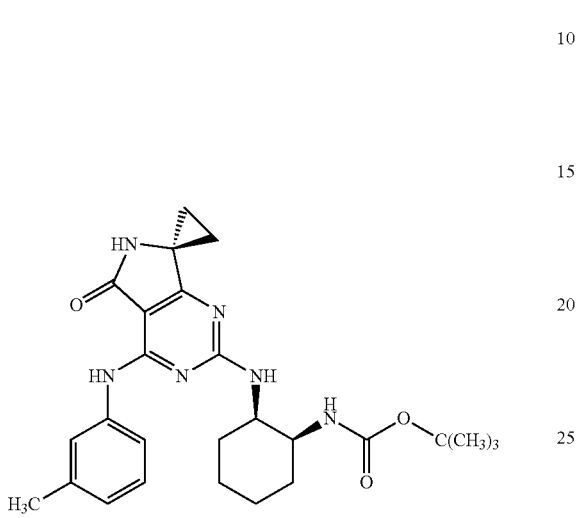

Ethylmagnesium bromide (0.069 mL, 0.208 mmol) was added at RT to a solution of methyl 2-((1R,2S)-2-(tert-butoxycarbonylamino)cyclohexylamino)-4-cyano-6-(m-tolylamino)pyrimidine-5-carboxylate (50 mg, 0.104 mmol) and tetraisopropylorthotitanate (0.091 mL, 0.312 mmol) in Et$_2$O (5 mL). The reaction mixture was stirred at RT for 20 h and was subsequently diluted with EtOAc. The organic phase was washed with saturated aq NaHCO$_3$, brine and water, was dried then concentrated to give a pink residue, which was purified by reverse phase preparative HPLC. The fractions were collected and concentrated to a residue, which was used in next step. [M+H] calc'd for C$_{26}$H$_{34}$N$_6$O$_3$, 479; found, 479.

B. 2'-((1R,2S)-2-Aminocyclohexylamino)-4'-(m-tolylamino)spiro[cyclopropane-1,7'-pyrrolo[3,4-d]pyrimidin]-5' (6'H)-one A solution of tert-Butyl (1S,2R)-2-(5'-oxo-4'-(m-tolylamino)-5',6'-dihydrospiro[cyclopropane-1,7'-pyrrolo[3,4-d]pyrimidine]-2'-ylamino)cyclohexylcarbamate (50 mg, 0.104 mmol) in DCM (5 mL) was treated with TFA (2 mL) for 1 h and was purified by reverse phase preparative HPLC. The collected fractions were lyophilized to give the TFA salt of the title compound (4 mg, 10% in two steps). $^1$H NMR (400 MHz, DMSO-d$_6$) δ ppm 1.12-1.31 (m, 1 H), 1.42 (m, 6 H), 1.63 (m, 3 H), 1.86 (m, 2 H), 2.33 (s, 3 H), 3.62 (br s, 1 H), 4.18 (br s, 1 H), 6.91 (d, J=7.33 Hz, 1 H), 7.24 (t, J=7.71 Hz, 1 H), 7.36-7.56 (m, 1 H), 7.60 (br s, 1 H), 7.73 (br s, 2 H), 8.33 (br s, 1 H), 8.65 (br s, 1 H). [M+H] calc'd for C$_{21}$H$_{26}$N$_6$O, 379; found, 379.

Example 40

2-(2-Aminoethylamino)-4-(m-tolylamino)-6,7-dihydro-5H-pyrrolo[3,4-d]pyrimidin-5-one

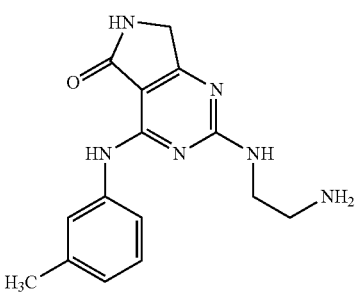 [SMILES: Cc1cccc(Nc2nc(NCCN)nc3c2C(=O)NC3)c1]

A. Methyl 4-methyl-2-(methylthio)-6-(m-tolylamino)pyrimidine-5-carboxylate

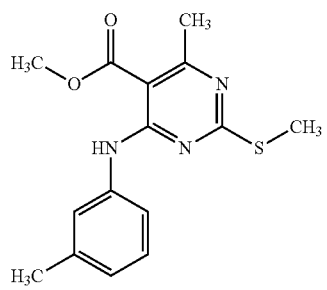

Methyl 2-chloro-4-methyl-6-(m-tolylamino)pyrimidine-5-carboxylate (0.078 g, 0.267 mmol) was dissolved in DMF (3 mL). Sodium thiomethoxide (0.019 g, 0.267 mmol) was added and the reaction mixture was allowed to stir at RT for 1 h. The reaction mixture was poured onto ice. The pH was adjusted to 7 with 1 N HCl. The title compound was isolated as a yellow solid by vacuum filtration (72.8 mg, 90%). [M+H] calc'd for C$_{15}$H$_{17}$N$_3$O$_2$S, 304; found, 304.

B. 6-(2,4-Dimethoxybenzyl)-2-(methylthio)-4-(m-tolylamino)-6,7-dihydro-5H-pyrrolo[3,4-d]pyrimidin-5-one

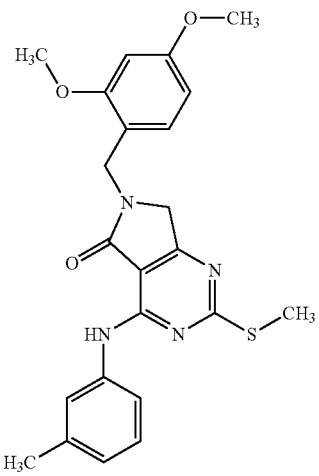

A mixture methyl 4-methyl-2-(methylthio)-6-(m-tolylamino)pyrimidine-5-carboxylate (0.44 g, 1.45 mmol) and selenium dioxide (0.32 g, 2.89 mmol) in dioxane (12 mL) was heated at 100° C. for 24 h. The reaction mixture was subsequently cooled and filtered. The filtrate was concentrated and dried to give a brown foam (0.459 g) which was dispersed in (2,4-dimethoxyphenyl)methanamine (0.217 mL, 1.446 mmol) in DCM (6 mL) and MeOH (3 mL). The resulting mixture was stirred at RT for 30 min. Sodium cyanoborohydride (0.227 g, 3.62 mmol) was added and the reaction mixture was stirred at RT for 20 h. The solid phase was filtered and washed with MeOH to give the title compound as a yellow solid (0.537 g, 85%). [M+H] calc'd for $C_{23}H_{24}N_4O_3S$, 437; found, 437.

C. 6-(2,4-dimethoxybenzyl)-2-(methylsulfonyl)-4-(m-tolylamino)-6,7-dihydro-5H-pyrrolo[3,4-d]pyrimidin-5-one

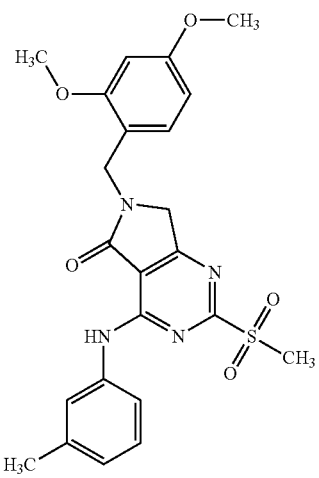

6-(2,4-Dimethoxybenzyl)-2-(methylthio)-4-(m-tolylamino)-6,7-dihydro-5H-pyrrolo[3,4-d]pyrimidin-5-one (0.432 g, 0.990 mmol) was dissolved in DCM (10 mL). The solution was chilled in an ice bath and m-chloroperoxybenzoic acid (0.256 g, 1.484 mmol) was added. The reaction was allowed to warm to RT with stirring for 3 h. A second aliquot of m-chloroperoxybenzoic acid (0.170 g, 0.990 mmol) was added to the reaction mixture, which was stirred for 1 h. A third aliquot of m-chloroperoxybenzoic acid (0.100 g, 0.579 mmol) was added. The reaction mixture was stirred for 30 min, diluted with DCM (20 mL), and quenched with saturated aq NaHCO₃ (20 mL). The organic phase was washed with saturated aq NaHCO₃ (20 mL) and brine (20 mL), and was dried over anhydrous Na₂SO₄. The solvent was removed in vacuo to give the title compound as a light brown glassy solid (330 mg, 71%). [M+H] calc'd for $C_{23}H_{24}N_4O_5S$, 469; found, 469.

D. tert-Butyl 2-(6-(2,4-dimethoxybenzyl)-5-oxo-4-(m-tolylamino)-6,7-dihydro-5H-pyrrolo[3,4-d]pyrimidin-2-ylamino)ethylcarbamate

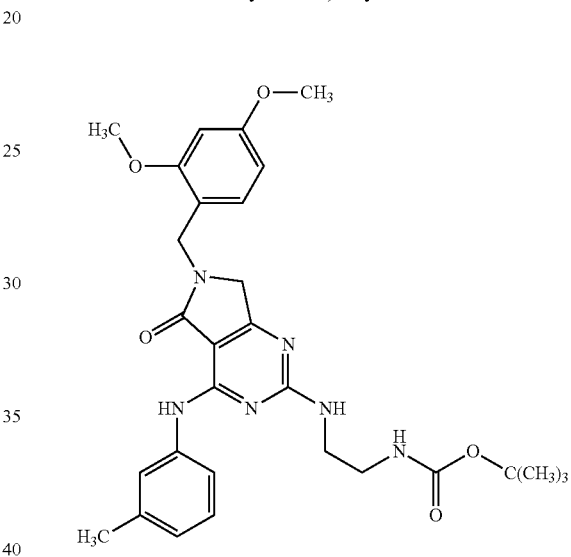

A mixture of 6-(2,4-dimethoxybenzyl)-2-(methylsulfonyl)-4-(m-tolylamino)-6,7-dihydro-5H-pyrrolo[3,4-d]pyrimidin-5-one (0.07 g, 0.149 mmol), tert-butyl 2-aminoethylcarbamate (0.024 g, 0.149 mmol), and Et₃N (0.104 mL, 0.747 mmol) in DMA (2 mL) was heated in a sealed tube at 90° C. for 4 h. The reaction mixture was poured slowly onto ice and its pH adjusted to about 7 through addition of 1 N HCl, resulting in precipitation of a tan solid. The solid was isolated by vacuum filtration, washed with water, and dried under vacuum to give the title compound as a tan brown solid (55 mg, 67%). [M+H] calc'd for $C_{29}H_{36}N_6O_5$, 549; found, 549.

E. 2-(2-Aminoethylamino)-4-(m-tolylamino)-6,7-dihydro-5H-pyrrolo[3,4-d]pyrimidin-5-one A mixture of tert-butyl 2-(6-(2,4-dimethoxybenzyl)-5-oxo-4-(m-tolylamino)-6,7-dihydro-5H-pyrrolo[3,4-d]pyrimidin-2-ylamino)ethylcarbamate (0.055 g, 0.100 mmol) in TFA (2 mL) was stirred at 70° C. for 1.5 h. Following reaction, the solvent was removed and the resulting residue was dispersed into a solution of DMSO and MeOH (1/1). The mixture was filtered and the filtrate was purified by preparative HPLC. The fractions were collected and dried in vacuo to give a TFA salt of the title compound as an off-white solid (28 mg, 93%). ¹H NMR (500 MHz, DMSO-d₆) δ ppm 2.21-2.40 (m, 3 H) 2.90-3.21 (m, 2 H) 3.57 (q, J=5.86 Hz, 2 H) 4.19 (br s, 2 H) 6.90 (br s, 1 H) 7.13-7.34 (m, 1 H) 7.54 (br s, 1 H) 7.56-7.74 (m, 2 H) 7.80 (br s, 2 H) 8.18 (d, J=13.67 Hz, 1 H) 8.54-8.82 (m, 1 H). [M+H] calc'd for $C_{15}H_{18}N_6O$, 299; found, 299.

Example 41

2-(2-Amino-2-methylpropylamino)-4-(m-tolylamino)-6,7-dihydro-5H-pyrrolo[3,4-d]pyrimidin-5-one

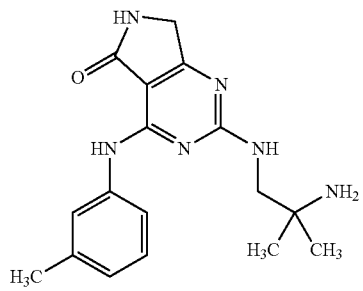 [SMILES: Cc1cccc(Nc2nc(NCC(C)(C)N)nc3c2C(=O)NC3)c1]

A TFA salt of the title compound was prepared in a manner similar to EXAMPLE 40 using tert-butyl 1-amino-2-methylpropan-2-ylcarbamate in place of tert-butyl 2-aminoethylcarbamate. $^1$H NMR (500 MHz, CD$_3$OD) δ ppm 1.14-1.53 (m, 6 H), 2.37 (br s, 3 H), 3.62 (br s, 2 H), 4.12-4.47 (m, 2 H), 6.77-7.15 (m, 1 H), 7.13-7.40 (m, 1 H), 7.40-7.79 (m, 2 H). [M+H] calc'd for $C_{17}H_{22}N_6O$, 327; found, 327.

Example 42

2-(5-Oxo-4-(m-tolylamino)-6,7-dihydro-5H-pyrrolo[3,4-d]pyrimidin-2-ylamino)acetamide

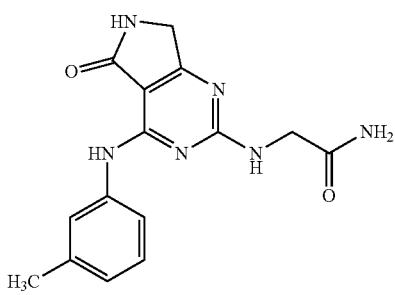 [SMILES: Cc1cccc(Nc2nc(NCC(N)=O)nc3c2C(=O)NC3)c1]

The title compound was prepared in a manner similar to EXAMPLE 40 using glycinamide hydrochloride in place of tert-butyl 2-aminoethylcarbamate. $^1$H NMR (500 MHz, CD$_3$OD) δ ppm 2.38 (s, 3 H), 4.11 (br s, 2 H), 4.41 (br s, 2 H), 7.02 (br s, 1 H), 7.27 (br s, 1 H), 7.51 (br s, 2 H). [M+H] calc'd for $C_{15}H_{16}N_6O_2$, 313; found, 313.

Example 43

2-((2-Aminoethyl)(methyl)amino)-4-(m-tolylamino)-6,7-dihydro-5H-pyrrolo[3,4-d]pyrimidin-5-one

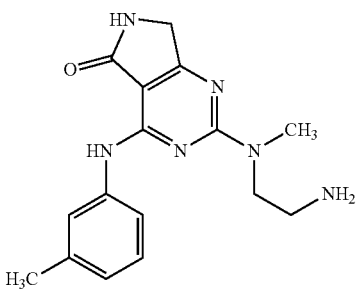 [SMILES: Cc1cccc(Nc2nc(N(C)CCN)nc3c2C(=O)NC3)c1]

A TFA salt of the title compound was prepared in a manner similar to EXAMPLE 40 using tert-butyl 2-(methylamino)ethylcarbamate hydrochloride in place of tert-butyl 2-aminoethylcarbamate. $^1$H NMR (500 MHz, CD$_3$OD) δ ppm 2.35 (s, 3 H), 3.26 (t, J=5.86 Hz, 2 H), 3.30 (s, 3 H), 3.89-4.04 (m, 2 H), 4.24 (s, 2 H), 6.94 (d, J=7.32 Hz, 1 H), 7.23 (t, J=7.81 Hz, 1 H), 7.55 (d, J=7.81 Hz, 2 H). [M+H] calc'd for $C_{16}H_{20}N_6O$, 313; found, 313.

Example 44

2-(Pyrrolidin-2-ylmethylamino)-4-(m-tolylamino)-6,7-dihydro-5H-pyrrolo[3,4-d]pyrimidin-5-one

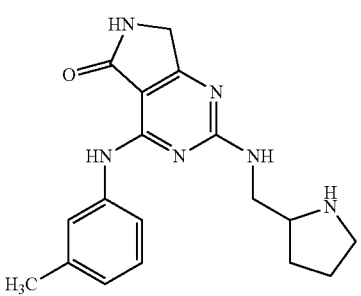 [SMILES: Cc1cccc(Nc2nc(NCC3CCCN3)nc3c2C(=O)NC3)c1]

A TFA salt of the title compound was prepared in a manner similar to EXAMPLE 40 using tert-butyl 2-(aminomethyl)pyrrolidine-1-carboxylate in place of tert-butyl 2-aminoethylcarbamate. $^1$H NMR (500 MHz, CD$_3$OD) δ ppm 1.80 (br s, 1 H), 1.91-2.26 (m, 3 H), 2.38 (br s, 3 H), 3.19 (br s, 1 H), 3.63

(d, J=7.32 Hz, 1 H), 3.71-4.03 (m, 2 H), 4.15-4.51 (m, 2 H), 6.74-7.16 (m, 1 H), 7.13-7.76 (m, 3 H). [M+H] calc'd for $C_{18}H_{22}N_6O$, 339; found, 339.

Example 45

2-(3-Aminopyrrolidin-1-yl)-4-(m-tolylamino)-6,7-dihydro-5H-pyrrolo[3,4-d]pyrimidin-5-one

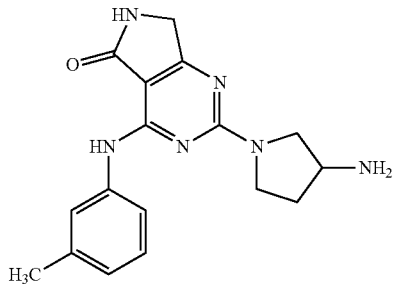 [SMILES: Cc1cccc(Nc2nc(N3CCC(N)C3)nc3c2C(=O)NC3)c1]

A TFA salt of the title compound was prepared in a manner similar to EXAMPLE 40 using tert-butyl pyrrolidin-3-ylcarbamate in place of tert-butyl 2-aminoethylcarbamate. $^1$H NMR (500 MHz, CD$_3$OD) δ ppm 2.13-2.28 (m, 1 H), 2.35 (s, 3 H), 2.51 (dd, J=13.42, 6.10 Hz, 1 H), 3.69-4.12 (m, 5 H), 4.22 (d, J=18.06 Hz, 2 H), 6.93 (d, J=7.32 Hz, 1 H), 7.21 (t, J=7.81 Hz, 1 H), 7.46-7.69 (m, 2 H). [M+H] calc'd for $C_{17}H_{20}N_6O$, 325; found, 325.

Preparation 15

Ethyl 4-chloro-6-methyl-2-(methylthio)pyrimidine-5-carboxylate

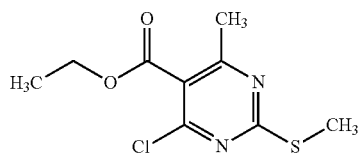

Ethyl 4-hydroxy-6-methyl-2-(methylthio)pyrimidine-5-carboxylate (0.2 g, 0.876 mmol), tetraethylammonium chloride (0.145 g, 0.876 mmol), and N,N-dimethylaniline (0.112 mL, 0.876 mmol) were dispersed in acetonitrile (10 mL). The reaction mixture was stirred briefly followed by the addition of phosphorous oxychloride (0.204 mL, 2.190 mmol). The reaction was heated at 100° C. for 4 h. The solvent was subsequently removed in vacuo. The residue was poured onto ice to give an off-white oil, which was extracted with DCM (2×15 mL), and dried over anhydrous Na$_2$SO$_4$. The solvent was removed in vacuo to give the title compound as a yellowish-green oil (0.179 g, 83%). [M+H] calc'd for $C_9H_{11}ClN_2O_2S$, 247; found, 247.

Example 46

2-((1R,2S)-2-Aminocyclohexylamino)-4-(1,5-dimethyl-1H-pyrazol-4-yl)-6,7-dihydro-5H-pyrrolo[3,4-d]pyrimidin-5-one

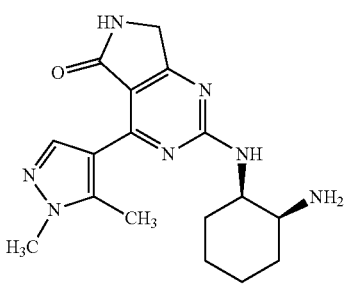 [SMILES: Cc1c(-c2nc(N[C@@H]3CCCC[C@@H]3N)nc3c2C(=O)NC3)cnn1C]

A. Ethyl 4-(1,5-dimethyl-1H-pyrazol-4-yl)-6-methyl-2-(methylthio)pyrimidine-5-carboxylate

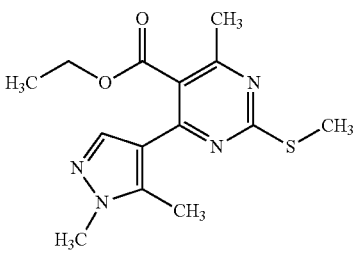 [SMILES: CCOC(=O)c1c(C)nc(SC)nc1-c1cnn(C)c1C]

Ethyl 4-chloro-6-methyl-2-(methylthio)pyrimidine-5-carboxylate (0.179 g, 0.726 mmol), 1,5-dimethyl-4-(4,4,5,5-tetramethyl-1,3,2-dioxaborolan-2-yl)-1H-pyrazole (0.242 g, 1.088 mmol), and PdCl$_2$(dppf) (0.106 g, 0.145 mmol) were dispersed in DMA (2 mL). After 10 min, 2 N sodium carbonate (1.814 mL, 3.63 mmol) was added to the reaction mixture. The reaction mixture was purged with nitrogen, sealed in a vial, and then heated at 80° C. for 5 h. The mixture was subsequently filtered through a pad of Celite, rinsed with MeOH, and the filtrate was purified via reverse phase preparative HPLC. The fractions were concentrated in vacuo to give the title compound as tan needles (0.159 g, 71%). [M+H] calc'd for $C_{14}H_{18}N_4O_2S$, 307; found, 307.

B. Ethyl 4-(1,5-dimethyl-1H-pyrazol-4-yl)-6-methyl-2-(methylsulfonyl)pyrimidine-5-carboxylate

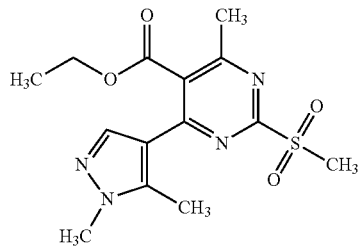 [SMILES: CCOC(=O)c1c(C)nc(S(C)(=O)=O)nc1-c1cnn(C)c1C]

Ethyl 4-(1,5-dimethyl-1H-pyrazol-4-yl)-6-methyl-2-(methylthio)pyrimidine-5-carboxylate (0.159 g, 0.519 mmol) was dissolved in DCM (10 mL). The solution was chilled in an ice bath and m-chloroperoxybenzoic acid (0.134 g, 0.778 mmol) was added. The reaction was allowed to warm to RT over a 30 min period with stirring. Another aliquot of m-chloroperoxybenzoic acid (0.159 g, 0.519 mmol) was added to the reaction mixture and it was stirred for an additional 45 min. The reaction mixture was subsequently diluted with DCM (10 mL) and was quenched with saturated aq NaHCO$_3$ (10 mL). The organic phase was washed with saturated aq NaHCO$_3$ (5 mL) and brine (5 mL) and was dried over anhydrous Na$_2$SO$_4$. The solvents were removed in vacuo to give the title compound as a yellow oil (173 mg, 98%). [M+H] calc'd for $C_{14}H_{18}N_4O_4S$, 339; found, 339.

C. Ethyl 2-((1R,2S)-2-(tert-butoxycarbonylamino)cyclohexylamino)-4-(1,5-dimethyl-1H-pyrazol-4-yl)-6-methylpyrimidine-5-carboxylate

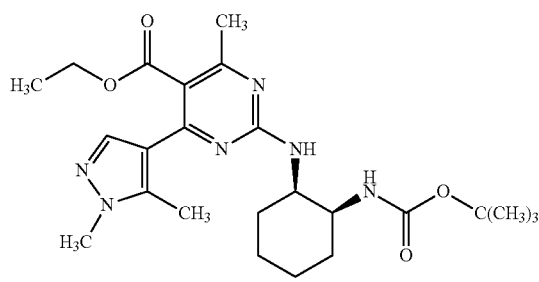 [SMILES: CCOC(=O)c1c(C)nc(N[C@@H]2CCCC[C@@H]2NC(=O)OC(C)(C)C)nc1-c1cnn(C)c1C]

A solution of ethyl 4-(1,5-dimethyl-1H-pyrazol-4-yl)-6-methyl-2-(methylsulfonyl)pyrimidine-5-carboxylate (0.07 g, 0.207 mmol), tert-butyl (1S,2R)-2-aminocyclohexylcarbamate (0.089 g, 0.414 mmol) and Et$_3$N (0.115 mL, 0.827 mmol) in DMA (3 mL) was heated in a sealed tube at 90° C. for 8 h. The reaction mixture was poured slowly onto ice to yield a pale yellow precipitate, which was isolated by vacuum filtration, washed with water, and dried under vacuum to give the title compound. [M+H] calc'd for $C_{24}H_{36}N_6O_4$, 473; found, 473.

D. tert-Butyl (1S,2R)-2-(6-(2,4-dimethoxybenzyl)-4-(1,5-dimethyl-1H-pyrazol-4-yl)-5-oxo-6,7-dihydro-5H-pyrrolo[3,4-d]pyrimidin-2-ylamino)cyclohexylcarbamate

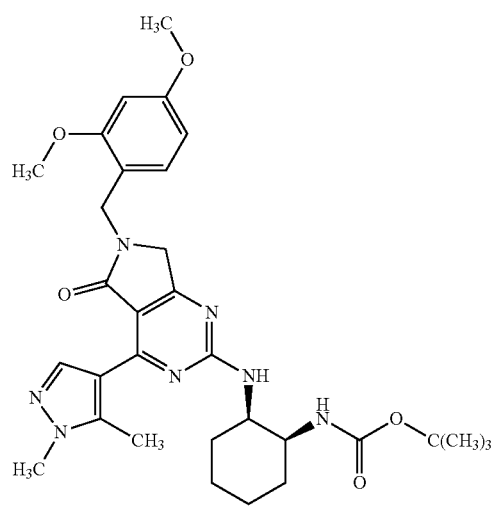 [SMILES: COc1ccc(CN2Cc3nc(N[C@@H]4CCCC[C@@H]4NC(=O)OC(C)(C)C)nc(-c4cnn(C)c4C)c3C2=O)c(OC)c1]

A mixture ethyl 2-((1R,2S)-2-(tert-butoxycarbonylamino)cyclohexylamino)-4-(1,5-dimethyl-1H-pyrazol-4-yl)-6-methylpyrimidine-5-carboxylate (0.098 g, 0.207 mmol) and selenium dioxide (0.046 g, 0.415 mmol) in dioxane (2 mL) was heated at 100° C. for 24 h. The mixture was subsequently cooled and filtered. The filtrate was concentrated and dried to give a brown foam (0.1 g, 0.206 mmol) which was combined with sodium acetate (0.051 g, 0.617 mmol) and (2,4-dimethoxyphenyl)methanamine (0.031 mL, 0.206 mmol) in DCM (2 mL) and MeOH (1 mL). The mixture was stirred at RT for 30 min, after which sodium cyanoborohydride (0.032 g, 0.514 mmol) was added. The reaction mixture was stirred at RT for 20 h, and then filtered through a pad of Celite, which was rinsed with MeOH. The filtrate was purified by reverse phase preparative HPLC and the fractions concentrated in vacuo to give the title compound as a tan solid. [M+H] calc'd for $C_{31}H_{41}N_7O_5$, 592; found, 592.

E. 2-((1R,2S)-2-Aminocyclohexylamino)-4-(1,5-dimethyl-1H-pyrazol-4-yl)-6,7-dihydro-5H-pyrrolo[3,4-d]pyrimidin-5-one

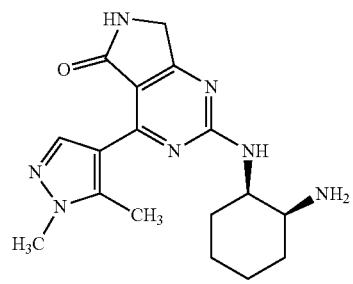 [SMILES: Cc1c(-c2nc(N[C@@H]3CCCC[C@@H]3N)nc3c2C(=O)NC3)cnn1C]

A mixture of tert-butyl (1S,2R)-2-(6-(2,4-dimethoxybenzyl)-4-(1,5-dimethyl-1H-pyrazol-4-yl)-5-oxo-6,7-dihydro-5H-pyrrolo[3,4-d]pyrimidin-2-ylamino)cyclohexylcarbamate obtained above in TFA (2 mL) was stirred at 70° C. for 2 h. The mixture was subsequently purified by reverse phase preparative HPLC. The fractions were collected and concentrated to give a TFA salt of the title compound as a white solid (0.5 mg). $^1$H NMR (500 MHz, CD$_3$OD) δ ppm 1.59 (br s, 2 H), 1.67-2.02 (m, 6 H), 2.66-2.72 (m, 3 H), 3.67 (br s, 1 H), 3.85 (s, 3 H), 4.29 (s, 2 H), 4.50-4.64 (m, 1 H), 8.64 (br s, 1 H). [M+H] calc'd for C$_{17}$H$_{23}$N$_7$O, 342; found, 342.

Example 47

2-((1R,2S)-2-Aminocyclohexylamino)-4-(1H-indol-2-yl)-6,7-dihydro-5H-pyrrolo[3,4-d]pyrimidin-5-one A TFA salt of the title compound was prepared in a manner similar to EXAMPLE 46 using 1-(tert-butoxycarbonyl)-1H-indol-2-ylboronic acid in place of 1,5-dimethyl-4-(4,4,5,5-tetramethyl-1,3,2-dioxaborolan-2-yl)-1H-pyrazole. $^1$H NMR (500 MHz, CD$_3$OD) δ ppm 1.46-1.72 (m, 2 H), 1.72-2.06 (m, 6 H), 3.56-3.89 (m, 1 H), 4.36 (s, 2 H), 4.52-4.77 (m, 1 H), 7.08 (t, J=7.57 Hz, 1 H), 7.25 (t, J=7.57 Hz, 1 H), 7.47 (d, J=8.30 Hz, 1 H), 7.58-7.79 (m, 2 H). [M+H] calc'd for C$_{20}$H$_{22}$N$_6$O, 363; found, 363.

Example 48

2-((1R,2S)-2-Aminocyclohexylamino)-4-(1H-pyrazol-5-yl)-6,7-dihydro-5H-pyrrolo[3,4-d]pyrimidin-5-one

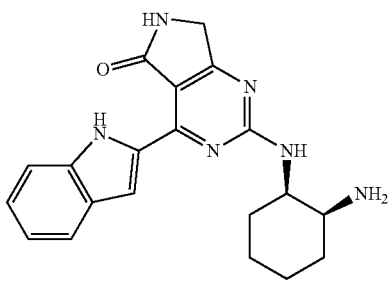 [SMILES: N[C@H]1CCCC[C@H]1Nc1nc2c(c(-c3cc4ccccc4[nH]3)n1)C(=O)NC2]

A TFA salt of the title compound was prepared in a manner similar to EXAMPLE 46 using tert-butyl 5-(5,5-dimethyl-1,3,2-dioxaborinan-2-yl)-1H-pyrazole-1-carboxylate in place of 1,5-dimethyl-4-(4,4,5,5-tetramethyl-1,3,2-dioxaborolan-2-yl)-1H-pyrazole. $^1$H NMR (500 MHz, CD$_3$OD) δ ppm 1.44-1.69 (m, 2 H), 1.68-1.94 (m, 6 H), 3.64 (br s, 1 H), 4.41 (s, 2 H), 4.65 (br s, 1 H), 7.11-7.55 (m, 1 H), 7.69 (d, J=1.77 Hz, 1 H). [M+H] calc'd for C$_{15}$H$_{19}$N$_7$O, 314; found, 314.

Example 49

2-(3-Aminopropyl)-4-(m-tolylamino)-6,7-dihydro-5H-pyrrolo[3,4-d]pyrimidin-5-one

A. Methyl 2-(3-(tert-butoxycarbonylamino)prop-1-ynyl)-4-methyl-6-(m-tolylamino)pyrimidine-5-carboxylate Methyl 2-chloro-4-methyl-6-(m-tolylamino)pyrimidine-5-carboxylate (0.4 g, 1.371 mmol), tert-butyl prop-2-ynylcarbamate (0.426 g, 2.74 mmol), tetrakis(triphenylphosphine) palladium (0.032 g, 0.027 mmol), and copper (I) iodide (0.026 g, 0.137 mmol) was dispersed in DMA (5 mL). Triethylamine (0.382 mL, 2.74 mmol) was added and the mixture was degassed with nitrogen for 5 min. The reaction mixture was placed in a sealed tube and heated at 90° C. for 4 h, after which it was filtered through a pad of Celite, which was rinsed with MeOH. The filtrate was purified via reverse phase preparative HPLC and the fractions were concentrated in vacuo to give the title compound as a brown oil (0.190 g, 34%). [M+H] calc'd for $C_{22}H_{26}N_4O_4$, 411; found, 411.

B. Methyl 2-(3-(tert-butoxycarbonylamino)propyl)-4-methyl-6-(m-tolylamino)pyrimidine-5-carboxylate

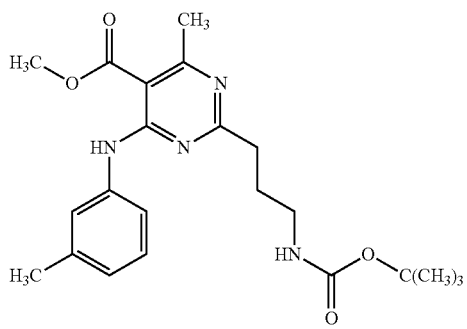 [SMILES: COC(=O)c1c(C)nc(CCCNC(=O)OC(C)(C)C)nc1Nc1cccc(C)c1]

Methyl 2-(3-(tert-butoxycarbonylamino)prop-1-ynyl)-4-methyl-6-(m-tolylamino)pyrimidine-5-carboxylate (0.190 g, 0.463 mmol) was dissolved in EtOH (4 mL). To this solution was added palladium on carbon (0.049 g, 0.046 mmol) and the resulting mixture was stirred overnight at RT under $H_2$ atmosphere. The mixture was filtered through a pad of Celite, and the filtrate was evaporated to give the title compound as a brown oil, which was used in next step without further purification. [M+H] calc'd for $C_{22}H_{30}N_4O_4$, 415; found, 415.

C. tert-Butyl 3-(6-(2,4-dimethoxybenzyl)-5-oxo-4-(m-tolylamino)-6,7-dihydro-5H-pyrrolo[3,4-d]pyrimidin-2-yl)propylcarbamate

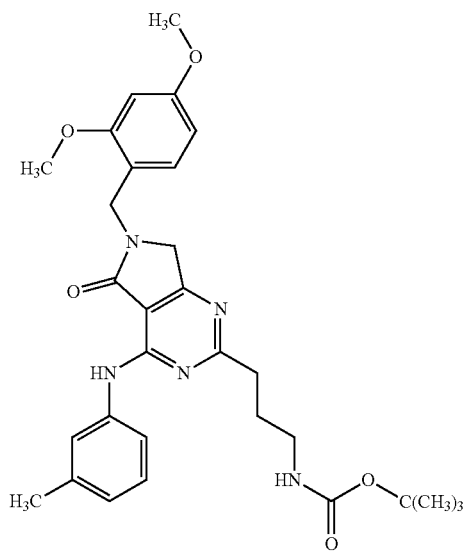 [SMILES: COc1ccc(CN2Cc3nc(CCCNC(=O)OC(C)(C)C)nc(Nc4cccc(C)c4)c3C2=O)c(OC)c1]

A mixture methyl 2-(3-(tert-butoxycarbonylamino)propyl)-4-methyl-6-(m-tolylamino)pyrimidine-5-carboxylate (0.124 g, 0.299 mmol) and selenium dioxide (0.033 g, 0.299 mmol) in dioxane (2 mL) was heated at 100° C. for 24 h. The reaction mixture was subsequently cooled and filtered. The filtrate was concentrated and dried to give a brown foam (0.128 g, 0.299 mmol), which was combined with (2,4-dimethoxyphenyl)methanamine (0.045 mL, 0.299 mmol), DCM (2 mL) and MeOH (1 mL). The mixture was stirred at RT for 30 min, after which sodium cyanoborohydride (0.047 g, 0.747 mmol) was added. The reaction mixture was stirred at RT for 20 h, and then filtered through a pad of Celite, which was rinsed with MeOH. The filtrate was purified via reverse phase preparative HPLC. The fractions were collected and concentrated in vacuo to yield the title compound as a tan solid (1.7 mg, 1%). [M+H] calc'd for $C_{30}H_{37}N_5O_5$, 548; found, 548.

D. 2-(3-Aminopropyl)-4-(m-tolylamino)-6,7-dihydro-5H-pyrrolo[3,4-d]pyrimidin-5-one A mixture of tert-butyl 3-(6-(2,4-dimethoxybenzyl)-5-oxo-4-(m-tolylamino)-6,7-dihydro-5H-pyrrolo[3,4-d]pyrimidin-2-yl)propylcarbamate (1.7 mg, 0.003 mmol) in TFA (2 mL) was stirred at 70° C. for 2 h. The mixture was purified by reverse phase preparative HPLC. The fractions were collected and concentrated to give a TFA salt of the title compound as a white solid (0.6 mg, 65%). $^1$H NMR (500 MHz, $CD_3OD$) δ ppm 2.11-2.26 (m, 2 H), 2.30-2.45 (m, 3 H), 2.92-3.09 (m, 4 H), 4.39 (s, 2 H), 6.98 (d, J=8.34 Hz, 1 H), 7.16-7.35 (m, 1 H), 7.51 (s, 1 H), 7.65 (d, J=8.59 Hz, 1 H). [M+H] calc'd for $C_{16}H_{19}N_5O$, 298; found, 298.

Example 50

6-((1R,2S)-2-Aminocyclohexylamino)-4-(benzofuran-3-yl)-7-fluoro-1H-pyrrolo[3,4-c]pyridin-3(2H)-one

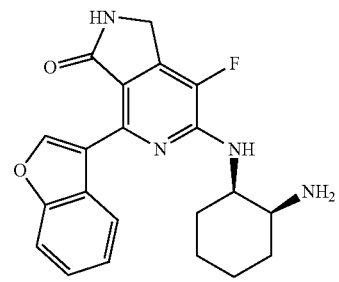 [SMILES: N[C@H]1CCCC[C@H]1Nc1nc(-c2coc3ccccc23)c2c(c1F)CNC2=O]

A. tert-Butyl (1S,2R)-2-(4-(benzofuran-3-yl)-2-(2,4-dimethoxybenzyl)-7-fluoro-3-oxo-2,3-dihydro-1H-pyrrolo[3,4-c]pyridin-6-ylamino)cyclohexylcarbamate

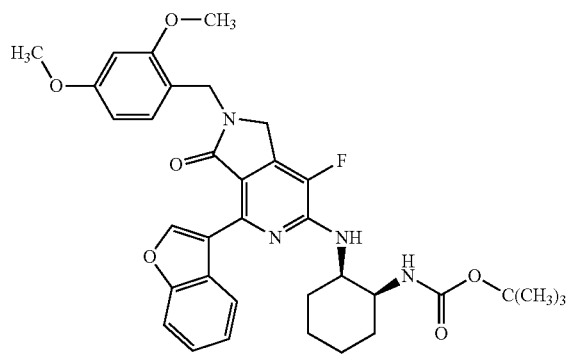 [SMILES: COc1ccc(CN2Cc3c(F)c(N[C@@H]4CCCC[C@@H]4NC(=O)OC(C)(C)C)nc(-c4coc5ccccc45)c3C2=O)c(OC)c1]

A mixture of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (65 mg, 0.118 mmol), aqueous sodium carbonate (2 N, 0.237 mL, 0.474 mmol), 2-(benzofuran-3-yl)-4,4,5,5-tetramethyl-1,3,2-dioxaborolane (43 mg, 0.178 mmol) and bis(triphenylphosphine)palladium chloride (17 mg, 0.024 mmol) in DME (2 mL) was placed in a vial. The vial was purged with nitrogen, sealed, and the reaction mixture heated at 120° C. for 1 h. The mixture was filtered through a pad of Celite, which was rinsed with MeOH. The solvent was removed in vacuo and the residue diluted with MeOH, passed through a microfiltration frit, and purified via preparative HPLC. The fractions were collected and concentrated in vacuo to give the title compound as a tan oil (36.3 mg, 48%). [M+H] calc'd for $C_{35}H_{39}FN_4O_6$, 632; found, 632.

B. 6-((1R,2S)-2-Aminocyclohexylamino)-4-(benzofuran-3-yl)-7-fluoro-1H-pyrrolo[3,4-c]pyridin-3(2H)-one A mixture of tert-butyl (1S,2R)-2-(4-(benzofuran-3-yl)-2-(2,4-dimethoxybenzyl)-7-fluoro-3-oxo-2,3-dihydro-1H-pyrrolo[3,4-c]pyridin-6-ylamino)cyclohexylcarbamate (75 mg, 0.119 mmol) and TFA (2 mL) was placed in a vial and heated at 125° C. for 3 h. The solvent was subsequently removed in vacuo to give a residue which was dispersed in DMSO and MeOH (1/1), passed through a microfiltration frit, and purified via preparative HPLC. The fractions were collected and the solvent removed in vacuo to give a TFA salt of the title compound as a gray solid (9.2 mg, 20%). $^1$H NMR (500 MHz, CD$_3$OD) δ ppm 1.67 (br s, 3 H), 1.79-2.05 (m, 5 H), 3.98 (br s, 1 H), 4.50 (s, 2 H), 4.69 (br s, 1 H), 7.28-7.47 (m, 2 H), 7.56 (d, J=7.81 Hz, 1 H), 8.31 (d, J=6.83 Hz, 1 H), 9.08 (s, 1 H). [M+H] calc'd for $C_{21}H_{21}FN_4O_2$, 381; found, 381.

Example 51

6-((1R,2S)-2-aminocyclohexylamino)-7-fluoro-4-(imidazo[1,2-a]pyridin-3-yl)-1H-pyrrolo[3,4-c]pyridin-3(2H)-one

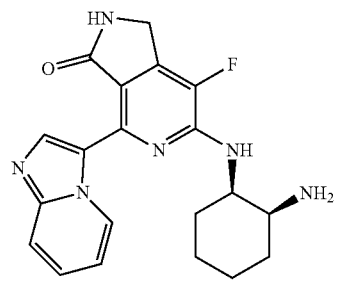 [SMILES: N[C@H]1CCCC[C@H]1Nc1nc(-c2cnc3ccccn23)c2c(c1F)CNC2=O]

A TFA salt of the title compound was prepared in a manner similar to EXAMPLE 50 using imidazo[1,2-a]pyridin-3-ylboronic acid in place of 2-(benzofuran-3-yl)-4,4,5,5-tetramethyl-1,3,2-dioxaborolane. $^1$H NMR (500 MHz, CD$_3$OD) δ ppm 1.50-1.75 (m, 3 H), 1.74-1.98 (m, 5 H), 3.78 (br s, 1 H), 4.58 (br s, 3 H), 7.57 (t, J=6.35 Hz, 1 H), 7.93-8.21 (m, 2 H), 8.78 (br s, 1 H), 9.45 (d, J=6.35 Hz, 1 H). [M+H] calc'd for $C_{20}H_{21}FN_6O$, 381; found, 381.

Example 52

6-((1R,2S)-2-aminocyclohexylamino)-4-(benzo[b]thiophen-3-yl)-7-fluoro-1H-pyrrolo[3,4-c]pyridin-3(2H)-one

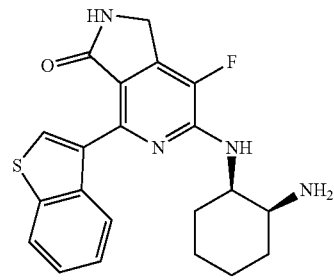 [SMILES: N[C@H]1CCCC[C@H]1Nc1nc(-c2csc3ccccc23)c2c(c1F)CNC2=O]

A TFA salt of the title compound was prepared in a manner similar to EXAMPLE 50 using benzo[b]thiophen-3-ylboronic acid in place of 2-(benzofuran-3-yl)-4,4,5,5-tetramethyl-1,3,2-dioxaborolane. $^1$H NMR (500 MHz, CD$_3$OD) δ ppm 1.50-1.93 (m, 8 H), 3.80 (br s, 1 H), 4.42-4.68 (m, 3 H), 7.38 (m, J=4.40 Hz, 2 H), 7.94 (br s, 1 H), 8.00-8.20 (m, 2 H). [M+H] calc'd for $C_{21}H_{21}FN_4OS$, 397; found, 397.

Example 53

6-((1S,2R)-2-Aminocyclohexylamino)-7-fluoro-4-(1-methyl-1H-pyrazol-4-yl)-1H-pyrrolo[3,4-c]pyridin-3(2H)-one

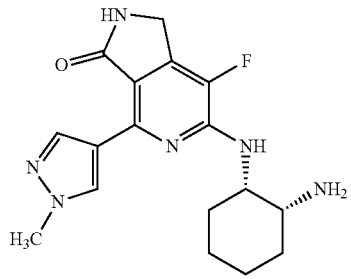 [SMILES: Cn1cc(-c2nc(N[C@H]3CCCC[C@H]3N)c(F)c3c2C(=O)NC3)cn1]

A. tert-Butyl (1R,2S)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate

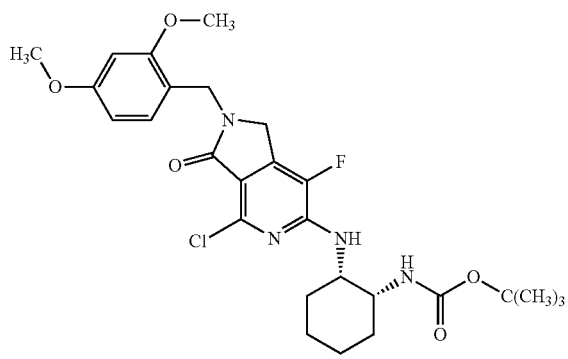 [SMILES: COc1ccc(CN2Cc3c(F)c(N[C@H]4CCCC[C@H]4NC(=O)OC(C)(C)C)nc(Cl)c3C2=O)c(OC)c1]

To a mixture of 4,6-dichloro-2-(2,4-dimethoxybenzyl)-7-fluoro-1H-pyrrolo[3,4-c]pyridin-3(2H)-one (200 mg, 0.539 mmol) and tert-butyl (1R,2S)-2-aminocyclohexylcarbamate (173 mg, 0.808 mmol) in ACN (5 mL) was added N,N-diisopropylethylamine (0.141 mL, 0.808 mmol). The reaction mixture was heated in a sealed vial at 100° C. for several hours after which additional amine (0.5 eq) was added. The mixture was heated overnight and the solvent was subsequently removed in vacuo. The residue was dispersed in DMSO and MeOH (1/1) and the resulting mixture was filtered. The filtrate was purified via preparative HPLC. The fractions were collected and dried in vacuo to give the title compound as a tan solid (60.7 mg, 21%). [M+H] calc'd for $C_{27}H_{34}ClFN_4O_5$, 550; found, 550

B. tert-Butyl (1R,2S)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate

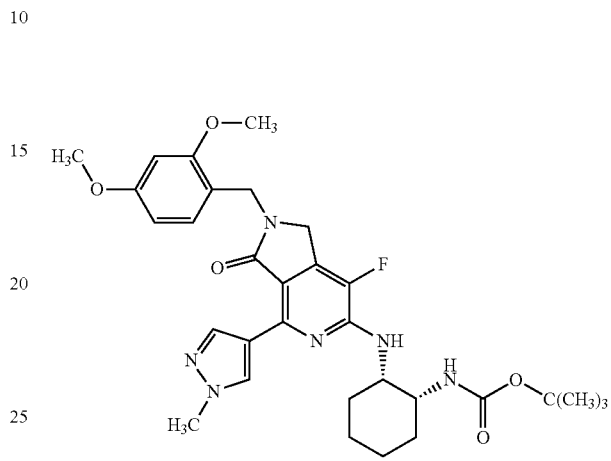

A mixture of tert-butyl (1R,2S)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (60 mg, 0.109 mmol), 1-methyl-4-(4,4,5,5-tetramethyl-1,3,2-dioxaborolan-2-yl)-1H-pyrazole (34 mg, 0.164 mmol) and bis(triphenylphosphine)palladium chloride (15 mg, 0.022 mmol) in DME (1 mL) was placed in a vial. The vial was purged with nitrogen and aqueous sodium carbonate (2 N, 0.219 mL, 0.437 mmol) was added. The vial was sealed and the reaction mixture heated in an oil bath at 85° C. for 3 h. The reaction mixture was filtered through a pad of Celite, which was rinsed with MeOH and DCM. The solvent was removed in vacuo and the residue was diluted with DMSO and MeOH (1/1). The resulting mixture was filtered to recover a white precipitate (31.3 mg). The mother liquor was purified via preparative HPLC. The fractions were collected and dried in vacuo to recover an additional white solid (10.2 mg). The two crops were combined to give the title compound as a white solid (41.5 mg, 64%). [M+H] calc'd for $C_{31}H_{39}FN_6O_5$, 595; found, 595.

C. 6-((1S,2R)-2-Aminocyclohexylamino)-7-fluoro-4-(1-methyl-1H-pyrazol-4-yl)-1H-pyrrolo[3,4-c]pyridin-3(2H)-one A mixture of tert-butyl (1R,2S)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate (41.5 mg, 0.070 mmol) and TFA (2 mL) was heated at 65° C. for 3 h. Following reaction, the solvent was removed in vacuo. The residue was diluted with DMSO and MeOH (1/1), passed through a microfiltration frit, and purified via preparative HPLC. The fractions were collected and dried in vacuo to give a TFA salt of the title compound as a white solid (22 mg, 92%). $^1$H NMR (500 MHz, $CD_3OD$) δ ppm 1.56-2.01 (m, 8 H), 3.85 (br s, 1 H), 3.94 (br s, 3 H), 4.45 (br s, 2 H), 4.67 (br s, 1 H), 8.31 (br s, 1 H), 8.81 (br s, 1 H). [M+H] calc'd for $C_{17}H_{21}FN_6O$, 345; found, 345.

Preparation 16

(R)-tert-Butyl 1-amino-3-ethoxypropan-2-ylcarbamate

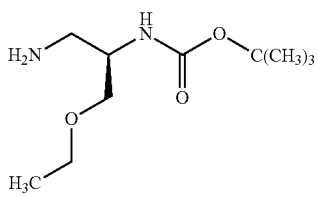

A. (S)-2-(tert-Butoxycarbonylamino)-3-ethoxypropanoic acid

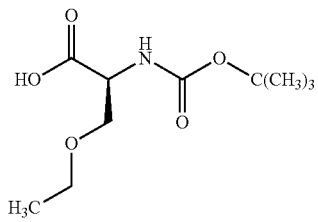

To a suspension of sodium hydride (17.73 g, 702 mmol) in THF (600 mL) at 0° C. was added MeOH (18 mL) dropwise. The mixture was stirred at RT for 1 h to yield a sodium methanolate solution. Iodoethane (25.5 mL, 316 mmol) and a portion of the sodium methanolate solution (120 mL) were added to a solution of (S)-2-(tert-butoxycarbonylamino)-3-hydroxypropanoic acid (18 g, 88 mmol) in THF (600 mL). After stirring at RT for 1 h, the remaining sodium methanolate solution (480 mL) was added, followed by additional iodoethane (9.9 mL, 123 mmol). The mixture was stirred at RT overnight. The mixture was subsequently concentrated and the residue was dissolved in water. The aqueous layer was washed with ether (250 mL), acidified to pH 2 using 1N HCl, and extracted with EtOAc (3×300 mL). The combined organic layers were washed with 1M $Na_2S_2O_3$ (300 mL), dried, and concentrated. The resulting crude material was reconstituted in MeOH, DCM and DMF (total volume: 50 mL) and purified via reverse phase preparative HPLC. The fractions were collected and the ACN was removed via rotary evaporation. The resulting aq solution was neutralized with saturated aq $NaHCO_3$, washed with EtOAc (2×200 mL), dried over $Na_2SO_4$, filtered, and the organic phase stripped to dryness via rotary evaporation to yield the title compound as a clear oil (1.81 g, 9%). [M+H] calc'd for $C_{10}H_{19}NO_5$, 234; found, 234.

B. (R)-tert-Butyl 1-ethoxy-3-hydroxypropan-2-ylcarbamate

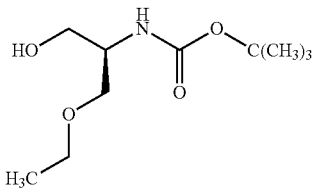

To a solution of (S)-2-(tert-butoxycarbonylamino)-3-ethoxypropanoic acid (1.81 g, 7.76 mmol) in THF (20 mL) at −15° C. was added isobutyl chloroformate (1.015 mL, 7.76 mmol) in THF (5 mL) and 4-methylmorpholine (0.853 mL, 7.76 mmol) in THF (5 mL). After stirring for 10 min at −15° C., the mixture was slowly added to a solution of sodium borohydride (0.881 g, 23.28 mmol) in $H_2O$ (7 mL). The mixture was stirred at −15° C. for 30 min and was diluted with EtOAc. The organic layer was washed with saturated aq $NaHCO_3$ and brine and dried. The residue was carried to next step without further purification (1.6 g, 94%). [M+H] calc'd for $C_{10}H_{21}NO_4$, 220; found, 220.

C. (R)-tert-Butyl 1-azido-3-ethoxypropan-2-ylcarbamate

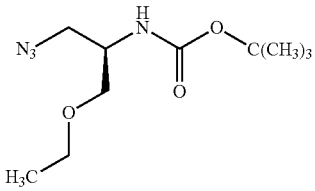 [SMILES: CCOC[C@@H](CN=[N+]=[N-])NC(=O)OC(C)(C)C]

Methanesulfonyl chloride (0.851 mL, 10.95 mmol) in DCM (1 mL) was added to a solution of (R)-tert-butyl 1-ethoxy-3-hydroxypropan-2-ylcarbamate (1.6 g, 7.30 mmol) and $Et_3N$ (1.538 mL, 10.95 mmol) in DCM (10 mL) at 0° C. After stirring at RT for 1 h, the mixture was diluted with EtOAc. The organic layer was washed with saturated aq $NaHCO_3$ solution, dried, and concentrated in vacuo. The residue was dissolved in DMF (10.00 mL). Sodium azide (2.372 g, 36.5 mmol) and tetrabutylammonium iodide (0.270 g, 0.730 mmol) were added, and the reaction mixture was stirred at 75° C. for 4 h. After cooling to RT, the mixture was diluted with EtOAc. The organic layer was washed with saturated aq $NaHCO_3$, dried, and concentrated in vacuo to give the title compound (1.2 g, 67%). [M+H] calc'd for $C_{10}H_{20}N_4O_3$, 245; found, 245.

D. (R)-tert-Butyl 1-amino-3-ethoxypropan-2-ylcarbamate

A mixture of (R)-tert-butyl 1-azido-3-ethoxypropan-2-yl-carbamate (1.2 g, 4.91 mmol) in MeOH (10 mL) was added palladium on carbon (0.523 g, 4.91 mmol). The mixture was stirred under hydrogen atmosphere overnight at RT. The resulting crude material was reconstituted in MeOH (1.0 mL) and purified via reverse phase preparative HPLC. The fractions were collected and solvent was stripped to dryness via rotary evaporation to give the title compound as clear oil (722 mg, 67%). [M+H] calc'd for $C_{10}H_{22}N_2O_3$, 219; found, 219.

Preparation 17

(R)-tert-Butyl 1-ethoxy-3-(3-oxo-4-(m-tolylamino)-2,3-dihydro-1H-pyrrolo[3,4-c]pyridin-6-ylamino)propan-2-ylcarbamate

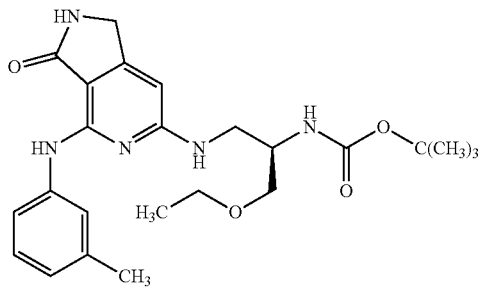 [SMILES: CCOC[C@@H](CNc1cc2c(c(Nc3cccc(C)c3)n1)C(=O)NC2)NC(=O)OC(C)(C)C]

A. (R)-Methyl 6-(2-(tert-butoxycarbonylamino)-3-ethoxypropylamino)-4-cyano-2-(m-tolylamino)nicotinate

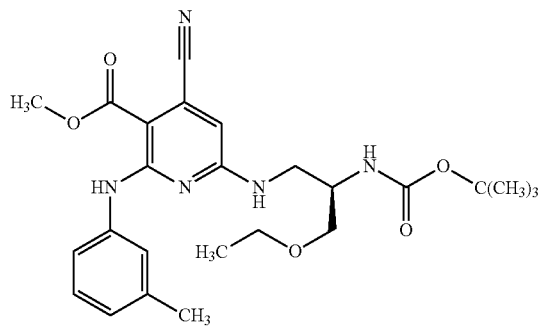 [SMILES: CCOC[C@@H](CNc1cc(C#N)c(C(=O)OC)c(Nc2cccc(C)c2)n1)NC(=O)OC(C)(C)C]

To a solution of methyl 6-chloro-4-cyano-2-(m-tolylamino)nicotinate (200 mg, 0.663 mmol) in DMF (5 mL) was added DIPEA (0.232 mL, 1.326 mmol) and (R)-tert-butyl 1-amino-3-ethoxypropan-2-ylcarbamate (174 mg, 0.795 mmol). The reaction mixture was stirred at RT overnight. Additional (R)-tert-butyl 1-amino-3-ethoxypropan-2-ylcarbamate (231.25 mg, 1.061 mmol) was added and the mixture was heated at 65° C. for 1 h. After cooling to RT, the reaction mixture was diluted with EtOAc (30 mL) and washed with water (2×20 mL) and brine (20 mL). The combined organic layers were dried over $Na_2SO_4$ and concentrated to thick yellow oil. The crude product was used in the next step without further purification (415 mg). [M+H] calc'd for $C_{25}H_{33}N_5O_5$, 484; found, 484.

B. (R)-tert-Butyl 1-ethoxy-3-(3-oxo-4-(m-tolylamino)-2,3-dihydro-1H-pyrrolo[3,4-c]pyridin-6-ylamino)propan-2-ylcarbamate In a flask containing (R)-methyl 6-(2-(tert-butoxycarbonylamino)-3-ethoxypropylamino)-4-cyano-2-(m-tolylamino)nicotinate (400 mg, 0.827 mmol) in HOAc (0.25 mL) and DCM (1 mL) was added platinum(IV) oxide (18.78 mg, 0.083 mmol). The flask was evacuated and filled with $H_2$ three times, and the reaction mixture was stirred vigorously at RT under $H_2$ atmosphere for 3-4 h. The mixture was subsequently filtered through Celite, and the solvent was removed in vacuo. The residue was kept under vacuum overnight to remove excess HOAc. The crude residue was dissolved in anhydrous DCM (20 mL). Potassium carbonate (572 mg, 4.14 mmol) was added, and the mixture was stirred at RT for 8 h. The mixture was filtered through Celite and concentrated in vacuo. The residue was reconstituted in a MeOH/DCM solution (1/1, 5 mL) and purified via reverse phase preparative HPLC. The collected fractions were concentrated in vacuo to give the title compound as a TFA salt (109 mg, 28.9%). [M+H] calc'd for $C_{24}H_{33}N_5O_4$, 456; found, 456.

Example 54

(R)-6-(2-Amino-3-ethoxypropylamino)-4-(m-tolylamino)-1H-pyrrolo[3,4-c]pyridin-3(2H)-one

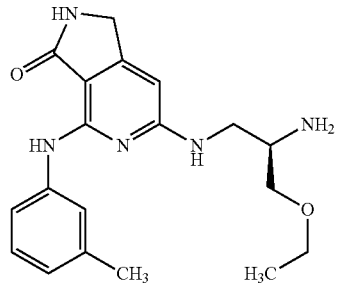 [SMILES: CCOC[C@H](N)CNc1cc2c(c(Nc3cccc(C)c3)n1)C(=O)NC2]

To a solution of (R)-tert-butyl 1-ethoxy-3-(3-oxo-4-(m-tolylamino)-2,3-dihydro-1H-pyrrolo[3,4-c]pyridin-6-ylamino)propan-2-ylcarbamate (109 mg, 0.239 mmol) in DCM (1 mL) was added a TFA/DCM solution (1/1, 10 mL). The mixture was stirred at RT for 2 h. After removal of the solvent, the resulting crude material was reconstituted in a solution of MeOH/DCM (1/1, 5 mL) and was purified via reverse phase preparative HPLC. The fractions were collected, and ACN was removed via rotary evaporation. The resulting aq solution was neutralized with saturated aq $NaHCO_3$, washed with EtOAc (2×200 mL), dried over $Na_2SO_4$, and filtered. The organic phase was stripped to dryness via rotary evaporation to give the title compound (11 mg, 13%). $^1H$ NMR (400 MHz, DMSO-$d_6$) δ ppm 1.08-1.18 (m, 3 H), 1.25-1.44 (m, 4 H), 2.26-2.32 (m, 3 H), 4.07-4.17 (m, 3 H), 4.19-4.29 (m, 2 H), 6.03 (s, 1 H), 6.78 (d, J=7.83 Hz, 1 H), 7.06 (br s, 1 H), 7.12-7.22 (m, 1 H), 7.48 (s, 1 H), 7.60 (d, J=7.83 Hz, 1 H), 7.66-7.75 (m, 2 H), 7.99 (s, 1 H), 8.83-8.97 (m, 1 H). [M+H] calc'd for $C_{19}H_{25}N_5O_2$, 356; found, 356.

Preparation 18

(R)-tert-Butyl 1-ethoxy-3-(7-fluoro-3-oxo-4-(m-tolylamino)-2,3-dihydro-1H-pyrrolo[3,4-c]pyridin-6-ylamino)propan-2-ylcarbamate

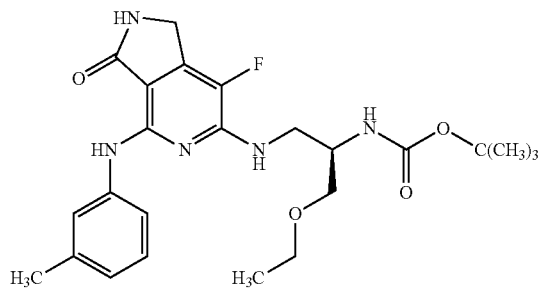 [SMILES: CCOC[C@@H](CNc1nc(Nc2cccc(C)c2)c2c(c1F)CNC2=O)NC(=O)OC(C)(C)C]

To a chilled solution of (R)-tert-butyl 1-ethoxy-3-(3-oxo-4-(m-tolylamino)-2,3-dihydro-1H-pyrrolo[3,4-c]pyridin-6-ylamino)propan-2-ylcarbamate (94.7 mg, 0.208 mmol) in $CH_2Cl_2$ (5 mL) at 0° C. was added SELECTFLUOR® (73.6 mg, 0.208 mmol). The mixture was left stirring in an ice bath and warmed slowly to RT for 6 h. Afterwards, the mixture was diluted with EtOAc (10 mL) and washed with saturated aq $NaHCO_3$ (5 mL) followed by water (5 mL) and brine (5 mL). The organic layers were combined, dried over $Na_2SO_4$, and concentrated to a brown residue. The resulting crude material was reconstituted in MeOH/DCM (5 mL) and purified via preparative HPLC. The collected fractions were collected and ACN was removed via rotary evaporation. The resulting aq solution was neutralized with saturated aq $NaHCO_3$ and washed with EtOAc (2×200 mL), dried over $Na_2SO_4$, filtered, and the organic phase stripped to dryness via rotary evaporation to yield the title compound. [M+H] calc'd for $C_{24}H_{32}FN_5O_4$, 474; found, 474.

Example 55

(R)-6-(2-Amino-3-ethoxypropylamino)-7-fluoro-4-(m-tolylamino)-1H-pyrrolo[3,4-c]pyridin-3(2H)-one

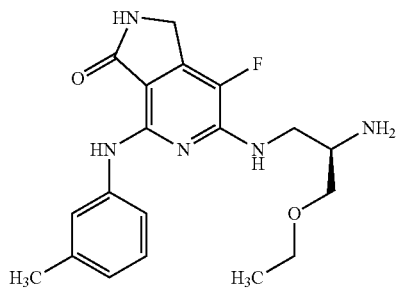 [SMILES: CCOC[C@H](N)CNc1nc(Nc2cccc(C)c2)c2c(c1F)CNC2=O]

A TFA salt of the title compound was prepared in a manner similar to EXAMPLE 54 using (R)-tert-butyl 1-ethoxy-3-(7-fluoro-3-oxo-4-(m-tolylamino)-2,3-dihydro-1H-pyrrolo[3,4-c]pyridin-6-ylamino)propan-2-ylcarbamate in place of (R)-tert-butyl 1-ethoxy-3-(3-oxo-4-(m-tolylamino)-2,3-dihydro-1H-pyrrolo[3,4-c]pyridin-6-ylamino)propan-2-ylcarbamate. $^1H$ NMR (400 MHz, DMSO-$d_6$) δ ppm 1.08-1.19 (m, 3 H), 2.25-2.36 (m, 3 H), 3.38-3.77 (m, 7 H), 4.40 (s, 2 H), 6.80 (d, J=7.58 Hz, 1 H), 7.07-7.25 (m, 2 H), 7.38 (s, 1 H), 7.54 (d, J=7.58 Hz, 1 H), 7.92 (br s, 2 H), 8.28 (s, 1 H), 8.83 (s, 1 H). [M+H] calc'd for $C_{19}H_{24}FN_5O_2$, 374; found, 374.

Preparation 19

3,3,3-Trifluoropropane-1,2-diamine

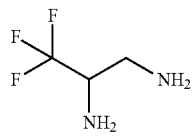

A. 3,3,3-Trifluoro-1-nitroprop-1-ene

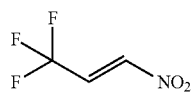

A mixture of 2,2,2-trifluoroethane-1,1-diol (75% aq solution, 20 g, 0.13 mol), $CH_3NO_2$ (24 g, 0.39 mol) and $Na_2CO_3$ (0.85 g, 8 mmol) was stirred overnight at RT. Water (50 mL) was added and the mixture was extracted with diethyl ether (3×30 mL) and dried over $Na_2SO_4$. After concentrating the organic extract at low temperature and under reduced pressure, $P_2O_5$ (20.0 g, 0.14 mol) was added to the residue oil, which was distilled at atmospheric pressure to give a green-yellow oil (4 g, 50% purity, 10% yield). Boiling point 85-90° C.; $^1H$ NMR (400 MHz, $CDCl_3$) δ ppm 7.09-7.17 (m, 1 H), 7.50 (dd, J=2.0 Hz, 12.0 Hz, 1 H).

B. N-Benzyl-1,1,1-trifluoro-3-nitropropan-2-amine

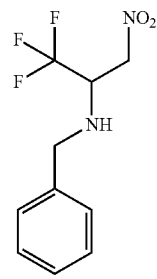

A mixture of 3,3,3-trifluoro-1-nitroprop-1-ene (4 g, 28.4 mmol) and benzylamine (3.2 g, 30.0 mmol) in toluene (50 mL) was stirred for RT or 1 h. The mixture was concentrated and the residue was purified by column chromatography (EtOAc/PE=1/10) to give the title compound (5.5 g, 78%). $^1H$ NMR (400 MHz, CDCl₃) δ ppm 3.91-3.95 (m, 1 H), 4.06-4.14 (m, 1 H), 4.45-4.51 (m, 1 H), 4.63-4.67 (m, 1 H), 7.30-7.39 (m, 5 H).

C. Di-tert-butyl N,N-(3,3,3-trifluoropropane-1,2-diyl)-biscarbamate

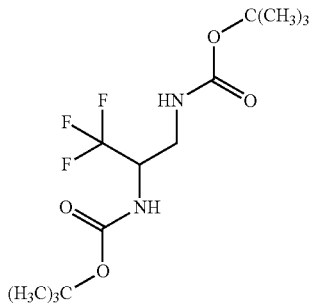 [SMILES: CC(C)(C)OC(=O)NCC(NC(=O)OC(C)(C)C)C(F)(F)F]

A mixture of N-benzyl-1,1,1-trifluoro-3-nitropropan-2-amine (5.5 g, 22.0 mmol) and Pd/C (3.0 g) in MeOH was stirred at RT overnight under H₂ atmosphere. The mixture was subsequently filtered and concentrated to afford an oil, which was combined with di-tert-butyl pyrocarbonate (11.0 g, 50.0 mmol) and Et₃N (5.0 g, 50.0 mmol) in DCM (100 mL). The mixture was stirred overnight and then concentrated. The residue was purified by column chromatography (EtOAc/PE=1/7) to give the title compound as a white solid (5.5 g).

D. 3,3,3-Trifluoropropane-1,2-diamine

A mixture of di-tert-butyl N,N-(3,3,3-trifluoropropane-1,2-diyl)-biscarbamate and 1.0 M HCl-EtOAc was stirred at RT overnight to give the title compound (1.5 g, 54%). ¹H NMR (400 MHz, CD₃OD) δ ppm 3.50-3.55 (m, 1 H), 3.61-3.66 (m, 1 H), 4.58-4.63 (m, 1 H). [M+H] calc'd for $C_3H_7F_3N_2$, 129; found, 129.

Example 56

6-(2-Amino-3,3,3-trifluoropropylamino)-4-(m-tolylamino)-1H-pyrrolo[3,4-c]pyridin-3(2H)-one

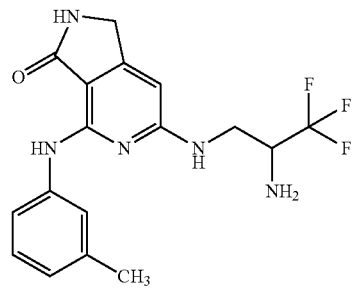 [SMILES: Cc1cccc(Nc2nc(NCC(N)C(F)(F)F)cc3c2C(=O)NC3)c1]

The title compound was prepared in a manner similar to EXAMPLE 54 using 3,3,3-trifluoropropane-1,2-diamine in place of (R)-tert-butyl 1-amino-3-ethoxypropan-2-ylcarbamate. ¹H NMR (400 MHz, DMSO-d₆) δ ppm 1.12-1.39 (m, 2 H), 1.91-2.15 (m, 1 H), 2.22-2.40 (m, 3 H), 3.47-3.66 (m, 1 H), 3.66-3.86 (m, 1 H), 4.14-4.27 (m, 1 H), 4.33-4.46 (m, 1 H), 4.74-4.89 (m, 1 H), 5.96-6.13 (m, 1 H), 6.71-6.86 (m, 1 H), 7.08-7.26 (m, 1 H), 7.38-7.70 (m, 2 H), 8.79-9.07 (m, 1 H). [M+H] calc'd for $C_{17}H_{18}F_3N_5O$, 366; found, 366.

Example 57

(R)-4-Methyl-2-(3-oxo-4-(m-tolylamino)-2,3-dihydro-1H-pyrrolo[3,4-c]pyridin-6-ylamino)pentanamide

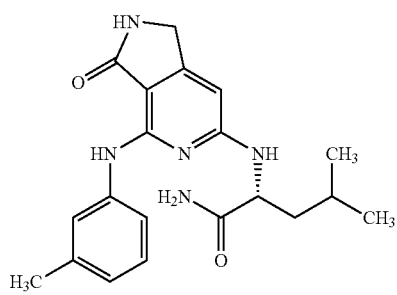 [SMILES: Cc1cccc(Nc2nc(N[C@H](CC(C)C)C(N)=O)cc3c2C(=O)NC3)c1]

The title compound was prepared in a manner similar to EXAMPLE 54 using (R)-2-amino-4-methylpentanamide (64.7 mg, 0.497 mmol) in place of (R)-tert-butyl 1-amino-3-ethoxypropan-2-ylcarbamate. ¹H NMR (400 MHz, DMSO-d₆) δ ppm 0.82-0.88 (m, 3 H), 0.91-0.96 (m, 3 H), 1.18-1.32 (m, 1 H), 1.61 (t, J=7.33 Hz, 2 H), 1.69-1.83 (m, 1 H), 2.24-2.34 (m, 3 H), 4.21 (s, 1 H), 4.37 (s, 1 H), 6.00-6.17 (m, 1 H), 6.69-6.80 (m, 1 H), 6.96 (br s, 1 H), 7.04 (d, J=7.83 Hz, 1 H), 7.10-7.26 (m, 2 H), 7.49 (s, 1 H), 7.58 (d, J=7.33 Hz, 1 H), 7.95 (s, 1 H), 8.82-8.97 (m, 1 H). [M+H] calc'd for $C_{20}H_{25}N_5O_2$, 368; found, 368.

Preparation 20

(3R,4S)-Tetrahydrofuran-3,4-diamine

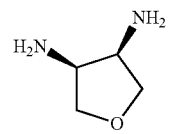

A. (3R,4S)-tetrahydrofuran-3,4-diyl dimethanesulfonate

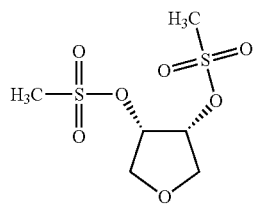

Methanesulfonyl chloride (1.642 mL, 21.13 mmol) in DCM (5 mL) was added to a solution of (3R,4S)-tetrahydrofuran-3,4-diol (0.787 mL, 9.61 mmol) and Et₃N (4.05 mL, 28.8 mmol) in DCM (10 mL) at 0° C. After stirring at 0° C. for 1 h, the mixture was diluted with DCM. The organic layer was washed with saturated aqueous NaHCO$_3$, dried, and concentrated in vacuo to give the title compound as a yellowish white solid (2.5 g, 100%). $^1$H NMR (400 MHz, CDCl$_3$) δ ppm 3.09-3.20 (m, 6 H), 3.90-4.07 (m, 2 H), 4.10-4.22 (m, 2 H), 5.19 (ddd, J=5.31, 3.54, 1.77 Hz, 2 H).

B. (3R,4S)-3,4-Diazidotetrahydrofuran

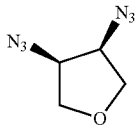 [SMILES: [N-]=[N+]=N[C@H]1COC[C@H]1N=[N+]=[N-]]

To a solution of (3R,4S)-tetrahydrofuran-3,4-diyl dimethanesulfonate (2.5 g, 9.60 mmol) in DMF (50 mL) was added sodium azide (3.75 g, 57.6 mmol) and tetrabutylammonium iodide (0.355 g, 0.960 mmol). The reaction mixture was heated at 100° C. overnight. After cooling to RT, the mixture was diluted with EtOAc, and the organic layer was washed with brine, dried over Na$_2$SO$_4$, and concentrated in vacuo. The residue was dispersed in toluene and the mixture was evaporated in vacuo to remove excess DMF and to give the title compound as brown oil which was used in the next step without further purification (2.2 g). $^1$H NMR (400 MHz, CDCl$_3$) δ ppm 3.72-3.87 (m, 2 H), 3.94-4.46 (m, 4 H).

C. (3R,4S)-Tetrahydrofuran-3,4-diamine

To a mixture of (3R,4S)-3,4-diazidotetrahydrofuran (2.2 g, 14.27 mmol) dispersed in MeOH (10 mL) and DCM (8 mL) was added palladium on carbon (1.519 g, 14.27 mmol). The reaction mixture was stirred under H$_2$ atmosphere overnight. Following hydrogenation, the mixture was filtered through Celite and the solvent was removed in vacuo to yield the title compound which was used without further purification (1.54 g).

Example 58

6-(cis-4-Aminotetrahydrofuran-3-ylamino)-4-(m-tolylamino)-1H-pyrrolo[3,4-c]pyridin-3(2H)-one

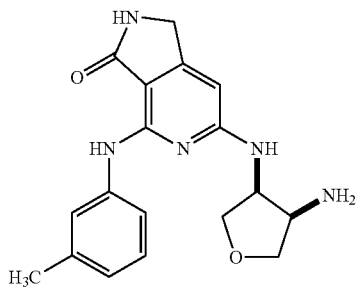

A. Methyl 6-(cis-4-Aminotetrahydrofuran-3-ylamino)-4-cyano-2-(m-tolylamino)nicotinate

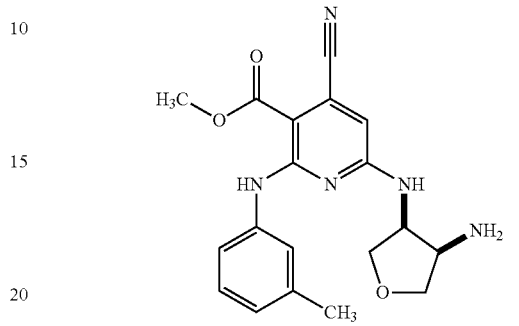

To a solution of methyl 6-chloro-4-cyano-2-(m-tolylamino)nicotinate (40 mg, 0.133 mmol) in DMF (1 mL) was added DIPEA (0.046 mL, 0.265 mmol) and (3R,4S)-tetrahydrofuran-3,4-diamine (13.54 mg, 0.133 mmol). The mixture was stirred at RT overnight. Additional amine was added and the reaction mixture was stirred at RT for an additional day. The reaction mixture was diluted in MeOH (10 mL) and purified by reverse phase preparative HPLC. The fractions were collected and ACN was removed via rotary evaporation. The resulting aq solution was neutralized with saturated aq NaHCO$_3$ and washed with EtOAc (2×200 mL), dried over Na$_2$SO$_4$, and filtered. The organic phase was stripped to dryness via rotary evaporation to yield the title compound (35.5 mg, 73%). [M+H] calc'd for C$_{19}$H$_{21}$N$_5$O$_3$, 368; found, 368.

B. 6-(cis-4-Aminotetrahydrofuran-3-ylamino)-4-(m-tolylamino)-1H-pyrrolo[3,4-c]pyridin-3(2H)-one To a vessel containing methyl 6-(cis-4-aminotetrahydrofuran-3-ylamino)-4-cyano-2-(m-tolylamino)nicotinate (35.5 mg, 0.097 mmol) in MeOH (5 mL) and HOAc (2.5 mL) was added palladium on carbon (1.028 mg, 9.66 μmol). The vessel was evacuated and filled with H$_2$ three times, and the mixture was then stirred vigorously at RT under H$_2$ atmosphere overnight. The mixture was subsequently filtered through Celite, and the solvent was removed in vacuo. The residue was dissolved in DCM (10 mL) and MeOH (5 mL) and potassium carbonate (26.7 mg, 0.193 mmol) was added. The mixture was stirred at RT overnight. Additional potassium carbonate (40.1 mg, 0.290 mmol) was added and the reaction mixture was stirred for 4 h at RT, and then heated at 50° C. for 30 min. The mixture was filtered to remove solid K$_2$CO$_3$ and the filtrate was diluted with MeOH (10 mL) and purified by reverse phase preparative HPLC. The fractions were collected and concentrated in vacuo to give a TFA salt of the title compound (4.5 mg, 13.7%). $^1$H NMR (500 MHz, DMSO-d$_6$) δ ppm 2.30 (s, 3 H), 2.52-2.58 (m, 2 H), 3.67-3.83 (m, 2 H), 3.90 (br s, 1 H), 3.98-4.14 (m, 2 H), 4.20-4.30 (m, 2 H), 4.58 (br s, 1 H), 6.16 (s, 1 H), 6.81 (d, J=7.32 Hz, 1 H), 7.11-7.27

(m, 2 H), 7.46 (d, J=7.32 Hz, 1 H), 7.59 (br s, 1 H), 8.08 (s, 1 H), 8.94 (s, 1 H). [M+H] calc'd for $C_{18}H_{21}N_5O_2$, 340; found, 340.

Preparation 21 tert-Butyl (1S,2R)-2-(4-(1-ethyl-1H-pyrazol-4-yl)-3-oxo-2,3-dihydro-1H-pyrrolo[3,4-c]pyridin-6-ylamino)cyclohexylcarbamate

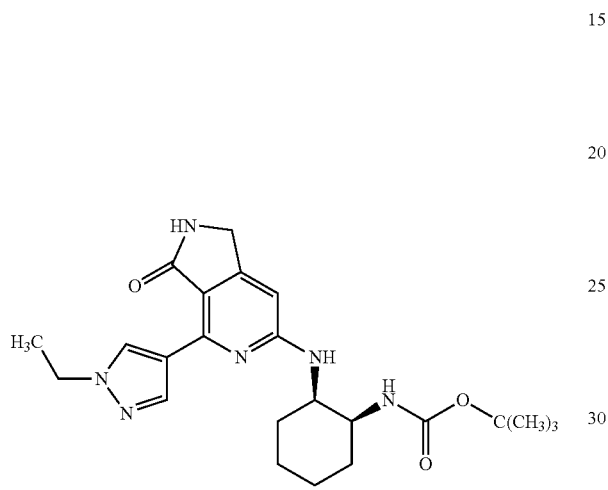

A. Methyl 4-cyano-2-(1-ethyl-1H-pyrazol-4-yl)nicotinate

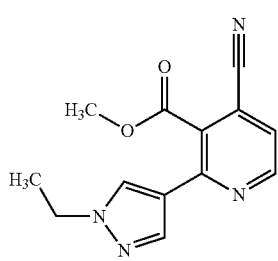 [SMILES: CCn1cc(-c2nccc(C#N)c2C(=O)OC)cn1]

A mixture of methyl 2-chloro-4-cyanonicotinate (207 mg, 1.053 mmol), 1-ethyl-4-(4,4,5,5-tetramethyl-1,3,2-dioxaborolan-2-yl)-1H-pyrazole (201 mg, 0.905 mmol) and tetrakis(triphenylphosphine)palladium(0) (122 mg, 0.105 mmol) in DME (2 mL), and saturated aq $Na_2CO_3$ (2 mL) was stirred at 80° C. for 3 h under $N_2$ atmosphere. Water and EtOAc were subsequently added. The organic phase was washed with $H_2O$ and brine, dried over $MgSO_4$, and evaporated to yield the title compound (265.3 mg, 98%). [M+H] calc'd for $C_{13}H_{12}N_4O_2$, 257; found, 257.

B. 4-Cyano-2-(1-ethyl-1H-pyrazol-4-yl)-3-(methoxycarbonyl)pyridine 1-oxide

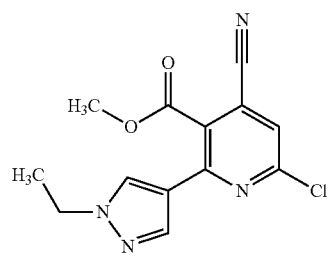 [SMILES: CCn1cc(-c2nc(Cl)cc(C#N)c2C(=O)OC)cn1]

To a mixture of methyl 4-cyano-2-(1-ethyl-1H-pyrazol-4-yl)nicotinate (207 mg, 0.808 mmol) in ACN (2 mL) was added urea hydrogen peroxide (380 mg, 4.04 mmol) and trifluoroacetic anhydride (0.456 mL, 3.23 mmol) at 0° C. The resulting mixture was stirred at RT overnight. Next, saturated aq $NaHCO_3$ solution and chloroform were added. The aqueous phase was extracted with chloroform (3×200 mL). The organic layers were combined and washed with brine, dried over $MgSO_4$, and evaporated to give the title compound which was used without further purification (210 mg, 95%). [M+H] calc'd for $C_{13}H_{12}N_4O_3$, 273.5; found, 273.5.

C. Methyl 6-chloro-4-cyano-2-(1-ethyl-1H-pyrazol-4-yl)nicotinate

A solution of 4-cyano-2-(1-ethyl-1H-pyrazol-4-yl)-3-(methoxycarbonyl)pyridine 1-oxide (210 mg, 0.771 mmol) in $POCl_3$ (2 mL) was heated at 80° C. for 3-4 h. The mixture was concentrated and purified by flash chromatography ($SiO_2$, 10-100% EtOAc in Hexane). The fractions were collected and the solvent was removed in vacuo to give the title compound (201 mg, 90%).

D. Methyl 6-((1R,2S)-2-(tert-butoxycarbonylamino) cyclohexylamino)-4-cyano-2-(1-ethyl-1H-pyrazol-4-yl)nicotinate

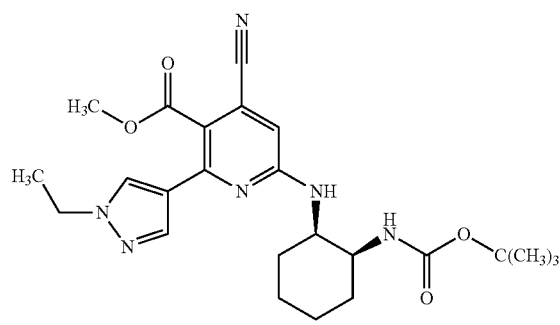 [SMILES: CCn1cc(-c2nc(N[C@@H]3CCCC[C@@H]3NC(=O)OC(C)(C)C)cc(C#N)c2C(=O)OC)cn1]

To a solution of methyl 6-chloro-4-cyano-2-(1-ethyl-1H-pyrazol-4-yl)nicotinate (201 mg, 0.691 mmol) in DMF (1 mL) was added DIPEA (0.242 mL, 1.383 mmol) and tert-butyl (1S,2R)-2-aminocyclohexylcarbamate (237 mg, 1.106 mmol). The reaction mixture was stirred at 100° C. overnight, after which the solvent was removed, and the resulting crude material was diluted in MeOH (5.0 mL) and purified via reverse phase preparative HPLC. The collected fractions were collected and ACN was removed via rotary evaporation. The resulting aq solution was neutralized with saturated aq NaHCO$_3$ and washed with EtOAc (2×200 mL), dried over Na$_2$SO$_4$, and filtered. The organic phase was stripped to dryness via rotary evaporation to yield the title compound (62 mg, 19%). [M+H] calc'd for C$_{24}$H$_{32}$N$_6$O$_4$, 469; found, 469.

E. tert-Butyl (1S,2R)-2-(4-(1-ethyl-1H-pyrazol-4-yl)-3-oxo-2,3-dihydro-1H-pyrrolo[3,4-c]pyridin-6-ylamino)cyclohexylcarbamate To a flask containing methyl 6-((1R,2S)-2-(tert-butoxycarbonylamino)cyclohexyl-amino)-4-cyano-2-(1-ethyl-1H-pyrazol-4-yl)nicotinate (62 mg, 0.132 mmol) in MeOH (2 mL) was added HOAc (1 mL) to give a yellow solution. Palladium on carbon was added (14.08 mg, 0.132 mmol). The flask was evacuated and filled with H$_2$ three times, after which the mixture was stirred vigorously at RT under a H$_2$ atmosphere overnight. The mixture was filtered through Celite, and the solvent was removed in vacuo to give a residue, which was dissolved in DCM (10 mL) and MeOH (10 mL). Potassium carbonate was added and the mixture was stirred for 5 h. The solids were filtered out and the filtrate concentrated to give the title compound (50 mg, 86%). [M+H] calc'd for C$_{23}$H$_{32}$N$_6$O$_3$, 441; found, 441.

Example 59

6-((1R,2S)-2-Aminocyclohexylamino)-4-(1-ethyl-1H-pyrazol-4-yl)-1H-pyrrolo[3,4-c]pyridin-3(2H)-one

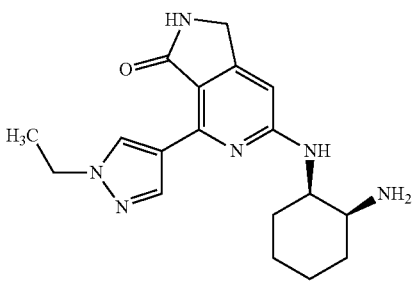 [SMILES: CCn1cc(-c2nc(N[C@@H]3CCCC[C@@H]3N)cc3c2C(=O)NC3)cn1]

To a solution of tert-butyl (1S,2R)-2-(4-(1-ethyl-1H-pyrazol-4-yl)-3-oxo-2,3-dihydro-1H-pyrrolo[3,4-c]pyridin-6-ylamino)cyclohexylcarbamate (50 mg, 0.113 mmol) in DCM (1 mL) was added DCM/TFA (1/1, 2 mL). The mixture was stirred at RT for 2 h. After removal of solvent, the resulting crude material was reconstituted in MeOH (5.0 mL) and was purified by preparative HPLC. The fractions were collected and the solvent stripped to dryness via rotary evaporation to yield the title compound as a TFA salt (10.5 mg, 27%). $^1$H NMR (500 MHz, DMSO-d$_6$) δ ppm 1.31-1.55 (m, 6 H), 1.58-1.86 (m, 8 H), 4.20-4.31 (m, 3 H), 6.56 (s, 1 H), 6.84 (d, J=7.32 Hz, 1 H), 7.56-7.76 (m, 2 H), 8.10 (s, 1 H), 8.38 (s, 1 H), 8.96 (s, 1 H). [M+H] calc'd for C$_{18}$H$_{24}$N$_6$O, 341; found, 341.

Example 60

6-((1R,2S)-2-Aminocyclohexylamino)-4-(1-ethyl-1H-pyrazol-4-yl)-7-fluoro-1H-pyrrolo[3,4-c]pyridin-3(2H)-one

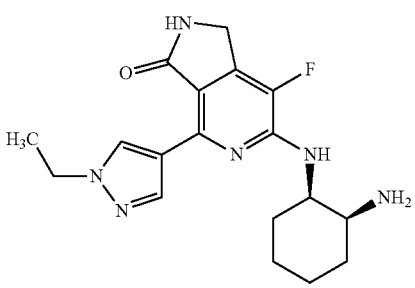 [SMILES: CCn1cc(-c2nc(N[C@@H]3CCCC[C@@H]3N)c(F)c3c2C(=O)NC3)cn1]

A. tert-Butyl (1S,2R)-2-(4-(1-ethyl-1H-pyrazol-4-yl)-7-fluoro-3-oxo-2,3-dihydro-1H-pyrrolo[3,4-c]pyridin-6-ylamino)cyclohexylcarbamate

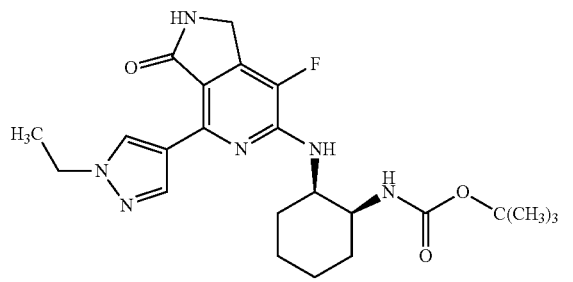 [SMILES: CCn1cc(-c2nc(N[C@@H]3CCCC[C@@H]3NC(=O)OC(C)(C)C)c(F)c3c2C(=O)NC3)cn1]

A solution of tert-Butyl (1S,2R)-2-(4-(1-ethyl-1H-pyrazol-4-yl)-3-oxo-2,3-dihydro-1H-pyrrolo[3,4-c]pyridin-6-ylamino)cyclohexylcarbamate (69.7 mg, 0.158 mmol) in DCM (5 mL) was cooled to 0° C. SELECTFLUOR® (84 mg, 0.237 mmol) was added. The mixture was left stirring in an ice bath and was allowed to warm slowly to RT with stirring overnight. Additional SELECTFLUOR® (2 eq) was added and the reaction was stopped after 2 h. After removal of solvent, the residue was diluted with EtOAc (10 mL) and washed with saturated aq NaHCO$_3$ (5 mL), water (5 mL), and brine (5 mL). The organic layers were combined, dried over Na$_2$SO$_4$, and concentrated to a brown residue. The resulting crude material was reconstituted in MeOH/DCM (6 mL) and was purified via preparative HPLC. The fractions were collected and ACN was removed via rotary evaporation. The resulting aq solution was neutralized with saturated aq NaHCO$_3$, washed with EtOAc (2×200 mL), dried over Na$_2$SO$_4$, and filtered. The organic phase was stripped to dryness via rotary evaporation to yield the title compound (20 mg, 28%). [M+H] calc'd for C$_{23}$H$_{31}$FN$_6$O$_3$, 459; found, 459.

B. 6-((1R,2S)-2-Aminocyclohexylamino)-4-(1-ethyl-1H-pyrazol-4-yl)-7-fluoro-1H-pyrrolo[3,4-c]pyridin-3(2H)-one To a solution of tert-butyl (1S,2R)-2-(4-(1-ethyl-1H-pyrazol-4-yl)-7-fluoro-3-oxo-2,3-dihydro-1H-pyrrolo[3,4-c]pyridin-6-ylamino)cyclohexylcarbamate (20 mg, 0.044 mmol) in DCM (1 mL) was added DCM/TFA (1/1, 2 mL). The mixture was stirred at RT for 2 h. After removal of solvent, the resulting crude material was reconstituted in MeOH (5.0 mL) and was purified by preparative HPLC. The fractions were collected and solvent stripped to dryness via rotary evaporation to yield the title compound as a TFA salt (7 mg, 45%). $^1$H NMR (500 MHz, DMSO-d$_6$) δ ppm 1.40 (t, J=7.08 Hz, 4 H), 1.54-1.72 (m, 2 H), 1.75-1.97 (m, 2 H), 3.47-3.60 (m, 2 H), 3.69 (br s, 1 H), 4.18 (q, J=7.32 Hz, 2 H), 4.33-4.52 (m, 3 H), 6.74 (d, J=6.83 Hz, 1 H), 7.77 (br s, 3 H), 8.26-8.44 (m, 2 H), 8.88 (s, 1 H). [M+H] calc'd for C$_{18}$H$_{23}$FN$_6$O, 359; found, 359.

Preparation 22

1-Isopropyl-4-(4,4,5,5-tetramethyl-1,3,2-dioxaborolan-2-yl)-1H-pyrazole

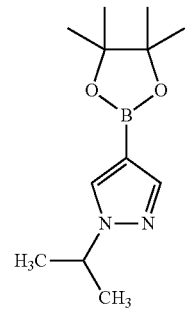 [SMILES: CC(C)n1cc(B2OC(C)(C)C(C)(C)O2)cn1]

In a microwave vial, a solution of 4-(4,4,5,5-tetramethyl-1,3,2-dioxaborolan-2-yl)-1H-pyrazole (1 g, 5.15 mmol) in DMF (10 mL) was added cesium carbonate (5.04 g, 15.46 mmol) and 2-iodopropane (2.58 mL, 25.8 mmol). The mixture was heated at 100° C. overnight. After cooling to RT, H$_2$O (300 mL) was added and the aqueous layer was extracted with EtOAC (2×200 mL). The organic extracts were combined, dried over Na$_2$SO$_4$, filtered, and solvent was removed in vacuo. The resulting crude material was reconstituted in MeOH (1.0 mL) and purified by HPLC. The fractions were collected and stripped to dryness via rotary evaporation to yield the title compound. [M+H] calc'd for C$_{12}$H$_{21}$BN$_2$O$_2$, 237; found 237.

Preparation 23

1-Cyclopropyl-4-(4,4,5,5-tetramethyl-1,3,2-dioxaborolan-2-yl)-1H-pyrazole

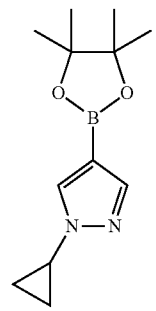 [SMILES: CC1(C)OB(c2cnn(C3CC3)c2)OC1(C)C]

The title compound was prepared in a manner similar to PREPARATION 22 using bromocyclopropane in place of iodopropane. [M+H] calc'd for $C_{12}H_{19}BN_2O_2$, 234; found, 234.

Preparation 24

1-(Difluoromethyl)-4-(4,4,5,5-tetramethyl-1,3,2-dioxaborolan-2-yl)-1H-pyrazole

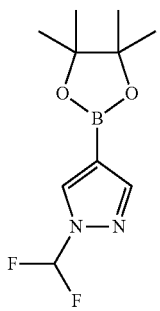 [SMILES: CC1(C)OB(c2cnn(C(F)F)c2)OC1(C)C]

The title compound was prepared in a manner similar to PREPARATION 22 using difluoroiodomethane in place of iodopropane and carrying out the reaction at 90° C. [M+H] calc'd for $C_{10}H_{15}BF_2N_2O_2$, 245; found, 245.

Example 61

6-((1R,2S)-2-Aminocyclohexylamino)-4-(1-cyclopropyl-1H-pyrazol-4-yl)-1H-pyrrolo[3,4-c]pyridin-3(2H)-one

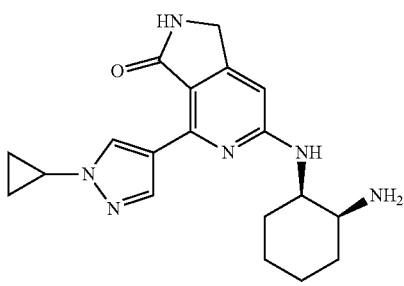 [SMILES: N[C@H]1CCCC[C@H]1Nc1cc2c(c(-c3cnn(C4CC4)c3)n1)C(=O)NC2]

A TFA salt of the title compound was prepared in a manner similar to EXAMPLE 59 using 1-cyclopropyl-4-(4,4,5,5-tetramethyl-1,3,2-dioxaborolan-2-yl)-1H-pyrazole in place of 1-ethyl-4-(4,4,5,5-tetramethyl-1,3,2-dioxaborolan-2-yl)-1H-pyrazole. $^1$H NMR (500 MHz, CD$_3$OD) δ ppm 1.47-1.67 (m, 4 H), 1.69-1.95 (m, 8 H), 3.63-3.74 (m, 3 H), 4.35 (s, 2 H), 6.65 (s, 1 H), 8.35 (s, 1 H), 8.96 (s, 1 H). [M+H] calc'd for $C_{19}H_{24}N_6O$, 353; found, 353.

Example 62

6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one

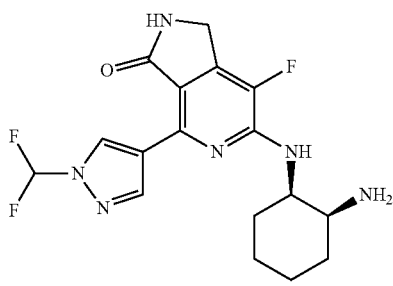 [SMILES: N[C@H]1CCCC[C@H]1Nc1nc(-c2cnn(C(F)F)c2)c2c(c1F)CNC2=O]

A. tert-Butyl (1S,2R)-2-(4-(1-(difluoromethyl)-1H-pyrazol-4-yl)-2-(2,4-dimethoxybenzyl)-7-fluoro-3-oxo-2,3-dihydro-1H-pyrrolo[3,4-c]pyridin-6-ylamino)cyclohexylcarbamate

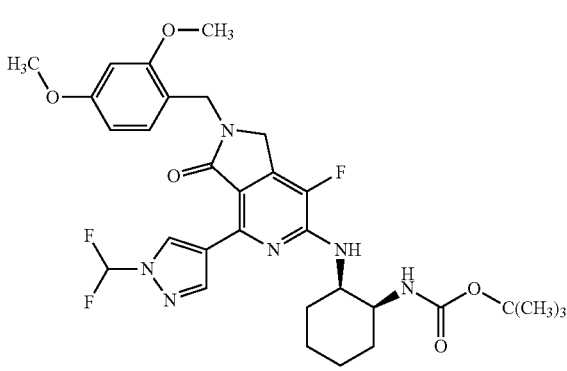 [SMILES: COc1ccc(CN2Cc3c(F)c(N[C@@H]4CCCC[C@@H]4NC(=O)OC(C)(C)C)nc(-c4cnn(C(F)F)c4)c3C2=O)c(OC)c1]

A solution of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (35 mg, 0.064 mmol), 1-(difluoromethyl)-4-(4,4,5,5-tetramethyl-1,3,2-dioxaborolan-2-yl)-1H-pyrazole (18.67 mg, 0.076 mmol) and bis(triphenylphosphine)palladium chloride (44.7 mg, 0.064 mmol) in dioxane (500 μL) and saturated aq Na$_2$CO$_3$ (500 μL) was heated at 85° C. for 2 h. After filtering out the solids, the solvent was removed and the residue was dissolved in MeOH and DCM and purified by preparative HPLC. The fractions were collected and ACN was removed via rotary evaporation. The resulting aq solution was neutralized with saturated aq NaHCO$_3$, washed with EtOAc (2×200 mL), dried over Na$_2$SO$_4$, and filtered. The organic phase was stripped to dryness via rotary evaporation to yield the title compound (36 mg, 90%). [M+H] calc'd for $C_{31}H_{37}F_3N_6O_5$, 631; found, 631.

B. 6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one A solution of tert-butyl (1S,2R)-2-(4-(1-(difluoromethyl)-1H-pyrazol-4-yl)-2-(2,4-dimethoxybenzyl)-7-fluoro-3-oxo- 2,3-dihydro-1H-pyrrolo[3,4-c]pyridin-6-ylamino)cyclohexylcarbamate (36 mg, 0.057 mmol) in TFA (2 mL) was heated at 60° C. for 2 h. After removal of the solvent, the residue was diluted in MeOH (2 mL) and was purified by preparative HPLC. The fractions were collected and stripped to dryness via rotary evaporation to yield the title compound as a TFA salt (18.7 mg, 86%). $^1$H NMR (500 MHz, DMSO-$d_6$) δ ppm 1.40-1.52 (m, 2 H), 1.58-1.76 (m, 3 H), 1.75-1.94 (m, 3 H), 3.67 (br s, 1 H), 4.44 (d, J=4.88 Hz, 2 H), 4.53 (br s, 1 H), 6.86 (d, J=6.83 Hz, 1 H), 7.71 (br s, 2 H), 7.79-8.12 (m, 1 H), 8.53 (s, 2 H), 9.41 (s, 1 H). [M+H] calc'd for $C_{17}H_{19}F_3N_6O$, 381; found, 381.

Example 63

6-((1R,2S)-2-Aminocyclohexylamino)-4-(1-cyclopropyl-1H-pyrazol-4-yl)-7-fluoro-1H-pyrrolo[3,4-c]pyridin-3(2H)-one

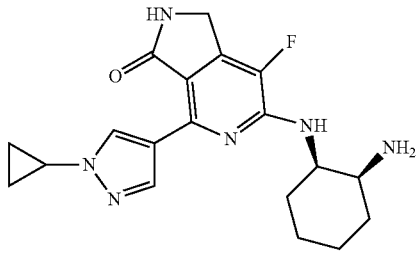 [SMILES: N[C@H]1CCCC[C@H]1Nc1nc(-c2cnn(C3CC3)c2)c2c(c1F)CNC2=O]

A TFA salt of the title compound was prepared in a manner similar to EXAMPLE 62 using 1-cyclopropyl-4-(4,4,5,5-tetramethyl-1,3,2-dioxaborolan-2-yl)-1H-pyrazole in place of 1-(difluoromethyl)-4-(4,4,5,5-tetramethyl-1,3,2-dioxaborolan-2-yl)-1H-pyrazole. $^1$H NMR (500 MHz, DMSO-$d_6$) δ ppm 0.94-1.11 (m, 4 H), 1.47 (d, J=6.35 Hz, 2 H), 1.56-1.97 (m, 6 H), 3.60-3.85 (m, 2 H), 4.28-4.53 (m, 3 H), 6.74 (d, J=6.35 Hz, 1 H), 7.70 (br s, 2 H), 8.25 (s, 1 H), 8.38 (s, 1 H), 8.94 (s, 1 H). [M+H] calc'd for $C_{19}H_{23}FN_6O$, 371; found, 371.

Example 64 cis-6-(2-Aminocyclohexylamino)-7-fluoro-4-(1-methyl-1H-pyrazol-4-yl)-1H-pyrrolo[3,4-c]pyridin-3(2H)-one

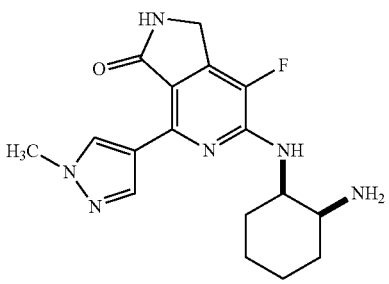

A. cis-tert-Butyl 2-(4-chloro-2-(2,4-dimethoxybenzyl)-7-fluoro-3-oxo-2,3-dihydro-1H-pyrrolo[3,4-c]pyridin-6-ylamino)cyclohexylcarbamate

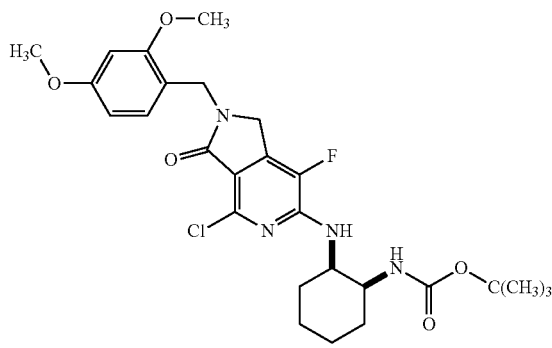 [SMILES: COc1ccc(CN2Cc3c(F)c(N[C@@H]4CCCC[C@@H]4NC(=O)OC(C)(C)C)nc(Cl)c3C2=O)c(OC)c1]

A mixture of 4,6-dichloro-2-(2,4-dimethoxybenzyl)-7-fluoro-1H-pyrrolo[3,4-c]pyridin-3(2H)-one (316 mg, 0.851 mmol) and cis-tert-butyl 2-aminocyclohexylcarbamate (365 mg, 1.703 mmol) and DIPEA (0.743 mL, 4.26 mmol) in ACN (2 mL) was stirred at 85° C. for 3 d. The resulting crude material was reconstituted in MeOH (1 mL) and purified by preparative HPLC. The fractions were collected and stripped to dryness via rotary evaporation to yield the title compound (161 mg, 34%). $^1$H NMR (500 MHz, DMSO-$d_6$) δ ppm 1.35 (br s, 10 H), 1.58 (br s, 2 H), 1.76 (br s, 2 H), 3.71-3.90 (m, 11 H), 4.33 (br s, 2 H), 4.51 (br s, 2 H), 6.43-6.72 (m, 3 H), 6.87 (br s, 1 H), 7.07 (br s, 1 H). [M+H] calc'd for $C_{27}H_{34}ClFN_4O_5$, 549; found, 549.

B. cis-tert-Butyl 2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate

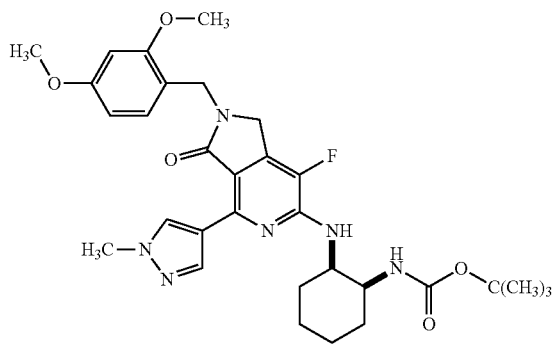 [SMILES: COc1ccc(CN2Cc3c(F)c(N[C@@H]4CCCC[C@@H]4NC(=O)OC(C)(C)C)nc(-c4cnn(C)c4)c3C2=O)c(OC)c1]

A solution of cis-tert-butyl 2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (135.8 mg, 0.247 mmol), 1-methyl-4-(4,4,5,5-tetramethyl-1,3,2-dioxaborolan-2-yl)-1H-pyrazole (154 mg, 0.742 mmol) and bis(triphenylphosphine)palladium chloride (174 mg, 0.247 mmol) in dioxane (2 mL) and saturated aq $Na_2CO_3$ (2 mL) was heated at 120° C. for 30 min. After filtering out the solids, the solvent was removed and the residue was dissolved in MeOH and DCM and the mixture was purified by preparative HPLC. The fractions were collected and the solvent was stripped to dryness via rotary evaporation to give the title compound (109 mg, 74%). $^1$H NMR (500 MHz, DMSO-$d_6$) δ ppm 0.97-1.98 (m, 10 H), 2.28-2.44 (m, 3 H), 2.56-2.72 (m, 4 H), 3.63-3.99 (m, 11 H), 4.36 (d, J=18.06 Hz, 2 H), 4.56 (br s, 2 H), 6.50 (br s, 1 H), 6.61 (br s, 1 H), 6.65-6.81 (m, 1 H), 7.08 (br s, 1 H), 7.70 (br s, 1 H), 8.30 (br s, 1 H), 8.75-9.02 (m, 1 H). [M+H] calc'd for $C_{31}H_{39}FN_6O_5$, 595; found, 595.

C. cis-6-(2-Aminocyclohexylamino)-7-fluoro-4-(1-methyl-1H-pyrazol-4-yl)-1H-pyrrolo[3,4-c]pyridin-3(2H)-one A solution of cis-tert-butyl 2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)cyclohexylcarbamate (109 mg, 0.183 mmol) in TFA (5 mL) was heated at 60° C. for 2 h. After removal of the solvent, the residue was diluted in MeOH (2 mL) and was purified by preparative HPLC. The fractions were collected and stripped to dryness via rotary evaporation to give the title compound as a TFA salt. $^1$H NMR (500 MHz, DMSO-$d_6$) δ ppm 1.47 (br s, 2 H), 1.57-1.75 (m, 3 H), 1.84 (br s, 2 H), 3.12-3.23 (m, 2 H), 3.87-3.94 (m, 3 H), 4.35-4.50 (m, 3 H), 6.73 (br s, 1 H), 7.71 (br s, 2 H), 8.28-8.44 (m, 2 H), 8.84 (d, J=3.91 Hz, 1 H). [M+H] calc'd for $C_{17}H_{21}FN_6O$, 345; found, 345.

Example 65

6-((3R,4R)-3-Aminotetrahydro-2H-pyran-4-ylamino)-7-fluoro-4-(1-methyl-1H-pyrazol-4-yl)-1H-pyrrolo[3,4-c]pyridin-3(2H)-one

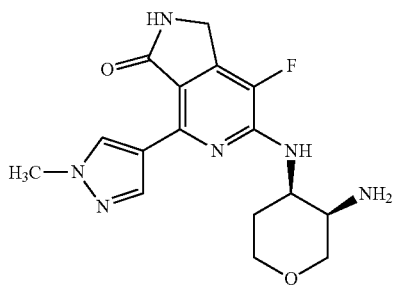 [SMILES: Cn1cc(-c2nc(N[C@@H]3CCOC[C@@H]3N)c(F)c3c2C(=O)NC3)cn1]

A TFA salt of the title compound was prepared in a manner similar to EXAMPLE 64 using (3R,4R)-tetrahydro-2H-pyran-3,4-diamine dihydrochloride in place of cis-tert-butyl 2-aminocyclohexylcarbamate. The desired stereoisomer was isolated using preparative HPLC. $^1$H NMR (500 MHz, CD$_3$OD) δ ppm 1.29 (br s, 2 H), 1.86-1.99 (m, 1 H), 3.84-3.99 (m, 4 H), 4.03-4.17 (m, 1 H), 4.45 (br s, 2 H), 8.29 (br s, 1 H), 8.79 (br s, 1 H). [M+H] calc'd for $C_{16}H_{19}FN_6O_{20}$, 347; found, 347.

Preparation 25 cis-4,4-Difluorocyclopentane-1,2-diamine

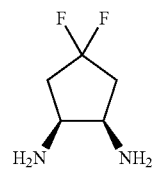

A. Cyclopenta-1,3-diene

A flask containing dicyclopentadiene was flushed with N$_2$ for 1 min and was then heated by oil bath to approximately 180° C. Cyclopentadiene distilled slowly at 40-45° C. The title compound (100 g) was collected and kept at −70° C. under N$_2$. $^1$H NMR (400 MHz, CDCl$_3$) δ ppm 3.02 (t, J=1.4 Hz, 2 H), 6.49-6.51 (m, 2 H), 6.61-6.62 (m, 2 H).

B. Cyclopent-3-enol

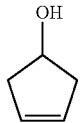

To cooled alpha-pinene (225.0 g, 1.65 mol) at 0° C. was added dropwise BH$_3$-THF (1 M, 750 mL) over a 30 min period under N$_2$ atmosphere. The reaction mixture was stirred for 3.5 h at 0° C. Distilled cyclopenta-1,3-diene (99.0 g, 1.50 mol) was added dropwise at 0° C. over a 40 min period. The resulting mixture was slowly warmed to RT and stirred for 20 h. Excess hydride was decomposed by adding water (30 mL) at a temperature below 10° C. Aqueous NaOH (3N, 300 mL) was added at a temperature below 5° C., followed by H$_2$O$_2$ (30%, 250 mL). The aqueous layer was salted out with NaCl, and the organic layer was separated and dried over Na$_2$SO$_4$. The product was distilled at 65° C. under a reduced pressure of 20 mm Hg to give the title compound as an oil (30.4 g, 24%). $^1$H NMR (400 MHz, CDCl$_3$) δ ppm 2.29 (d, J=17.6 Hz, 2 H), 2.61 (dd, J=6.0, 16.4 Hz, 2 H), 4.82 (s, 1 H), 5.68 (s, 2 H).

C. ((Cyclopent-3-enyloxy)methyl)benzene

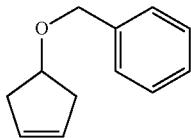 [SMILES: C1=CCC(OCc2ccccc2)C1]

To a cooled solution of cyclopent-3-enol (30.40 g, 0.36 mol) in THF (300 mL) at 0° C. was added NaH (18.82 g, 0.47 mol, 60% in mineral oil). After effervescence had ceased, benzyl bromide (80.45 g, 0.47 mol) was added dropwise at 0° C. over a 45 min period. The reaction mixture was allowed to warm to RT over a 6 h period. Excess NaH was quenched with MeOH (120 mL) at a temperature below 5° C. The mixture was warmed to RT, diluted with H$_2$O, and the two layers were separated. The aqueous layer was extracted with EtOAc. The organic layers were combined, concentrated, and purified by column chromatography eluting with petroleum ether and EtOAc (PE/EA=40/1 to 30/1) to give the title compound as an oil (45.28 g, 72%). $^1$H NMR (400 MHz, CDCl$_3$) δ ppm 2.38-2.41 (m, 2 H), 2.49-2.54 (m, 2 H), 4.20-4.24 (m, 1 H), 4.42 (s, 2 H), 5.62 (s, 2 H), 7.17-7.28 (m, 5 H).

D. (1R,3s,5S)-3-(Benzyloxy)-6-oxabicyclo[3.1.0]hexane and (1R,3r,5S)-3-(Benzyloxy)-6-oxabicyclo[3.1.0]hexane

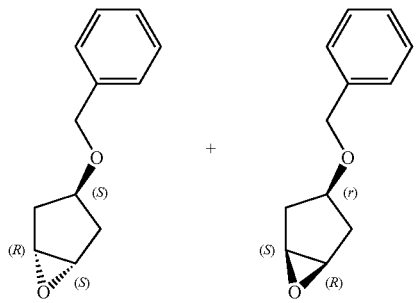

To a cooled solution of ((cyclopent-3-enyloxy)methyl)benzene (45.28 g, 260 mmol) in DCM (300 mL) at 0° C. was added m-chloroperoxybenzoic acid (111.9 g, 520 mmol) in one portion. The mixture was stirred at a temperature from 0° C. to RT overnight. The reaction mixture was filtered and excess m-chloroperoxybenzoic acid was reduced by the addition of saturated aq Na$_2$S$_2$O$_3$ until a negative starch iodide test was observed. The mixture was neutralized with saturated NaHCO$_3$ to pH 8-9 and filtered. The filtrate was separated with DCM, washed with brine, dried over Na$_2$SO$_4$, and purified by column chromatography eluting with petroleum ether and EtOAc (PE/EtOAc=30/1, 20/1 to 10/1) to give the title compounds as oils ((1R,3s,5S): 14.41 g, 76 mmol; ((1R,3r, 5S): 21.38 g, 113 mmol). $^1$H NMR of (1R,3s,5S) (400 MHz, CDCl$_3$) δ ppm 1.69 (dd, J=6.8, 14.0 Hz, 2 H), 2.49 (dd, J=7.2, 14.0 Hz, 2 H), 3.49 (s, 2 H), 3.85 (quintet J=7.0 Hz, 1 H), 4.43 (s, 2 H), 7.25-7.34 (m, 5 H); $^1$H NMR of (1R,3r,5S) (400 MHz, CDCl$_3$) δ ppm 1.99 (dd, J=7.6, 15.6 Hz, 2 H), 2.23 (d, J=16.6 Hz, 2 H), 3.55 (s, 2 H), 4.08 (t, J=7.2 Hz, 1 H), 4.49 (s, 2 H), 7.27-7.35 (m, 5 H).

E. (1S,2S,4R)-2-Azido-4-(benzyloxy)cyclopentanol

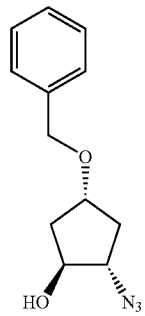 [SMILES: [N-]=[N+]=N[C@H]1C[C@@H](OCc2ccccc2)C[C@@H]1O]

To a solution of (1R,3s,5S)-3-(benzyloxy)-6-oxabicyclo[3.1.0]hexane (14.41 g, 76 mmol) in EtOH/H$_2$O (550 mL/160 mL) was added NH$_4$Cl (15.06 g, 284 mmol) and sodium azide (18.47 g, 284 mmol), The mixture was refluxed overnight and then cooled to RT. After removing EtOH, water was added and the residue was extracted with EtOAc. The organic layer was washed with brine, dried over Na$_2$SO$_4$, and purified by column chromatography eluting with petroleum ether and EtOAc (PE/EtOAc=20/1, 10/1 to 6/1) to give the title compound as an oil (18.24 g, 78.3 mmol). $^1$H NMR (400 MHz, CDCl$_3$) δ ppm 1.65-1.79 (m, 2 H), 2.01-2.07 (m, 1 H), 2.30-2.37 (m, 1 H), 3.49-3.54 (m 1 H), 3.97-4.06 (m, 2 H), 4.11-4.13 (br, 1 H), 4.33-4.40 (m, 2 H), 7.18-7.27 (m, 5 H).

F. (1R,2R,4R)-2-Azido-4-(benzyloxy)cyclopentyl methanesulfonate

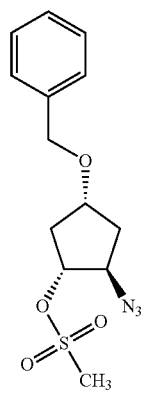 [SMILES: CS(=O)(=O)O[C@@H]1C[C@H](OCc2ccccc2)C[C@H]1N=[N+]=[N-]]

To a cooled mixture of Et$_3$N (9.49 g, 94.0 mmol) and (1S,2S,4R)-2-azido-4-(benzyloxy)cyclopentanol (18.25 g, 78.3 mmol) in DCM (500 mL) was added dropwise methanesulfonyl chloride (9.87 g, 86.2 mmol) in DCM (50 mL) at 0° C. The mixture was stirred overnight at a temperature of 0° C. to RT. After complete conversion, aq NaHCO$_3$ (5%, 300 mL) was added. The mixture was extracted with DCM, washed with brine, and dried over Na$_2$SO$_4$ to give the title compound as an oil (23.58 g, 75.8 mmol). $^1$H NMR (400 MHz, CDCl$_3$) δ ppm 1.83-1.89 (m, 1 H), 2.06-2.13 (m, 1 H), 2.34-2.49 (m, 2 H), 3.04 (s, 3 H), 3.94-3.99 (m, 1 H), 4.08-4.13 (m, 1 H), 4.64 (s, 2 H), 4.93-4.98 (q, J=5.6/7.0 Hz, 1 H), 7.25-7.36 (m, 5 H).

G. (((1s,3R,4S)-3,4-Diazidocyclopentyloxy)methyl)benzene

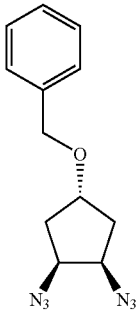 [SMILES: [N-]=[N+]=N[C@H]1C[C@H](OCc2ccccc2)C[C@H]1N=[N+]=[N-]]

To a mixture of (1R,2R,4R)-2-azido-4-(benzyloxy)cyclopentyl methanesulfonate (23.58 g 75.8 mmol), pyridine (25 mL), water (140 mL), and DMA (350 mL) was added NaN₃ (10.84 g, 166.8 mmol). The mixture was heated at 130° C. under N₂ atmosphere overnight. The reaction mixture was cooled to RT and quenched with cold water (300 mL). The mixture was extracted with EtOAc, washed with H₂O (several times) and with brine, dried over Na₂SO₄, and purified by column chromatography eluting with petroleum ether and EtOAc (PE/EA=40/1 to 30/1) to give the title compound as an oil (15.35 g, 59.5 mmol). ¹H NMR (400 MHz, CDCl₃) δ ppm 1.99-2.08 (m. 2 H), 2.23-2.30 (m, 2 H), 3.75-3.80 (m, 2 H), 3.99-4.04 (m, 1 H), 4.49 (s, 2 H), 7.26-7.35 (m, 5 H).

H. Di-tert-butyl N,N-((1R,2S,4s)-4-hydroxycyclopentane-1,2-diyl)-biscarbamate

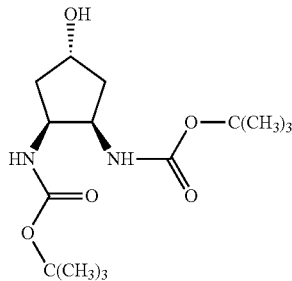 [SMILES: CC(C)(C)OC(=O)N[C@H]1C[C@H](O)C[C@H]1NC(=O)OC(C)(C)C]

To a solution of (((1s,3R,4S)-3,4-diazidocyclopentyloxy)methyl)benzene (15.35 g, 59.5 mmol) and di-tert-butyl pyrocarbonate (31.69 g, 145.4 mmol) in MeOH (200 mL) was added Pd/C (50% wet, 8.0 g) in an autoclave. The autoclave was charged with H₂ to 2.2 MPa. The reaction mixture was stirred at RT overnight. After conversion, the mixture was filtered and solvent removed to give the title compound, which was used without further purification (14.8 g, 46.8 mmol). ¹H NMR (400 MHz, CDCl₃) δ ppm 1.45 (s, 18 H), 1.72-1.75 (m, 2 H), 2.20 (m, 2 H), 4.04 (br, 2 H), 4.34-4.37 (m, 1 H), 4.45 (br, 2 H), 5.21 (br, 1H).

I. Di-tert-butyl N,N-(cis-4-oxocyclopentane-1,2-diyl)-biscarbamate

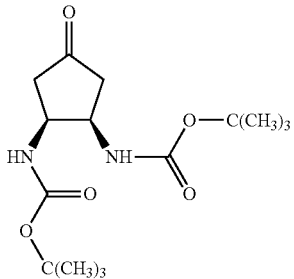 [SMILES: CC(C)(C)OC(=O)N[C@H]1CC(=O)C[C@H]1NC(=O)OC(C)(C)C]

To a cooled solution of di-tert-butyl N,N-((1R,2S,4s)-4-hydroxycyclopentane-1,2-diyl)-biscarbamate (5.35 g, 16.9 mmol) in DCM 90 (mL) at 0° C. was added Dess-Martin periodinane reagent (24.4 g, 57.6 mmol). The mixture was stirred from 0° C. to RT for 1.5 h. After the reaction was completed, the mixture was filtered and the residue was purified by column chromatography eluting with petroleum ether and EtOAc (PE/EtOAc=6/1 to 2/1) to give the title compound as a solid (5.03 g, 15.9 mmol). ¹H NMR (400 MHz, CDCl₃) δ ppm 1.38 (s, 18 H), 2.30-2.50 (m, 4 H), 4.29 (s, 2 H).

J. Di-tert-butyl N,N-(cis-4,4-difluorocyclopentane-1,2-diyl)-biscarbamate

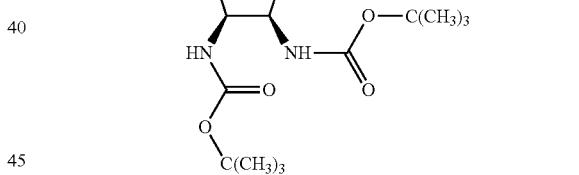

To a cooled solution of di-tert-butyl N,N-(cis-4-oxocyclopentane-1,2-diyl)-biscarbamate (5.00 g, 15.9 mmol) in DCM (100 mL) was added dropwise a mixture of diethylaminosulfur trifluoride (12.82 g, 79.6 mmol) in DCM (10 mL) at 0° C. The mixture was stirred at a temperature of from 0° C. to RT overnight. The mixture was subsequently cooled to 0° C. and its pH adjusted to 9-10 with saturated aq K₂CO₃, while maintaining the temperature of the mixture below 5° C. Di-tert-butyl pyrocarbonate (7.60 g, 2.2 eq) was added and the mixture was stirred at a temperature of from 0° C. to RT for 3 h. After removing DCM, the residue was purified by column chromatography eluting with petroleum ether and EtOAc (PE/EtOAc=20/1 to 15/1 to 12/1) to give the title compound as a solid (2.40 g, 7.10 mmol). ¹H NMR (400 MHz, CDCl₃) δ ppm 1.45 (br, 18 H), 2.15-2.19 (m, 2 H), 2.47-2.52 (m, 2 H), 4.22 (br, 2 H), 4.87 (br, 2 H).

K. cis-4,4-Difluorocyclopentane-1,2-diamine

To a cooled solution of di-tert-butyl N,N-(cis-4,4-difluorocyclopentane-1,2-diyl)-biscarbamate (2.40 g, 7.10 mmol)

in EtOAc (30 mL) at 0° C. was added 1N HCl-EtOAc (10 mL) while maintaining the temperature of the mixture below 5° C. The mixture was stirred at RT overnight. The mixture was subsequently filtered, washed with EtOAc several times, and dried in vacuo to give a hydrochloride salt of the title compound as a solid (0.98 g, 4.7 mmol). $^1$H NMR (400 MHz, CD$_3$OD) δ ppm 2.63-2.67 (m, 2 H), 2.76-2.86 (m, 2 H), 4.15-4.17 (m, 2 H). [M+H] calc'd for C$_5$H$_{10}$F$_2$N$_2$, 137; found 137.

Example 66

6-(cis-2-Amino-4,4-difluorocyclopentylamino)-7-fluoro-4-(1-methyl-1H-pyrazol-4-yl)-1H-pyrrolo[3,4-c]pyridin-3(2H)-one

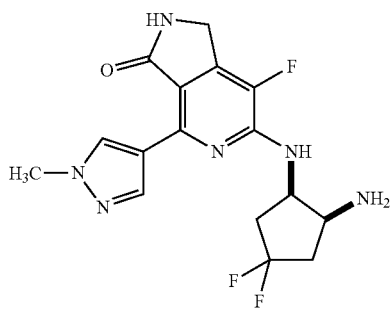 [SMILES: Cn1cc(-c2nc(N[C@@H]3CC(F)(F)C[C@@H]3N)c(F)c3c2C(=O)NC3)cn1]

A TFA salt of the title compound was prepared in a manner similar to EXAMPLE 64 using cis-4,4-difluorocyclopentane-1,2-diamine in place of cis-tert-butyl 2-aminocyclohexylcarbamate. $^1$H NMR (500 MHz, DMSO-d$_6$) δ ppm 2.62-2.69 (m, 2 H), 2.87 (td, J=16.84, 8.79 Hz, 2 H), 3.89 (s, 3 H), 4.14 (br s, 1 H), 4.32-4.48 (m, 2 H), 4.79 (d, J=9.76 Hz, 1 H), 7.28 (d, J=5.37 Hz, 1 H), 7.93 (br s, 2 H), 8.41 (d, J=7.32 Hz, 2 H), 8.87 (s, 1 H). [M+H] calc'd for C$_{16}$H$_{17}$F$_3$N$_6$O, 367; found, 367.

Preparation 26 cis-3,3-Difluorocyclohexane-1,2-diamine

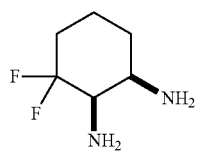

A. tert-Butyl(cyclohex-2-enyloxy)dimethylsilane

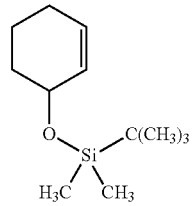

Pyridine (4.74 g, 60 mmol) and tert-butyldimethylsilyl chloride (4.83 g, 32 mmol) were added to a solution of cyclohex-2-enol (1.96 g, 20 mmol) in DCM (40 mL). The reaction mixture was stirred at RT overnight. The mixture was concentrated and the residue was dispersed in EtOAc and water. The organic phase was separated and washed with brine, dried over anhydrous Na$_2$SO$_4$, concentrated, and purified by silica flash chromatography eluting with EtOAc and petroleum ether (5-10% EtOAc) to give the title compound as an oil (4.1 g, 97%). $^1$H NMR (400 MHz, CDCl$_3$) δ ppm 0.06-0.09 (m, 6 H), 0.92 (s, 9 H), 1.50-1.57 (m, 2 H), 1.74-1.89 (m, 2 H), 1.93-2.03 (m, 2 H), 4.21-4.23 (m, 1 H), 5.61-5.64 (m, 1 H), 5.72-5.76 (m, 1 H).

B. (1S,2S,3S)-3-(tert-Butyldimethylsilyloxy)cyclohexane-1,2-diol and (1R,2R,3R)-3-(tert-butyldimethylsilyloxy)cyclohexane-1,2-diol

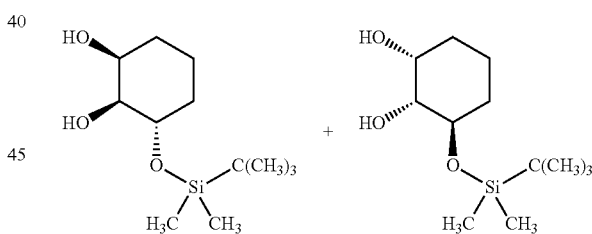

tert-Butyl(cyclohex-2-enyloxy)dimethylsilane (12.72 g, 60 mmol) was dissolved in CH$_3$CN (100 mL). A solution of N-methylmorpholine-N-oxide (14 g, 120 mmol) in H$_2$O (20 mL) and OsO$_4$ (0.5 g) in acetone (5 mL) was added, and the mixture was stirred at RT overnight. The mixture was then diluted with EtOAc (800 mL), washed with brine and saturated aq NaHCO$_3$, dried over anhydrous Na$_2$SO$_4$, concentrated, and purified by silica flash chromatography eluting with EtOAC and petroleum ether (20-40% EtOAc) to give the title compounds as an oil (12.8 g, 87%). $^1$H NMR (400 MHz, CDCl$_3$) δ ppm 0.06-0.09 (m, 6 H), 0.90 (s, 9 H), 1.25-1.28 (m, 2 H), 1.44-1.62 (m, 2 H), 1.80-1.84 (m, 2 H), 2.28 (s, 1 H), 2.51 (s, 1 H), 3.40-3.44 (m, 1 H), 3.77-3.82 (m, 1 H), 4.08-4.11 (m, 1 H).

C. (1S,2R,3S)-3-(tert-Butyldimethylsilyloxy)cyclohexane-1,2-diyl dimethanesulfinate and (1R,2S,3R)-3-(tert-Butyldimethylsilyloxy)cyclohexane-1,2-diyl dimethanesulfinate

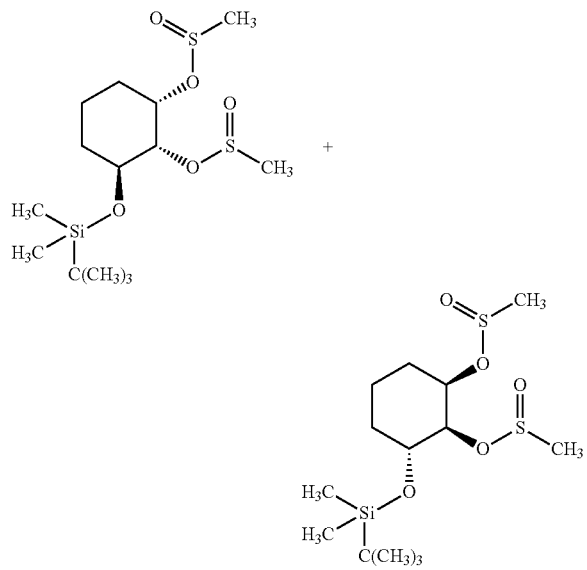

(1S,2S,3S)/(1R,2R,3R)-3-(tert-Butyldimethylsilyloxy)cyclohexane-1,2-diol (1.9 g, 7.7 mmol) was dissolved in DCM (40 mL). The mixture was placed in an ice bath. Pyridine (3.1 mL, 38.5 mmol) and methanesulfonyl chloride (1.44 mL, 18.5 mmol) were added and the reaction mixture was stirred at RT overnight. Next, the mixture was diluted with DCM, washed with brine, dried over anhydrous $Na_2SO_4$, concentrated, and purified by silica flash chromatography eluting with EtOAC and petroleum ether (20-30% EtOAc) to give the title compounds as an oil (2.6 g, 84%). $^1$H NMR (400 MHz, $CDCl_3$) δ ppm 0.06-0.09 (m, 6 H), 0.90 (s, 9 H), 1.58-1.64 (m, 2 H), 1.70-1.78 (m, 2 H), 1.85-1.90 (m, 2 H), 3.12 (s, 6 H), 4.08-4.12 (m, 1 H), 4.51-4.55 (m, 1 H), 5.06-5.10 (m, 1 H).

D. (1S,2R,6S)-2-Azido-6-(tert-butyldimethylsilyloxy)cyclohexyl methanesulfonate and (1R,2S,6R)-2-Azido-6-(tert-butyldimethylsilyloxy)cyclohexyl methanesulfinate

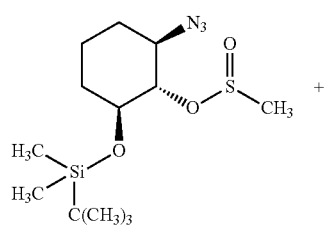

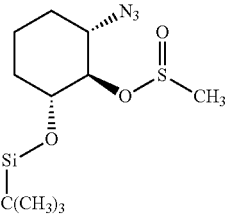

(1S,2R,3S)/(1R,2S,3R)-3-(tert-Butyldimethylsilyloxy)cyclohexane-1,2-diyl dimethanesulfinate (12.0 g, 29.8 mmol) was dissolved in DMF (80 mL) and hexamethylphosphoramide (20 mL). Sodium azide (10.0 g, 154 mmol) was added and the mixture was stirred at 75° C. overnight. The mixture was diluted with EtOAc, washed with water and brine, dried over anhydrous $Na_2SO_4$, and concentrated. The solid was washed petroleum ether and dried in vacuo to give the title compounds (7 g, 68%). $^1$H NMR (400 MHz, $CDCl_3$) δ ppm 0.06-0.09 (m, 6 H), 0.90 (s, 9 H), 1.32-1.47 (m, 3 H), 1.76-1.81 (m, 1 H), 1.97-2.01 (m, 1 H), 2.10-2.14 (m, 1 H), 3.14 (s, 3 H), 3.33-3.39 (m, 1 H), 3.55-3.61 (m, 1 H), 4.23-4.28 (m, 1 H).

E. tert-Butyl((1S,2R,3R)-2,3-diazidocyclohexyloxy)dimethylsilane and tert-Butyl((1R,2S,3S)-2,3-diazidocyclohexyloxy)dimethylsilane

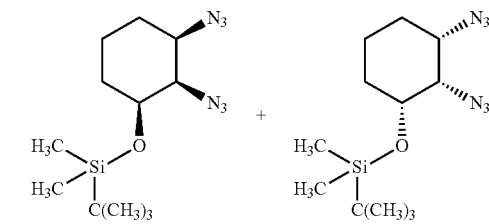 [SMILES: CC(C)(C)[Si](C)(C)O[C@H]1CCC[C@@H](N=[N+]=[N-])[C@H]1N=[N+]=[N-] ; CC(C)(C)[Si](C)(C)O[C@@H]1CCC[C@H](N=[N+]=[N-])[C@@H]1N=[N+]=[N-]]

(1S,2R,6S)/(1R,2S,6R)-2-Azido-6-(tert-butyldimethylsilyloxy)cyclohexyl methanesulfonate (7 g, 20 mmol) was dissolved in DMF (80 mL) and hexamethylphosphoramide (20 mL). Sodium azide (15.0 g, 230 mmol) was added and the mixture was stirred at 120° C. for 24 h. The mixture was diluted with EtOAc, washed with water and brine, dried over anhydrous $Na_2SO_4$, concentrated, and purified by silica flash chromatography eluting with EtOAc and petroleum ether (3% EtOAc) to give the title compounds as an oil (3.52 g, 60%). $^1$H NMR (400 MHz, $CDCl_3$) δ ppm 0.06-0.09 (m, 6 H), 0.90 (s, 9 H), 1.66-1.70 (m, 2 H), 1.72-1.76 (m, 2 H), 1.80-1.85 (m, 2 H), 3.16 -3.21 (m, 1 H), 3.71-3.76 (m, 1 H), 3.80-3.85 (m, 1 H).

F. (1S,2R,3R)-2,3-Diazidocyclohexanol and (1R,2S,3S)-2,3-Diazidocyclohexanol

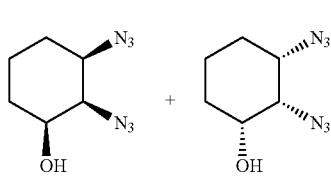 [SMILES: [N-]=[N+]=N[C@H]1[C@@H](O)CCC[C@H]1N=[N+]=[N-] ; [N-]=[N+]=N[C@@H]1[C@H](O)CCC[C@@H]1N=[N+]=[N-]]

Tetrabutylammonium fluoride (16.0 g, 61.3 mmol) dissolved in THF was added to tert-butyl((1S,2R,3R)/(1R,2S,3S)-2,3-diazidocyclohexyloxy)dimethylsilane (12.0 g, 40.5 mmol) in THF (300 mL). The reaction mixture was stirred at RT for 3 h and was then quenched with MeOH. The mixture was concentrated and the residue was purified by column chromatography (EtOAc/PE=4/1) to give the title compounds as an oil (5 g, 68%).

G. (1S,2R,3R)-2,3-Diaminocyclohexanol and (1R,2S,3S)-2,3-Diaminocyclohexanol

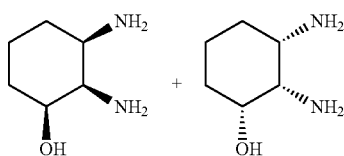 [SMILES: N[C@@H]1[C@H](N)CCC[C@@H]1O ; N[C@@H]1[C@H](O)CCC[C@@H]1N]

A mixture of (1S,2R,3R)/(1R,2S,3S)-2,3-diazidocyclohexanol (5.0 g, 27.5 mmol) and Pd/C (2.0 g) in MeOH was stirred at RT overnight under $H_2$ atmosphere. Following reaction, the mixture was filtered and concentrated to give the title compounds as an oil, which was used without further purification (3.18 g).

H. Dibenzyl N,N-((1R,2R,3S)-3-hydroxycyclohexane-1,2-diyl)-biscarbamate and Dibenzyl N,N-((1S,2S,3R)-3-hydroxycyclohexane-1,2-diyl)-biscarbamate

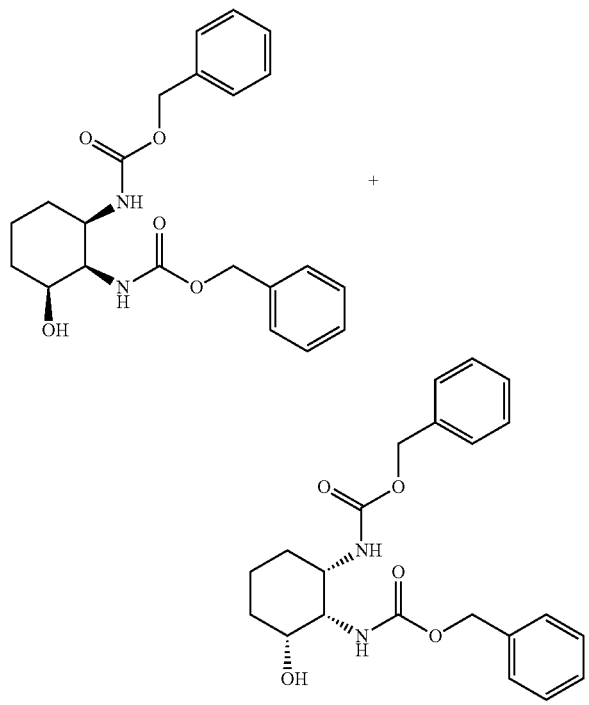

To a solution of (1S,2R,3R)/(1R,2S,3S)-2,3-diaminocyclohexanol (3.1 g, 24.5 mmol) and $Et_3N$ (7.4 g, 73.5 mmol) in DCM (50 mL) at −10° C. was added benzyl carbonochloridate (9.6 g, 56.3 mmol). The progress of the reaction was monitored by TLC and LCMS. Following completion of the reaction, the mixture was washed with water, dried over $Na_2SO_4$, and concentrated. The residue was purified by column chromatography (EtOAc/PE=2/1) to give the title compounds as an oil (2.2 g, 22%). $^1H$ NMR (400 MHz, $CDCl_3$) δ ppm 1.59-1.84 (m, 6 H), 3.80 (br, 1 H), 4.05-4.16 (m, 2 H), 5.12 (s, 4 H), 5.4 (s, 1 H), 6.4 (s, 1 H), 7.33-7.37 (m, 10 H).

I. Dibenzyl N,N-(cis-3-oxocyclohexane-1,2-diyl)-biscarbamate

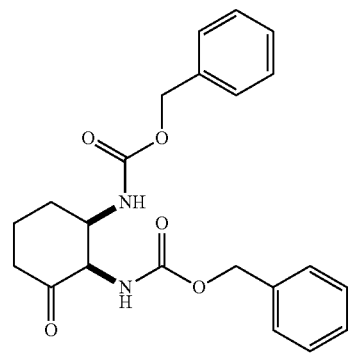 [SMILES: O=C(N[C@@H]1CCCC(=O)[C@@H]1NC(=O)OCc1ccccc1)OCc1ccccc1]

To a solution of dibenzyl N,N-((1R,2R,3S)/(1S,2S,3R)-3-hydroxycyclohexane-1,2-diyl)-biscarbamate (2.2 g, 5.5 mmol) in DCM (30 mL) at −0° C. was added Dess-Martin periodinane reagent (5.9 g, 13.8 mmol). The suspension was stirred at RT for 3 h. The mixture was concentrated and the residue was purified by column chromatography (EtOAc/PE=2/1) to give the title compound as a solid (2.0 g, 93%). $^1H$ NMR (400 MHz, $CDCl_3$) δ ppm 1.60-1.70 (m, 3 H), 2.00-2.04 (m, 1 H), 2.35-2.58 (m, 2 H), 4.27-4.31 (m, 1 H), 5.12 (s, 4 H), 5.82-5.92 (m, 1 H), 7.33-7.38 (m, 10 H).

J. Dibenzyl N,N-(cis-3,3-difluorocyclohexane-1,2-diyl)-biscarbamate

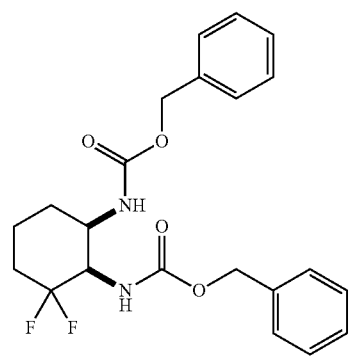 [SMILES: O=C(N[C@@H]1[C@H](NC(=O)OCc2ccccc2)CCCC1(F)F)OCc1ccccc1]

To a solution of dibenzyl N,N-(cis-3-oxocyclohexane-1,2-diyl)-biscarbamate (2.0 g, 5.1 mmol) in DCM (30 mL) at −0° C. was added diethylaminosulfur trifluoride (4 mL, 1.22 g/cm³). The reaction mixture was stirred at −0° C. overnight. The reaction mixture was neutralized with sodium bicarbonate, concentrated, and the residue was purified by column chromatography (EtOAc/PE=2/1) to give the title compound as a solid (1.0 g, 47%). $^1H$ NMR (400 MHz, $CD_3OD$) δ ppm 1.43-2.01 (m, 6 H), 3.83-3.84 (m, 1 H), 4.23-4.24 (m, 1 H), 4.97 (s, 4 H), 7.16-7.24 (m, 10 H).

K. cis-3,3-Difluoro cyclohexane-1,2-diamine

A mixture of dibenzyl N,N-(cis-3,3-difluorocyclohexane-1,2-diyl)-biscarbamate (1.0 g, 2.4 mmol) and Pd/C (0.9 g) in MeOH was stirred at RT overnight under $H_2$ atmosphere. Following reaction, the mixture was filtered and concentrated to an oil, which was reacted with EtOAc—HCl to give a hydrochloride salt of the title compound as a white solid (280 mg, 77%). $^1$H NMR (400 MHz, CD$_3$OD) δ ppm 1.84-2.31 (m, 6 H), 4.01 (m, 1 H), 4.20-4.26 (m, 1 H). [M+H] calc'd for $C_6H_{12}F_2N_2$, 151; found, 151.

Preparation 27

6-(cis-2-Amino-3,3-difluorocyclohexylamino)-4-chloro-2-(2,4-dimethoxybenzyl)-7-fluoro-1H-pyrrolo[3,4-c]pyridin-3(2H)-one

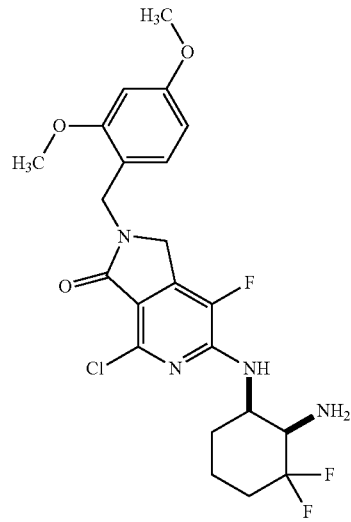

A mixture of 4,6-dichloro-2-(2,4-dimethoxybenzyl)-7-fluoro-1H-pyrrolo[3,4-c]pyridin-3(2H)-one (100 mg, 0.269 mmol) and cis-3,3-difluorocyclohexane-1,2-diamine hydrochloride (75 mg, 0.404 mmol) and DIPEA (118 μL, 0.674 mmol) in acetonitrile (449 μL) was stirred at 100° C. for 3 d. The reaction mixture was concentrated to a brown oil and reconstituted in DMF (1 mL). The residue was purified by preparative HPLC, the appropriate fraction was collected, and excess acetonitrile was evaporated. The residue was treated with saturated aq sodium carbonate and extracted with EtOAc (3×20 mL). The organic layers were combined, dried over sodium sulfate, and concentrated to give the title compound as a colorless residue (13.7 mg, 10%). [M+H] calc'd for $C_{22}H_{24}ClF_3N_4O_3$, 485; found, 485.

Example 67

6-(cis-2-Amino-3,3-difluorocyclohexylamino)-7-fluoro-4-(1-methyl-1H-pyrazol-4-yl)-1H-pyrrolo[3,4-c]pyridin-3(2H)-one

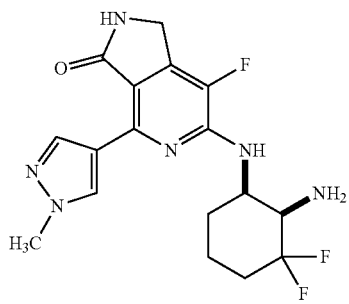

A. 6-(cis-2-Amino-3,3-difluorocyclohexylamino)-2-(2,4-dimethoxybenzyl)-7-fluoro-4-(1-methyl-1H-pyrazol-4-yl)-1H-pyrrolo[3,4-c]pyridin-3(2H)-one

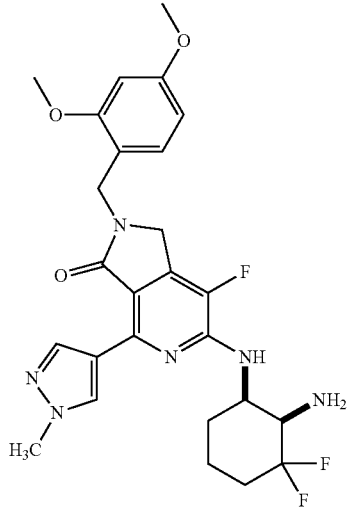

A microwave vial was charged with 6-(cis-2-amino-3,3-difluorocyclohexylamino)-4-chloro-2-(2,4-dimethoxybenzyl)-7-fluoro-1H-pyrrolo[3,4-c]pyridin-3(2H)-one (13.7 mg, 0.028 mmol) and 1-methyl-4-(4,4,5,5-tetramethyl-1,3,2-dioxaborolan-2-yl)-1H-pyrazole (8.82 mg, 0.042 mmol) and bis(triphenylphosphine)palladium chloride (3.97 mg, 5.65 μmol) and placed under an inert environment. DME (283 μL) was added to the mixture and the resulting yellow slurry was degassed for 5 min. Sodium carbonate was added (56.5 μL, 0.113 mmol) and the slurry degassed for an additional 3 min. The vessel was capped and the mixture was heated at 80° C. for 4 h, cooled to ambient temperature, diluted with EtOAc (5 mL), and washed with water (3 mL) and brine (3 mL). The organic layer was collected, dried over sodium sulfate, and concentrated to give the title compound as a dark brown residue which was used in the next step without further purification (21 mg). [M+H] calc'd for $C_{26}H_{29}F_3N_6O_3$, 531; found, 531.

B. 6-(cis-2-Amino-3,3-difluorocyclohexylamino)-7-fluoro-4-(1-methyl-1H-pyrazol-4-yl)-1H-pyrrolo[3,4-c]pyridin-3(2H)-one To a solution of 6-(cis-2-amino-3,3-difluorocyclohexylamino)-2-(2,4-dimethoxybenzyl)-7-fluoro-4-(1-methyl-1H-pyrazol-4-yl)-1H-pyrrolo[3,4-c]pyridin-3(2H)-one (21 mg, 0.040 mmol) in DCM (300 µL) was added TFA (500 µL, 6.49 mmol). The reaction mixture was stirred at ambient temperature for 12 h then an additional 3 h at 50° C. The mixture was subsequently concentrated to a dark oil and diluted with DMF (1 mL) which was purified via preparative HPLC and lyophilized to give a TFA salt of the title compound as a fluffy white solid (3.6 mg, 19%). $^1$H NMR (400 MHz, DMSO-$d_6$) δ ppm 8.89 (s, 1 H), 8.43 (s, 3 H), 8.16 (s, 1 H), 6.89 (br s, 1 H), 6.54 (br s, 1 H), 4.65-4.52 (m, 1 H), 4.49-4.32 (m, 2 H), 4.17 (br s, 1 H), 3.89 (s, 3 H), 2.37-2.03 (m, 2 H), 1.84 (br s, 3 H), 1.63 (br s, 1 H). [M+H] calc'd for $C_{17}H_{19}F_3N_6O$, 381; found, 381.

Example 68

6-(cis-2-Amino-3,3-difluorocyclohexylamino)-4-(1-(difluoromethyl)-1H-pyrazol-4-yl)-7-fluoro-1H-pyrrolo[3,4-c]pyridin-3(2H)-one

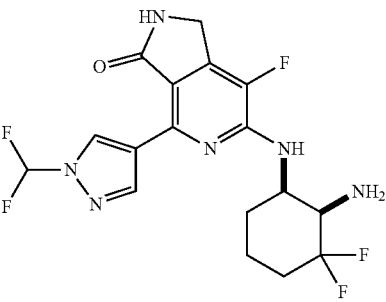

A TFA salt of the title compound was prepared in a manner similar to EXAMPLE 67 using 1-(difluoromethyl)-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (400 MHz, DMSO-$d_6$) δ ppm 1.64 (br s, 1 H), 1.83 (br s, 3 H), 2.00-2.29 (m, 2 H), 2.33 (t, J=1.77 Hz, 1 H), 2.63-2.72 (m, 1 H), 4.11 (br s, 1 H), 4.40-4.50 (m, 2 H), 4.62 (br s, 1 H), 6.93 (d, J=5.31 Hz, 1 H), 7.74-8.14 (m, 1 H), 8.45 (s, 1 H), 8.56 (s, 1 H), 9.40 (s, 1 H). [M+H] calc'd for $C_{17}H_{17}F_5N_6O$, 417; found, 417.

Example 69

6-(cis-2-amino-3,3-difluorocyclohexylamino)-4-(1-cyclopropyl-1H-pyrazol-4-yl)-7-fluoro-1H-pyrrolo[3,4-c]pyridin-3(2H)-one

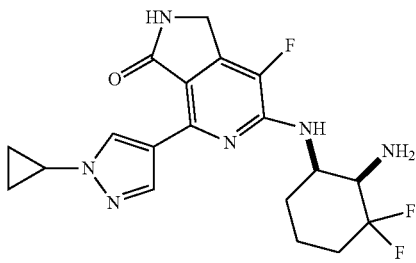

A TFA salt of the title compound was prepared in a manner similar to EXAMPLE 67 using 1-cyclopropyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (400 MHz, DMSO-$d_6$) δ ppm 1.63 (br s, 1 H), 1.75-1.92 (m, 3 H), 2.00-2.29 (m, 2 H), 2.33 (dt, J=3.73, 1.80 Hz, 1 H), 2.62-2.74 (m, 1 H), 4.34-4.46 (m, 2 H), 4.57 (br s, 1 H), 4.81 (d, J=5.56 Hz, 2 H), 5.08-5.30 (m, 2 H), 5.93-6.10 (m, 1 H), 6.83 (d, J=6.06 Hz, 1 H), 8.22 (s, 1 H), 8.39 (s, 2 H), 8.84-9.05 (m, 1 H). [M+H] calc'd for $C_{19}H_{21}F_3N_6O$, 407; found, 407.

Preparation 28

(R)-2-(4-Chloro-2-(2,4-dimethoxybenzyl)-7-fluoro-3-oxo-2,3-dihydro-1H-pyrrolo[3,4-c]pyridin-6-ylamino)-4-methylpentanamide

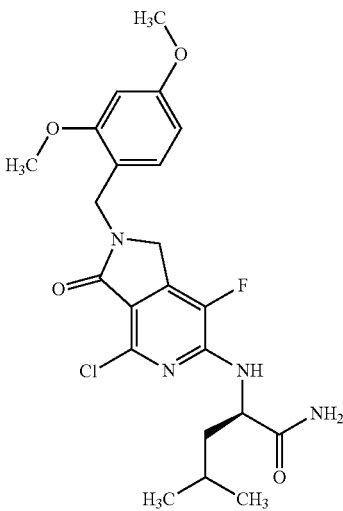 [SMILES: COc1ccc(CN2Cc3c(F)c(N[C@H](CC(C)C)C(N)=O)nc(Cl)c3C2=O)c(OC)c1]

A mixture of 4,6-dichloro-2-(2,4-dimethoxybenzyl)-7-fluoro-1H-pyrrolo[3,4-c]pyridin-3(2H)-one (200 mg, 0.539 mmol), (R)-2-amino-4-methylpentanamide (140 mg, 1.078 mmol), and N-isopropyl-N-methylpropan-2-amine (310 mg, 2.69 mmol) in acetonitrile (2 mL) was stirred at 85° C. for 3 d. The resulting crude material was reconstituted in MeOH/DCM/DMF (10.0 mL) and purified via preparative HPLC. The fractions were collected and stripped to dryness via rotary evaporation to yield the title compound (83 mg, 33%). [M+H] calc'd for $C_{22}H_{26}ClFN_4O_4$, 465; found, 465.

Example 70

(R)-2-(7-Fluoro-4-(1-methyl-1H-pyrazol-4-yl)-3-oxo-2,3-dihydro-1H-pyrrolo[3,4-c]pyridin-6-ylamino)-4-methylpentanamide

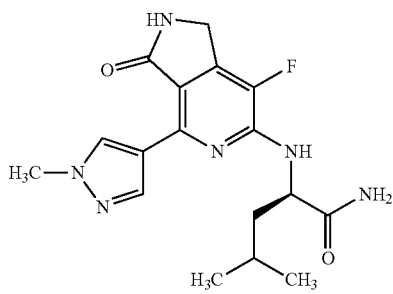 [SMILES: CC(C)C[C@@H](Nc1nc(-c2cnn(C)c2)c2c(c1F)CNC2=O)C(N)=O]

A. (R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)-4-methylpentanamide

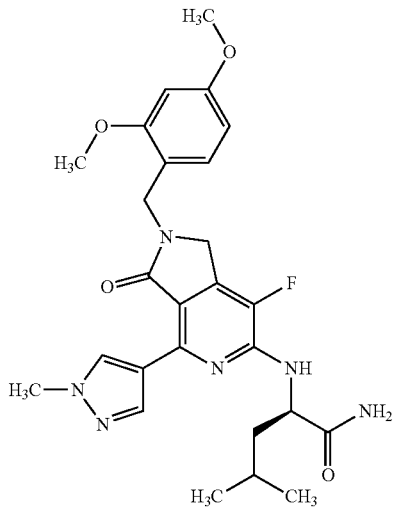 [SMILES: COc1ccc(CN2Cc3c(F)c(N[C@H](CC(C)C)C(N)=O)nc(-c4cnn(C)c4)c3C2=O)c(OC)c1]

A solution of (R)-2-(4-chloro-2-(2,4-dimethoxybenzyl)-7-fluoro-3-oxo-2,3-dihydro-1H-pyrrolo[3,4-c]pyridin-6-ylamino)-4-methylpentanamide (83 mg, 0.179 mmol), 1-methyl-4-(4,4,5,5-tetramethyl-1,3,2-dioxaborolan-2-yl)-1H-pyrazole (111 mg, 0.536 mmol), and bis(triphenylphosphine)palladium chloride (12.53 mg, 0.018 mmol) in dioxane (2 mL) and saturated aq $Na_2CO_3$ (2 mL) was heated at 120° C. for 30 min. After filtering off the solid, the solvent was removed, and the residue was dissolved in MeOH and DCM and was purified by preparative HPLC. The fractions were collected and the solvent was stripped to dryness via rotary evaporation to yield the title compound (40 mg, 44%). [M+H] calc'd for $C_{26}H_{31}FN_6O_4$, 511; found, 511.

B. (R)-2-(7-Fluoro-4-(1-methyl-1H-pyrazol-4-yl)-3-oxo-2,3-dihydro-1H-pyrrolo[3,4-c]pyridin-6-ylamino)-4-methylpentanamide A solution of (R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)-4-methylpentanamide (39.8 mg, 0.078 mmol) in TFA (5 mL) was heated at 60° C. for 2 h. After removal of solvent, the residue was diluted in MeOH (2 mL) and was purified by preparative HPLC. The fractions were collected and the solvent stripped to dryness via rotary evaporation to yield the title compound (12.8 mg, 46%). $^1$H NMR (500 MHz, DMSO-$d_6$) δ ppm 0.82-1.00 (m, 6 H), 1.45-1.60 (m, 1 H), 1.67-1.83 (m, 2 H), 3.87 (s, 3 H), 4.36 (s, 2 H), 4.50-4.64 (m, 1 H), 6.88-7.02 (m, 2 H), 7.44 (s, 1 H), 8.28 (s, 2 H), 8.83 (s, 1 H). [M+H] calc'd for $C_{17}H_{21}FN_6O_2$, 361; found, 361.

Example 71

(R)-2-(4-(1-(Difluoromethyl)-1H-pyrazol-4-yl)-7-fluoro-3-oxo-2,3-dihydro-1H-pyrrolo[3,4-c]pyridin-6-ylamino)-4-methylpentanamide

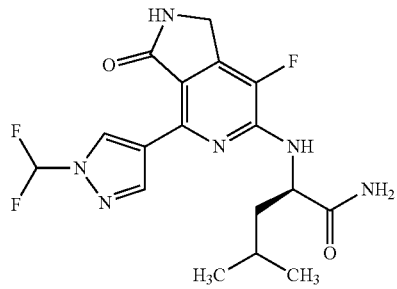 [SMILES: CC(C)C[C@@H](Nc1nc(-c2cnn(C(F)F)c2)c2c(c1F)CNC2=O)C(N)=O]

The title compound was prepared in a manner similar to EXAMPLE 70 using 1-(difluoromethyl)-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^1$H NMR (400 MHz, DMSO-$d_6$) δ ppm 1.63 (br s, 1 H), 1.75-1.92 (m, 3 H), 2.00-2.29 (m, 2 H), 2.33 (dt, J=3.73, 1.80 Hz, 1 H), 2.62-2.74 (m, 1 H), 4.34-4.46 (m, 2 H), 4.57 (br s, 1 H), 4.81 (d, J=5.56 Hz, 2 H), 5.08-5.30 (m, 2 H), 5.93-6.10 (m, 1 H), 6.83 (d, J=6.06 Hz, 1 H), 8.22 (s, 1 H), 8.39 (s, 2 H), 8.84-9.05 (m, 1 H). [M+H] calc'd for $C_{17}H_{19}F_3N_6O_2$, 397; found, 397.

Example 72

(R)-2-(4-(1-Cyclopropyl-1H-pyrazol-4-yl)-7-fluoro-3-oxo-2,3-dihydro-1H-pyrrolo[3,4-c]pyridin-6-ylamino)-4-methylpentanamide

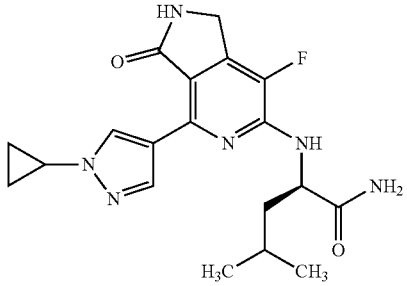 [SMILES: CC(C)C[C@@H](Nc1nc(-c2cnn(C3CC3)c2)c2c(c1F)CNC2=O)C(N)=O]

The title compound was prepared in a manner similar to EXAMPLE 70 using 1-cyclopropyl-4-(4,4,5,5-tetramethyl-1,3,2-dioxaborolan-2-yl)-1H-pyrazole in place of 1-methyl-4-(4,4,5,5-tetramethyl-1,3,2-dioxaborolan-2-yl)-1H-pyrazole. $^{1}$H NMR (400 MHz, DMSO-$d_6$) δ ppm 0.70-1.07 (m, 7 H), 1.15-1.35 (m, 1 H), 1.48-1.64 (m, 1 H), 1.67-1.93 (m, 2 H), 4.25-4.43 (m, 2 H), 4.54 (d, J=9.60 Hz, 1 H), 4.79 (d, J=5.81 Hz, 1 H), 5.11-5.31 (m, 1 H), 5.91-6.16 (m, 1 H), 6.80-7.07 (m, 2 H), 7.42 (br s, 1 H), 8.25 (s, 1 H), 8.34-8.43 (m, 1 H), 8.83-8.97 (m, 1 H). [M+H] calc'd for $C_{19}H_{23}FN_6O_2$, 387; found, 387.

Example 73

(R)-2-(4-(Benzofuran-3-yl)-7-fluoro-3-oxo-2,3-dihydro-1H-pyrrolo[3,4-c]pyridin-6-ylamino)-4-methylpentanamide

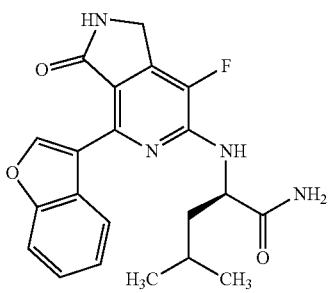 [SMILES: CC(C)C[C@@H](Nc1nc(-c2coc3ccccc23)c2c(c1F)CNC2=O)C(N)=O]

The title compound was prepared in a manner similar to EXAMPLE 70 using 2-(benzofuran-3-yl)-4,4,5,5-tetramethyl-1,3,2-dioxaborolane in place of 1-methyl-4-(4,4,5,5-tetramethyl-1,3,2-dioxaborolan-2-yl)-1H-pyrazole. $^{1}$H NMR (400 MHz, DMSO-$d_6$) δ ppm 0.73-0.96 (m, 6 H), 1.57-1.91 (m, 3 H), 4.42 (s, 2 H), 4.63-4.77 (m, 1 H), 6.99-7.17 (m, 2 H), 7.24-7.42 (m, 3 H), 7.62 (d, J=7.83 Hz, 1 H), 8.32-8.48 (m, 2 H), 9.28 (s, 1 H). [M+H] calc'd for $C_{21}H_{21}FN_4O_3$, 397; found, 397.

Example 74

(R)-2-(7-Fluoro-3-oxo-4-(pyrazolo[1,5-a]pyridin-3-yl)-2,3-dihydro-1H-pyrrolo[3,4-c]pyridin-6-ylamino)-4-methylpentanamide

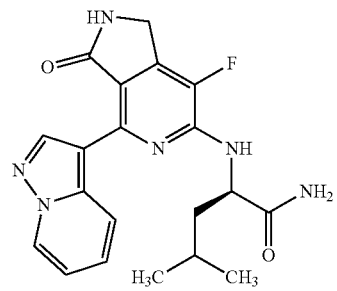 [SMILES: CC(C)C[C@@H](Nc1nc(-c2cnn3ccccc23)c2c(c1F)CNC2=O)C(N)=O]

The title compound was prepared in a manner similar to EXAMPLE 70 using 3-(4,4,5,5-tetramethyl-1,3,2-dioxaborolan-2-yl)pyrazolo[1,5-a]pyridine in place of 1-methyl-4-(4,4,5,5-tetramethyl-1,3,2-dioxaborolan-2-yl)-1H-pyrazole. $^{1}$H NMR (400 MHz, DMSO-$d_6$) δ ppm 0.77-0.99 (m, 6 H), 1.57-1.70 (m, 1 H), 1.71-1.90 (m, 2 H), 4.33-4.45 (m, 2 H), 4.56-4.68 (m, 1 H), 6.93-7.12 (m, 3 H), 7.27-7.42 (m, 2 H), 8.27 (s, 1 H), 8.47 (d, J=8.84 Hz, 1 H), 8.72 (d, J=6.82 Hz, 1 H), 9.30 (s, 1 H). [M+H] calc'd for $C_{20}H_{21}FN_6O_2$, 397; found, 397.

Preparation 29 tert-Butyl (1S,2R)-2-(7-chloro-3-oxo-4-(m-tolylamino)-2,3-dihydro-1H-pyrrolo[3,4-c]pyridin-6-ylamino)cyclohexylcarbamate

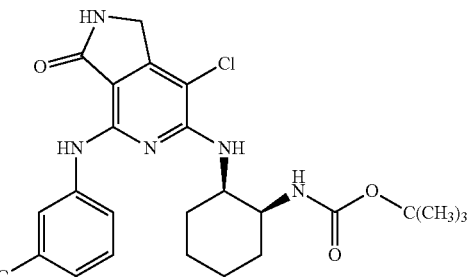

A vial was charged with tert-butyl (1S,2R)-2-(3-oxo-4-(m-tolylamino)-2,3-dihydro-1H-pyrrolo[3,4-c]pyridin-6-ylamino)cyclohexylcarbamate (63 mg, 0.140 mmol) and N-chlorosuccinimide (18.63 mg, 0.140 mmol) in DCM (1.4 mL) to give a yellow solution. The solution was stirred for 1 h at RT. The crude reaction mixture was diluted with DCM (20 mL) and washed with saturated aq NaHCO$_3$ (2×10 mL) followed by water (10 mL) and brine (10 mL). The organic layers were combined, dried over sodium sulfate, and concentrated to a residue which was purified by flash column chromatography. The collected fractions were concentrated to a brown residue to give the title compound as a cream colored solid upon drying (38.1 mg, 56%). [M+H] calc'd for C$_{25}$H$_{32}$ClN$_5$O$_3$, 486; found, 486.

Example 75

6-((1R,2S)-2-Aminocyclohexylamino)-7-chloro-4-(m-tolylamino)-1H-pyrrolo[3,4-c]pyridin-3(2H)-one

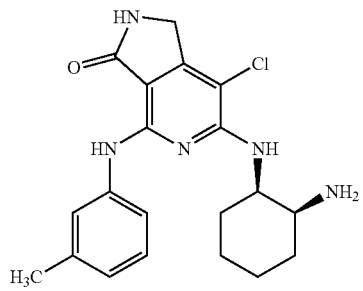 [SMILES: Cc1cccc(Nc2nc(N[C@@H]3CCCC[C@@H]3N)c(Cl)c3c2C(=O)NC3)c1]

To a solution of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate (20 mg, 0.041 mmol) in DCM (0.8 mL) was added trifluoroacetic acid (0.31 mL). The reaction mixture was stirred at RT for 1 h, then concentrated to a brown residue which was diluted in MeOH (2 mL) and purified via preparative HPLC to give a TFA salt of the title compound as a fluffy white solid (12.3 mg, 61.9%). $^1$H NMR (400 MHz, DMSO-d$_6$) δ ppm 8.85 (s, 1 H), 8.36 (s, 1 H), 7.83 (br s, 3 H), 7.39-7.57 (m, 2 H), 7.12-7.32 (m, 1 H), 6.84 (d, J=7.6 Hz, 1 H), 6.22 (d, J=6.8 Hz, 1 H), 4.19-4.43 (m, 3 H), 3.71 (br s, 1 H), 2.32 (s, 3 H), 1.37-1.99 (m, 8 H). [M+H] calc'd for C$_{20}$H$_{24}$ClN$_5$O, 386; found, 386.

Preparation 30 tert-Butyl (1S,2R)-2-(7-iodo-3-oxo-4-(m-tolylamino)-2,3-dihydro-1H-pyrrolo[3,4-c]pyridin-6-ylamino)cyclohexylcarbamate

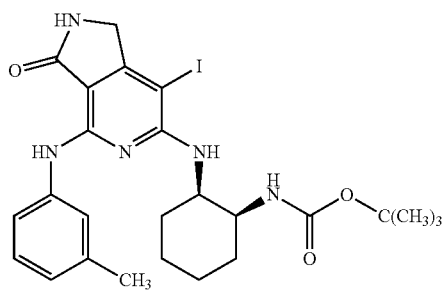 [SMILES: Cc1cccc(Nc2nc(N[C@@H]3CCCC[C@@H]3NC(=O)OC(C)(C)C)c(I)c3c2C(=O)NC3)c1]

To a screw-top vial was added tert-butyl (1S,2R)-2-(3-oxo-4-(m-tolylamino)-2,3-dihydro-1H-pyrrolo[3,4-c]pyridin-6-ylamino)cyclohexylcarbamate (73 mg, 0.162 mmol) and 1-iodopyrrolidine-2,5-dione (36.4 mg, 0.162 mmol) in DCM (1.6 mL) to give a yellow solution. The reaction was stirred 0.5 h at RT. The reaction mixture was diluted with DCM (10 mL) and washed with saturated aq NaHCO$_3$ (10 mL), water (10 mL), and brine (10 mL). The collected organic layers were dried with sodium sulfate and concentrated to give the title compound as a brown solid, which was used without further purification (85.7 mg, 92%). [M+H] calc'd for C$_{25}$H$_{32}$IN$_5$O$_3$, 578; found, 578.

Preparation 31 tert-Butyl (1S,2R)-2-(7-cyano-3-oxo-4-(m-tolylamino)-2,3-dihydro-1H-pyrrolo[3,4-c]pyridin-6-ylamino)cyclohexylcarbamate

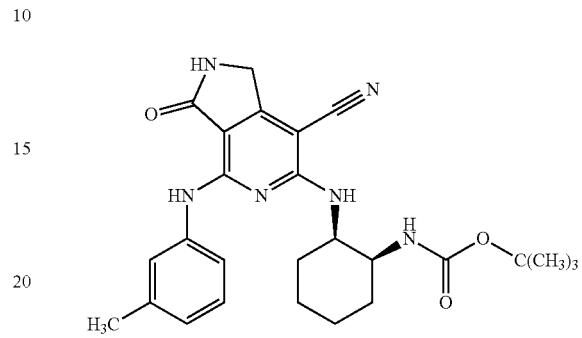

To an oven-dried microwave vial was added tert-butyl (1S,2R)-2-(7-iodo-3-oxo-4-(m-tolylamino)-2,3-dihydro-1H-pyrrolo[3,4-c]pyridin-6-ylamino)cyclohexylcarbamate (47.0 mg, 0.081 mmol), dicyanozinc (5.74 mg, 0.049 mmol), zinc powder (0.532 mg, 8.14 μmol), dppf (0.451 mg, 0.814 μmol), and Pd$_2$(dba)$_3$ (0.745 mg, 0.814 μmol). N,N-Dimethylacetamide (814 μL) was added and the resulting dark brown solution was degassed with nitrogen for 3 min. The vial was capped and heated at 80° C. with stirring for 1 h. The temperature was increased to 110° C., and the mixture was stirred for an additional 3 h, then cooled to RT, diluted with EtOAc (10 mL), and washed with water (2×10 mL) and brine (10 mL). The organic phase was dried with sodium sulfate and concentrated to give the title compound as a brown residue, which was used without further purification (40 mg, 103%). [M+H] calc'd for C$_{26}$H$_{32}$N$_6$O$_3$, 477; found, 477.

Example 76

6-((1R,2S)-2-Aminocyclohexylamino)-3-oxo-4-(m-tolylamino)-2,3-dihydro-1H-pyrrolo[3,4-c]pyridine-7-carbonitrile

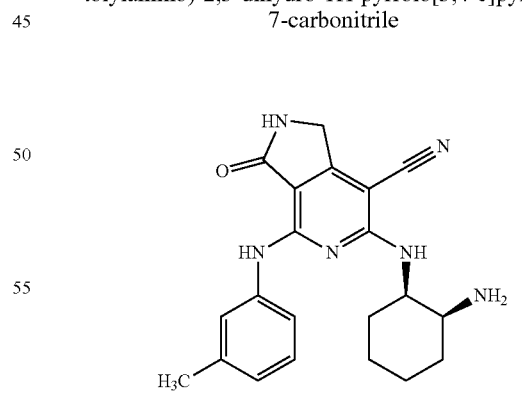

A TFA salt of the title compound was prepared in a manner similar to EXAMPLE 75 using tert-butyl (1S,2R)-2-(7-cyano-3-oxo-4-(m-tolylamino)-2,3-dihydro-1H-pyrrolo[3,4-c]pyridin-6-ylamino)cyclohexylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, DMSO-d$_6$) δ ppm 9.22 (s, 1 H), 8.48 (s, 1 H), 7.80 (br s, 3 H), 7.40-7.59 (m, 2 H), 7.26 (t, J=7.7 Hz, 1 H), 6.91 (dd, J=13.0, 6.9 Hz, 2 H), 4.43 (s, 2 H), 4.26-4.38 (m, 1 H), 3.68 (br s, 1 H), 2.33 (s, 3 H), 1.78-1.96 (m, 2 H), 1.35-1.79 (m, 6 H). [M+H] calc'd for $C_{21}H_{24}N_6O$, 377; found, 377.

Preparation 32

(R)-tert-Butyl 1-amino-3-methoxypropan-2-ylcarbamate

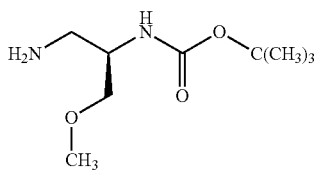

A. (S)-2-(tert-Butoxycarbonylamino)-3-methoxypropanoic acid

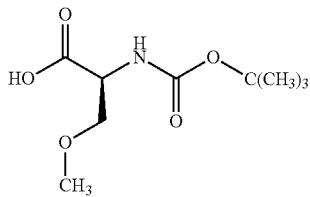

A sodium methanolate (NaOMe) solution was prepared by slowly adding MeOH (50 mL) to a suspension of sodium hydride (60% in mineral oil, 28 g, 0.71 mol) in dry THF (1.2 L) at 0° C. The resulting mixture was stirred at RT for 2 h. A portion of the NaOMe solution (320 mL) was added to (S)-2-(tert-butoxycarbonylamino)-3-hydroxypropanoic acid (36 g, 175 mmol) in dry THF (1.6 L), and the mixture was stirred at RT for 1 h. Methyl iodine (16 mL) was then added and the mixture was stirred at RT for 1 h. Another aliquot of NaOMe solution (540 mL) was added and the reaction mixture stirred at RT for 1 h. Additional methyl iodine (38 mL) in THF (200 mL) was added and the reaction mixture was stirred at RT for 36 h. Following reaction, the mixture was concentrated and the residue was dissolved in water and washed with diethyl ether (2×100 mL). The aqueous layer was acidified to pH 2 by the addition of solid citric acid and was extracted with EtOAc (3×200 mL) and dried over $Na_2SO_4$. The organic phase was concentrated, and the residue was dissolved in water and extracted with DCM (4×150 mL). The organic layers were combined and concentrated to give the title compound as an oil, which was used without further purification (10.9 g, 28%).

B. (R)-tert-Butyl 1-hydroxy-3-methoxypropan-2-ylcarbamate

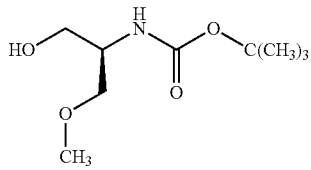

To a mixture of (S)-2-(tert-butoxycarbonylamino)-3-methoxypropanoic acid (10.9 g) and N-methylmorpholine (5.6 g, 55 mmol) in THF (50 mL) was added 2-methylpropylchloroformate (7.48 g, 55 mmol) in THF at −15° C. The reaction mixture was stirred −15° C. for 15 min, after which $NaBH_4$ (6.0 g, 159 mmol) in water (10 mL) was added. The reaction mixture was stirred for 30 min, then diluted with EtOAc, and neutralized with dilute HCl. The organic layer was dried over $Na_2SO_4$ and concentrated. The residue was purified by column chromatography on silica gel eluting with EtOAc and petroleum ether (EtOAc/PE=1.5/1) to give the title compound (6.0 g, 58%). $^1$H NMR (400 MHz, $CDCl_3$) δ ppm 5.23 (s, 1 H), 3.80 (d, J=8.0 Hz, 2 H), 3.72-3.68 (m, 1 H), 3.60-3.52 (m, 2 H), 3.38 (s, 3 H), 2.85 (s, 1 H), 1.47 (s, 9H).

C. (R)-tert-Butyl 1-azido-3-methoxypropan-2-ylcarbamate

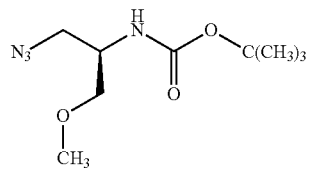 [SMILES: COC[C@@H](CN=[N+]=[N-])NC(=O)OC(C)(C)C]

Methanesulfonyl chloride (4.0 g, 35 mmol) in DCM (50 mL) was slowly added to a solution of (R)-tert-butyl 1-hydroxy-3-methoxypropan-2-ylcarbamate (6.0 g, 29 mmol) and $Et_3N$ (3.64 g, 36 mmol) in DCM (150 mL) at 0° C. The reaction mixture was stirred at RT for 2 h. The organic phase was washed with water and saturated aq $NaHCO_3$, concentrated, and dissolved in DMF. Sodium azide (2.34 g, 36.0 mmol) was added, and the reaction mixture was stirred at 75° C. for 4 h. The reaction mixture was diluted by EtOAc and washed with water. The crude product was purified by column chromatography on silica gel eluting with EtOAc and petroleum ether (EtOAc/PE=2/1) to give the title compound (4.3 g, 64%). $^1$H NMR (400 MHz, $CDCl_3$) δ ppm 4.92 (s, 1 H), 3.91 (m, 1 H), 3.53-3.48 (m, 2 H), 3.45-3.40 (m, 2 H), 3.38 (s, 3 H), 1.47 (s, 9 H).

D. (R)-tert-Butyl 1-amino-3-methoxypropan-2-ylcarbamate

A mixture of (R)-tert-butyl 1-azido-3-methoxypropan-2-ylcarbamate (4.3 g, 18.7 mmol) and 10% Pd/C (1.5 g) in MeOH was stirred at RT under $H_2$ atmosphere overnight.

After filtration, the crude product was purified by amino-protected silica gel chromatography eluting with EtOAc and petroleum ether (EtOAc/PE=1/1) to give the title compound (740 mg, 19.4%). $^1$H NMR (400 MHz, CD$_3$OD) δ ppm 5.00 (s, 1 H), 3.67-3.66 (m, 1 H), 3.51-3.47 (m, 1H), 3.42-3.38 (m, 1 H), 3.35 (s, 1 H), 2.82-2.78 (m, 2 H), 1.46 (s, 9 H). [M+H] calc'd for C$_9$H$_{20}$N$_2$O$_3$, 205; found, 205.

Preparation 33

(R)-Methyl 6-(2-(tert-butoxycarbonylamino)-3-methoxypropylamino)-4-cyano-2-(m-tolylamino)nicotinate

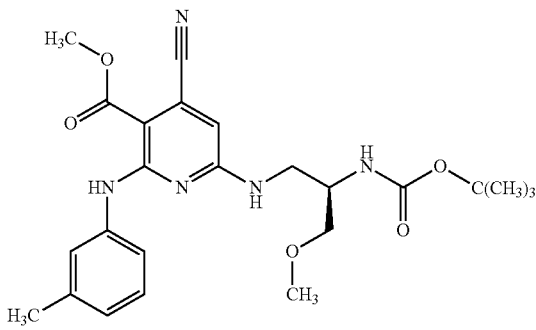 [SMILES: COC[C@@H](CNc1cc(C#N)c(C(=O)OC)c(Nc2cccc(C)c2)n1)NC(=O)OC(C)(C)C]

To a screw-top vial was added methyl 6-chloro-4-cyano-2-(m-tolylamino)nicotinate (0.28 g, 0.928 mmol), (R)-tert-Butyl 1-amino-3-methoxypropan-2-ylcarbamate (0.227 g, 1.114 mmol), and DIPEA (0.211 mL, 1.206 mmol) in DMF (3 mL). The resulting yellow solution was stirred at RT for 12 h, diluted with EtOAc (30 mL) and washed with water (2×20 mL) and brine (20 mL). The organic phase was dried with Na$_2$SO$_4$ and concentrated to give the title compound as thick yellow oil, which was used without further purification (470 mg). [M+H] calc'd for C$_{24}$H$_{31}$N$_5$O$_5$, 470; found, 470.

Preparation 34

(R)-tert-Butyl 1-methoxy-3-(3-oxo-4-(m-tolylamino)-2,3-dihydro-1H-pyrrolo[3,4-c]pyridin-6-ylamino)propan-2-ylcarbamate

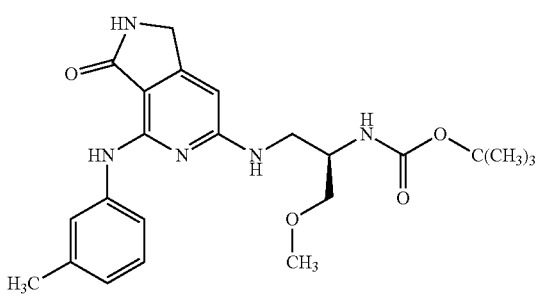 [SMILES: COC[C@@H](CNc1cc2c(c(Nc3cccc(C)c3)n1)C(=O)NC2)NC(=O)OC(C)(C)C]

To a round-bottomed flask was added (R)-methyl 6-(2-(tert-butoxycarbonylamino)-3-methoxypropylamino)-4-cyano-2-(m-tolylamino)nicotinate (84.5 mg, 0.180 mmol) in acetic acid (3 mL) and DCM (10 mL). To the resulting yellow solution was added platinum(IV) oxide (4.09 mg, 0.018 mmol). The flask was evacuated and back filled with hydrogen (3×1 atm). The reaction mixture was stirred vigorously at RT for 16 h, subsequently diluted with DCM (10 mL), and filtered through Celite. The filtrate was concentrated to an oil, which was diluted with DCM (10 mL). Potassium carbonate (24.87 mg, 0.180 mmol) was added and the reaction mixture was stirred at RT for 12 h. The crude reaction was diluted with DCM (10 mL), filtered through Celite, and concentrated to give the title compound as a thick yellow oil, which was used without further purification (26.5 mg, 33.4%). [M+H] calc'd for C$_{23}$H$_{31}$N$_5$O$_4$, 442; found, 442.

Example 77

(R)-6-(2-Amino-3-methoxypropylamino)-4-(m-tolylamino)-1H-pyrrolo[3,4-c]pyridin-3(2H)-one

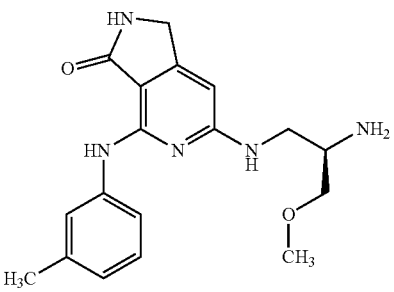 [SMILES: COC[C@H](N)CNc1cc2c(c(Nc3cccc(C)c3)n1)C(=O)NC2]

A TFA salt of the title compound was prepared in a manner similar to EXAMPLE 75 using (R)-tert-butyl 1-methoxy-3-(3-oxo-4-(m-tolylamino)-2,3-dihydro-1H-pyrrolo[3,4-c]pyridin-6-ylamino)propan-2-ylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, CD$_3$OD) δ ppm 7.57 (d, J=8.3 Hz, 1 H), 7.36 (s, 1 H), 7.22 (t, J=7.8 Hz, 1 H), 6.87 (d, J=7.3 Hz, 1 H), 6.07 (s, 1 H), 4.30 (s, 2 H), 3.70-3.82 (m, 2 H), 3.50-3.65 (m, 3 H), 3.40 (s, 3 H), 2.35 (s, 3 H). [M+H] calc'd for C$_{18}$H$_{23}$N$_5$O$_2$, 342; found, 342.

Preparation 35

(R)-tert-Butyl 1-(7-cyano-3-oxo-4-(m-tolylamino)-2,3-dihydro-1H-pyrrolo[3,4-c]pyridin-6-ylamino)-3-methoxypropan-2-ylcarbamate

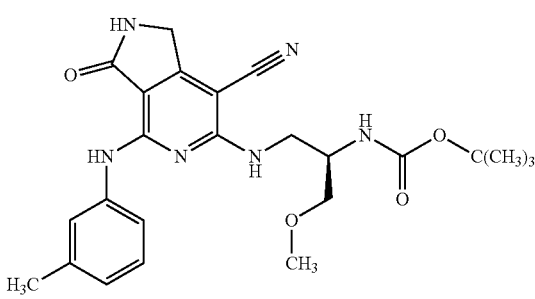 [SMILES: COC[C@@H](CNc1nc(Nc2cccc(C)c2)c2c(c1C#N)CNC2=O)NC(=O)OC(C)(C)C]

A. (R)-tert-Butyl 1-(7-iodo-3-oxo-4-(m-tolylamino)-2,3-dihydro-1H-pyrrolo[3,4-c]pyridin-6-ylamino)-3-methoxypropan-2-ylcarbamate

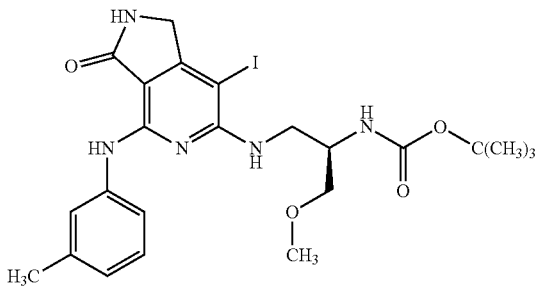 [SMILES: COC[C@@H](CNc1nc(Nc2cccc(C)c2)c2c(c1I)CNC2=O)NC(=O)OC(C)(C)C]

The title compound was prepared in a manner similar to PREPARATION 30 using (R)-tert-butyl 1-methoxy-3-(3-oxo-4-(m-tolylamino)-2,3-dihydro-1H-pyrrolo[3,4-c]pyridin-6-ylamino)propan-2-ylcarbamate in place of tert-butyl (1S,2R)-2-(3-oxo-4-(m-tolylamino)-2,3-dihydro-1H-pyrrolo[3,4-c]pyridin-6-ylamino)cyclohexylcarbamate. [M+H] calc'd for $C_{23}H_{30}IN_5O_4$, 568; found, 568.

B. (R)-tert-Butyl 1-(7-cyano-3-oxo-4-(m-tolylamino)-2,3-dihydro-1H-pyrrolo[3,4-c]pyridin-6-ylamino)-3-methoxypropan-2-ylcarbamate The title compound was prepared in a manner similar to PREPARATION 31 using (R)-tert-butyl 1-(7-iodo-3-oxo-4-(m-tolylamino)-2,3-dihydro-1H-pyrrolo[3,4-c]pyridin-6-ylamino)-3-methoxypropan-2-ylcarbamate in place of tert-butyl (1S,2R)-2-(7-iodo-3-oxo-4-(m-tolylamino)-2,3-dihydro-1H-pyrrolo[3,4-c]pyridin-6-ylamino)cyclohexylcarbamate. [M+H] calc'd for $C_{24}H_{30}N_6O_4$, 467; found, 467.

Example 78

(R)-6-(2-Amino-3-methoxypropylamino)-3-oxo-4-(m-tolylamino)-2,3-dihydro-1H-pyrrolo[3,4-c]pyridine-7-carbonitrile

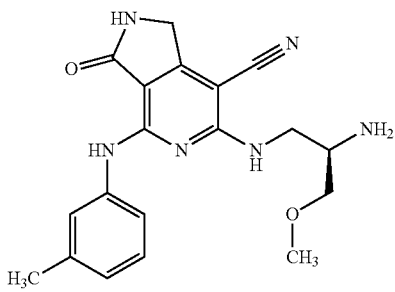 [SMILES: COC[C@H](N)CNc1nc(Nc2cccc(C)c2)c2c(c1C#N)CNC2=O]

A TFA salt of the title compound was prepared in a manner similar to EXAMPLE 75 using (R)-tert-butyl 1-(7-cyano-3-oxo-4-(m-tolylamino)-2,3-dihydro-1H-pyrrolo[3,4-c]pyridin-6-ylamino)-3-methoxypropan-2-ylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, DMSO-$d_6$) δ ppm 9.25 (s, 1 H), 8.47 (s, 1 H), 7.93 (br s, 3 H), 7.58 (d, J=7.8 Hz, 1 H), 7.51 (t, J=5.4 Hz, 1 H), 7.42 (s, 1 H), 7.27 (t, J=7.8 Hz, 1 H), 6.93 (d, J=7.3 Hz, 1 H), 4.43 (s, 2 H), 3.71-3.80 (m, 1 H), 3.60-3.70 (m, 1 H), 3.44-3.60 (m, 3 H), 3.29 (s, 3 H), 2.33 (s, 3 H). [M+H] calc'd for $C_{19}H_{22}N_6O_2$, 367; found, 367.

Preparation 36

(R)-tert-Butyl 1-(7-fluoro-3-oxo-4-(m-tolylamino)-2,3-dihydro-1H-pyrrolo[3,4-c]pyridin-6-ylamino)-3-methoxypropan-2-ylcarbamate

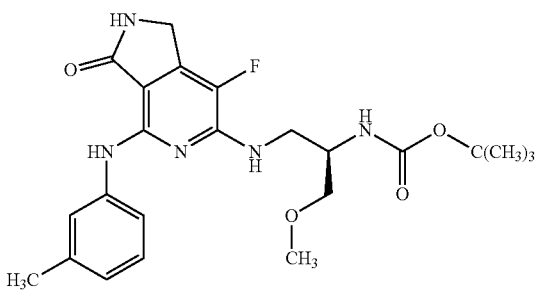 [SMILES: COC[C@@H](CNc1nc(Nc2cccc(C)c2)c2c(c1F)CNC2=O)NC(=O)OC(C)(C)C]

To a screw-top vial was added (R)-tert-butyl 1-methoxy-3-(3-oxo-4-(m-tolylamino)-2,3-dihydro-1H-pyrrolo[3,4-c]pyridin-6-ylamino)propan-2-ylcarbamate (27 mg, 0.061 mmol) in a mixture of DCM and MeOH (1/1, 1.2 mL). The resulting colorless solution was cooled to 0° C. SELECTFLUOR® (21.66 mg, 0.061 mmol) was added and the reaction mixture was stirred at 0° C. for 2 h. Next, the reaction mixture was diluted with EtOAc (10 mL) and washed with saturated aq sodium bicarbonate (5 mL), water (5 mL), and brine (5 mL). The organic layer was collected, dried over $Na_2SO_4$, and concentrated to give the title compound as a brown residue, which was used without further purification (32 mg, 114%). [M+H] calc'd for $C_{23}H_{30}FN_5O_4$, 460; found, 460.

Example 79

(R)-6-(2-Amino-3-methoxypropylamino)-7-fluoro-4-(m-tolylamino)-1H-pyrrolo[3,4-c]pyridin-3(2H)-one

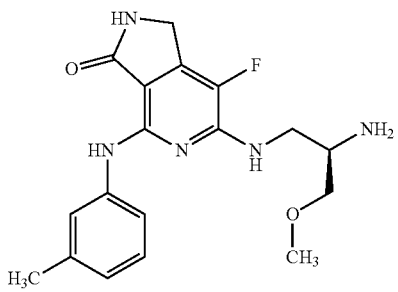 [SMILES: COC[C@H](N)CNc1nc(Nc2cccc(C)c2)c2c(c1F)CNC2=O]

A TFA salt of the title compound was prepared in a manner similar to EXAMPLE 75 using (R)-tert-butyl 1-(7-fluoro-3-oxo-4-(m-tolylamino)-2,3-dihydro-1H-pyrrolo[3,4-c]pyridin-6-ylamino)-3-methoxypropan-2-ylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, DMSO-$d_6$) δ ppm 8.84 (s, 1 H), 8.28 (s, 1 H), 7.97 (br s, 3 H), 7.47-7.62 (m, 1 H), 7.40 (s, 1 H), 7.11-7.29 (m, 2 H), 6.80 (d, J=7.6 Hz, 1 H), 4.40 (s, 2 H), 3.62-3.78 (m, 2 H), 3.46-3.61 (m, 3 H), 3.31 (s, 3 H), 2.31 (s, 3 H). [M+H] calc'd for $C_{18}H_{22}FN_5O_2$, 360; found, 360.

Preparation 37 tert-Butyl (1S,2R)-2-(7-(3-hydroxyprop-1-ynyl)-3-oxo-4-(m-tolylamino)-2,3-dihydro-1H-pyrrolo[3,4-c]pyridin-6-ylamino)cyclohexylcarbamate

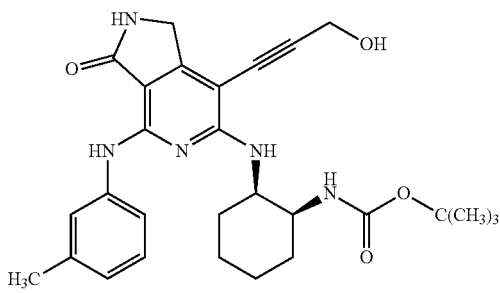 [SMILES: Cc1cccc(Nc2nc(N[C@@H]3CCCC[C@@H]3NC(=O)OC(C)(C)C)c(C#CCO)c3c2C(=O)NC3)c1]

To an oven dried glass pressure vessel was added tert-butyl (1S,2R)-2-(7-iodo-3-oxo-4-(m-tolylamino)-2,3-dihydro-1H-pyrrolo[3,4-c]pyridin-6-ylamino)cyclohexylcarbamate (25 mg, 0.043 mmol), copper(I) iodide (12.37 mg, 0.065 mmol), bis(triphenylphosphine) palladium(II)chloride (9.12 mg, 0.013 mmol), butylated hydroxytoluene (one granule), THF (866 µL), and Et₃N (121 µL, 0.866 mmol). The mixture was degassed 3 min with nitrogen. Propargyl alcohol (31 µL, 0.520 mmol) was added and the vessel was capped and heated at 80° C. with stirring for 2 h and then at RT for 12 h. The reaction mixture was diluted with EtOAc (10 mL) and washed with water (5 mL) and brine (5 mL). The organic layer was collected, dried with Na₂SO₄, and concentrated to give the title compound as a brown residue, which was used without further purification (22 mg, 101%). [M+H] calc'd for $C_{28}H_{35}N_5O_4$, 506; found, 506.

Example 80

7-Acryloyl-6-((1R,2S)-2-aminocyclohexylamino)-4-(m-tolylamino)-1H-pyrrolo[3,4-c]pyridin-3(2H)-one

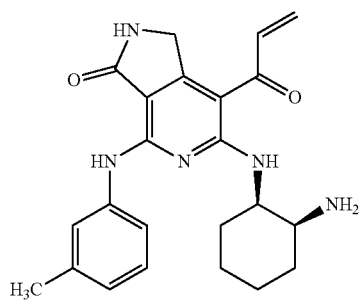 [SMILES: C=CC(=O)c1c(N[C@@H]2CCCC[C@@H]2N)nc(Nc2cccc(C)c2)c2c1CNC2=O]

A TFA salt of the title compound was prepared in a manner similar to EXAMPLE 75 using tert-butyl (1S,2R)-2-(7-(3-hydroxyprop-1-ynyl)-3-oxo-4-(m-tolylamino)-2,3-dihydro-1H-pyrrolo[3,4-c]pyridin-6-ylamino)cyclohexylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. ¹H NMR (400 MHz, DMSO-d₆) δ ppm 10.53 (d, J=7.8 Hz, 1 H), 9.81 (s, 1 H), 8.65 (s, 1 H), 7.85 (br s, 3 H), 7.60 (s, 1 H), 7.51 (s, 1 H), 7.27 (t, J=7.8 Hz, 1 H), 7.08 (dd, J=16.5, 10.5 Hz, 1 H), 6.93 (d, J=7.6 Hz, 1 H), 6.19 (dd, J=16.7, 2.0 Hz, 1 H), 5.68-5.90 (m, 1 H), 4.50-4.80 (m, 3 H), 3.65 (br s, 1 H), 2.34 (s, 3 H), 1.78-2.01 (m, 2 H), 1.75 (s, 3 H), 1.43-1.58 (m, 3 H). [M+H] calc'd for $C_{23}H_{27}N_5O_2$, 406; found, 406.

Example 81

6-((1R,2S)-2-Aminocyclohexylamino)-7-iodo-4-(m-tolylamino)-1H-pyrrolo[3,4-c]pyridin-3(2H)-one

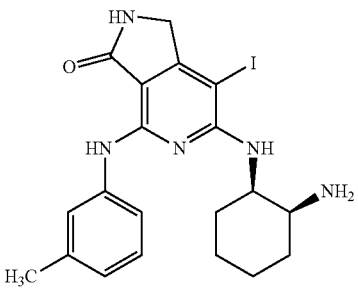 [SMILES: Cc1cccc(Nc2nc(N[C@@H]3CCCC[C@@H]3N)c(I)c3c2C(=O)NC3)c1]

A TFA salt of the title compound was prepared in a manner similar to EXAMPLE 75 using tert-butyl (1S,2R)-2-(7-iodo-3-oxo-4-(m-tolylamino)-2,3-dihydro-1H-pyrrolo[3,4-c]pyridin-6-ylamino)cyclohexylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. ¹H NMR (400 MHz, CD₃OD) δ ppm 7.48 (d, J=8.1 Hz, 1 H), 7.39 (s, 1 H), 7.23 (t, J=7.8 Hz, 1 H), 6.90 (d, J=7.6 Hz, 1 H), 4.47 (d, J=9.1 Hz, 1 H), 4.18 (d, J=3.0 Hz, 2 H), 3.80-3.87 (m, 1 H), 2.36 (s, 3 H), 1.87 (d, J=5.6 Hz, 4 H), 1.66 (br s, 4 H). [M+H] calc'd for $C_{20}H_{24}IN_5O$, 478; found, 478.

Preparation 38 tert-Butyl 4-(6-((1R,2S)-2-(tert-butoxycarbonylamino)cyclohexylamino)-3-oxo-4-(m-tolylamino)-2,3-dihydro-1H-pyrrolo[3,4-c]pyridin-7-yl)-1H-pyrazole-1-carboxylate

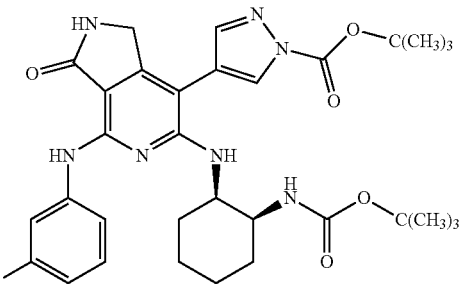

To an oven dried vial was added tert-butyl (1S,2R)-2-(7-iodo-3-oxo-4-(m-tolylamino)-2,3-dihydro-1H-pyrrolo[3,4-c]pyridin-6-ylamino)cyclohexylcarbamate (40 mg, 0.069 mmol), tert-butyl 3-(4,4,5,5-tetramethyl-1,3,2-dioxaborolan-2-yl)-1H-pyrazole-1-carboxylate (30.6 mg, 0.104 mmol), and sodium carbonate (0.104 mL, 0.208 mmol) in DMF (1 mL). The resulting tan mixture was degassed 15 min. Bis(triphenylphosphine) palladium(II)chloride (4.86 mg, 6.93 µmol) was added and the mixture was degassed an additional 5 min. The vial was capped and was heated at 80° C. for 12 h. The reaction mixture was diluted with EtOAc (10 mL) and washed with water (5 mL) and brine (5 mL). The organic layer was collected, dried with Na$_2$SO$_4$ and concentrated to give a brown residue, which was used without further purification (55 mg). LCMS indicated the desired mass less one of the Boc protecting groups. [M+H-Boc] calc'd for C$_{33}$H$_{43}$N$_7$O$_5$, 518; found, 518.

Example 82

6-((1R,2S)-2-Aminocyclohexylamino)-7-(1H-pyrazol-4-yl)-4-(m-tolylamino)-1H-pyrrolo[3,4-c]pyridin-3(2H)-one

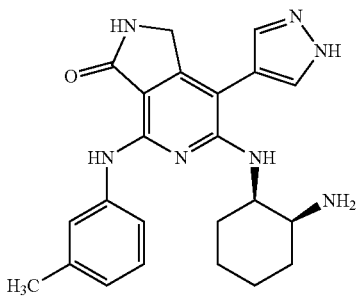 [SMILES: Cc1cccc(Nc2nc(N[C@@H]3CCCC[C@@H]3N)c(-c3cn[nH]c3)c3c2C(=O)NC3)c1]

A TFA salt of the title compound was prepared in a manner similar to EXAMPLE 75 using tert-Butyl 4-(6-((1R,2S)-2-(tert-butoxycarbonylamino)cyclohexylamino)-3-oxo-4-(m-tolylamino)-2,3-dihydro-1H-pyrrolo[3,4-c]pyridin-7-yl)-1H-pyrazole-1-carboxylate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, DMSO-d$_6$) δ ppm 13.13 (br s, 1 H), 8.97 (s, 1 H), 8.19 (s, 1 H), 8.06 (br s, 1 H), 7.75 (br s, 4 H), 7.42-7.58 (m, 2 H), 7.21 (t, J=8.1 Hz, 1 H), 6.81 (d, J=7.3 Hz, 1 H), 5.55 (d, J=6.6 Hz, 1 H), 4.25 (s, 3 H), 3.77 (br s, 1 H), 2.32 (s, 3 H), 1.63-1.89 (m, 4 H), 1.36-1.63 (m, 4 H). [M+H] calc'd for C$_{23}$H$_{27}$N$_7$O, 418; found, 418.

Example 83

6-(cis-2-Amino-3,3-difluorocyclohexylamino)-4-(m-tolylamino)-1H-pyrrolo[3,4-c]pyridin-3(2H)-one

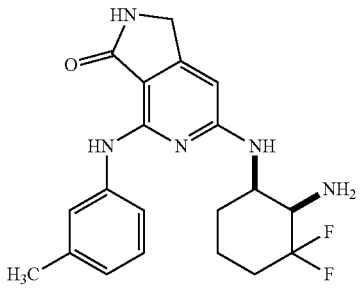

A. Methyl 6-(cis-2-Amino-3,3-difluorocyclohexylamino)-4-cyano-2-(m-tolylamino)nicotinate

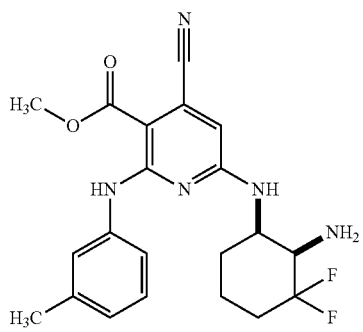

To a screw-cap vial was added methyl 6-chloro-4-cyano-2-(m-tolylamino)nicotinate (200 mg, 0.663 mmol), cis-3,3-difluorocyclohexane-1,2-diamine hydrochloride (148 mg, 0.795 mmol), and DIPEA (347 µL, 1.989 mmol) in DMF (3.9 mL). The resulting brownish-yellow mixture was stirred at RT for 2 h and then at 60° C. for 12 h. The reaction mixture was cooled to RT, diluted with EtOAc (30 mL) and washed with water (2×10 mL) and brine (20 mL). The organic layer was collected, dried over Na$_2$SO$_4$, and concentrated to give a thick brown oil, which included the title compound and isomers (328 mg, 119%). The crude product was used without further purification. [M+H] calc'd for C$_{21}$H$_{23}$F$_2$N$_5$O$_2$, 416; found, 416.

B. 6-(cis-2-Amino-3,3-difluorocyclohexylamino)-4-(m-tolylamino)-1H-pyrrolo[3,4-c]pyridin-3(2H)-one A round-bottomed flask was charged with methyl 6-(cis-2-amino-3,3-difluorocyclohexylamino)-4-cyano-2-(m-tolylamino)nicotinate (275 mg, 0.662 mmol) in HOAc (2.6 mL) and DCM (10.6 mL). To the resulting brown solution was added platinum(IV) oxide (15.03 mg, 0.066 mmol). The flask was evacuated and back filled with hydrogen (3×1 atm). The reaction mixture was stirred vigorously under H$_2$ atmosphere (1 atm) at RT for 16 h and then filtered through Celite. The filtrate was washed with DCM (20 mL) and concentrated to a residue, which was diluted in MeOH (3 mL) and purified via preparative HPLC to give a TFA salt of the title compound as a light green solid. $^1$H NMR (400 MHz, DMSO-d$_6$) δ ppm 8.97 (s, 1 H), 8.48 (br s, 3 H), 8.09 (s, 1 H), 7.62 (d, J=8.8 Hz, 1 H), 7.32 (s, 1 H), 7.14 (t, J=7.8 Hz, 1 H), 6.87 (br s, 1 H), 6.79 (d, J=7.3 Hz, 1 H), 6.15 (s, 1 H), 4.45 (br s, 1 H), 4.24 (d, 2 H), 4.15 (br s, 1 H), 2.29 (s, 3 H), 2.01-2.25 (m, 2 H), 1.74-1.89 (m, 3 H), 1.60 (d, J=10 Hz, 1 H). [M+H] calc'd for $C_{20}H_{23}F_2N_5O$, 388; found, 388.

Preparation 39 tert-Butyl (1S,2R)-2-(7-(1-methyl-1H-pyrazol-5-yl)-3-oxo-4-(m-tolylamino)-2,3-dihydro-1H-pyrrolo[3,4-c]pyridin-6-ylamino)cyclohexylcarbamate

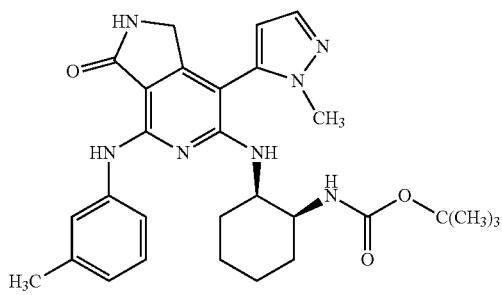 [SMILES: Cc1cccc(Nc2nc(N[C@@H]3CCCC[C@@H]3NC(=O)OC(C)(C)C)c(-c3ccnn3C)c3c2C(=O)NC3)c1]

The title compound was prepared in a manner similar to PREPARATION 36 using 1-methyl-5-(4,4,5,5-tetramethyl-1,3,2-dioxaborolan-2-yl)-1H-pyrazole in place of tert-butyl 3-(4,4,5,5-tetramethyl-1,3,2-dioxaborolan-2-yl)-1H-pyrazole-1-carboxylate. [M+H] calc'd for $C_{29}H_{37}N_7O_3$, 532; found, 532.

Example 84

6-((1R,2S)-2-Aminocyclohexylamino)-7-(1-methyl-1H-pyrazol-5-yl)-4-(m-tolylamino)-1H-pyrrolo[3,4-c]pyridin-3(2H)-one

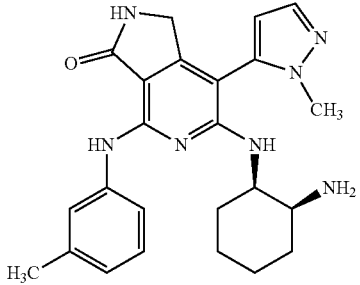 [SMILES: Cc1cccc(Nc2nc(N[C@@H]3CCCC[C@@H]3N)c(-c3ccnn3C)c3c2C(=O)NC3)c1]

A TFA salt of the title compound was prepared in a manner similar to EXAMPLE 75 using tert-butyl (1S,2R)-2-(7-(1-methyl-1H-pyrazol-5-yl)-3-oxo-4-(m-tolylamino)-2,3-dihydro-1H-pyrrolo[3,4-c]pyridin-6-ylamino)cyclohexylcarbamate in place of tert-butyl (1S,2R)-2-(7-chloro-3-oxo-4-(m-tolylamino)-2,3-dihydro-1H-pyrrolo[3,4-c]pyridin-6-ylamino)cyclohexylcarbamate. $^1$H NMR (400 MHz, DMSO-$d_6$) δ ppm 2.33 (d, J=1.26 Hz, 3 H), 3.64 (d, J=14.15 Hz, 3 H), 3.89-4.00 (m, 1 H), 4.02-4.21 (m, 1 H), 5.23-5.58 (m, 1 H), 6.29-6.47 (m, 1 H), 6.85 (d, J=7.58 Hz, 1 H), 7.23 (td, J=7.77, 4.93 Hz, 1 H), 7.47-7.56 (m, 2 H), 7.58 (dd, J=9.35, 1.77 Hz, 1 H), 7.64-7.83 (m, 2 H), 8.21 (d, J=2.27 Hz, 1 H), 9.04 (s, 1 H). [M+H] calc'd for $C_{24}H_{29}N_7O$, 432; found, 432.

Example 85

6-((3R,4R)-3-Aminotetrahydro-2H-pyran-4-ylamino)-4-(m-tolylamino)-1H-pyrrolo[3,4-c]pyridin-3(2H)-one

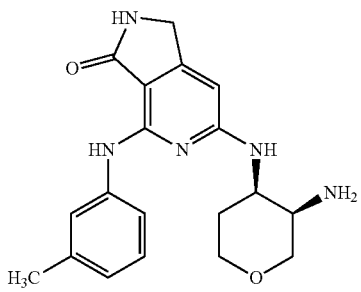 [SMILES: Cc1cccc(Nc2nc(N[C@@H]3CCOC[C@@H]3N)cc3c2C(=O)NC3)c1]

A. Methyl 6-((3R,4R)-3-Aminotetrahydro-2H-pyran-4-ylamino)-4-cyano-2-(m-tolylamino)nicotinate and Methyl 6-((3R,4R)-4-Aminotetrahydro-2H-pyran-3-ylamino)-4-cyano-2-(m-tolylamino)nicotinate

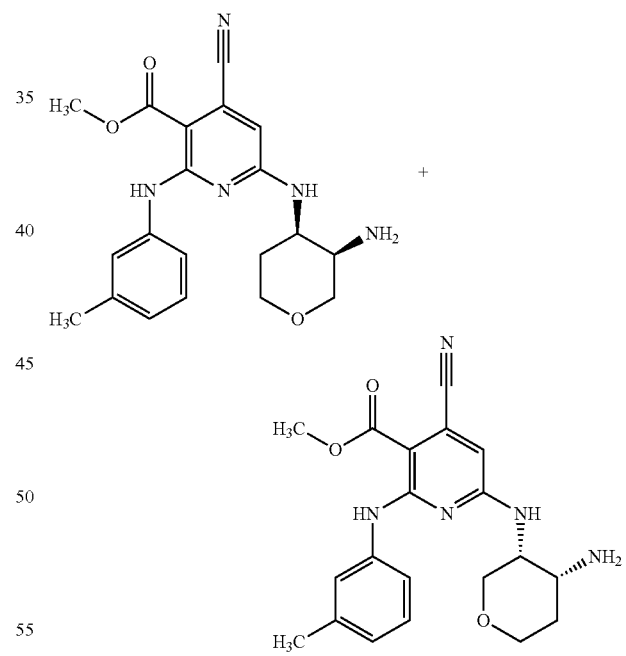

To a screw-cap vial was added methyl 6-chloro-4-cyano-2-(m-tolylamino)nicotinate (500 mg, 1.657 mmol), (3R,4R)-tetrahydro-2H-pyran-3,4-diamine hydrochloride (303.0 mg, 1.989 mmol), and DIPEA (868 μL, 4.97 mmol) in DMF (9748 μL). The resulting yellow suspension, which became a solution upon adding base, was stirred at 50° C. for 12 h. The reaction mixture was cooled to RT, diluted with EtOAc (30 mL), and washed with water (20 mL) and brine (20 mL). The organic layer was collected, dried with $Na_2SO_4$, and concentrated to give a yellow oil, which included the title compounds (350 mg, 55.4%). The crude product was used in the next step without further purification. [M+H] calc'd for $C_{20}H_{23}N_5O_3$, 382; found, 382.

B. 6-((3R,4R)-3-Aminotetrahydro-2H-pyran-4-ylamino)-4-(m-tolylamino)-1H-pyrrolo[3,4-c]pyridin-3(2H)-one To a 50 mL round-bottomed flask was added a mixture of methyl 6-((3R,4R)-3-aminotetrahydro-2H-pyran-4-ylamino)-4-cyano-2-(m-tolylamino)nicotinate and methyl 6-((3R,4R)-4-aminotetrahydro-2H-pyran-3-ylamino)-4-cyano-2-(m-tolylamino)nicotinate (100 mg, 0.262 mmol) and platinum(IV) oxide (11.91 mg, 0.052 mmol) in DCM (4195 µL) and HOAc (1049 µL). The vessel was evacuated and back filled with hydrogen (1 atm) and the mixture was stirred at RT for 12 h. The reaction mixture was diluted with DCM (10 mL) and MeOH (20 mL), filtered through Celite, and concentrated to a residue, which was diluted with DCM (50 mL). Potassium carbonate (217 mg, 1.573 mmol) was added and the mixture was stirred at RT for 12 h. The mixture was filtered through Celite, concentrated to a residue, diluted with a mixture of DMF and MeOH (1/1, 3 mL), and purified via preparative HPLC. The appropriate isomer peak was collected and lyophilized to give a TFA salt of the title compound as a light grey solid (20.3 mg, 21.9%). $^1$H NMR (400 MHz, DMSO-$d_6$) δ ppm 8.92 (s, 1 H), 8.05 (s, 1 H), 7.95 (br s, 3 H), 7.50 (d, J=8.1 Hz, 1 H), 7.43 (s, 1 H), 7.21 (t, J=7.8 Hz, 1 H), 7.09 (d, J=4.8 Hz, 1 H), 6.80 (d, J=7.6 Hz, 1 H), 6.11 (s, 1 H), 4.20-4.32 (m, 3 H), 3.91-4.06 (m, 2 H), 3.76 (br s, 1 H), 3.53-3.72 (m, 2 H), 2.31 (s, 3 H), 1.99 (qd, J=12.6, 4.7 Hz, 1 H), 1.70-1.80 (m, 1 H). [M+H] calc'd for $C_{19}H_{23}N_5O_2$, 354; found, 354.

Example 86

6-((3R,4R)-4-Aminotetrahydro-2H-pyran-3-ylamino)-4-(m-tolylamino)-1H-pyrrolo[3,4-c]pyridin-3(2H)-one A TFA salt of the title compound was prepared in a manner similar to EXAMPLE 85, collecting the fractions corresponding to 6-((3R,4R)-4-aminotetrahydro-2H-pyran-3-ylamino)-4-(m-tolylamino)-1H-pyrrolo[3,4-c]pyridin-3(2H)-one in place 6-((3R,4R)-3-aminotetrahydro-2H-pyran-4-ylamino)-4-(m-tolylamino)-1H-pyrrolo[3,4-c]pyridin-3(2H)-one. $^1$H NMR (400 MHz, DMSO-$d_6$) δ ppm 8.91 (s, 1 H), 7.94-8.15 (m, 4 H), 7.52 (s, 1 H), 7.43 (d, J=8.3 Hz, 1 H), 7.18 (t, J=7.8 Hz, 1 H), 7.03 (d, J=8.3 Hz, 1 H), 6.79 (d, J=7.6 Hz, 1 H), 6.21 (s, 1 H), 4.44 (br s, 1 H), 4.20-4.30 (m, 2 H), 3.84-3.95 (m, 2 H), 3.67-3.81 (m, 1 H), 3.62 (dd, J=11.6, 1.8 Hz, 1 H), 3.50 (td, J=11.2, 2.4 Hz, 1 H), 2.30 (s, 3 H), 1.98-2.13 (m, 1 H), 1.71-1.82 (m, 1 H). [M+H] calc'd for $C_{19}H_{23}N_5O_2$, 354; found, 354.

Example 87 tert-Butyl (1S,2R)-2-(3-oxo-7-phenyl-4-(m-tolylamino)-2,3-dihydro-1H-pyrrolo[3,4-c]pyridin-6-ylamino)cyclohexylcarbamate

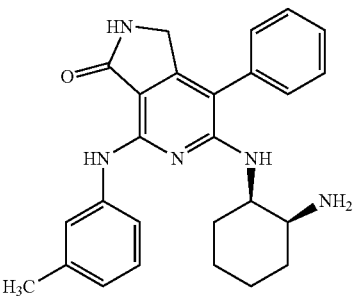 [SMILES: Cc1cccc(Nc2nc(N[C@@H]3CCCC[C@@H]3N)c(-c3ccccc3)c3c2C(=O)NC3)c1]

A TFA salt of the title compound was prepared in a manner similar to EXAMPLE 82 using phenylboronic acid in place of tert-butyl 3-(4,4,5,5-tetramethyl-1,3,2-dioxaborolan-2-yl)-1H-pyrazole-1-carboxylate. $^1$H NMR (400 MHz, DMSO-$d_6$) δ ppm 9.03 (s, 1 H), 8.15 (s, 1 H), 7.72 (br s, 3 H), 7.51 (d, J=4.5 Hz, 6 H), 7.35-7.45 (m, 1 H), 7.22 (dd, J=8.7, 7.5 Hz, 1 H), 6.83 (d, J=7.6 Hz, 1 H), 5.33 (d, J=6.8 Hz, 1 H), 4.30 (br s, 1 H), 4.17-4.27 (m, 1 H), 4.04 (d, J=17.7 Hz, 1 H), 3.76 (br s, 1 H), 2.33 (s, 3 H), 1.59-1.85 (m, 4 H), 1.37-1.59 (m, 4 H). [M+H] calc'd for $C_{26}H_{29}N_5O$, 428; found, 428.

Preparation 40 tert-Butyl (1S,2R)-2-(7-methyl-3-oxo-4-(m-tolylamino)-2,3-dihydro-1H-pyrrolo[3,4-c]pyridin-6-ylamino)cyclohexylcarbamate

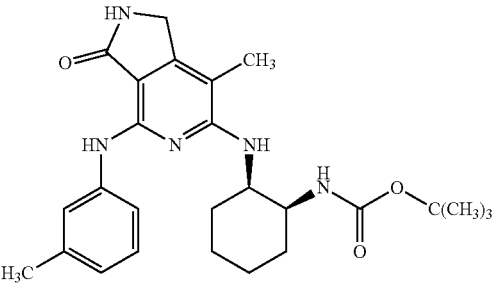

To an oven dry flask was added tert-butyl (1S,2R)-2-(7-bromo-3-oxo-4-(m-tolylamino)-2,3-dihydro-1H-pyrrolo[3,4-c]pyridin-6-ylamino)cyclohexylcarbamate (40 mg, 0.075 mmol), 2,4,6-trimethyl-1,3,5,2,4,6-trioxatriborinane (20.99 µL, 0.151 mmol), and potassium carbonate (31.3 mg, 0.226 mmol) in dioxane (1959 µL) and water (196 µL). The resulting tan solution was degassed with nitrogen for 5 min. Palladium chloride (dppf) (5.52 mg, 7.54 µmol) was added and the mixture was degassed for an additional 2 min. The vessel was capped and the reaction mixture was heated at 100° C. with stirring overnight. The reaction mixture was cooled to RT, diluted with EtOAc (5 mL), and washed with water (5 mL)

and brine (5 mL). The organic layer was collected, dried over Na₂SO₄ and concentrated to give the title compound as a brown viscous oil, which was used without purification (45 mg). [M+H] calc'd for C₂₆H₃₅N₅O₃, 466; found, 466.

Example 88

6-((1R,2S)-2-Aminocyclohexylamino)-7-methyl-4-(m-tolylamino)-1H-pyrrolo[3,4-c]pyridin-3(2H)-one

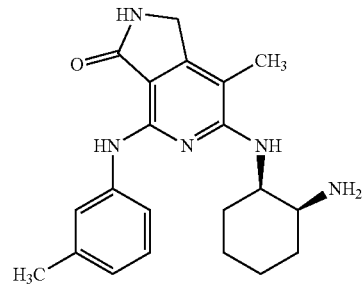 [SMILES: Cc1cccc(Nc2nc(N[C@@H]3CCCC[C@@H]3N)c(C)c3c2C(=O)NC3)c1]

A TFA salt of the title compound was prepared in a manner similar to EXAMPLE 75 using tert-butyl (1S,2R)-2-(7-methyl-3-oxo-4-(m-tolylamino)-2,3-dihydro-1H-pyrrolo[3,4-c]pyridin-6-ylamino)cyclohexylcarbamate in place of tert-butyl (1S,2R)-2-(7-chloro-3-oxo-4-(m-tolylamino)-2,3-dihydro-1H-pyrrolo[3,4-c]pyridin-6-ylamino) cyclohexylcarbamate. ¹H NMR (400 MHz, DMSO-d₆) δ ppm 8.79 (s, 1 H), 8.10 (s, 1 H), 7.73 (br s, 3 H), 7.48 (d, J=2.0 Hz, 2 H), 7.14-7.21 (m, 1 H), 6.77 (d, J=7.6 Hz, 1 H), 5.69 (d, J=6.6 Hz, 1 H), 4.36 (br s, 1 H), 4.18-4.29 (m, 2 H), 3.72 (br s, 1 H), 2.31 (s, 3 H), 2.01 (s, 3 H), 1.88 (d, J=9.1 Hz, 2 H), 1.55-1.79 (m, 4 H), 1.39-1.55 (m, 2 H). [M+H] calc'd for C₂₁H₂₇N₅O, 366; found, 366.

Preparation 41 tert-Butyl (3R,4R)-4-(7-fluoro-3-oxo-4-(m-tolylamino)-2,3-dihydro-1H-pyrrolo[3,4-c]pyridin-6-ylamino)tetrahydro-2H-pyran-3-ylcarbamate

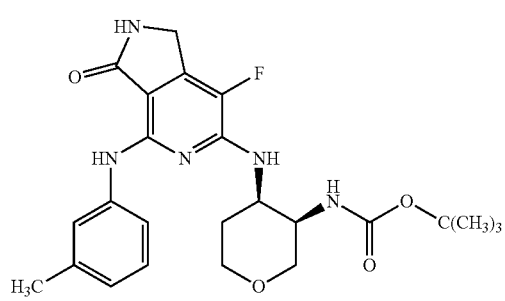 [SMILES: Cc1cccc(Nc2nc(N[C@@H]3CCOC[C@@H]3NC(=O)OC(C)(C)C)c(F)c3c2C(=O)NC3)c1]

A. tert-Butyl (3R,4R)-4-(3-oxo-4-(m-tolylamino)-2,3-dihydro-1H-pyrrolo[3,4-c]pyridin-6-ylamino)tetrahydro-2H-pyran-3-ylcarbamate

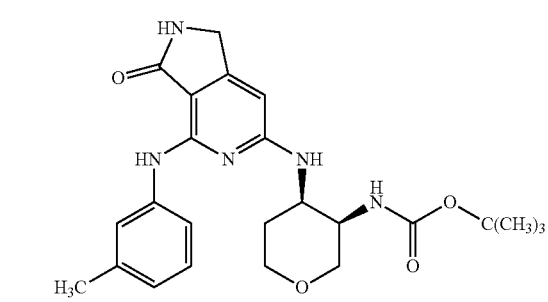

To a suspension of 6-((3R,4R)-3-aminotetrahydro-2H-pyran-4-ylamino)-4-(m-tolylamino)-1H-pyrrolo[3,4-c]pyridin-3(2H)-one (13.0 mg, 0.037 mmol) in DCM (368 μL) was added Et₃N (6.05 μL, 0.043 mmol) and di-tert-butyl dicarbonate (Boc anhydride) (39.0 μL, 0.039 mmol). The suspension was sonicated for 5 min and then stirred at RT for 12 h. The solution was diluted with DCM (15 mL) and washed with water (10 mL) and brine (10 mL). The organic layer was collected, dried over Na₂SO₄ and concentrated to give the title compound as a light yellow residue, which was used without further purification (15.2 mg, 91%). [M+H] calc'd for C₂₄H₃₁N₅O₄, 454; found, 454.

B. tert-Butyl (3R,4R)-4-(7-fluoro-3-oxo-4-(m-tolylamino)-2,3-dihydro-1H-pyrrolo[3,4-c]pyridin-6-ylamino)tetrahydro-2H-pyran-3-ylcarbamate To a screw-cap vial was added tert-butyl (3R,4R)-4-(3-oxo-4-(m-tolylamino)-2,3-dihydro-1H-pyrrolo[3,4-c]pyridin-6-ylamino)tetrahydro-2H-pyran-3-ylcarbamate (15.2 mg, 0.034 mmol) and SELECTFLUOR® (11.87 mg, 0.034 mmol) in DCM (335 μL) and MeOH (335 μL). The reaction mixture was stirred at RT for 2 h, diluted with EtOAc (10 mL) and washed with saturated aq NaHCO₃ (5 mL), water (5 mL), and brine (5 mL). The organic layer was collected, concentrated to a residue, and purified via preparative HPLC. The appropriate fractions were collected and concentrated to yield a TFA salt of the title compound as a colorless residue (4.2 mg, 26.6%). [M+H] calc'd for $C_{24}H_{30}FN_5O_4$, 472; found, 472.

Example 89

6-((3R,4R)-3-Aminotetrahydro-2H-pyran-4-ylamino)-7-fluoro-4-(m-tolylamino)-1H-pyrrolo[3,4-c]pyridin-3(2H)-one

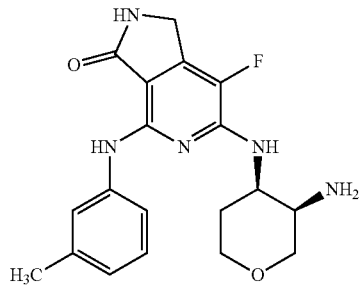 [SMILES: Cc1cccc(Nc2nc(N[C@@H]3CCOC[C@@H]3N)c(F)c3c2C(=O)NC3)c1]

A solution of tert-butyl (3R,4R)-4-(7-fluoro-3-oxo-4-(m-tolylamino)-2,3-dihydro-1H-pyrrolo[3,4-c]pyridin-6-ylamino)tetrahydro-2H-pyran-3-ylcarbamate (4.5 mg, 9.54 µmol) in 4 M HCl-dioxane (2 mL) was stirred for 0.5 h at RT. The reaction mixture was concentrated to a residue, which was diluted in DMF (1 mL) and purified via preparative HPLC. The appropriate fractions were collected and lyophilized to give a TFA salt of the title compound as a white solid (2.6 mg, 73%). $^1$H NMR (400 MHz, DMSO-$d_6$) δ ppm 8.81 (s, 1 H), 8.25 (s, 1 H), 7.57 (s, 1 H), 7.40 (d, J=8.1 Hz, 1 H), 7.04-7.28 (m, 2 H), 6.79 (d, J=7.3 Hz, 1 H), 6.62-6.76 (m, 2 H), 4.26-4.46 (m, 3 H), 3.85-3.96 (m, 2 H), 2.32 (s, 3 H), 1.94-2.13 (m, 1 H), 1.59-1.70 (m, 1 H), 1.07-1.28 (m, 4 H). [M+H] calc'd for $C_{19}H_{22}FN_5O_2$, 372; found, 372.

Preparation 42 tert-Butyl (1S,2R)-2-(7-bromo-4-(1-methyl-1H-pyrazol-4-yl)-3-oxo-2,3-dihydro-1H-pyrrolo[3,4-c]pyridin-6-ylamino)cyclohexylcarbamate

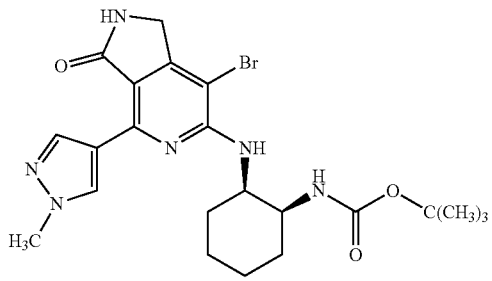

To a round bottomed flask was added tert-butyl (1S,2R)-2-(4-(1-methyl-1H-pyrazol-4-yl)-3-oxo-2,3-dihydro-1H-pyrrolo[3,4-c]pyridin-6-ylamino)cyclohexylcarbamate (124 mg, 0.291 mmol) in DCM (30 mL). The resulting white suspension was heated with a heat gun while stirring until all the starting material was dissolved. The solution was cooled to 0° C., and while stirring, 1-bromopyrrolidine-2,5-dione (51.7 mg, 0.291 mmol) was added. The reaction mixture was allowed to warm to RT and was stirred for 30 min. The solution was diluted with DCM (20 mL) and was washed with saturated aq NaHCO₃ (20 mL), water (20 mL), and brine (20 mL). The organic layer was collected and concentrated to an orange solid, which was treated with Et₂O (5 mL). Solids began to precipitate after the solution was allowed to sit undisturbed for 5 min. The mixture was allowed to sit for 1 h and was then filtered through paper. The solids were washed with Et₂O (5 mL) and collected to give the title compound as a tan solid (137.3 mg, 93%). [M+H] calc'd for $C_{22}H_{29}BrN6O_3$, 505; found, 505.

Preparation 43 tert-Butyl (1S,2R)-2-(7-methyl-4-(1-methyl-1H-pyrazol-4-yl)-3-oxo-2,3-dihydro-1H-pyrrolo[3,4-c]pyridin-6-ylamino)cyclohexylcarbamate

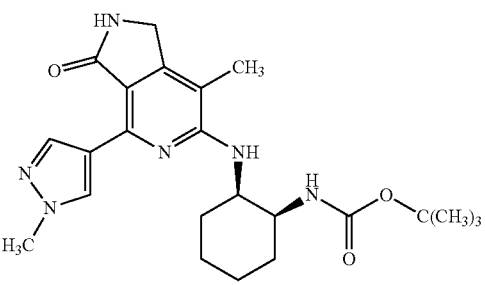

The title compound was prepared in a manner similar to PREPARATION 40 using tert-butyl (1S,2R)-2-(7-bromo-4-(1-methyl-1H-pyrazol-4-yl)-3-oxo-2,3-dihydro-1H-pyrrolo[3,4-c]pyridin-6-ylamino)cyclohexylcarbamate in place of tert-butyl (1S,2R)-2-(7-bromo-3-oxo-4-(m-tolylamino)-2,3-dihydro-1H-pyrrolo[3,4-c]pyridin-6-ylamino)cyclohexylcarbamate. [M+H] calc'd for $C_{23}H_{32}N_6O_3$, 441; found, 441.

Example 90

6-((1R,2S)-2-Aminocyclohexylamino)-7-methyl-4-(1-methyl-1H-pyrazol-4-yl)-1H-pyrrolo[3,4-c]pyridin-3(2H)-one

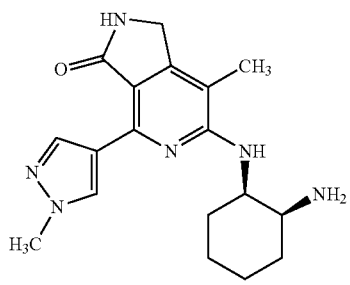

A TFA salt of the title compound was prepared in a manner similar to EXAMPLE 89 using tert-butyl (1S,2R)-2-(7-methyl-4-(1-methyl-1H-pyrazol-4-yl)-3-oxo-2,3-dihydro-1H-pyrrolo[3,4-c]pyridin-6-ylamino)cyclohexylcarbamate in place of tert-butyl (3R,4R)-4-(7-fluoro-3-oxo-4-(m-tolylamino)-2,3-dihydro-1H-pyrrolo[3,4-c]pyridin-6-ylamino)tetrahydro-2H-pyran-3-ylcarbamate. $^1$H NMR (400 MHz, DMSO-d$_6$) δ ppm 8.87 (s, 1 H), 8.30 (s, 1 H), 8.17 (s, 1 H), 7.71 (br s, 3 H), 5.71 (d, J=6.3 Hz, 1 H), 4.49 (d, J=2.8 Hz, 1 H), 4.24 (s, 2 H), 3.91 (br s, 3 H), 3.71 (br s, 1 H), 2.08 (s, 3 H), 1.77-1.93 (m, 3 H), 1.69 (d, J=8.6 Hz, 3 H), 1.40-1.53 (m, 2 H). [M+H] calc'd for $C_{18}H_{24}N_6O$, 341; found, 341.

Preparation 44: (R)-Methyl 6-(2-(tert-butoxycarbonylamino)-3-methoxypropylamino)-4-cyano-2-(1-methyl-1H-pyrazol-4-yl)nicotinate

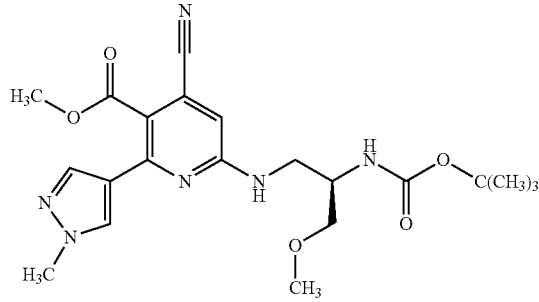 [SMILES: COC[C@@H](CNc1cc(C#N)c(C(=O)OC)c(-c2cnn(C)c2)n1)NC(=O)OC(C)(C)C]

To a screw-top vial was added methyl 6-chloro-4-cyano-2-(1-methyl-1H-pyrazol-4-yl)nicotinate (115 mg, 0.416 mmol), (R)-tert-butyl 1-amino-3-methoxypropan-2-ylcarbamate (93 mg, 0.457 mmol), and DIPEA (87 µL, 0.499 mmol) in DMF (308 µL). The resulting yellow solution was stirred for 12 h at 45° C. and then at 50° C. for 6 h. The reaction mixture was diluted with EtOAc (20 mL) and was washed with water (10 mL) and brine (20 mL). The organic layer was collected and dried over Na$_2$SO$_4$ and was concentrated to a yellow oil. The concentrate was purified via standard phase column chromatography eluting with EtOAc and hexanes (50-100% EtOAc gradient) to give the title compound as a light yellow residue (36.5 mg, 20%). [M+H] calc'd for $C_{21}H_{28}N_6O_5$, 445; found, 445.

Preparation 45

(R)-tert-Butyl 1-methoxy-3-(4-(1-methyl-1H-pyrazol-4-yl)-3-oxo-2,3-dihydro-1H-pyrrolo[3,4-c]pyridin-6-ylamino)propan-2-ylcarbamate

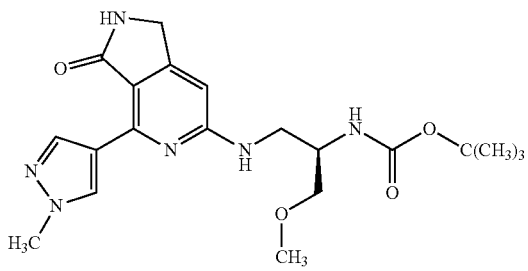 [SMILES: COC[C@@H](CNc1cc2c(c(-c3cnn(C)c3)n1)C(=O)NC2)NC(=O)OC(C)(C)C]

The title compound was prepared in a manner similar to PREPARATION 34 using (R)-methyl 6-(2-(tert-butoxycarbonylamino)-3-methoxypropylamino)-4-cyano-2-(1-methyl-1H-pyrazol-4-yl)nicotinate in place of (R)-methyl 6-(2-(tert-butoxycarbonylamino)-3-methoxypropylamino)-4-cyano-2-(m-tolylamino)nicotinate (84.5 mg, 0.180 mmol). [M+H] calc'd for $C_{20}H_{28}N_6O_4$, 417; found, 417.

Example 91

(R)-6-(2-Amino-3-methoxypropylamino)-4-(1-methyl-1H-pyrazol-4-yl)-1H-pyrrolo[3,4-c]pyridin-3(2H)-one

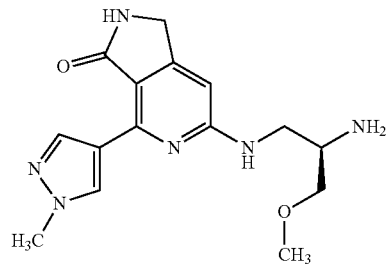 [SMILES: COC[C@H](N)CNc1cc2c(c(-c3cnn(C)c3)n1)C(=O)NC2]

A TFA salt of the title compound was prepared in a manner similar to EXAMPLE 89 using (R)-tert-butyl 1-methoxy-3-(4-(1-methyl-1H-pyrazol-4-yl)-3-oxo-2,3-dihydro-1H-pyrrolo[3,4-c]pyridin-6-ylamino)propan-2-ylcarbamate in place of tert-butyl (3R,4R)-4-(7-fluoro-3-oxo-4-(m-tolylamino)-2,3-dihydro-1H-pyrrolo[3,4-c]pyridin-6-ylamino)tetrahydro-2H-pyran-3-ylcarbamate. $^1$H NMR (400 MHz, DMSO-d$_6$) δ ppm 8.97 (s, 1 H), 8.40 (s, 1 H), 8.09 (s, 1 H), 8.00 (br s, 3 H), 7.17-7.26 (m, 1 H), 6.42 (s, 1 H), 4.24 (s, 2 H), 3.89 (s, 3 H), 3.54-3.60 (m, 5 H), 3.33 (s, 3 H). [M+H] calc'd for $C_{15}H_{20}N_6O_2$, 317; found, 317.

Preparation 46

6-((3R,4R)-3-Aminotetrahydro-2H-pyran-4-ylamino)-4-chloro-2-(2,4-dimethoxybenzyl)-7-fluoro-1H-pyrrolo[3,4-c]pyridin-3(2H)-one

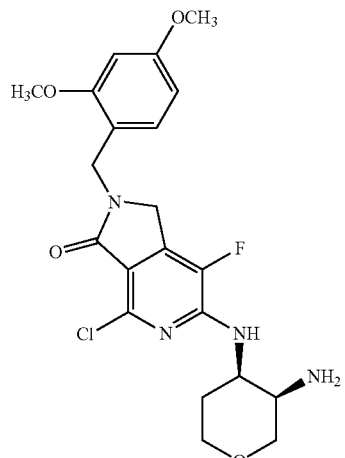

A mixture of 4,6-dichloro-2-(2,4-dimethoxybenzyl)-7-fluoro-1H-pyrrolo[3,4-c]pyridin-3(2 H)-one (2.5 g, 6.74 mmol), (3R,4R)-tetrahydro-2H-pyran-3,4-diamine (0.711 g, 6.12 mmol), and DIPEA (5.35 mL, 30.6 mmol) in ACN (30 mL) was stirred at 85° C. for 3 d in a sealed tube. Additional (3R,4R)-tetrahydro-2H-pyran-3,4-diamine (0.356 g, 3.06 mmol) and DIPEA (2.14 mL, 12.2 mmol) were added and the mixture was heated at 100° C. overnight. The mixture was concentrated and purified via preparative HPLC. The fractions corresponding to the desired regioisomer were collected to give the title compound (265 mg, 9.60%). $^1$H NMR (400 MHz, DMSO-d$_6$) δ ppm 1.64-1.65 (m, 1 H), 1.80-1.82 (s, 1 H), 3.40 (td, J=11.47, 2.44 Hz, 1 H), 3.53 (dd, J=11.23, 1.95 Hz, 1 H), 3.67 (dd, J=11.47, 2.20 Hz, 1 H), 3.71-3.73 (m, 1 H), 3.75 (s, 3 H), 3.77-3.79 (m, 1 H), 3.81 (s, 3 H), 4.09-4.11 (m, 1 H), 4.33 (s, 2 H), 4.50 (s, 2 H), 6.48 (dd, J=8.30, 2.44 Hz, 1 H), 6.58 (d, J=2.44 Hz, 1 H), 6.90 (br s, 1 H), 7.06 (d, J=8.30 Hz, 1 H). [M+H] calc'd for $C_{21}H_{24}ClFN_4O_4$, 451; found, 451.

Example 92

6-((3R,4R)-3-Aminotetrahydro-2H-pyran-4-ylamino)-7-fluoro-4-(pyrazolo[1,5-a]pyridin-3-yl)-1H-pyrrolo[3,4-c]pyridin-3(2H)-one

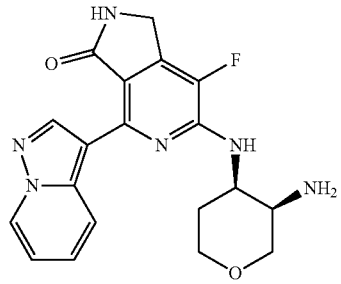 [SMILES: N[C@H]1COCC[C@H]1Nc1nc(-c2cnn3ccccc23)c2c(c1F)CNC2=O]

A. 6-((3R,4R)-3-Aminotetrahydro-2H-pyran-4-ylamino)-2-(2,4-dimethoxybenzyl)-7-fluoro-4-(pyrazolo[1,5-a]pyridin-3-yl)-1H-pyrrolo[3,4-c]pyridin-3(2H)-one

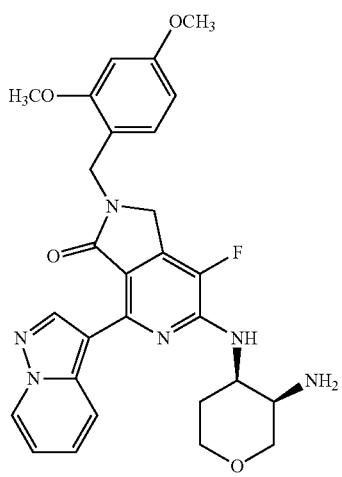 [SMILES: COc1ccc(CN2Cc3c(F)c(N[C@@H]4CCOC[C@@H]4N)nc(-c4cnn5ccccc45)c3C2=O)c(OC)c1]

To a 5 mL microwave vial with a stir bar was added bis(triphenylphosphine)palladium chloride (11.68 mg, 0.017 mmol), 6-((3R,4R)-3-aminotetrahydro-2H-pyran-4-ylamino)-4-chloro-2-(2,4-dimethoxybenzyl)-7-fluoro-1H-pyrrolo[3,4-c]pyridin-3(2H)-one (75 mg, 0.166 mmol), pyrazolo[1,5-a]pyridin-3-ylboronic acid (135 mg, 0.832 mmol) in dioxane (2 mL), and saturated aq NaHCO$_3$ (2 mL). The mixture was heated in a Biotage Initiator microwave at 120° C. for 30 min. The mixture was concentrated and purified via preparative HPLC to give the title compound (89 mg, 100%). $^1$H NMR (400 MHz, DMSO-d$_6$) δ ppm 1.82-1.84 (m, 1 H), 2.10-2.12 (m, 1 H), 3.68-3.72 (m, 3 H), 3.75 (s, 3 H), 3.82 (s, 3 H), 3.92-3.95 (m, 1 H), 4.01-4.02 (m, 1 H), 4.39 (s, 2 H), 4.55-4.58 (m, 1 H), 4.59 (s, 2 H), 6.50 (dd, J=8.30, 1.95 Hz, 1 H), 6.60 (d, J=2.44, 1 H), 7.04-7.08 (m, 2 H), 7.16 (d, J=5.86 Hz, 1 H), 7.48-7.51 (m, 1 H), 7.93 (br s, 1 H), 8.37 (d, J=9.27 Hz, 1 H), 8.79 (d, J=6.83 Hz, 1 H), 9.36 (s, 1 H). [M+H] calc'd for $C_{28}H_{29}FN_6O_4$, 533; found, 533.

B. 6-((3R,4R)-3-Aminotetrahydro-2H-pyran-4-ylamino)-7-fluoro-4-(pyrazolo[1,5-a]pyridin-3-yl)-1H-pyrrolo[3,4-c]pyridin-3(2H)-one To a 25 mL round bottom flask with a stir bar was added 6-((3R,4R)-3-aminotetrahydro-2H-pyran-4-ylamino)-2-(2,4-dimethoxybenzyl)-7-fluoro-4-(pyrazolo[1,5-a]pyridin-3-yl)-1H-pyrrolo[3,4-c]pyridin-3(2H)-one (85 mg, 0.160 mmol) in TFA (5 mL). The mixture was heated at 60° C. for 1.5 h and then cooled to RT. The mixture was concentrated and purified via preparative HPLC to give a TFA salt of the title compound as a white solid (27 mg, 44.2%). $^1$H NMR (400 MHz, DMSO-d$_6$) δ ppm 1.83-1.85 (m, 1 H), 2.12-2.14 (m, 1 H), 3.65-3.73 (m, 2 H), 3.81-3.82 (m, 1 H), 3.93-3.95 (m, 1 H), 4.01-4.03 (m, 1 H), 4.43 (s, 2 H), 4.53-4.55 (m, 1 H), 7.04 (t, J=6.83 Hz, 1 H), 7.13 (d, J=4.88 Hz, 1 H), 7.49 (t, J=8.05 Hz, 1 H), 7.94 (br s, 1 H), 8.36-8.42 (m, 2 H), 8.78 (d, J=6.83 Hz, 1 H), 9.33 (s, 1 H). [M+H] calc'd for $C_{19}H_{19}FN_6O_2$, 383; found, 383.

Example 93

6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one

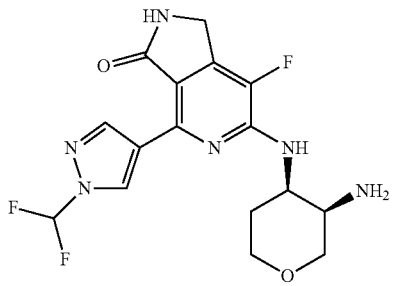 [SMILES: N[C@H]1COCC[C@H]1Nc1nc(-c2cnn(C(F)F)c2)c2c(c1F)CNC2=O]

A TFA salt of the title compound was prepared in a manner similar to EXAMPLE 92 using 1-(difluoromethyl)-1H-pyrazol-4-ylboronic acid in place of pyrazolo[1,5-a]pyridin-3-ylboronic acid. $^1$H NMR (400 MHz, DMSO-d$_6$) δ ppm 1.75-1.77 (m, 1 H), 2.09-2.12 (m, 1 H), 3.60-3.63 (m, 1 H), 3.76-3.77 (m, 1 H), 3.88-3.98 (m, 3 H), 4.44 (d, J=6.35 Hz, 2 H), 4.54-4.55 (m, 1 H), 7.17 (d, J=5.86 Hz, 1 H), 7.89 (br s, 1 H), 8.54 (s, 1 H), 8.58 (s, 1 H), 9.43 (s, 1 H). [M+H] calc'd for C$_{16}$H$_{17}$F$_3$N$_6$O$_2$, 383; found, 383.

Example 94

6-((3R,4R)-3-Aminotetrahydro-2H-pyran-4-ylamino)-4-(benzofuran-3-yl)-7-fluoro-1H-pyrrolo[3,4-c]pyridin-3(2H)-one

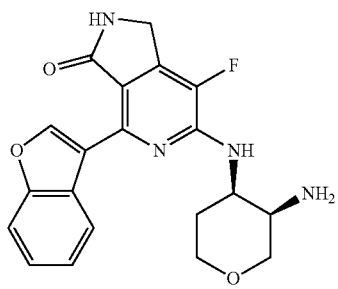 [SMILES: N[C@H]1COCC[C@H]1Nc1nc(-c2coc3ccccc23)c2c(c1F)CNC2=O]

A TFA salt of the title compound was prepared in a manner similar to EXAMPLE 92 using benzofuran-3-ylboronic acid in place of pyrazolo[1,5-a]pyridin-3-ylboronic acid. $^1$H NMR (400 MHz, DMSO-d$_6$) δ ppm 1.84-1.88 (m, 2 H), 3.68-3.73 (m, 1 H), 3.76-4.02 (m, 4 H), 4.47 (s, 2 H), 4.58-4.59 (m, 1 H), 7.25 (d, J=6.35 Hz, 1 H), 7.40-7.42 (m, 2 H), 7.67-7.69 (m, 1 H), 7.93 (br s, 1 H), 8.33 (d, J=9.76 Hz, 1 H), 8.56 (s, 1 H), 9.38 (s, 1 H). [M+H] calc'd for C$_{20}$H$_{19}$FN$_4$O$_3$, 383; found, 383.

Example 95

(S)-6-(3-Aminopyrrolidin-1-yl)-7-fluoro-4-(1-methyl-1H-pyrazol-4-yl)-1H-pyrrolo[3,4-c]pyridin-3(2H)-one

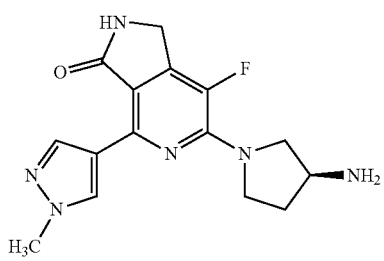 [SMILES: Cn1cc(-c2nc(N3CC[C@H](N)C3)c(F)c3c2C(=O)NC3)cn1]

A. (S)-tert-Butyl 1-(4-chloro-2-(2,4-dimethoxybenzyl)-7-fluoro-3-oxo-2,3-dihydro-1H-pyrrolo[3,4-c]pyridin-6-yl)pyrrolidin-3-ylcarbamate

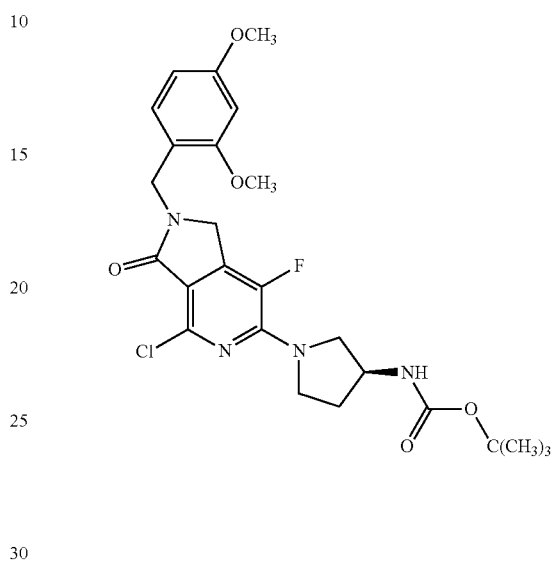

A tube containing 4,6-dichloro-2-(2,4-dimethoxybenzyl)-7-fluoro-1H-pyrrolo[3,4-c]pyridin-3(2H)-one (300 mg, 0.808 mmol) and (S)-tert-butyl pyrrolidin-3-ylcarbamate (301 mg, 1.616 mmol) dissolved in ACN (4 mL) was sealed and heated at 100° C. for 2 d. The reaction mixture was concentrated and dissolved in EtOAc (20 mL) and washed with saturated aq NaHCO$_3$ (10 mL) and brine (10 mL). The organic extracts were dried over Na$_2$SO$_4$ and evaporated to give a crude product, which was purified via preparative HPLC. Pure fractions were collected and evaporated to give the title compound (235 mg, 55.8%). [M+H] calc'd for C$_{25}$H$_{30}$ClFN$_4$O$_5$, 521; found, 521.

B. (S)-6-(3-Aminopyrrolidin-1-yl)-7-fluoro-4-(1-methyl-1H-pyrazol-4-yl)-1H-pyrrolo[3,4-c]pyridin-3(2H)-one To a 30 mL tube charged with (S)-tert-butyl 1-(4-chloro-2-(2,4-dimethoxybenzyl)-7-fluoro-3-oxo-2,3-dihydro-1H-pyrrolo[3,4-c]pyridin-6-yl)pyrrolidin-3-ylcarbamate (225 mg, 0.43 mmol) 1-methyl-4-(4,4,5,5-tetramethyl-1,3,2-dioxaborolan-2-yl)-1H-pyrazole (145 mg, 0.695 mmol), and PdCl$_2$(PPh$_3$) dispersed in dioxane (5 mL) was added 2 N Na$_2$CO$_3$ (0.5 mL). The tube was sealed and the reaction mixture was heated at 85° C. for 4 h. The mixture was diluted with water (5 mL) and extracted into EtOAc (2×30 mL). The organic layer was dried over Na$_2$SO$_4$ and evaporated to afford a residue, which was treated with TFA (1 mL) and heated at 85° C. for 1 h to remove the protecting groups. TFA was evaporated and the mixture was dissolved in DMSO (8 mL) and purified via preparative HPLC. Pure fractions were collected, evaporated to a minimal volume, and lyophilized to give a TFA salt of the title compound as a pale yellow solid (46 mg, 27.2%). $^1$H NMR (400 MHz, DMSO-d$_6$) δ ppm 2.05-2.39 (m, 3 H), 3.75-4.04 (m, 6H), 3.89 (s, 3 H), 4.38 (s, 2 H), 8.02 (br s, 2 H), 8.26 (d, J=0.51 Hz, 1 H), 8.39 (s, 1 H), 8.85 (s, 1H);). [M+H] calc'd for $C_{15}H_{17}FN_6O$, 317; found, 317.

Example 96

(S)-6-(3-Aminopiperidin-1-yl)-7-fluoro-4-(1-methyl-1H-pyrazol-4-yl)-1H-pyrrolo[3,4-c]pyridin-3(2H)-one

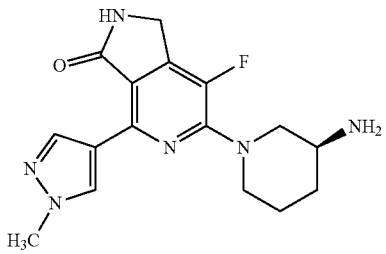 [SMILES: Cn1cc(-c2nc(N3CCC[C@H](N)C3)c(F)c3c2C(=O)NC3)cn1]

A TFA salt of the title compound was prepared in a manner similar to EXAMPLE 95 using (S)-tert-butyl piperidin-3-ylcarbamate in place of (S)-tert-butyl pyrrolidin-3-ylcarbamate. $^1$H NMR (400 MHz, DMSO-$d_6$) δ ppm 1.61 (m, 2 H), 1.83 (d, J=8.34 Hz, 1 H), 2.03 (br s, 1 H), 2.53-2.55 (m, 2 H), 3.16-3.35 (m, 3 H), 3.90 (s, 3 H), 3.92 (m, 1 H), 4.33 (m, 1 H), 4.39 (s, 2 H), 8.04 (br s, 3 H), 8.36 (s, 1 H), 8.51 (s, 1 H), 8.90 (s, 1 H). [M+H] calc'd for $C_{16}H_{19}FN_6O$, 331; found, 331.

Example 97

6-((1R,2S)-2-Aminocyclohexylamino)-7-fluoro-4-(1-isopropyl-1H-pyrazol-4-yl)-1H-pyrrolo[3,4-c]pyridin-3(2H)-one

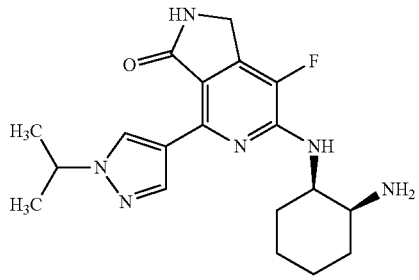 [SMILES: CC(C)n1cc(-c2nc(N[C@@H]3CCCC[C@@H]3N)c(F)c3c2C(=O)NC3)cn1]

A TFA salt of the title compound was prepared in a manner similar to EXAMPLE 62 using 1-isopropyl-4-(4,4,5,5-tetramethyl-1,3,2-dioxaborolan-2-yl)-1H-pyrazole in place of 1-(difluoromethyl)-4-(4,4,5,5-tetramethyl-1,3,2-dioxaborolan-2-yl)-1H-pyrazole. $^1$H NMR (500 MHz, CDCl$_3$) δ ppm 1.14-1.33 (m, 6 H), 1.47-1.64 (m, 8 H), 1.76 (br. s., 2 H), 1.94-2.01 (m, 2 H), 3.86 (br. s., 1 H), 4.36 (s, 2 H), 4.53 (d, J=6.83 Hz, 2 H), 8.15 (s, 1 H), 8.88 (s, 1 H). [M+H] calc'd for $C_{19}H_{25}FN_6O$, 373; found, 373.

Preparation 47 tert-Butyl 4,6-dichloro-7-fluoro-3-oxo-1H-pyrrolo[3,4-c]pyridine-2(3H)-carboxylate

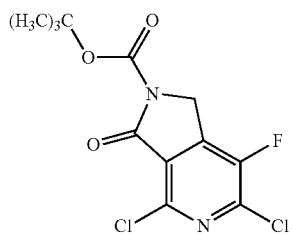 [SMILES: CC(C)(C)OC(=O)N1Cc2c(F)c(Cl)nc(Cl)c2C1=O]

A. 2,6-Dichloro-5-fluoronicotinamide

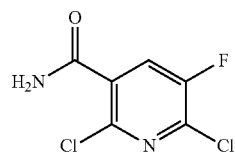 [SMILES: NC(=O)c1cc(F)c(Cl)nc1Cl]

A 12-L 3-neck round bottom flask equipped with overhead stirrer, refluxing condenser, and N$_2$ inlet/outlet was charged with 2,6-dichloro-5-fluoronicotinonitrile (2.0 kg, 1.0 eq). Concentrated sulfuric acid (4.93 L) was added and the mixture was stirred at RT until most of the brown solids had dissolved. Next, the reaction mixture was stirred at 65° C. for 1 h. The dark-brown solution was cooled to a temperature<10° C. using an ice bath. The reaction mixture was added to a 50-L round bottom flask, which contained de-ionized water (24.7 L) that had been cooled to a temperature<10° C., using a peristaltic pump. The reaction mixture was added to the water quench over a 2.3 h period, which kept the internal temperature of the mixture below 21° C. The resulting slurry was filtered through a Buchner funnel fitted with a Sharkskin filter paper. The 50-L RBF was rinsed with water (3×4 L) and the rinses were used to wash the filter cake. The filter cake was conditioned for 50 min, transferred to a drying tray, and was dried under high vacuum at 40-50° C. for 24 h and then at 20-25° C. for 18 h to give the title compound as a beige solid (896.4 g, 82%). $^1$H NMR (500 MHz, DMSO-$d_6$) δ ppm 7.94

(s, 1 H), 8.10 (s, 1 H), 8.24 (d, 1 H). [M+H] calc'd for C$_6$H$_3$Cl$_2$FN$_2$O, 209; found, 209.

B. 4,6-Dichloro-7-fluoro-1-hydroxy-1H-pyrrolo[3,4-c]pyridin-3(2H)-one

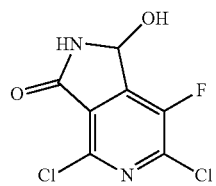 [SMILES: O=C1NC(O)c2c(F)c(Cl)nc(Cl)c21]

A 22-L multi-neck RBF equipped with an overhead stirrer, temperature probe, and N$_2$ inlet/outlet was charged with LiHMDS (10.65 L, 2.5 eq) by N$_2$ pressure. The orange solution was cooled to <0° C. using an ice/brine bath. A separate 12-L RBF was sequentially charged with 2,6-dichloro-5-fluoronicotinamide (890 g, 1.0 eq), anhydrous THF (6.0 L), and anhydrous DMF (1.0 L, 3.0 eq). The resulting solution was added to the LiHMDS solution via a peristaltic pump over a 1 h period, which kept the internal temperature below 5° C. The 12-L flask was rinsed with THF (1.6 L), and the rinse was transferred to the reaction mixture. The mixture was stirred at a temperature<5° C. for 1 h, and the reaction was added to a pre-cooled 2N HCl aq solution via a peristaltic pump at a rate that kept the temperature of the mixture below 22° C. Following the quench, IPAc (14 L) was added and the mixture was stirred for 10 min. The biphasic mixture was separated and the organic layer was stored in a carboy at RT overnight. The organic layer was subsequently washed with water (8.9 L) and was concentrated under reduced pressure to a volume of about 4.5 L. The distillation was continued the next day. Isopropyl acetate (16 L) was added to the slurry and the distillation was continued until about 4.5 L of material remained. The off-white slurry was transferred into a 50-L multi-neck RBF to which was charged heptanes (18 L) via a peristaltic pump over a 45 min period. The resultant slurry was stirred at RT overnight and then filtered through a Buchner funnel with a Sharkskin filter paper. The filter cake was washed with heptanes (2×4.5 L) and then dried under high vacuum at RT for 24 h to afford title compound (913.0 g, 90%). $^1$H NMR (300 MHz, DMSO-d$_6$) δ ppm 6.11 (dd, J=9.3 Hz, 1.5 Hz, 1 H), 6.95 (d, J=9.3 Hz, 1 H), 9.54 (s, 1 H). [M+H] calc'd for C$_7$H$_3$Cl$_2$FN$_2$O$_2$, 237; found, 237.

C. 4,6-Dichloro-7-fluoro-1H-pyrrolo[3,4-c]pyridin-3(2H)-one

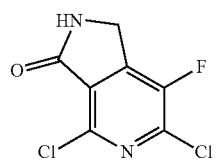 [SMILES: O=C1NCc2c(F)c(Cl)nc(Cl)c21]

A 22-L 3-neck RBF equipped with overhead stirrer, refluxing condenser, and N$_2$ inlet/outlet, and having all glass or PTFE-coated parts, was sequentially charged with 4,6-dichloro-7-fluoro-1-hydroxy-1H-pyrrolo[3,4-c]pyridin-3(2H)-one (908 g), DCM (4.55 L), and TFA (3.46 L, 11.76 eq).

Agitation was started and Et$_3$SiH (3.05 L, 4.97 eq) was added. The cloudy mixture was heated to reflux, resulting in a clear solution that was stirred at refluxing conditions for 24 h. The mixture was cooled to RT and stirred overnight. The orange solution was cooled to <10° C. using an ice bath. Methyl tert-butyl ether (14.0 L) was added via a peristaltic pump within a 1 h period. The resultant slurry was stirred at <10° C. for 1 h and then filtered through a coarse fitted glass funnel. The filter cake was washed with MTBE (2×4 L). The solid was dried under high vacuum at RT for 19 h to afford the title compound (802 g, 94%). $^1$H NMR (500 MHz, DMSO-d$_6$) δ ppm 4.55 (s, 2 H), 9.15 (s, 1 H). [M+H] calc'd for C$_7$H$_3$Cl$_2$FN$_2$O, 221; found, 221.

D. tert-Butyl 4,6-dichloro-7-fluoro-3-oxo-1H-pyrrolo[3,4-c]pyridine-2(3H)-carboxylate A 12 L 3-neck RBF was charged with 4,6-dichloro-7-fluoro-1H-pyrrolo[3,4-c]pyridin-3(2H)-one (745.0 g, 1.0 eq), DCM (3.0 L), Et$_3$N (940 mL, 2.0 eq), and DMAP (20.59 g, 0.05 eq). To a separate 2-L flask containing di-tert-butyl dicarbonate (882.8 g, 1.2 eq) was added DCM (0.75 L), and the resulting clear solution was added dropwise to the reaction mixture over a 20 min period via a peristaltic pump. The 2-L flask was rinsed with DCM (0.75 L) and the rinse was added to the reaction mixture, which was stirred at RT for 28 min. Ethanol (7.5 L) was added and the mixture was concentrated under reduced pressure to a volume of about 4.5 L. A second volume of EtOH (7.5 L) was added to the mixture and distillation was continued until about 4.5 L of the material remained. The resultant slurry was stirred at 15-20° C. for 10 min and was then filtered through a Buchner funnel. The filter cake was washed with EtOH (3×1.5 L) and dried under high vacuum at RT overnight to give the title compound as a pink solid (873 g, 81% yield). $^1$H (300 MHz, CDCl$_3$) δ ppm 1.61 (s, 9 H), 4.82 (d, J=0.9 Hz, 2 H), $^{19}$F NMR (282 MHz, CDCl$_3$) δ ppm −128.36. [M−H] calc'd for C$_{12}$H$_{11}$C$_{12}$FN$_2$O$_3$, 319; found, 319.

Example 98

7-Fluoro-4,6-bis(1-methyl-1H-pyrazol-4-yl)-1H-pyrrolo[3,4-c]pyridin-3(2H)-one

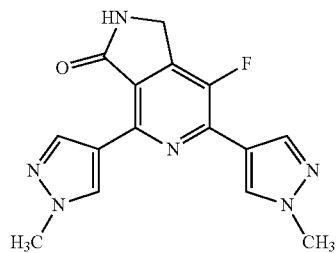 [SMILES: Cn1cc(-c2nc(-c3cnn(C)c3)c3c(c2F)CNC3=O)cn1]

A mixture of tert-butyl 4,6-dichloro-7-fluoro-3-oxo-1H-pyrrolo[3,4-c]pyridine-2(3H)-carboxylate (30.0 mg, 0.093 mmol), 1-methyl-4-(4,4,5,5-tetramethyl-1,3,2-dioxaborolan-2-yl)-1H-pyrazole (19.4 mg, 0.093 mmol), tris(dibenzylideneacetone)dipalladium (3.42 mg, 0.003 mmol), tricyclohexylphosphine (3.90 mg, 0.001 mmol) and potassium phosphate (35.7 mg, 0.168 mmol) in dioxane (1 mL) and deionized water (0.3 mL) were heated at 120° C. in a microwave for 20 min. The mixture was concentrated and purified via preparative HPLC to give a TFA salt of the title compound as a pale yellow solid (4.1 mg, 14%). ¹H NMR (400 MHz, DMSO-d₆) δ ppm 3.92 (s, 3 H), 3.96 (s, 3 H), 4.53 (s, 2 H), 8.17 (s, 1 H), 8.49 (s, 1 H), 8.50 (s, 1 H), 8.81 (s, 1 H), 8.92 (s, 1 H). [M+H] calc'd for $C_{15}H_{13}FN_6O$, 313; found, 313.

Example 99

6-((1R,2S)-2-Aminocyclohexylamino)-7-bromo-4-(1-methyl-1H-pyrazol-4-yl)-1H-pyrrolo[3,4-c]pyridin-3(2H)-one

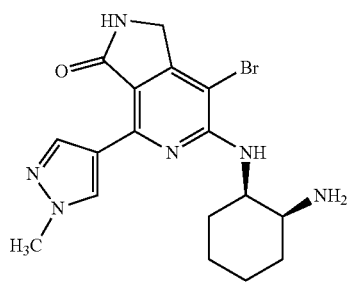 [SMILES: Cn1cc(-c2nc(N[C@@H]3CCCC[C@@H]3N)c(Br)c3c2C(=O)NC3)cn1]

A solution of tert-butyl (1S,2R)-2-(7-bromo-4-(1-methyl-1H-pyrazol-4-yl)-3-oxo-2,3-dihydro-1H-pyrrolo[3,4-c]pyridin-6-ylamino)cyclohexylcarbamate (10 mg, 0.020 mmol) in HCl-dioxane (999 µL, 4.00 mmol) was stirred at RT for 2 h. The mixture was concentrated to a residue, diluted with Et₂O (3 mL), and sonicated to yield a white precipitate, which was filtered and dried overnight in a lyophilizer to give an HCl salt of the title compound as a white solid (1.8 mg, 21%). [M+H] calc'd for $C_{17}H_{21}BrN_6O$, 406; found, 406.

Example 100

2-((1R,2S)-2-Aminocyclohexylamino)-4-(1-(4-fluorophenyl)-1H-pyrazol-4-yl)-6,7-dihydro-5H-pyrrolo[3,4-d]pyrimidin-5-one

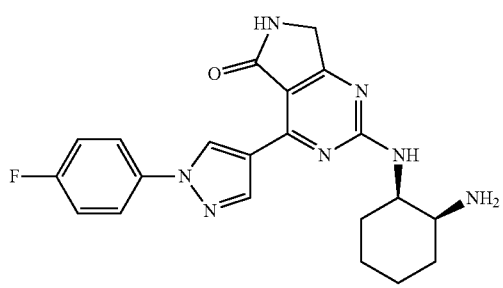 [SMILES: N[C@H]1CCCC[C@H]1Nc1nc2c(c(-c3cnn(-c4ccc(F)cc4)c3)n1)C(=O)NC2]

A TFA salt of the title compound was prepared in a manner similar to EXAMPLE 14 using 1-(4-fluorophenyl)-1H-pyrazol-4-ylboronic acid in place of 1-methyl-4-(4,4,5,5-tetramethyl-1,3,2-dioxaborolan-2-yl)-1H-pyrazole. ¹H NMR (500 MHz, DMSO-d₆) δ ppm 1.43 (br s, 2 H), 1.55-1.98 (m, 6 H), 4.10-4.35 (m, 2 H), 4.34-4.70 (m, 1 H), 7.43 (t, J=8.79 Hz, 2 H), 7.65 (d, J=7.81 Hz, 1 H), 7.68-7.83 (m, 3 H), 7.87 (br s, 2 H), 8.39 (s, 1 H), 8.58-9.00 (m, 1 H), 9.62-9.86 (m, 1 H). [M+H] calc'd for $C_{21}H_{22}FN_7O$, 408; found, 408.

Example 101

(R)-6-(2-Amino-3-methoxypropylamino)-7-fluoro-4-(1-methyl-1H-pyrazol-4-yl)-1H-pyrrolo[3,4-c]pyridin-3(2M-one

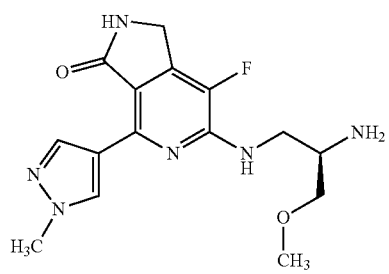 [SMILES: COC[C@H](N)CNc1nc(-c2cnn(C)c2)c2c(c1F)CNC2=O]

To a 20 mL round-bottomed flask was added (R)-tert-butyl 1-methoxy-3-(4-(1-methyl-1H-pyrazol-4-yl)-3-oxo-2,3-dihydro-1H-pyrrolo[3,4-c]pyridin-6-ylamino)propan-2-ylcarbamate (19.7 mg, 0.047 mmol) and SELECTFLUOR® (21.78 mg, 0.061 mmol) in DCM (473 µL) and MeOH (473 µL). The resulting yellow solution was stirred at RT for 3 h and concentrated to a residue, which was dissolved in 4 N HCl-dioxane (2 mL) and stirred at RT for 2 h. The mixture was concentrated, dissolved in DMF (1 mL) and purified via preparative HPLC to give a TFA salt of the title compound. [M+H] calc'd for $C_{15}H_{19}FN_6O_2$, 335; found, 335.

Preparation 48 cis-tert-butyl 2-aminocyclohexylcarbamate

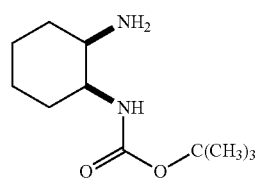 [SMILES: CC(C)(C)OC(=O)N[C@H]1CCCC[C@H]1N]

A. trans-tert-Butyl 2-hydroxycyclohexylcarbamate

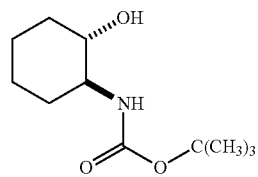 [SMILES: CC(C)(C)OC(=O)N[C@H]1CCCC[C@@H]1O]

To a stirred slurry of trans-2-aminohexanol hydrochloride (15.0 g, 98.92 mmol) in EtOAc (75 mL) was added a solution of NaOH (9.1 g, 0.227 mol) in water (150 mL). A solution of di-tert-butyl dicarbonate (25.9 g, 118.70 mmol) in EtOAc (75 mL) was added in one portion and the mixture was heated to 45° C. and stirred for 16 h. The phases were separated and the aqueous phase was extracted with EtOAc (60 mL). The combined organic extracts were washed with water (45 mL) and phase separated. The organic phase was distilled at atmospheric pressure until approximately 75 mL of solution remained. Heptane (90 mL) was added and the solution was distilled until approximately 75 mL of solution remained. Heptane (150 mL) was added and the mixture was heated to 98-100° C. The heat was switched off and the mixture was allowed to cool to RT. Seeds of pure product were added at 70° C. and crystallization occurred at about 65° C. Once the slurry reached RT, the mixture was cooled to about 5° C. and was stirred for 30 min. The solids were filtered, washed with heptane (2×45 mL), and dried to give the title compound as a white crystalline solid (19.6 g, 92%).

B. cis-tert-Butyl 2-(1,3-dioxoisoindolin-2-yl)cyclohexylcarbamate

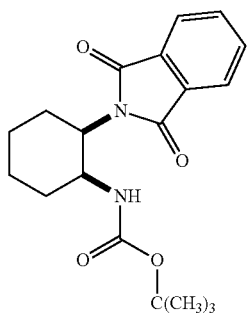 [SMILES: CC(C)(C)OC(=O)N[C@H]1CCCC[C@H]1N1C(=O)c2ccccc2C1=O]

To a stirred slurry of trans-tert-butyl 2-hydroxycyclohexylcarbamate (1.00 g, 4.64 mmol), PPh$_3$ (1.34 g, 5.10 mmol) and phthalimide (1.50 g, 10.20 mmol) in a 2:1 mixture of toluene and THF (15 mL) was added diisopropyl azodicarboxylate (1.0 mL, 5.10 mmol) dropwise over a period of 1 h. Once the addition was complete, the mixture was stirred at about 0° C. for 7 h and was then warmed slowly to 7° C. over a period of 14 h. The mixture was filtered, and the filtrate was concentrated under reduced pressure to give the title compound as a yellow oil (3.90 g). The crude product was used in the next step without further purification.

C. cis-tert-Butyl 2-aminocyclohexylcarbamate

Crude cis-tert-butyl 2-(1,3-dioxoisoindolin-2-yl)cyclohexylcarbamate (3.90 g) was dissolved in toluene (20 mL) and charged to a round bottom flask. Hydrazine hydrate (0.70 mL) was added and the mixture was heated to 80° C. for 2 h whereupon TLC analysis indicated the reaction was complete. The reaction was cooled to RT and the solids were filtered and washed with toluene (2×5 mL). The filtrates were washed with 2 N NaOH aq (10 mL) and phase separated. The aqueous phase was extracted with toluene (2×5 mL) and the combined organic extracts were washed with 10% HOAc aq (2×10 mL). The combined aqueous washes were basified with 2 N NaOH aq (13 mL). The product was extracted with IPAc (2×10 mL) and the combined organic extracts were washed with water (5 mL). The organic phase was concentrated to dryness to give 0.78 g of crude product. The oil was re-dissolved in IPAc (12 mL), heated to about 75° C., and maleic acid (423 mg) was added. Precipitation of solids occurred immediately and the thick mixture was diluted with IPAc (5 mL). The slurry was cooled to RT and allowed to stand for 20 min. The solids were filtered, washed with IPAc (10 mL), and dried to give a maleic acid salt of the title compound as white crystalline solid (730 mg, 44%). $^1$H NMR (300 MHz, DMSO-d$_6$) δ ppm 1.34-1.42 (m, 2 H), 1.50 (s, 9 H), 1.50-1.64 (m, 6 H), 3.22 (m, 1 H), 3.83 (br s, 1 H), 6.02 (s, 2 H), 6.86 (d, J=7.5 Hz, 1 H), 7.68 (br s, 3 H).

Preparation 49 tert-Butyl (1S,2R)-2-aminocyclohexylcarbamate, (S)-mandelic acid salt

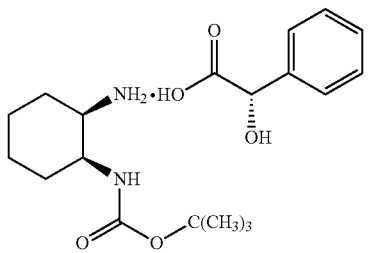

A. cis-N-(2-Aminocyclohexyl)-2,2,2-trifluoroacetamide

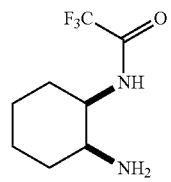 [SMILES: N[C@H]1CCCC[C@H]1NC(=O)C(F)(F)F]

cis-Cyclohexane-1,2-diamine (5.00 g, 43.9 mmol, 1.00 eq) was charged to a 250 mL three-neck round bottom flask equipped with an overhead stirrer and a thermocouple. Ethanol (50 mL) was added and the solution was cooled to <0° C. using an ice-brine bath. A solution of ethyl trifluoroacetate (6.23 g, 1.00 eq) in EtOH (25 mL) was added via a syringe pump over a one hour period. Once the addition was complete, the cooling bath was removed and the solution was slowly warmed to RT and stirred for 3.5 hours to afford the title compound in EtOH. Half (41 mL, about 21.9 mmol) of the total solution (about 82 mL) was carried into the next step.

B. cis-tert-Butyl 2-(2,2,2-trifluoroacetamido)cyclohexylcarbamate

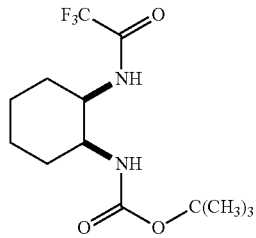 [SMILES: CC(C)(C)OC(=O)N[C@H]1CCCC[C@H]1NC(=O)C(F)(F)F]

Triethylamine (3.1 mL, 22.05 mmol, 1.0 eq) was added to a solution of cis-N-(2-aminocyclohexyl)-2,2,2-trifluoroacetamide in EtOH (41 mL, 21.9 mmol). Di-tert-butyl dicarbonate (5.74 g, 26.3 mmol, 1.2 eq) was added in one portion at RT. An ice bath was used to control a modest exotherm and the internal reaction temperature was maintained at <25° C. Once the exotherm subsided the ice bath was removed, and the mixture was stirred at RT for 16 h to give the title compound in EtOH.

C. cis-tert-Butyl 2-aminocyclohexylcarbamate

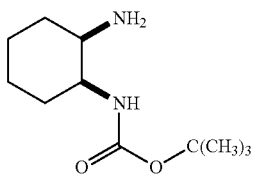 [SMILES: CC(C)(C)OC(=O)N[C@H]1CCCC[C@H]1N]

Aqueous sodium hydroxide (50%, 10 g, 0.125 mole, 5.7 eq) was added to a solution of cis-tert-butyl 2-(2,2,2-trifluoroacetamido)cyclohexylcarbamate in EtOH (about 21.9 mmol). An exotherm from 20 to 37° C. was observed and a fine white slurry formed. The reaction mixture was stirred overnight, during which further solids precipitated out of solution. The solvent volume was concentrated under reduced pressure to about 10 to 15 mL and then IPAc (40 mL) and water (30 mL) were added to form a clean bi-phasic solution. Following phase separation the aqueous phase was extracted with IPAc (15 mL) and the organic extracts were combined and washed with water (15 mL) to give the title compound as a crude racemic product in IPAc.

D. tert-Butyl (1S,2R)-2-aminocyclohexylcarbamate

Crude cis-tert-butyl 2-aminocyclohexylcarbamate in IPAc (70 mL, about 21.9 mmol) was charged to a 100 mL three-neck RBF equipped with a short-path distillation unit, thermocouple, and stir bar. Vacuum was applied and the solution was heated and the solvent volume was distilled at 43-44° C. until the volume reached about 45 mL (10 volumes relative to theoretical crude yield of racemic product). Karl Fisher analysis indicated a water content of 4.9%. The vacuum was released and the solution was heated to 60° C. The solution was then slowly cooled to RT and seeds of tert-butyl (1S,2R)-2-aminocyclohexylcarbamate, (S)-mandelic acid salt (from small scale resolution experiments) were added at 5° C. intervals. All the seeds dissolved while cooling, but remained when RT was reached. The solution was cooled in an ice-brine bath (−15° C.) for 30 min. The solution was reheated, and following the addition of IPAc (40 mL), was redistilled under vacuum at 45-46° C. to about 45 mL of volume. The reaction was cooled to RT and stirred overnight. The solids were filtered, washed with IPAc (2×12.5 mL) and dried to afford an (S)-mandelic acid salt of the title compound as a white solid (2.21 g, 28%, 98% ee). $^1$H NMR (500 MHz, DMSO-$d_6$) δ ppm 1.24-1.30 (m, 2 H), 1.35 (s, 9 H), 1.35-1.64 (m, 6 H), 3.15 (m, 1 H), 3.71 (br s, 1 H), 4.55 (s, 1 H), 6.85-7.11 (br s, 3 H), 6.95 (br d, 1 H, J=7.5 Hz), 7.15 (m 1 H), 7.23 (m, 2 H), 7.37 (m, 2 H).

Example 102

6-((1R,2S)-2-Aminocyclohexylamino)-7-fluoro-4-(1-methyl-1H-pyrazol-4-yl)-1H-pyrrolo[3,4-c]pyridin-3(2H)-one (HCl salt)

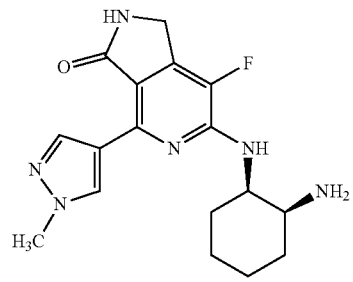

A. tert-Butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate

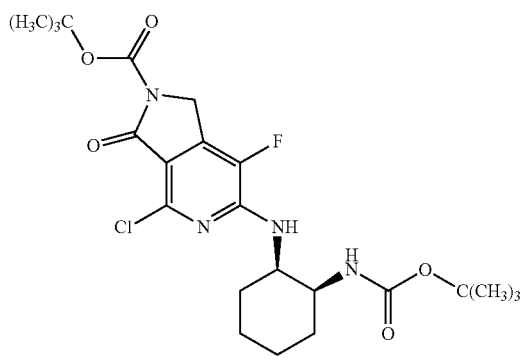 [SMILES: CC(C)(C)OC(=O)N[C@H]1CCCC[C@H]1Nc1nc(Cl)c2c(c1F)CN(C(=O)OC(C)(C)C)C2=O]

To a stirred suspension of tert-butyl 4,6-dichloro-7-fluoro-3-oxo-1H-pyrrolo[3,4-c]pyridine-2(3H)-carboxylate (12.5 g, 38.9 mmol) in 2-propanol (72 mL) was added a solution of tert-butyl (1S,2R)-2-aminocyclohexylcarbamate (10.01 g, 46.7 mmol) in DMSO (12.00 mL) and DIPEA (8.84 mL, 50.6 mmol). The reaction mixture was heated to 90° C. for 16 h at which point it was cooled to 50° C. and water (50 mL) was added dropwise to give a precipitate. The suspension was stirred at 50° C. for 1 h then cooled to RT. The suspension was reheated to 50° C. for 15 min and cooled to RT for two more cycles. The solids were subsequently filtered and washed with isopropanol (20 mL) and dried on a filter to give the title compound (9.538 g, 49%). $^1$H NMR (400 MHz, DMSO-$d_6$) δ ppm 1.18-1.76 (br m, 26 H), 3.83 (br s, 1 H), 4.12 (br s, 1 H), 4.72 (s, 2 H), 6.71 (d, J=7.58 Hz, 1 H), 7.22 (d, J=6.32 Hz, 1 H).

B. tert-Butyl 6-((1R,2S)-2-(tert-butoxycarbonylamino)cyclohexylamino)-7-fluoro-4-(1-methyl-1H-pyrazol-4-yl)-3-oxo-1H-pyrrolo[3,4-c]pyridine-2(3H)-carboxylate

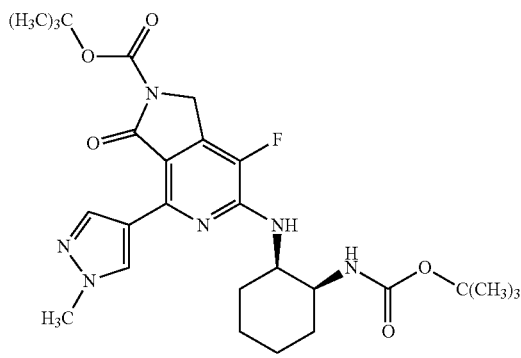 [SMILES: Cn1cc(-c2nc(N[C@@H]3CCCC[C@@H]3NC(=O)OC(C)(C)C)c(F)c3c2C(=O)N(C(=O)OC(C)(C)C)C3)cn1]

A 50 mL, 2-neck round bottom flask was charged with tert-butyl 6-((1R,2S)-2-(tert-butoxycarbonylamino)cyclohexylamino)-4-chloro-7-fluoro-3-oxo-1H-pyrrolo[3,4-c]pyridine-2(3H)-carboxylate (520 mg, 1.042 mmol), 1-methyl-4-(4,4,5,5-tetramethyl-1,3,2-dioxaborolan-2-yl)-1H-pyrazole (282 mg, 1.355 mmol), potassium carbonate (504 mg, 3.65 mmol), and DMA (3 mL). The reaction flask was degassed followed by addition of 1,1-bis(di-tert-butylphosphino)ferrocene palladium chloride (21 mg, 0.032 mmol). Under $N_2$ atmosphere, the reaction mixture was heated in an oil bath at 80° C. for 2.5 h and then allowed to cool to RT. In a separate 50 mL recovery flask was added de-ionized $H_2O$ (12 mL) and the vessel was cooled in an ice/water bath. When the internal temperature of the water reached 2° C., the reaction mixture was transferred to the recovery flask at a rate which kept the internal temperature below 10° C. Following the addition, the reaction vessel was rinsed with DMA (1 mL). The rinse was added to the recovery flask and the resulting aqueous slurry was stirred in an ice bath for 10 min and was then allowed to warm to RT with stirring. When the internal temperature reached 22° C., the mixture was filtered. The filter cake was rinsed with de-ionized $H_2O$ (2×5 mL) and air-dried under suction. The solids were re-suspended in glacial acetic acid (3 mL) and stirred at RT for 1 h. Isopropanol (1 mL) was added and the mixture was stirred at RT. De-ionized water (3.4 mL) was added to induce crystallization. Precipitation occurred, but some solids were sticky, so the mixture was heated in a 40° C. oil bath, with stirring, for 20 min. The mixture was allowed to cool to RT with stirring and then filtered. The filter cake was rinsed with a 3:3:1 mixture of HOAc/$H_2$O/IPA (2.1 mL), briefly air-dried under suction, and then dried in a vacuum oven at 60° C. to give the title compound as a tan solid (352 mg, 62%). $^1$H NMR (400 MHz, DMSO-$d_6$) δ ppm 1.35 (s, 9 H), 1.53 (s, 9 H), 1.65 (m, 3 H), 1.76 (m, 3 H), 3.94 (s, 3 H), 4.03 (br s, 1 H), 4.38 (br s, 1 H), 4.67 (s, 2 H), 5.12 (br s, 1 H), 5.77 (br s, 1 H), 8.25 (br s, 1 H), 8.96 (br s, 1 H). [M+H] calc'd for $C_{27}H_{37}FN_6O_5$, 545; found, 545.

C. 6-((1R,2S)-2-Aminocyclohexylamino)-7-fluoro-4-(1-methyl-1H-pyrazol-4-yl)-1H-pyrrolo[3,4-c]pyridin-3(2H)-one A suspension of tert-butyl 6-((1R,2S)-2-(tert-butoxycarbonylamino)cyclohexyl-amino)-7-fluoro-4-(1-methyl-1H-pyrazol-4-yl)-3-oxo-1H-pyrrolo[3,4-c]pyridine-2(3H)-carboxylate (2.148 g, 3.94 mmol) in IPA (21 mL) was heated to 70° C. at which point 2M HCl aq (9.86 mL, 19.72 mmol) was added. The reaction mixture was heated at 65° C. for approximately 3 h, cooled in an ice water bath for 1 h, and then filtered. The solids were rinsed with cold IPA (15 mL) and then dried in a 50° C. vacuum oven overnight to give an HCL salt of the title compound as a light yellow solid (1.404 g, 3.37 mmol) having 1.5-2 eq of associated water (by $^1$H NMR). $^1$H NMR (400 MHz, DMSO-$d_6$) δ ppm 1.46 (d, J=7.07 Hz, 2 H), 1.57-1.76 (m, 3 H), 1.76-2.04 (m, 3 H), 3.31 (s, 3 H), 3.67 (br s, 1 H), 3.90 (s, 3 H), 4.39 (d, J=2.53 Hz, 2 H), 4.41-4.60 (m, 1 H), 6.75 (d, J=6.57 Hz, 1 H), 7.96 (br s, 3 H), 8.22-8.31 (m, 1 H), 8.34 (s, 1 H), 8.84 (s, 1H). [M+H] calc'd for $C_{17}H_{21}FN_6O$, 345; found 345.

Example 103

6-((3R,4R)-3-Aminotetrahydro-2H-pyran-4-ylamino)-7-fluoro-4-(thiophen-3-yl)-1H-pyrrolo[3,4-c]pyridin-3(2H)-one

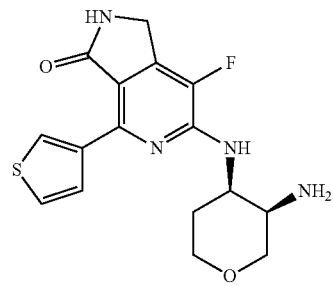 [SMILES: N[C@H]1COCC[C@H]1Nc1nc(-c2ccsc2)c2c(c1F)CNC2=O]

A TFA salt of the title compound was prepared in a manner similar to EXAMPLE 92 using thiophene-3-boronic acid in place of pyrazolo[1,5-α]pyridin-3-ylboronic acid. $^1$H NMR (400 MHz, DMSO-$d_6$) δ ppm 3.16-3.17 (m, 2 H), 3.61-3.63 (m, 1 H), 3.77-3.79 (m, 2 H), 3.81-3.83 (m, 2 H), 4.41-4.43 (m, 2 H), 4.49-5.10 (m, 1 H), 7.12-7.13 (m, 1 H), 7.52-7.54 (m, 1 H), 7.90-7.97 (m, 3 H), 8.48 (s, 1 H), 8.88 (s, 1 H). [M+H] calc'd for $C_{16}H_{17}FN_4O_2S$, 349; found, 349.

Example 104

6-((3R,4R)-3-Aminotetrahydro-2H-pyran-4-ylamino)-7-fluoro-4-(4-methylthiophen-2-yl)-1H-pyrrolo[3,4-c]pyridin-3(2H)-one

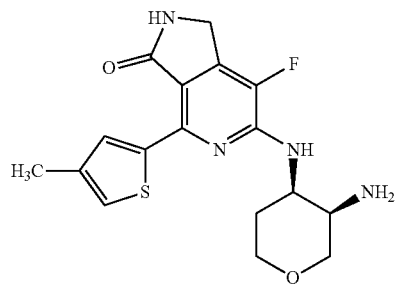 [SMILES: Cc1csc(-c2nc(N[C@@H]3CCOC[C@@H]3N)c(F)c3c2C(=O)NC3)c1]

A TFA salt of the title compound was prepared in a manner similar to EXAMPLE 92 using 4-methylthiophene-2-boronic acid in place of pyrazolo[1,5-α]pyridin-3-ylboronic acid. ¹H NMR (400 MHz, DMSO-d₆) δ ppm 2.24 (s, 3 H), 3.17 (d, J=4.04 Hz, 2 H), 3.35-3.39 (m, 1 H), 3.62-3.64 (m, 1 H), 3.74-3.75 (m, 2 H), 4.00-4.03 (m, 2 H), 4.42 (d, J=11.62 Hz, 2 H), 6.46 (s, 1 H), 7.20-7.22 (m, 3 H), 8.46 (s, 1 H), 8.85 (s, 1 H). [M+H] calc'd for C₁₇H₁₉FN₄O₂S, 363; found, 363.

Example 105

6-((1R,2S)-2-Aminocyclohexylamino)-7-fluoro-4-(4-methylthiophen-2-yl)-1H-pyrrolo[3,4-c]pyridin-3(2H)-one

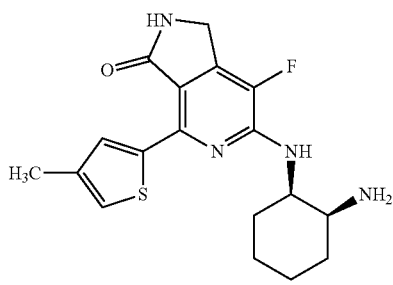 [SMILES: Cc1csc(-c2nc(N[C@@H]3CCCC[C@@H]3N)c(F)c3c2C(=O)NC3)c1]

A TFA salt of the title compound was prepared in a manner similar to EXAMPLE 62 using 4,4,5,5-tetramethyl-2-(4-methylthiophen-2-yl)-1,3,2-dioxaborolane in place of 1-(difluoromethyl)-4-(4,4,5,5-tetramethyl-1,3,2-dioxaborolan-2-yl)-1H-pyrazole. ¹H NMR (500 MHz, DMSO-d₆) δ ppm 1.31-2.04 (m, 8 H), 2.24 (s, 3 H), 3.83 (br s, 1 H), 4.22 (br s, 1 H), 4.36-4.49 (m, 2 H), 6.98 (d, J=5.37 Hz, 1 H), 7.22 (s, 1 H), 7.75 (br s, 2 H), 8.47 (s, 1 H), 8.85 (s, 1 H). [M+H] calc'd for C₁₈H₂₁FN₄OS, 361; found, 361.

Example 106

6-((1R,2S)-2-Aminocyclohexylamino)-7-fluoro-4-(thiophen-3-yl)-1H-pyrrolo[3,4-c]pyridin-3(2H)-one

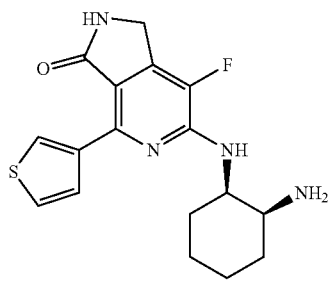 [SMILES: N[C@H]1CCCC[C@H]1Nc1nc(-c2ccsc2)c2c(c1F)CNC2=O]

A TFA salt of the title compound was prepared in a manner similar to EXAMPLE 62 using 4,4,5,5-tetramethyl-2-(thiophen-3-yl)-1,3,2-dioxaborolane in place of 1-(difluoromethyl)-4-(4,4,5,5-tetramethyl-1,3,2-dioxaborolan-2-yl)-1H-pyrazole. ¹H NMR (500 MHz, DMSO-d₆) δ ppm 1.31-2.05 (m, 8 H), 3.84 (br s, 1 H), 4.25 (d, J=3.42 Hz, 1 H), 4.36-4.50 (m, 2 H), 7.01 (d, J=5.86 Hz, 1 H), 7.15 (dd, J=5.37, 3.91 Hz, 1 H), 7.64 (dd, J=4.88, 0.98 Hz, 1 H), 7.75 (br s, 2 H), 8.50 (s, 1 H), 8.95-9.07 (m, 1 H). [M+H] calc'd for C₁₇H₁₉FN₄OS, 347; found, 347.

Example 107

(R)-2-(7-Fluoro-4-(1-methyl-1H-pyrazol-4-yl)-3-oxo-2,3-dihydro-1H-pyrrolo[3,4-c]pyridin-6-ylamino)-N,4-dimethylpentanamide

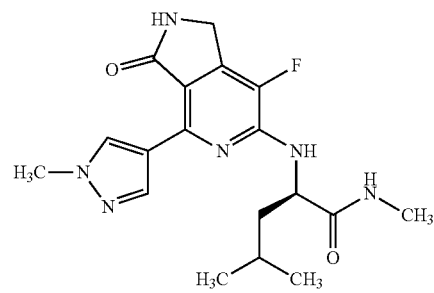

A. (R)-Methyl 2-(4-chloro-2-(2,4-dimethoxybenzyl)-7-fluoro-3-oxo-2,3-dihydro-1H-pyrrolo[3,4-c]pyridin-6-ylamino)-4-methylpentanoate

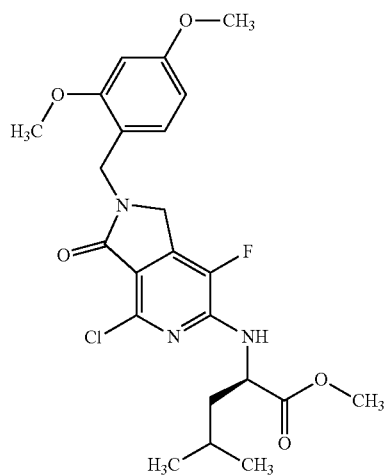

A mixture of 4,6-dichloro-2-(2,4-dimethoxybenzyl)-7-fluoro-1H-pyrrolo[3,4-c]pyridin-3(2H)-one (3 g, 8.08 mmol), (S)-methyl 2-amino-4-methylpentanoate hydrochloride (2.94 g, 16.16 mmol), and N-isopropyl-N-methylpropan-2-amine (3.76 mL, 24.25 mmol) in ACN (50 mL) was stirred at 100° C. for 3 d. The solvent was removed and the resulting residue was used in the next step without further purification. [M+H] calc'd for $C_{23}H_{27}ClFN_3O_5$, 480; found, 480.

B. (R)-2-(4-Chloro-2-(2,4-dimethoxybenzyl)-7-fluoro-3-oxo-2,3-dihydro-1H-pyrrolo[3,4-c]pyridin-6-ylamino)-4-methylpentanoic acid

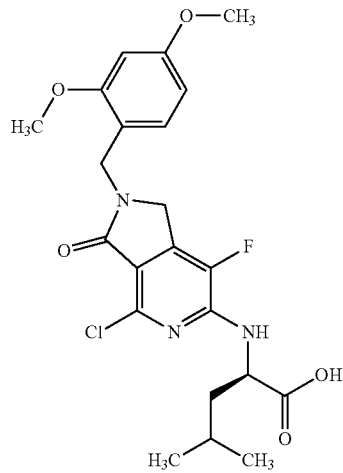 [SMILES: COc1ccc(CN2Cc3c(F)c(N[C@H](CC(C)C)C(=O)O)nc(Cl)c3C2=O)c(OC)c1]

A mixture of (R)-methyl 2-(4-chloro-2-(2,4-dimethoxybenzyl)-7-fluoro-3-oxo-2,3-dihydro-1H-pyrrolo[3,4-c]pyridin-6-ylamino)-4-methylpentanoate (2.9 g, 6.04 mmol) in MeOH (10 mL) and 1N NaOH (40.0 mL) was stirred at 50° C. for 2 h. UPLC showed 30% starting material remained. Additional saturated NaOH solution (5 mL) was added and the reaction mixture was stirred for 3 h at 50° C. The solvent was removed and the resulting residue was dispersed in $H_2O$ (100 mL) and acidified to pH 3 using HCl. After stirring at RT for 2 h, the solid was filtered to give the title compound. [M+H] calc'd for $C_{22}H_{25}ClFN_3O_5$, 466; found, 466.

C. (R)-2-(2-(2,4-Dimethoxybenzyl)-7-fluoro-4-(1-methyl-1H-pyrazol-4-yl)-3-oxo-2,3-dihydro-1H-pyrrolo[3,4-c]pyridin-6-ylamino)-4-methylpentanoic acid

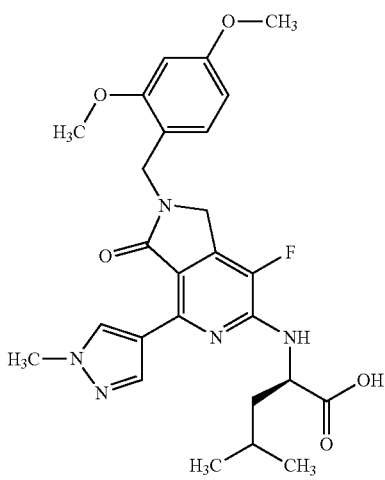 [SMILES: COc1ccc(CN2Cc3c(F)c(N[C@H](CC(C)C)C(=O)O)nc(-c4cnn(C)c4)c3C2=O)c(OC)c1]

A solution of (R)-2-(4-chloro-2-(2,4-dimethoxybenzyl)-7-fluoro-3-oxo-2,3-dihydro-1H-pyrrolo[3,4-c]pyridin-6-ylamino)-4-methylpentanoic acid (1.1 g, 2.361 mmol), 1-methyl-4-(4,4,5,5-tetramethyl-1,3,2-dioxaborolan-2-yl)-1H-pyrazole (2.456 g, 11.81 mmol) and bis(triphenylphosphine)palladium chloride (1.657 g, 2.361 mmol) in dioxane (10 mL) and saturated aq $Na_2CO_3$ (10.00 mL) was heated to 120° C. for 30 min. After filtering out the solids, the solvent was removed from the filtrate. The resulting residue was dissolved in MeOH and DCM and was purified via preparative HPLC eluting with water (0.05% TFA) and ACN (40-70% gradient, 0.035% TFA). The collected fractions were combined and the solvent stripped to dryness via rotary evaporation to yield the title compound. [M+H] calc'd for $C_{26}H_{30}FN_5O_5$, 512; found, 512.

D. (R)-2-(2-(2,4-Dimethoxybenzyl)-7-fluoro-4-(1-methyl-1H-pyrazol-4-yl)-3-oxo-2,3-dihydro-1H-pyrrolo[3,4-c]pyridin-6-ylamino)-N,4-dimethylpentanamide

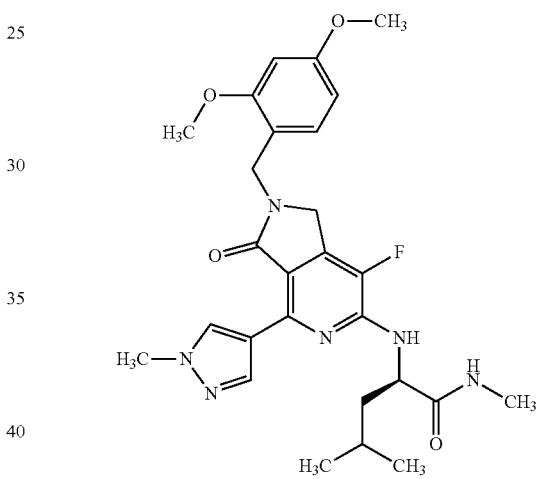

A solution of (R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)-4-methylpentanoic acid (48 mg, 0.094 mmol), methylamine hydrochloride (31.7 mg, 0.469 mmol) and DIPEA (49.2 µL, 0.281 mmol) in DMF (1 mL) was stirred at RT for 10 min. HATU (71.4 mg, 0.188 mmol) was added and the mixture was stirred at RT for 1 h, after which UPLC showed about 80% starting material remained. Additional methylamine (58.4 µL, 0.469 mmol, 33% in EtOH) was added, which resulted in little conversion of the starting material. The solvent was stripped off and the residue was dissolved in DMF (1 mL). To this solution was added EDCI hydrochloride (54.0 mg, 0.281 mmol), HOBT monohydrate (43.1 mg, 0.281 mmol), and methylamine hydrochloride (31.7 mg, 0.469 mmol). The reaction mixture was heated to 60° C. for 4 h. UPLC subsequently showed the reaction mixture contained 95% of desired product. The reaction mixture was allowed to cool to RT. Water (50 mL) was added and the mixture was extracted with DCM (3×50 mL). The organic layers were collected, dried over $Na_2SO_4$, filtered, and the solvent was stripped to dryness via rotary evaporation to yield the title compound, which was used without further purification. [M+H] calc'd for $C_{27}H_{33}FN_6O_4$, 525; found, 525.

E. (R)-2-(7-Fluoro-4-(1-methyl-1H-pyrazol-4-yl)-3-oxo-2,3-dihydro-1H-pyrrolo[3,4-c]pyridin-6-ylamino)-N,4-dimethylpentanamide A solution of (R)-2-(2-(2,4-dimethoxybenzyl)-7-fluoro-4-(1-methyl-1H-pyrazol-4-yl)-3-oxo-2,3-dihydro-1H-pyrrolo[3,4-c]pyridin-6-ylamino)-N,4-dimethylpentanamide (38 mg, 0.072 mmol) in TFA (5 mL) was heated to 65° C. for 4 h. After removal of the solvent, the residue was diluted in MeOH (2 mL) and was purified by preparative HPLC eluting with water (0.05% TFA) and ACN (25-30%, gradient, 0.035% TFA). The collected fractions were stripped to dryness to give the title compound. $^1$H NMR (500 MHz, DMSO-$d_6$) δ ppm 0.84-0.93 (m, 6 H), 1.63-1.81 (m, 2 H), 2.57 (d, J=4.39 Hz, 3 H), 3.88 (s, 3 H), 4.04-4.19 (m, 2 H), 4.36 (s, 2 H), 6.99 (d, J=7.32 Hz, 1 H), 7.61-7.76 (m, 1 H), 7.93 (d, J=4.39 Hz, 1 H), 8.30 (s, 1 H), 8.83 (s, 1 H). [M+H] calc'd for $C_{18}H_{23}FN_6O_2$, 375; found, 375.

Example 108

6-((1R,2S)-2-Aminocyclohexylamino)-7-fluoro-4-(5-methylthiophen-2-yl)-1H-pyrrolo[3,4-c]pyridin-3(2H)-one

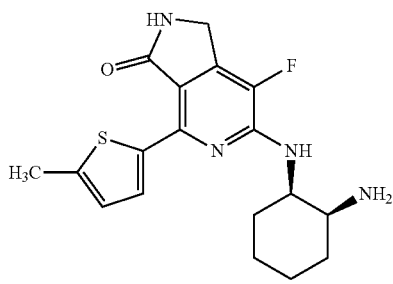 [SMILES: Cc1ccc(-c2nc(N[C@@H]3CCCC[C@@H]3N)c(F)c3c2C(=O)NC3)s1]

A TFA salt of the title compound was prepared in a manner similar to EXAMPLE 62 using 4,4,5,5-tetramethyl-2-(5-methylthiophen-2-yl)-1,3,2-dioxaborolane in place of 1-(difluoromethyl)-4-(4,4,5,5-tetramethyl-1,3,2-dioxaborolan-2-yl)-1H-pyrazole. $^1$H NMR (400 MHz, DMSO-$d_6$) δ ppm 1.31-2.01 (m, 8 H), 2.46 (d, J=0.51 Hz, 3 H), 3.80 (br s, 1 H), 4.25 (d, J=4.55 Hz, 1 H), 4.36-4.50 (m, 2 H), 6.83 (dd, J=3.79, 1.01 Hz, 1 H), 6.91 (d, J=6.06 Hz, 1 H), 7.73 (br s, 2 H), 8.43 (s, 1 H), 8.82 (d, J=3.54 Hz, 1 H). [M+H] calc'd for $C_{18}H_{21}FN_4OS$, 361; found, 361.

Example 109

(R)-2-(7-Fluoro-4-(4-methylthiophen-2-yl)-3-oxo-2,3-dihydro-1H-pyrrolo[3,4-c]pyridin-6-ylamino)-4-methylpentanamide

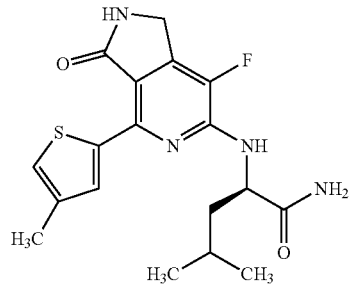 [SMILES: Cc1csc(-c2nc(N[C@H](CC(C)C)C(N)=O)c(F)c3c2C(=O)NC3)c1]

The title compound was prepared in a manner similar to EXAMPLE 70 using 4,4,5,5-tetramethyl-2-(4-methylthiophen-2-yl)-1,3,2-dioxaborolane in place of 1-methyl-4-(4,4,5,5-tetramethyl-1,3,2-dioxaborolan-2-yl)-1H-pyrazole. $^1$H NMR (400 MHz, DMSO-$d_6$) δ ppm 0.82-0.95 (m, 6 H), 1.20-1.32 (m, 2 H), 2.23 (s, 3 H), 4.38 (s, 2 H), 4.59-4.72 (m, 2 H), 6.94-6.99 (m, 1 H), 7.02-7.08 (m, 1 H), 7.15-7.23 (m, 1 H), 7.27-7.34 (m, 1 H), 8.35 (s, 1 H), 8.78 (d, J=1.26 Hz, 1 H). [M+H] calc'd for $C_{18}H_{21}FN_4O_2S$, 377; found, 377.

Example 110

(R)-2-(7-Fluoro-3-oxo-4-(thiophen-3-yl)-2,3-dihydro-1H-pyrrolo[3,4-c]pyridin-6-ylamino)-4-methylpentanamide

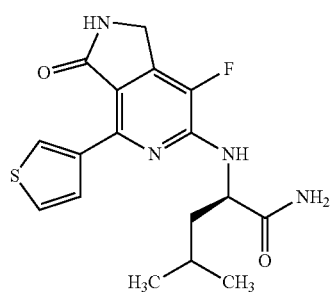 [SMILES: CC(C)C[C@@H](Nc1nc(-c2ccsc2)c2c(c1F)CNC2=O)C(N)=O]

The title compound was prepared in a manner similar to EXAMPLE 70 using 4,4,5,5-tetramethyl-2-(thiophen-3-yl)-1,3,2-dioxaborolane in place of 1-methyl-4-(4,4,5,5-tetramethyl-1,3,2-dioxaborolan-2-yl)-1H-pyrazole. $^1$H NMR (400 MHz, DMSO-$d_6$) δ ppm 0.75-1.00 (m, 6 H), 1.50-1.63 (m, 1 H), 1.69-1.83 (m, 2 H), 4.39 (s, 2 H), 4.52-4.61 (m, 1 H), 6.93 (br s, 1 H), 7.01 (d, J=7.58 Hz, 1 H), 7.38 (br s, 1 H), 7.49 (dd, J=5.05, 3.03 Hz, 1 H), 8.04 (dd, J=5.05, 1.26 Hz, 1 H), 8.36 (s, 1 H), 8.94 (dd, J=3.03, 1.01 Hz, 1 H). [M+H] calc'd for $C_{17}H_{19}FN_4O_2S$, 363; found, 363.

Example 111

(R)-2-(7-Fluoro-4-(5-methylthiophen-2-yl)-3-oxo-2,3-dihydro-1H-pyrrolo[3,4-c]pyridin-6-ylamino)-4-methylpentanamide

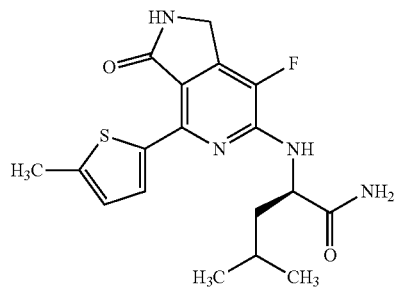

The title compound was prepared in a manner similar to EXAMPLE 70 using 4,4,5,5-tetramethyl-2-(5-methylthiophen-2-yl)-1,3,2-dioxaborolane in place of 1-methyl-4-(4,4,5,5-tetramethyl-1,3,2-dioxaborolan-2-yl)-1H-pyrazole. $^1$H NMR (400 MHz, DMSO-d$_6$) δ ppm 0.71-0.96 (m, 6 H), 1.52-1.85 (m, 3 H), 2.45 (s, 3 H), 4.38 (s, 2 H), 4.56-4.74 (m, 1 H), 6.80 (dd, J=3.66, 1.14 Hz, 1 H), 6.93-7.10 (m, 2 H), 7.30 (br s, 1 H), 8.32 (s, 1 H), 8.78 (d, J=3.79 Hz, 1 H). [M+H] calc'd for $C_{18}H_{21}FN_4O_2S$, 377; found, 377.

Example 112

6-((1R,2S)-2-Aminocyclohexylamino)-4-(2-aminothiazol-5-yl)-7-fluoro-1H-pyrrolo[3,4-c]pyridin-3(2H)-one

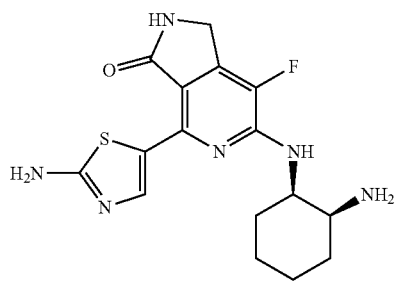

A. tert-Butyl (5-(6-(((1R,2S)-2-((tert-butoxycarbonyl)amino)cyclohexyl)amino)-2-(2,4-dimethoxybenzyl)-7-fluoro-3-oxo-2,3-dihydro-1H-pyrrolo[3,4-c]pyridin-4-yl)-1,3-thiazol-2-yl)carbamate

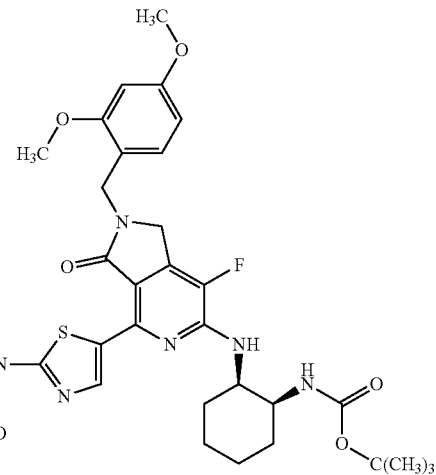

A solution of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (50 mg, 0.091 mmol), tert-butyl 5-(tributylstannyl)thiazol-2-ylcarbamate (53.5 mg, 0.109 mmol), and tetrakis(triphenylphosphine)palladium(0) (105 mg, 0.091 mmol) in toluene (1 mL) was heated to 102° C. for 24 h. After removal of the solvent, the resulting crude material was reconstituted in MeOH/DMF (6.0 mL) and purified via preparative HPLC eluting with water (0.05% TFA) and ACN (70-75% gradient, 0.035% TFA). The collected fractions were stripped to dryness via rotary evaporation to yield the title compound (42 mg, 64%). [M+H] calc'd for $C_{35}H_{45}FN_6O_7S$, 713; found, 713.

B. 6-((1R,2S)-2-Aminocyclohexylamino)-4-(2-aminothiazol-5-yl)-7-fluoro-1H-pyrrolo[3,4-c]pyridin-3(2H)-one A solution of tert-butyl (5-(6-(((1R,2S)-2-((tert-butoxycarbonyl)amino)cyclo-hexyl)amino)-2-(2,4-dimethoxybenzyl)-7-fluoro-3-oxo-2,3-dihydro-1H-pyrrolo[3,4-c]pyridin-4-yl)-1,3-thiazol-2-yl)carbamate (41.5 mg, 0.058 mmol) in TFA (5 mL) was heated to 65° C. for 3 h. After removal of the solvent, the resulting crude material was reconstituted in MeOH/DMF (6.0 mL) and purified via preparative HPLC eluting with water (0.05% TFA) and ACN (10-20% gradient, 0.035% TFA). The collected fractions were stripped to dryness via rotary evaporation to yield the title compound as a TFA salt (6.7 mg, 32%). $^1$H NMR (400 MHz, DMSO-d$_6$) δ ppm 1.12-2.11 (m, 9 H), 3.73 (br s, 2 H), 4.19 (d, J=3.79 Hz, 1 H), 4.41

(d, J=3.03 Hz, 2 H), 6.95 (d, J=3.03 Hz, 1 H), 7.77 (br s, 2 H), 8.44 (s, 1 H), 8.93 (s, 1 H). [M+H] calc'd for $C_{16}H_{19}FN_6OS$, 363; found, 363.

Preparation 50

(R)-2-(4-Chloro-2-(2,4-dimethoxybenzyl)-7-fluoro-3-oxo-2,3-dihydro-1H-pyrrolo[3,4-c]pyridin-6-ylamino)-4-methylpentanamide

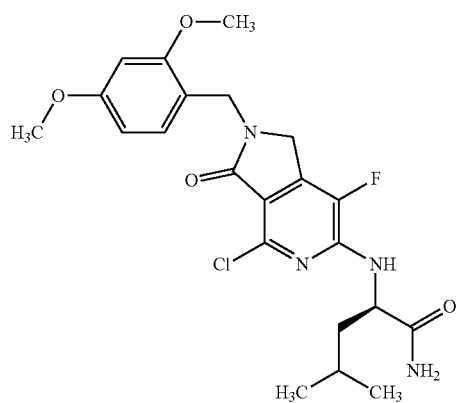 [SMILES: COc1ccc(CN2Cc3c(F)c(N[C@H](CC(C)C)C(N)=O)nc(Cl)c3C2=O)c(OC)c1]

A mixture of 4,6-dichloro-2-(2,4-dimethoxybenzyl)-7-fluoro-1H-pyrrolo[3,4-c]pyridin-3(2H)-one (7 g, 18.86 mmol), N-isopropyl-N-methylpropan-2-amine (14.64 mL, 94 mmol), and N-isopropyl-N-methylpropan-2-amine (14.64 ml, 94 mmol) in ACN (100 mL) was stirred at 100° C. for 3 d. UPLC showed about 10% starting material remained. The reaction was stopped, the solvent was removed, and the crude product was reconstituted in MeOH/DCM and dispersed on silica gel (10 g). The solvent was evaporated and the residue was purified on a silica gel column eluting with 1-3% MeOH in DCM over a 45 min period. The collected fractions were combined and stripped to dryness via rotary evaporation to yield the title compound (5.3 g, 61%). [M+H] calc'd for $C_{22}H_{26}ClFN_4O_4$, 465; found 465.

Example 113

(R)-2-(7-Fluoro-4-(furan-2-yl)-3-oxo-2,3-dihydro-1H-pyrrolo[3,4-c]pyridin-6-ylamino)-4-methylpentanamide

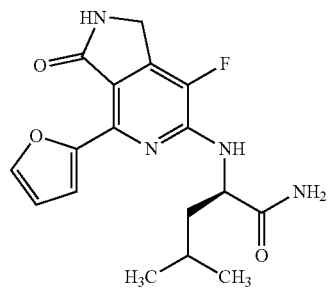 [SMILES: CC(C)C[C@@H](Nc1nc(-c2ccco2)c2c(c1F)CNC2=O)C(N)=O]

A. (R)-2-(2-(2,4-Dimethoxybenzyl)-7-fluoro-4-(furan-2-yl)-3-oxo-2,3-dihydro-1H-pyrrolo[3,4-c]pyridin-6-ylamino)-4-methylpentanamide

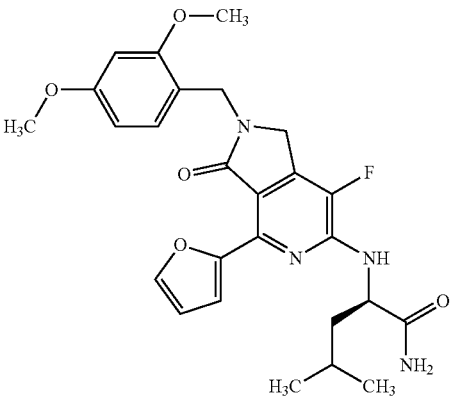 [SMILES: COc1ccc(CN2Cc3c(F)c(N[C@H](CC(C)C)C(N)=O)nc(-c4ccco4)c3C2=O)c(OC)c1]

A solution of (R)-2-(4-chloro-2-(2,4-dimethoxybenzyl)-7-fluoro-3-oxo-2,3-dihydro-1H-pyrrolo[3,4-c]pyridin-6-ylamino)-4-methylpentanamide (150 mg, 0.323 mmol), tributyl(furan-2-yl)stannane (138 mg, 0.387 mmol), and tetrakis(triphenylphosphine)palladium(0) (373 mg, 0.323 mmol) in toluene (1 mL) was heated to 102° C. overnight. After removal of the solvent, the residue was diluted in MeOH/DCM (10 mL) and was purified via preparative HPLC eluting with water (0.05% TFA) and ACN (45-60% gradient, 0.035% TFA). The collected fractions were stripped to dryness via rotary evaporation to give the title compound (93.1 mg, 58%). [M+H] calc'd for $C_{26}H_{29}FN_4O_5$, 498; found 498.

B. (R)-2-(7-Fluoro-4-(furan-2-yl)-3-oxo-2,3-dihydro-1H-pyrrolo[3,4-c]pyridin-6-ylamino)-4-methylpentanamide A solution of (R)-2-(2-(2,4-dimethoxybenzyl)-7-fluoro-4-(furan-2-yl)-3-oxo-2,3-dihydro-1H-pyrrolo[3,4-c]pyridin-6-ylamino)-4-methylpentanamide (93.1 mg, 0.188 mmol) in TFA (5 mL) was heated to 65° C. for 3 h. The solvent was removed and the resulting residue was diluted in MeOH/DCM (10 mL) and was purified via preparative HPLC eluting with water (0.05% TFA) and ACN (30%, 0.035% TFA). The collected fractions were stripped to dryness via rotary evaporation to afford the title compound. $^1$H NMR (400 MHz, DMSO-$d_6$) δ ppm 0.79-0.97 (m, 6 H), 1.52-1.87 (m, 3 H), 4.38 (s, 2 H), 4.66-4.85 (m, 1 H), 6.61 (dd, J=3.54, 1.77 Hz, 1 H), 6.92-7.07 (m, 2 H), 7.36 (br s, 1 H), 7.79 (dd, J=1.64, 0.63

Hz, 1 H), 8.04 (dd, J=3.54, 0.51 Hz, 1 H), 8.32 (s, 1 H). [M+H] calc'd for $C_{17}H_{19}FN_4O_3$, 347; found, 347.

Example 114

(R)-2-(7-Fluoro-4-(furan-3-yl)-3-oxo-2,3-dihydro-1H-pyrrolo[3,4-c]pyridin-6-ylamino)-4-methylpentanamide

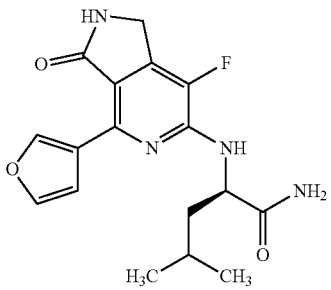 [SMILES: CC(C)C[C@@H](Nc1nc(-c2ccoc2)c2c(c1F)CNC2=O)C(N)=O]

The title compound was prepared in a manner similar to EXAMPLE 70 using 2-(furan-3-yl)-4,4,5,5-tetramethyl-1,3,2-dioxaborolane in place of 1-methyl-4-(4,4,5,5-tetramethyl-1,3,2-dioxaborolan-2-yl)-1H-pyrazole. $^1$H NMR (500 MHz, DMSO-d$_6$) δ ppm 0.80-0.99 (m, 6 H), 1.21-1.33 (m, 1 H), 1.50-1.60 (m, 1 H), 1.74-1.81 (m, 1 H), 4.38 (s, 2 H), 4.47-4.61 (m, 1 H), 6.89-6.98 (m, 1 H), 7.03 (d, J=7.81 Hz, 1 H), 7.35 (s, 1 H), 7.42 (s, 1 H), 7.68 (s, 1 H), 8.35 (s, 1 H), 8.98 (s, 1 H). [M+H] calc'd for $C_{17}H_{19}FN_4O_3$, 347; found, 347.

Example 115

(R)-2-(7-Fluoro-4-(5-methylfuran-2-yl)-3-oxo-2,3-dihydro-1H-pyrrolo[3,4-c]pyridin-6-ylamino)-4-methylpentanamide

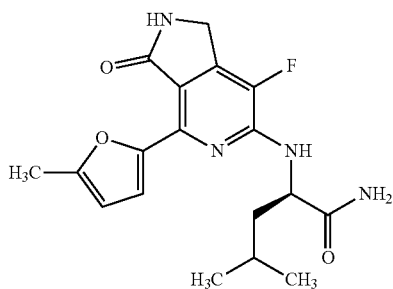

The title compound was prepared in a manner similar to EXAMPLE 113 using tributyl(5-methylfuran-2-yl)stannane in place of tributyl(furan-2-yl)stannane. $^1$H NMR (400 MHz, DMSO-d$_6$) δ ppm 0.84-0.97 (m, 6 H), 1.51-1.78 (m, 3 H), 2.29-2.36 (m, 3 H), 4.36 (s, 2 H), 4.64-4.86 (m, 1 H), 6.22 (dd, J=3.28, 1.01 Hz, 1 H), 6.92 (d, J=8.08 Hz, 1 H), 7.01 (br s, 1 H), 7.41 (br s, 1 H), 7.97 (d, J=3.03 Hz, 1 H), 8.26 (s, 1 H). [M+H] calc'd for $C_{18}H_{21}FN_4O_3$, 361; found, 361.

Example 116

(R)-2-(4-(5-Cyanothiophen-2-yl)-7-fluoro-3-oxo-2,3-dihydro-1H-pyrrolo[3,4-c]pyridin-6-ylamino)-4-methylpentanamide

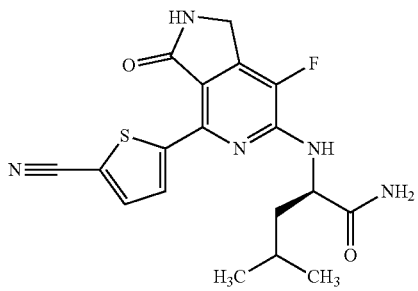 [SMILES: CC(C)C[C@@H](Nc1nc(-c2ccc(C#N)s2)c2c(c1F)CNC2=O)C(N)=O]

A. (R)-2-(4-(5-Cyanothiophen-2-yl)-2-(2,4-dimethoxybenzyl)-7-fluoro-3-oxo-2,3-dihydro-1H-pyrrolo[3,4-c]pyridin-6-ylamino)-4-methylpentanamide

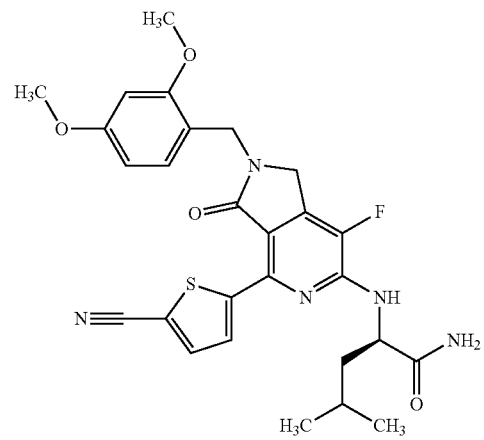 [SMILES: COc1ccc(CN2Cc3c(F)c(N[C@H](CC(C)C)C(N)=O)nc(-c4ccc(C#N)s4)c3C2=O)c(OC)c1]

A solution of (R)-2-(4-chloro-2-(2,4-dimethoxybenzyl)-7-fluoro-3-oxo-2,3-dihydro-1H-pyrrolo[3,4-c]pyridin-6-ylamino)-4-methylpentanamide (114 mg, 0.245 mmol), 5-cyanothiophen-2-ylboronic acid (113 mg, 0.736 mmol), tris(dibenzylideneacetone)di-palladium(0) (13.47 mg, 0.015 mmol), and 2-(dicyclohexylphosphino)biphenyl (5.16 mg, 0.015 mmol) in dioxane (2 mL) and DMF (0.5 mL) was heated to 160° C. under microwave irradiation for 45 min. UPLC showed 50% conversion. The reaction mixture was subsequently heated at 160° C. under microwave irradiation for 45 min. Additional 5-cyanothiophen-2-ylboronic acid (113 mg, 0.736 mmol) was added and the reaction mixture was heated at 160° C. under microwave irradiation for 60 min. After removal of the solvent, the resulting crude material was reconstituted in MeOH/DMF (6.0 mL) and purified via preparative HPLC eluting with water (0.05% TFA) and ACN (40-80% gradient, 0.035% TFA). The collected fractions were stripped to dryness via rotary evaporation to yield the title compound. [M+H] calc'd for $C_{27}H_{28}FN_5O_4S$, 538; found, 538.

B. (R)-2-(4-(5-Cyanothiophen-2-yl)-7-fluoro-3-oxo-2,3-dihydro-1H-pyrrolo[3,4-c]pyridin-6-ylamino)-4-methylpentanamide A solution of (R)-2-(4-(5-cyanothiophen-2-yl)-2-(2,4-dimethoxybenzyl)-7-fluoro-3-oxo-2,3-dihydro-1H-pyrrolo[3,4-c]pyridin-6-ylamino)-4-methylpentanamide (68 mg, 0.126 mmol) in TFA (2 mL) was heated to 65° C. for 3 h. After removal of the solvent, the resulting crude material was reconstituted in MeOH/DCM (3.0 mL) and purified via preparative HPLC eluting with water (0.05% TFA) and ACN (40%, 0.035% TFA). The collected fractions were combined and the solvent was removed via rotary evaporation to yield the title compound (8.3 mg, 17%). $^1$H NMR (500 MHz, DMSO-$d_6$) δ ppm 0.86-0.96 (m, 6 H), 1.53-1.62 (m, 1 H), 1.67-1.88 (m, 2 H), 4.45 (s, 2 H), 4.50-4.57 (m, 1 H), 6.96-7.06 (m, 1 H), 7.32-7.54 (m, 2 H), 7.86-8.02 (m, 1 H), 8.61 (s, 1 H), 9.00-9.15 (m, 1 H). [M+H] calc'd for $C_{18}H_{18}FN_5O_2S$, 388; found, 388.

Example 117

(R)-2-(4-(4-Cyanothiophen-2-yl)-7-fluoro-3-oxo-2,3-dihydro-1H-pyrrolo[3,4-c]pyridin-6-ylamino)-4-methylpentanamide

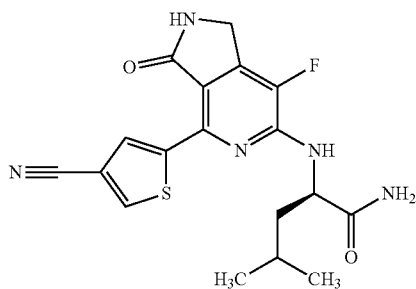 [SMILES: CC(C)C[C@@H](Nc1nc(-c2cc(C#N)cs2)c2c(c1F)CNC2=O)C(N)=O]

The title compound was prepared in a manner similar to EXAMPLE 116 using 4-cyanothiophen-2-ylboronic acid in place of 5-cyanothiophen-2-ylboronic acid. $^1$H NMR (500 MHz, DMSO-$d_6$) δ ppm 0.80-0.96 (m, 6 H), 1.55-1.66 (m, 1 H), 1.65-1.86 (m, 2 H), 4.44 (s, 2 H), 4.51-4.64 (m, 1 H), 6.99 (s, 1 H), 7.04-7.20 (m, 1 H), 7.32 (d, J=8.30 Hz, 1 H), 7.37 (s, 1 H), 8.53-8.68 (m, 1 H), 9.24 (s, 1 H). [M+H] calc'd for $C_{18}H_{18}FN_5O_2S$, 388; found, 388.

Example 118

(R)-2-(7-Fluoro-3-oxo-4-(thiazol-5-yl)-2,3-dihydro-1H-pyrrolo[3,4-c]pyridin-6-ylamino)-4-methylpentanamide

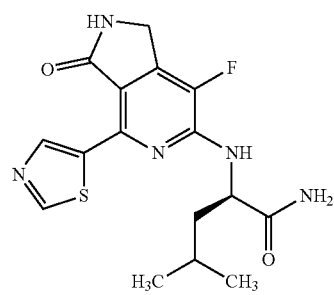 [SMILES: CC(C)C[C@@H](Nc1nc(-c2cncs2)c2c(c1F)CNC2=O)C(N)=O]

The title compound was prepared in a manner similar to EXAMPLE 113 using 5-(tributylstannyl)thiazole in place of tributyl(furan-2-yl)stannane. $^1$H NMR (400 MHz, DMSO-$d_6$) δ ppm 0.77-0.98 (m, 6 H), 1.53-1.68 (m, 1 H), 1.71-1.84 (m, 2 H), 4.42 (s, 2 H), 4.52-4.66 (m, 1 H), 6.95 (br s, 1 H), 7.18 (d, J=8.59 Hz, 1 H), 7.34 (br s, 1 H), 8.46 (s, 1 H), 9.11 (s, 1 H), 9.46 (s, 1 H). [M+H] calc'd for $C_{16}H_{18}FN_5O_2S$, 364; found, 364.

Example 119

(R)-2-(7-Fluoro-4-(isothiazol-5-yl)-3-oxo-2,3-dihydro-1H-pyrrolo[3,4-c]pyridin-6-ylamino)-4-methylpentanamide

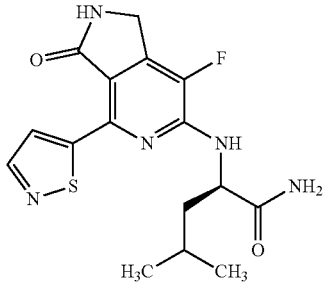 [SMILES: CC(C)C[C@@H](Nc1nc(-c2ccns2)c2c(c1F)CNC2=O)C(N)=O]

The title compound was prepared in a manner similar to EXAMPLE 116 using 5-(4,4,5,5-tetramethyl-1,3,2-dioxaborolan-2-yl)isothiazole in place of 5-cyanothiophen-2-ylboronic acid. $^1$H NMR (500 MHz, DMSO-$d_6$) δ ppm 0.77-0.97 (m, 6 H), 1.56-1.64 (m, 1 H), 1.67-1.86 (m, 2 H), 4.45 (s, 2 H), 4.49-4.62 (m, 1 H), 7.00 (s, 1 H), 7.33 (d, J=8.30 Hz, 1

H), 7.44 (s, 1 H), 8.53-8.65 (m, 2 H), 8.91 (d, J=1.46 Hz, 1 H). [M+H] calc'd for $C_{16}H_{18}FN_5O_2S$, 364; found, 364.

Example 120

6-((1R,2S)-2-Aminocyclohexylamino)-7-fluoro-1,1-dimethyl-4-(1-methyl-1H-pyrazol-4-yl)-1H-pyrrolo[3,4-c]pyridin-3(2H)-one

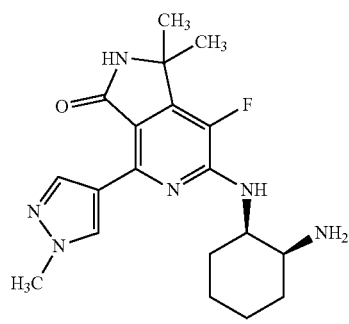 [SMILES: Cn1cc(-c2nc(N[C@@H]3CCCC[C@@H]3N)c(F)c3c2C(=O)NC3(C)C)cn1]

A. 4,6-Dichloro-2-(2,4-dimethoxybenzyl)-7-fluoro-1,1-dimethyl-1H-pyrrolo[3,4-c]pyridin-3(2H)-one

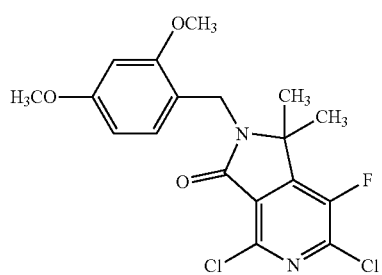 [SMILES: COc1ccc(CN2C(=O)c3c(Cl)nc(Cl)c(F)c3C2(C)C)c(OC)c1]

To a solution of 4,6-dichloro-2-(2,4-dimethoxybenzyl)-7-fluoro-1H-pyrrolo[3,4-c]pyridin-3(2H)-one (500 mg, 1.347 mmol) in DMF (5 mL) at 0° C. was added sodium hydride (53.9 mg, 1.347 mmol) and iodomethane (0.084 mL, 1.347 mmol). The mixture was stirred at 0° C. for 1 h, then diluted to EtOAc (200 mL) and washed with brine (200 mL) and water (200 mL). The organic phase was dried and concentrated to a residue, which was purified by reverse phase preparative HPLC to give the title compound as one of the products (50 mg, 9%, mono-methylated product was observed). [M+H] calc'd for $C_{18}H_{17}Cl_2FN_2O_3$, 400.2; found, 399.4.

B. tert-Butyl (1S,2R)-2-(4-chloro-2-(2,4-dimethoxybenzyl)-7-fluoro-1,1-dimethyl-3-oxo-2,3-dihydro-1H-pyrrolo[3,4-c]pyridin-6-ylamino)cyclohexylcarbamate

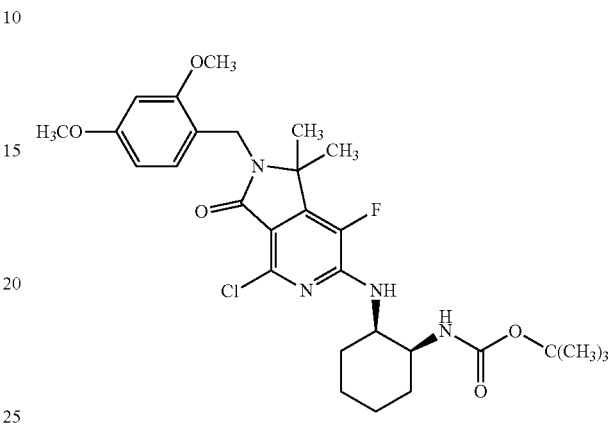

In a 10 mL sealed cap glass vial, 4,6-dichloro-2-(2,4-dimethoxybenzyl)-7-fluoro-1,1-dimethyl-1H-pyrrolo[3,4-c]pyridin-3(2H)-one (50 mg, 0.125 mmol) and tert-butyl (1S,2R)-2-aminocyclohexylcarbamate (53.2 mg, 0.250 mmol) were dissolved in ACN (2 mL). N-ethyldiisopropylamine (0.033 mL, 0.188 mmol) was added, the cap was sealed, and the reaction mixture heated at 95° C. for 72 h. The reaction mixture was subsequently purified by preparative HPLC and basified to give the title compound as a light yellow solid (40 mg, 55%). [M+H] calc'd for $C_{29}H_{38}ClFN_4O_5$, 578.1; found, 577.4.

C. tert-Butyl (1S,2R)-2-(2-(2,4-dimethoxybenzyl)-7-fluoro-1,1-dimethyl-4-(1-methyl-1H-pyrazol-4-yl)-3-oxo-2,3-dihydro-1H-pyrrolo[3,4-c]pyridin-6-ylamino)cyclohexylcarbamate

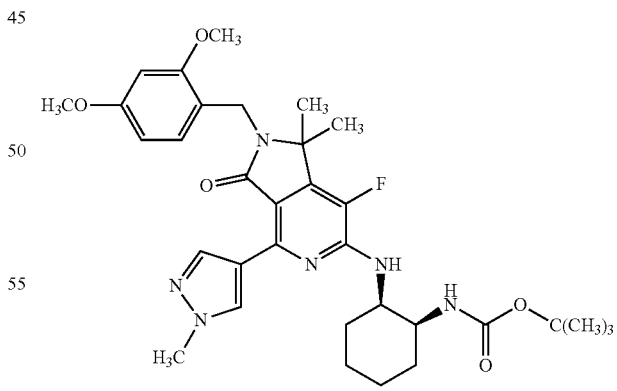

In a sealed tube, a mixture of tert-butyl (1S,2R)-2-(4-chloro-2-(2,4-dimethoxybenzyl)-7-fluoro-1,1-dimethyl-3-oxo-2,3-dihydro-1H-pyrrolo[3,4-c]pyridin-6-ylamino)cyclohexylcarbamate (30 mg, 0.052 mmol), $Na_2CO_3$ aq (2M, 0.065 mL, 0.130 mmol), 1-methyl-4-(4,4,5,5-tetramethyl-1,3,2-dioxaborolan-2-yl)-1H-pyrazole (12.98 mg, 0.062 mmol), bis(triphenylphosphine)palladium chloride (3.65 mg, 5.20 µmol), and DMF (1 mL) was heated at 160° C. for 0.5 h in a microwave oven. The reaction mixture was then heated at 160° C. for an additional 4 h in a microwave oven and was subsequently purified by preparative HPLC to give the title compound as a light yellow solid (5 mg, 18%). [M+H] calc'd for $C_{28}H_{35}FN_6O_3$, 524; found 524.

D. 6-((1R,2S)-2-Aminocyclohexylamino)-7-fluoro-1,1-dimethyl-4-(1-methyl-1H-pyrazol-4-yl)-1H-pyrrolo[3,4-c]pyridin-3(2H)-one A solution of tert-butyl (1S,2R)-2-(2-(2,4-dimethoxybenzyl)-7-fluoro-1,1-dimethyl-4-(1-methyl-1H-pyrazol-4-yl)-3-oxo-2,3-dihydro-1H-pyrrolo[3,4-c]pyridin-6-ylamino)cyclo-hexylcarbamate (5 mg, 9.57 µmol) in TFA (1 mL) was heated at 60° C. for 0.5 h. The reaction mixture was subsequently purified by preparative HPLC and the product lyophilized to give the title compound as a TFA salt (2 mg, 56%). [M+H] calc'd for $C_{19}H_{25}FN_6$, 374; found, 374.

Example 121

((1R,2S)-2-Aminocyclohexylamino)-7-fluoro-4-(1-methyl-1H-pyrazol-3-yl)-1H-pyrrolo[3,4-c]pyridin-3(2H)-one

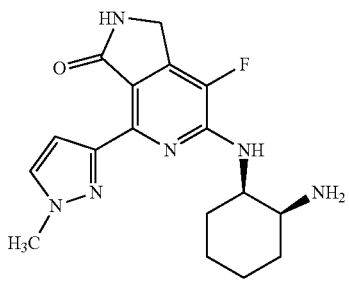 [SMILES: Cn1ccc(-c2nc(N[C@@H]3CCCC[C@@H]3N)c(F)c3c2C(=O)NC3)n1]

In a 30 mL sealed cap glass vial, tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (350 mg, 0.637 mmol), 1-methyl-3-(4,4,5,5-tetramethyl-1,3,2-dioxaborolan-2-yl)-1H-pyrazole (172 mg, 0.829 mmol) and $PdCl_2(PPh_3)_2$ (44.7 mg, 0.064 mmol) were dissolved in dioxane (5 mL). An aqueous solution of $Na_2CO_3$ (2M, 0.5 mL) was added and the cap was sealed. The reaction mixture was heated at 85° C. for 4 h, then diluted with water (5 mL), and extracted with EtOAc (2×30 mL). The organic phase was dried over $Na_2SO_4$ and the solvent evaporated. The resulting residue was treated with TFA (4 mL) and heated at 80° C. for 1.5 h to remove the protecting groups. Next, TFA was evaporated and the product was dissolved in DMSO (8 mL) and purified by preparative HPLC. The pure fractions were combined, concentrated, and lyophilized to give a TFA salt of the title compound as a white solid (52.3 mg, 24%). $^1$H NMR (400 MHz, DMSO-$d_6$) δ ppm 1.40-1.95 (m, 8 H), 3.64 (br s, 1 H), 3.92 (s, 2 H), 4.28-4.49 (m, 3 H), 6.76 (d, J=5.31 Hz, 1 H), 7.42 (d, J=2.27 Hz, 1 H), 7.72 (d, J=2.27 Hz, 1 H), 7.98 (br s, 3 H), 8.39 (s, 1 H). [M+H] calc'd for $C_{17}H_{21}FN_6O$, 345; found, 345.

Example 122

6-((1R,2S)-2-Aminocyclohexylamino)-7-fluoro-4-(2-methylthiazol-5-yl)-1H-pyrrolo[3,4-c]pyridin-3(2H)-one

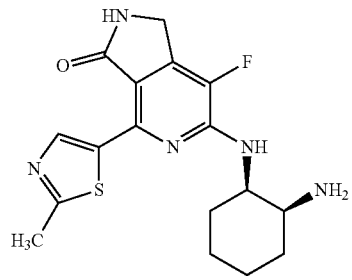 [SMILES: Cc1ncc(-c2nc(N[C@@H]3CCCC[C@@H]3N)c(F)c3c2C(=O)NC3)s1]

A. 6-((1R,2S)-2-Aminocyclohexylamino)-4-bromo-7-fluoro-1H-pyrrolo[3,4-c]pyridin-3(2H)-one

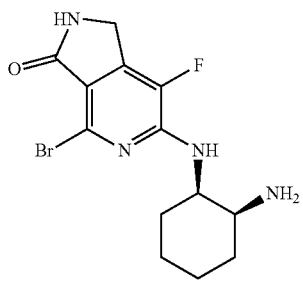 [SMILES: N[C@H]1CCCC[C@H]1Nc1nc(Br)c2c(c1F)CNC2=O]

A mixture of tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (200 mg, 0.364 mmol) and hydrobromic acid in HOAc (10 mL) was stirred at 90° C. for 6 h. The mixture was concentrated under reduced pressure, and the resulting crude material was reconstituted in MeOH (1.0 mL) and was purified via preparative HPLC eluting with water (0.05% TFA) and ACN (15-30% gradient, 0.035% TFA). The collected fractions were combined and ACN was removed via rotary evaporation. The resulting aqueous solution was neutralized with saturated aqueous $NaHCO_3$, washed with EtOAc (2×200 mL), dried over $Na_2SO_4$, and filtered. The organic phase was stripped to dryness via rotary evaporation to yield the title compound (38 mg, 30%). [M+H] calc'd for $C_{13}H_{16}BrFN_4O$, 343; found, 343.

B. 6-((1R,2S)-2-Aminocyclohexylamino)-7-fluoro-4-(2-methylthiazol-5-yl)-1H-pyrrolo[3,4-c]pyridin-3(2H)-one A solution of 6-((1R,2S)-2-aminocyclohexylamino)-4-bromo-7-fluoro-1H-pyrrolo[3,4-c]pyridin-3(2H)-one (38 mg, 0.111 mmol), 2-methylthiazole-5-carboxylic acid (15.85 mg, 0.111 mmol), silver(I) acetate (18.48 mg, 0.111 mmol), and copper(II) chloride (14.89 mg, 0.111 mmol) in toluene (1.8 mL) and DMA (0.2 mL) was heated to 135° C. overnight. The reaction mixture was filtered through a pad of Celite and the solvent was removed in vacuo. The resulting crude material was reconstituted in MeOH/DMF (10.0 mL) and purified via preparative HPLC eluting with water (0.05% TFA) and ACN (50-90% gradient, 0.035% TFA). The collected fractions were combined and the solvent was stripped to dryness via rotary evaporation to yield the title compound as a TFA salt (2.3 mg, 6%). $^1$H NMR (500 MHz, CDCl$_3$) δ ppm 1.37-1.85 (m, 8 H) 2.93 (s, 2 H) 2.97-3.08 (m, 3 H) 4.22-4.42 (m, 2 H) 6.52 (s, 1 H) 7.53 (d, J=4.39 Hz, 1 H) 7.72 (br s, 1 H) 8.08 (br s, 1 H) 8.27 (s, 1 H) [M+H] calc'd for C$_{17}$H$_{20}$FN$_5$OS, 362; found, 362.

Example 123

6-((3R,4R)-3-Aminotetrahydro-2H-pyran-4-ylamino)-7-fluoro-4-(5-methylthiophen-2-yl)-1H-pyrrolo[3,4-c]pyridin-3(2H)-one

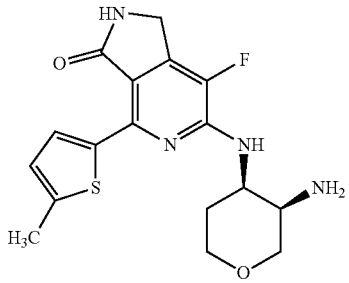 [SMILES: Cc1ccc(-c2nc(N[C@@H]3CCOC[C@@H]3N)c(F)c3c2C(=O)NC3)s1]

A. tert-Butyl (3R,4R)-4-(4-chloro-2-(2,4-dimethoxybenzyl)-7-fluoro-3-oxo-2,3-dihydro-1H-pyrrolo[3,4-c]pyridin-6-ylamino)tetrahydro-2H-pyran-3-ylcarbamate

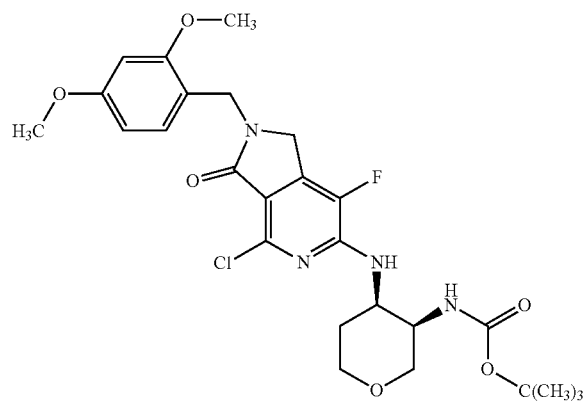 [SMILES: COc1ccc(CN2Cc3c(F)c(N[C@@H]4CCOC[C@@H]4NC(=O)OC(C)(C)C)nc(Cl)c3C2=O)c(OC)c1]

A mixture of 4,6-dichloro-2-(2,4-dimethoxybenzyl)-7-fluoro-1H-pyrrolo[3,4-c]pyridin-3(2H)-one (320 mg, 0.862 mmol), tert-butyl (3R,4R)-4-aminotetrahydro-2H-pyran-3-ylcarbamate (280 mg, 1.293 mmol) and DIPEA (0.226 mL, 1.293 mmol) in ACN (5 mL) was stirred at 85° C. overnight. UPLC indicated the presence of starting material, so the mixture was stirred at 85° C. overnight. UPLC showed about 50% conversion. Additional stirring at 85° C. for 3 d and at 100° C. overnight did not appreciably increase the conversion, so the reaction was stopped and the solvent was removed. The resulting crude material was reconstituted in MeOH/DMF (10 mL) and purified via preparative HPLC eluting with water (0.05% TFA) and ACN (50%, 0.035% TFA). The collected fractions were combined and the ACN was removed via rotary evaporation. The resulting aqueous solution was neutralized with saturated aqueous NaHCO$_3$, washed with EtOAc (2×200 mL), dried over Na$_2$SO$_4$, and filtered. The organic phase was stripped to dryness via rotary evaporation to give the title compound (51 mg, 11%). [M+H] calc'd for C$_{26}$H$_{32}$ClFN$_4$O$_6$, 552; found, 552.

B. tert-Butyl (3R,4R)-4-(2-(2,4-dimethoxybenzyl)-7-fluoro-4-(5-methylthiophen-2-yl)-3-oxo-2,3-dihydro-1H-pyrrolo[3,4-c]pyridin-6-ylamino)tetrahydro-2H-pyran-3-ylcarbamate

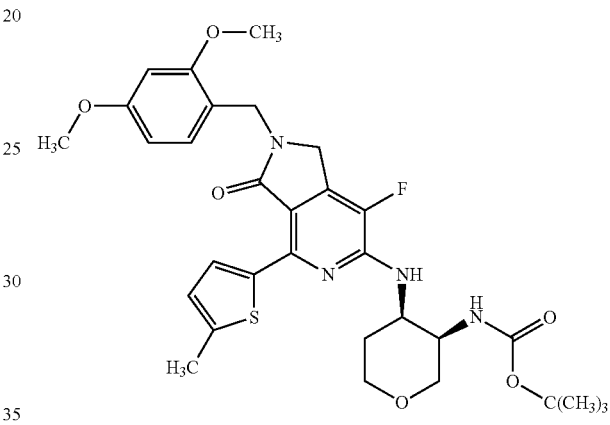

A solution of tert-butyl (3R,4R)-4-(4-chloro-2-(2,4-dimethoxybenzyl)-7-fluoro-3-oxo-2,3-dihydro-1H-pyrrolo[3,4-c]pyridin-6-ylamino)tetrahydro-2H-pyran-3-ylcarbamate (51 mg, 0.093 mmol), 4,4,5,5-tetramethyl-2-(5-methylthiophen-2-yl)-1,3,2-dioxaborolane (104 mg, 0.463 mmol), and bis(triphenylphosphine)palladium chloride (65.0 mg, 0.093 mmol) in dioxane (1 mL) and saturated Na$_2$CO$_3$ aq (1 mL) was heated to 140° C. for 40 min. After filtering out the solids, the solvent was removed from the filtrate. The resulting residue was dissolved in MeOH and DCM (10 mL) and was purified via preparative HPLC eluting with water (0.05% TFA) and ACN (80%, 0.035% TFA). The collected fractions were combined and solvent was stripped to dryness via rotary evaporation to give the title compound (31 mg, 55%). [M+H] calc'd for C$_{31}$H$_{37}$FN$_4$O$_6$S, 613; found, 613.

C. 6-((3R,4R)-3-Aminotetrahydro-2H-pyran-4-ylamino)-7-fluoro-4-(5-methylthiophen-2-yl)-1H-pyrrolo[3,4-c]pyridin-3(2H)-one A solution of tert-butyl (3R,4R)-4-(2-(2,4-dimethoxybenzyl)-7-fluoro-4-(5-methylthiophen-2-yl)-3-oxo-2,3-dihydro-1H-pyrrolo[3,4-c]pyridin-6-ylamino)tetrahydro-2H-pyran-3-ylcarbamate (31 mg, 0.051 mmol) in TFA (10 mL) was heated to 80° C. for 1 h. After the solvent was removed, the residue was dissolved in MeOH and DCM (8 mL) and was purified via preparative HPLC eluting with water (0.05% TFA) and ACN (15-30% gradient, 0.035% TFA). The collected fractions were combined and the solvent was stripped to dryness via rotary evaporation to give the title compound as a TFA salt (13.5 mg, 74%). $^1$H NMR (500 MHz, DMSO-d$_6$)

δ ppm 1.78 (d, J=13.18 Hz, 1 H), 2.03-2.18 (m, 1 H), 2.46 (s, 3 H), 3.17 (d, J=4.88 Hz, 1 H), 3.55-3.65 (m, 1 H), 3.75 (d, J=13.18 Hz, 1 H), 3.85 (br s, 1 H), 3.96-4.06 (m, 2 H), 4.41 (d, J=7.81 Hz, 2 H), 6.84 (d, J=2.44 Hz, 1 H), 7.22 (d, J=4.88 Hz, 1 H), 7.92 (br s, 2 H), 8.47 (s, 1 H), 8.83 (d, J=3.42 Hz, 1 H). [M+H] calc'd for $C_{17}H_{19}FN_4O_2S$, 363; found, 363.

Example 124

6-((1R,2S)-2-Aminocyclohexylamino)-7-fluoro-1-methyl-4-(1-methyl-1H-pyrazol-4-yl)-1H-pyrrolo[3,4-c]pyridin-3(2H)-one

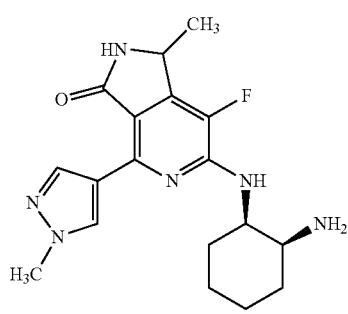 [SMILES: CC1NC(=O)c2c(-c3cnn(C)c3)nc(N[C@@H]3CCCC[C@@H]3N)c(F)c21]

A. 2,6-Dichloro-4-((3,5-dimethoxybenzylimino) methyl)-5-fluoronicotinic acid

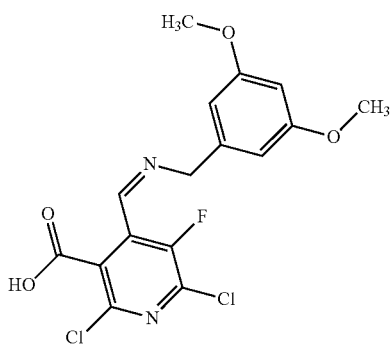 [SMILES: COc1cc(C/N=C\c2c(F)c(Cl)nc(Cl)c2C(=O)O)cc(OC)c1]

A. To a solution of (2,4-dimethoxyphenyl)methanamine (4.4 g, 26.6 mmol) in MeOH (50 mL) was added 4,6-dichloro-7-fluoro-1-hydroxyfuro[3,4-c]pyridin-3(1H)-one (6.0 g, 25.3 mmol). The mixture was stirred for 0.5 h, filtered, and washed with petroleum ether to give the title compound as a white solid (5.8 g, 60%). $^1$H-NMR (CDCl$_3$, 400 MHz) δ 3.75 (s, 3H), 3.79 (s, 3 H), 3.93 (s, 2 H), 6.30 (s, 1 H), 6.40-6.42 (m, 2 H), 7.12 (d, J=8.4 Hz, 1 H).

B. 4,6-Dichloro-2-(3,5-dimethoxybenzyl)-7-fluoro-1-methyl-1H-pyrrolo[3,4-c]pyridin-3(2H)-one

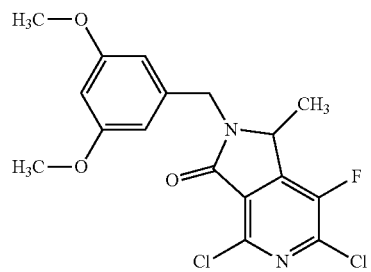 [SMILES: COc1cc(CN2C(=O)c3c(Cl)nc(Cl)c(F)c3C2C)cc(OC)c1]

To a mixture of 2,6-dichloro-4-((3,5-dimethoxybenzylimino)methyl)-5-fluoronicotinic acid (5.8 g, 25.3 mmol) in THF (120 mL) was added methyl-lithium (60.0 mL, 126.6 mmol) drop wise at −78° C. After the addition was completed, the mixture was stirred for an additional 2 h. The reaction mixture was acidified with 1N HCl to pH 7 and THF was removed under reduced pressure. The mixture was extracted with EtOAc, washed with brine, dried over anhydrous Na$_2$SO$_4$, and purified by silica gel chromatography eluting with PE-EtOAc (5:1) to give the title compound as a white solid (0.93 g, 16%). $^1$H-NMR (CDCl$_3$, 400 MHz) δ 1.58 (d, J=6.8 Hz, 3 H), 3.79 (s, 3 H), 3.84 (s, 3 H), 4.35 (d, J=14.4 Hz, 1 H), 4.52 (q, J=6.8 Hz, 1 H), 5.07 (d, J=14.4 Hz, 1 H), 6.43-6.45 (m, 2 H), 7.28 (d, J=9.2 Hz, 1 H). [M+H] calc'd for $C_{17}H_{15}Cl_2FN_2O_3$, 386; found, 385.

C. 6-((1R,2S)-2-Aminocyclohexylamino)-7-fluoro-1-methyl-4-(1-methyl-1H-pyrazol-4-yl)-1H-pyrrolo[3,4-c]pyridin-3(2H)-one A mixture of 6-((1R,2S)-2-aminocyclohexylamino)-2-(2,4-dimethoxybenzyl)-7-fluoro-1-methyl-4-(1-methyl-1H-pyrazol-4-yl)-1H-pyrrolo[3,4-c]pyridin-3(2H)-one (20 mg, 0.039 mmol) and TFA (1 mL) was heated at 60° C. for 2 h. Following reaction, the mixture was purified by preparative HPLC eluting with water (0.05% TFA) and ACN (15-25% gradient, 0.035% TFA) to give the title compound as a TFA salt (10 mg, 71%). $^1$H NMR (500 MHz, DMSO-d$_6$) δ ppm 1.41 (d, J=6.59 Hz, 3 H), 1.46 (d, J=7.02 Hz, 2 H), 1.60-1.84 (m, 5 H), 3.68 (br s, 1 H), 3.89 (s, 2 H), 4.44 (br s, 1 H), 4.71 (q, J=6.65 Hz, 1 H), 6.52 (br s, 1 H), 6.73 (d, J=6.53 Hz, 1 H), 7.72 (br s, 2 H), 8.24-8.32 (m, 1 H), 8.46 (s, 1 H), 8.82 (s, 1 H). [M+H] calc'd for $C_{18}H_{23}FN_6O$, 359; found, 359.

Example 125

6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one

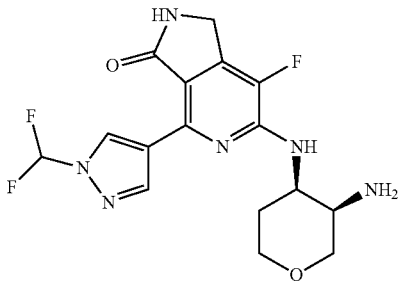 [SMILES: N[C@H]1COCC[C@H]1Nc1nc(-c2cnn(C(F)F)c2)c2c(c1F)CNC2=O]

A. tert-Butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate

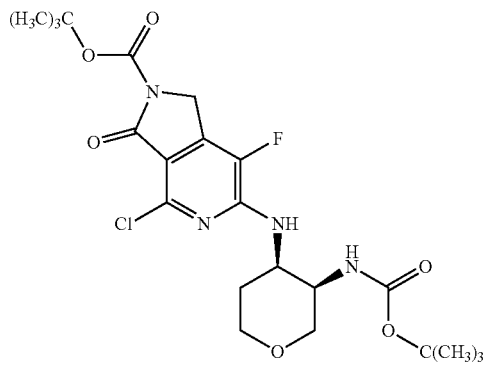 [SMILES: CC(C)(C)OC(=O)N[C@H]1COCC[C@H]1Nc1nc(Cl)c2c(c1F)CN(C(=O)OC(C)(C)C)C2=O]

A mixture of tert-butyl 4,6-dichloro-7-fluoro-3-oxo-1H-pyrrolo[3,4-c]pyridine-2(3H)-carboxylate (1.42 g, 4.43 mmol), tert-butyl (3R,4R)-4-aminotetrahydro-2H-pyran-3-ylcarbamate (1.15 g, 5.52 mmol), diisopropylethylamine (3.87 mL, 22.16 mmol) in DMSO (10 mL) and 2-propanol (40 mL) were heated to 100° C. in an oil bath for 20 h. The solution was then concentrated and the resulting oil was dissolved in water (50 mL) and heated in an oil bath to 50° C. for 1 h then allowed to cool to RT. The solution was subsequently heated to 50° C. for 15 min, allowed to cool to RT, again heated to 50° C. for 15 min, and allowed to cool to RT. The resulting precipitate was filtered and rinsed with water to give the title compound as a pale pinkish-white solid (1.90 g, 86%, 4:1 mixture with regioisomer) which was used in the next step without further purification. $^1$H NMR (400 MHz, DMSO-d$_6$) δ ppm 1.36 (s, 9 H), 1.50 (s, 3 H), 1.59-1.61 (m, 1 H), 1.97-1.99 (m, 1 H), 1.97-1.99 (m, 1 H), 3.46-3.49 (m, 2 H), 3.80-3.83 (m, 3 H), 4.31-4.33 (m, 1 H), 4.73 (s, 1 H), 6.59 (d, J=7.30 Hz, 1 H), 7.43 (d, J=7.30 Hz, 1 H). [M+H] calc'd for $C_{22}H_{30}ClFN_4O_6$, 501; found, 501.

B. tert-Butyl 6-((3R,4R)-3-(tert-butoxycarbonylamino)tetrahydro-2H-pyran-4-ylamino)-4-(1-(difluoromethyl)-1H-pyrazol-4-yl)-7-fluoro-3-oxo-1H-pyrrolo[3,4-c]pyridine-2(3H)-carboxylate

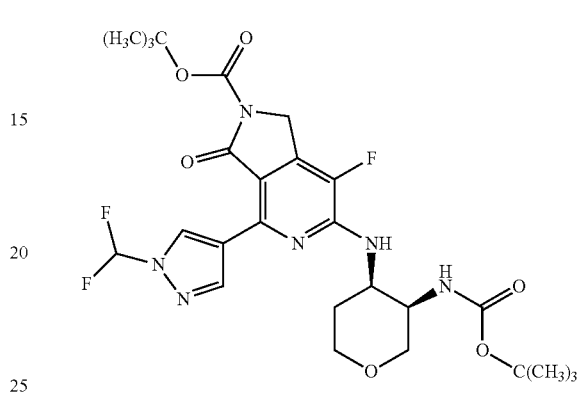

A mixture of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (500 mg, 0.998 mmol), 1-(difluoromethyl)-1H-pyrazol-4-ylboronic acid (808 mg, 4.99 mmol), bis(triphenylphosphine)palladium chloride (70.1 mg, 0.100 mmol) in dioxane (15 mL) and 2M saturated sodium carbonate (2 mL) were heated to 100° C. in a microwave for 30 min. The solution was concentrated and was purified by preparatory HPLC eluting with water (10 mM NH$_4$HCO$_3$) and ACN/water (80/20 v/v, 15-30% gradient, 10 mM NH$_4$HCO$_3$) to give the title compound as a white solid (132 mg, 23%). $^1$H NMR (400 MHz, DMSO-d$_6$) δ ppm 1.35 (s, 9 H), 1.52 (s, 9 H), 1.55-1.56 (m, 1 H), 2.46-2.47 (m, 1 H), 3.57-3.59 (m, 2 H), 3.81-3.84 (m, 3 H), 4.61-4.62 (m, 1 H), 4.78 (s, 2 H), 6.61 (d, J=6.35 Hz, 1 H), 7.15 (d, J=6.83 Hz, 1 H), 7.97 (s, 1 H), 8.54 (s, 1 H), 9.24 (s, 1 H). [M+H] calc'd for $C_{26}H_{33}F_3N_6O_6$, 583; found, 583.

C. 6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one tert-Butyl 6-((3R,4R)-3-(tert-butoxycarbonylamino)tetrahydro-2H-pyran-4-ylamino)-4-(1-(difluoromethyl)-1H-pyrazol-4-yl)-7-fluoro-3-oxo-1H-pyrrolo[3,4-c]pyridine-2(3H)-carboxylate (126 mg, 0.998 mmol) was dissolved in 2-propanol (5 mL) and the solution was heated to 75° C. with a heating block. Then 2M HCl (2.5 mL) was added, the temperature was lowered to 65° C., and the reaction mixture was stirred for 3 h. The solution was concentrated and purified by preparatory HPLC eluting with water (10 mM NH$_4$HCO$_3$) and ACN/water (80/20 v/v, 10-50% gradient, 10 mM NH$_4$HCO$_3$) to give the title compound as a white solid (79 mg, 96%). $^1$H NMR (400 MHz, DMSO-d$_6$) δ ppm 1.75-1.77 (m, 1 H), 2.09-2.12 (m, 1 H), 3.60-3.63 (m, 1 H), 3.76-3.77 (m, 1 H), 3.88-3.98 (m, 3 H), 4.44 (d, J=6.35 Hz, 2 H), 4.54-4.55 (m, 1 H), 7.17 (d, J=5.86 Hz, 1 H), 7.89 (br s, 1 H),

Example 126

(R)-2-(7-Fluoro-3-oxo-4-(thiophen-2-yl)-2,3-dihydro-1H-pyrrolo[3,4-c]pyridin-6-ylamino)-4-methylpentanamide

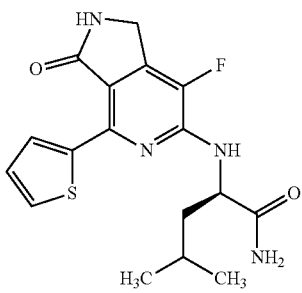 [SMILES: CC(C)C[C@@H](Nc1nc(-c2cccs2)c2c(c1F)CNC2=O)C(N)=O]

The title compound was prepared in a manner similar to EXAMPLE 113 using tributyl(thiophen-2-yl)stannane in place of tributyl(furan-2-yl)stannane. $^1$H NMR (500 MHz, DMSO-$d_6$) δ ppm 0.80-0.99 (m, 6 H), 1.51-1.84 (m, 3 H), 4.40 (s, 2 H), 4.59-4.76 (m, 1 H), 6.99 (br s, 1 H), 7.06-7.17 (m, 2 H), 7.34 (br s, 1 H), 7.61 (d, J=4.88 Hz, 1 H), 8.40 (s, 1 H), 8.93-9.05 (m, 1 H). [M+H] calc'd for $C_{17}H_{19}FN_4O_2S$, 363; found, 363.

Preparation 51 tert-Butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate

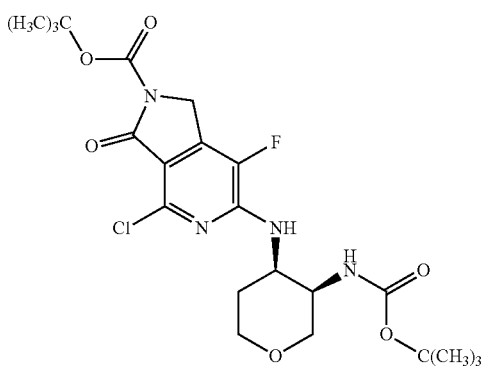 [SMILES: CC(C)(C)OC(=O)N[C@H]1COCC[C@H]1Nc1nc(Cl)c2c(c1F)CN(C(=O)OC(C)(C)C)C2=O]

A mixture of tert-butyl 4,6-dichloro-7-fluoro-3-oxo-1H-pyrrolo[3,4-c]pyridine-2(3H)-carboxylate (1.24 g, 3.85 mmol), tert-butyl (3R,4R)-4-aminotetrahydro-2H-pyran-3-ylcarbamate (1.00 g, 4.62 mmol), diisopropylethylamine (3.36 mL, 19.27 mmol) in DMSO (10 mL) and 2-propanol (40 mL) were heated to 100° C. in an oil bath for 20 h. The reaction was repeated on the same scale and both reaction solutions were combined and concentrated. The mixture was purified via silica gel flash chromatography eluting with EtOAc and hexanes (10-50% EtOAc gradient) to give the title compound as a pale pinkish-white solid (510 mg, 13%). $^1$H NMR (400 MHz, DMSO-$d_6$) δ ppm 1.36 (s, 9 H), 1.50 (s, 3 H), 1.59-1.61 (m, 1 H), 1.97-1.99 (m, 1 H), 1.97-1.99 (m, 1 H), 3.46-3.49 (m, 2 H), 3.80-3.83 (m, 3 H), 4.31-4.33 (m, 1 H), 4.73 (s, 1 H), 6.59 (d, J=7.30 Hz, 1 H), 7.43 (d, J=7.30 Hz, 1 H). [M+H] calc'd for $C_{22}H_{30}ClFN_4O_6$, 501; found, 501.

Example 127

6-((3R,4R)-3-Aminotetrahydro-2H-pyran-4-ylamino)-7-fluoro-4-(thiophen-2-yl)-1H-pyrrolo[3,4-c]pyridin-3(2H)-one

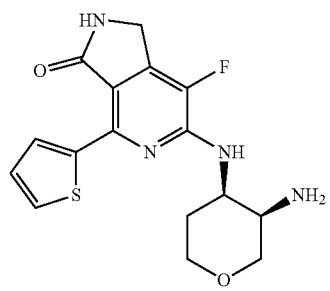 [SMILES: N[C@H]1COCC[C@H]1Nc1nc(-c2cccs2)c2c(c1F)CNC2=O]

A. tert-Butyl 6-((3R,4R)-3-(tert-butoxycarbonylamino)tetrahydro-2H-pyran-4-ylamino)-7-fluoro-3-oxo-4-(thiophen-2-yl)-1H-pyrrolo[3,4-c]pyridine-2(3H)-carboxylate

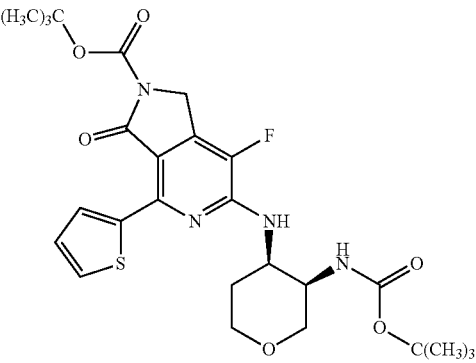 [SMILES: CC(C)(C)OC(=O)N[C@H]1COCC[C@H]1Nc1nc(-c2cccs2)c2c(c1F)CN(C(=O)OC(C)(C)C)C2=O]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (50 mg, 0.1 mmol), tributyl(thiophen-2-yl)stannane (44.7 mg, 0.12 mmol) and tetrakis(triphenylphosphine)palladium(0) (115 mg, 0.1 mmol) in toluene (3 mL) was heated to 102° C. for 24 h. The solid was filtered though a pad of Celite, and resulting crude material was reconstituted in MeOH/DCM (20 mL) and purified via preparative HPLC. The collected fractions were combined and stripped to dryness via rotary evaporation to yield the title compound (30 mg, 55%).

B. 6-((3R,4R)-3-Aminotetrahydro-2H-pyran-4-ylamino)-7-fluoro-4-(thiophen-2-yl)-1H-pyrrolo[3,4-c]pyridin-3(2H)-one A solution of tert-butyl 6-((3R,4R)-3-(tert-butoxycarbonylamino)tetrahydro-2H-pyran-4-ylamino)-7-fluoro-3-oxo-4-(thiophen-2-yl)-1H-pyrrolo[3,4-c]pyridine-2(3H)-carboxylate (30 mg, 0.055 mmol) in TFA/DCM (1:1, 10 mL) was stirred at RT for 2 h. The solvent was removed and the resulting crude material was reconstituted in MeOH/DCM (20 mL) and purified via preparative HPLC. The collected fractions were combined and stripped to dryness via rotary evaporation to yield the title compound (16 mg, 85%). $^1$H NMR (500 MHz, DMSO-$d_6$) δ ppm 1.79 (d, J=9.76 Hz, 1 H), 2.12 (qd, J=12.94, 5.13 Hz, 1 H), 3.56-3.68 (m, 1 H), 3.75 (d, J=11.72 Hz, 1 H), 3.89 (br s, 1 H), 4.02 (d, J=11.72 Hz, 2 H), 4.28-4.37 (m, 1 H), 4.38-4.49 (m, 2 H), 7.10-7.20 (m, 1 H), 7.28 (d, J=4.88 Hz, 1 H), 7.59-7.70 (m, 1 H), 7.93 (br s, 2 H), 8.52 (s, 1 H), 9.02 (dd, J=3.91, 0.98 Hz, 1 H). [M+H] calc'd for $C_{16}H_{17}FN_4O_2S$, 349; found, 349.

Example 128

6-((3R,4R)-3-Aminotetrahydro-2H-pyran-4-ylamino)-7-fluoro-4-(thiazol-5-yl)-1H-pyrrolo[3,4-c]pyridin-3(2H)-one

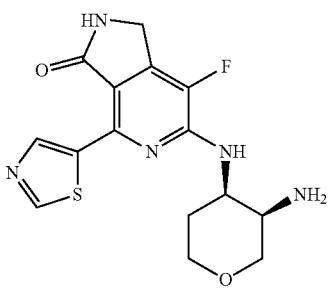 [SMILES: N[C@H]1COCC[C@H]1Nc1nc(-c2cncs2)c2c(c1F)CNC2=O]

A TFA salt of the title compound was prepared in a manner similar to EXAMPLE 127 using 5-(tributylstannyl)thiazole in place of tributyl(thiophen-2-yl)stannane. $^1$H NMR (500 MHz, DMSO-$d_6$) δ ppm 1.78 (dd, J=13.67, 4.39 Hz, 1 H), 2.04-2.20 (m, 1 H), 3.53-3.66 (m, 1 H), 3.69-3.85 (m, 2 H), 4.01 (d, J=11.72 Hz, 2 H), 4.25-4.38 (m, 1 H), 4.41-4.55 (m, 2 H), 7.38 (s, 1 H), 7.94 (br s, 2 H), 8.62 (s, 1 H), 9.15 (s, 1 H), 9.52 (s, 1 H). [M+H] calc'd for $C_{15}H_{16}FN_5O_2S$, 350; found, 350.

Example 129

6-((1R,2S)-2-Aminocyclohexylamino)-7-fluoro-4-(thiophen-2-yl)-1H-pyrrolo[3,4-c]pyridin-3(2H)-one

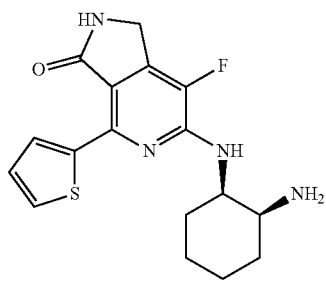 [SMILES: N[C@H]1CCCC[C@H]1Nc1nc(-c2cccs2)c2c(c1F)CNC2=O]

In a 30 mL sealed cap glass vial, tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (300 mg, 0.546 mmol), 4,4,5,5-tetramethyl-2-(thiophen-2-yl)-1,3,2-dioxaborolane (172 mg, 0.820 mmol), and trans-dichloro-bis(triphenylphosphine)palladium-II (38.4 mg, 0.055 mmol) were dissolved in dioxane (5 mL). An aqueous solution of 2N $Na_2CO_3$ (0.5 mL) was added, the cap was sealed, and the mixture was allowed to react at 85° C. for 3 h. The reaction mixture was subsequently diluted with water (5 mL) and extracted into EtOAc (2×30 mL). The organic layer was dried over sodium sulfate and evaporated. The resulting residue was treated with TFA (4 mL) and heated at 80° C. for 1 h to remove the protecting groups. Next, TFA was evaporated from the reaction mixture. The product was reconstituted in DMSO (8 mL) and was then purified via preparative HPLC eluting with water (0.05% TFA) and ACN (15-45% gradient, 0.035% TFA). The pure fractions were combined and evaporated to a minimal volume. Saturated aq $NaHCO_3$ (10 mL) was added and the mixture was extracted with EtOAc (3×25 mL). The organic layers were combined, dried over sodium sulfate, and evaporated to give the title compound as a pale yellow solid (83 mg, 44%). $^1$H NMR (400 MHz, DMSO-$d_6$) δ ppm 1.16-1.80 (m, 8 H), 3.18 (br s, 1 H), 3.86-4.11 (m, 1 H), 4.39 (s, 2 H), 6.60 (d, J=6.57 Hz, 1 H), 7.13 (dd, J=5.05, 3.79 Hz, 1 H), 7.60 (dd, J=5.18, 1.14 Hz, 1 H), 8.39 (s, 1 H), 9.00 (dd, J=3.79, 1.01 Hz, 1 H). [M+H] calc'd for $C_{17}H_{19}FN_4OS$, 347; found, 347.

Example 130

6-((3R,4R)-3-Aminotetrahydro-2H-pyran-4-ylamino)-7-fluoro-4-(4-(trifluoromethyl)-1H-imidazol-1-yl)-1H-pyrrolo[3,4-c]pyridin-3(2H)-one

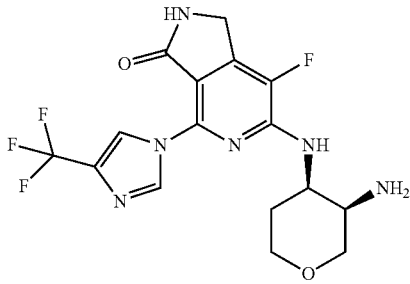 [SMILES: N[C@H]1COCC[C@H]1Nc1nc(-n2cnc(C(F)(F)F)c2)c2c(c1F)CNC2=O]

In a 10 mL sealed cap glass vial, tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (60 mg, 0.120 mmol), 4-(trifluoromethyl)-1H-imidazole (48.9 mg, 0.359 mmol) and $K_2CO_3$ (66.2 mg, 0.479 mmol) were dissolved in ACN (2 mL). The cap was sealed and the mixture was reacted at 100° C. for 16 h. The reaction mixture was subsequently filtered through a Buchner funnel to remove un-dissolved $K_2CO_3$. The solids were washed with ACN (2×5 mL) and the filtrate was evaporated to give a residue, which was treated with TFA (2 mL) at RT for 20 min to remove the protecting groups. Next, TFA was evaporated from the reaction mixture. The product was reconstituted in DMSO (5 mL) and was then purified by preparative HPLC eluting with water (0.05% TFA) and ACN (15-45% gradient, 0.035% TFA). The pure fractions were combined, evaporated to a minimal volume, and lyophilized to give a TFA salt of the title compound as a brown solid (4.2 mg, 8.8%). $^1$H NMR (400 MHz, DMSO-$d_6$) δ ppm 1.67 (m, 1 H), 2.05 (td, J=12.88, 7.33 Hz, 1 H), 3.30-3.90 (m, 4 H), 3.78-3.99 (m, 2 H), 4.44 (s, 2 H), 6.49 (br s, 2 H), 7.54 (d, J=5.56 Hz, 1 H), 7.85 (br s, 2 H), 8.67-8.80 (m, 2 H). [M+H] calc'd for $C_{16}H_{16}F_4N_6O_2$, 401; found, 401.

Example 131

6-((1R,2S)-2-Aminocyclohexylamino)-7-fluoro-4-(4-methyl-1H-imidazol-1-yl)-1H-pyrrolo[3,4-c]pyridin-3(2H)-one

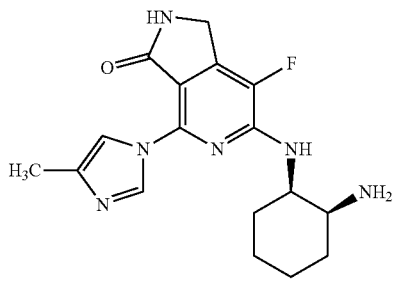 [SMILES: Cc1cn(-c2nc(N[C@@H]3CCCC[C@@H]3N)c(F)c3c2C(=O)NC3)cn1]

In a 10 mL sealed cap glass vial, tert-butyl (1S,2R)-2-(4-chloro-2-(2,4-dimethoxybenzyl)-7-fluoro-3-oxo-2,3-dihydro-1H-pyrrolo[3,4-c]pyridin-6-ylamino)cyclohexylcarbamate (50 mg, 0.091 mmol), 4-methyl-1H-imidazole (22.43 mg, 0.273 mmol) and $K_2CO_3$ (50.3 mg, 0.364 mmol) were dissolved in ACN (2 mL). The cap was sealed and the mixture was reacted at 100° C. for 16 h. The reaction mixture was subsequently filtered through a Buchner funnel to remove un-dissolved solids. The solids were washed with ACN (2×5 mL) and the filtrate was evaporated to give a residue, which was treated with TFA (4 mL) and heated at 80° C. for 1 h to remove the protecting groups. Next, TFA was evaporated from the reaction mixture. The resulting residue was reconstituted in DMSO (5 mL) and purified via preparative HPLC eluting with water (0.05% TFA) and ACN (15-65% gradient, 0.035% TFA). The pure fractions were combined, evaporated to a minimal volume, and lyophilized to give a TFA salt of the title compound as a white solid (7.2 mg, 23%). $^1$H NMR (400 MHz, DMSO-$d_6$) δ ppm 1.20-1.65 (m., 8 H), 3.65-3.79 (m, 5 H), 4.15 (s, 2 H), 6.40 (d, 1 H), 6.51 (d, 1 H), 6.73 (m, 1 H), 6.97 (d, 1 H), 7.26 (d, 1 H), 8.68 (br s, 1 H). [M+H] calc'd for $C_{17}H_{21}FN_6O$, 345; found, 345.

Preparation 52

3-Methyl-5-(tributylstannyl)isothiazole

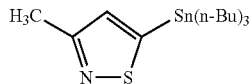

To a cold (−78° C.) solution of 3-methylisothiazole (100 mg, 1.0 mmol) in anhydrous THF (2.0 mL) was added n-butyllithium (0.693 mL, 1.1 mmol) dropwise. After stirring for 60 min at −78° C., a solution of tributylchlorostannane (0.326 mL, 1.210 mmol) in anhydrous THF (0.5 mL) was added to the reaction mixture. The reaction mixture was stirred for 30 min at −78° C. and then allowed to warm to RT over a 2 to 3 h period. Saturated aq $NaHCO_3$ was added and the aqueous phase was extracted with EtOAc (3×50 mL). The combined organic phase was dried over anhydrous $Na_2SO_4$, filtered, and evaporated in vacuo. The residue was purified by silica gel column chromatography (9:1 Hexane/EtOAc, Flash 60 column) to give the title compound. $^1$H NMR (500 MHz, $CDCl_3$) δ ppm 0.86-0.94 (m, 9 H), 1.05-1.21 (m, 6 H), 1.26-1.38 (m, 6 H), 1.44-1.65 (m, 6 H), 2.56 (s, 3 H), 6.97-7.04 (m, 1 H).

Example 132

6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one

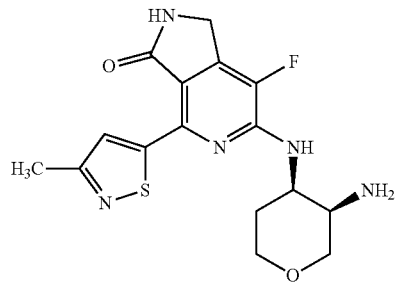 [SMILES: Cc1cc(-c2nc(N[C@@H]3CCOC[C@@H]3N)c(F)c3c2C(=O)NC3)sn1]

A. tert-Butyl 6-((3R,4R)-3-(tert-butoxycarbonylamino)tetrahydro-2H-pyran-4-ylamino)-7-fluoro-4-(3-methylisothiazol-5-yl)-3-oxo-1H-pyrrolo[3,4-c]pyridine-2(3H)-carboxylate

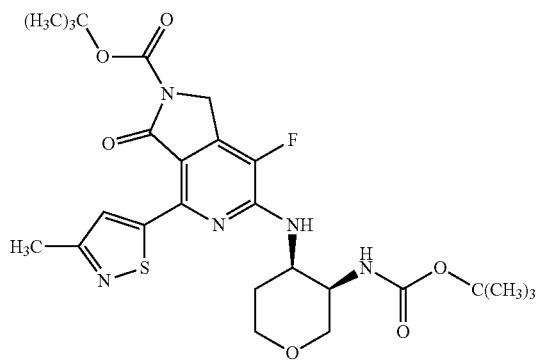 [SMILES: Cc1cc(-c2nc(N[C@@H]3CCOC[C@@H]3NC(=O)OC(C)(C)C)c(F)c3c2C(=O)N(C(=O)OC(C)(C)C)C3)sn1]

A solution of tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (10 mg, 0.02 mmol), 3-methyl-5-(tributylstannyl)isothiazole (23.25 mg, 0.06 mmol) and tetrakis(triphenylphosphine)palladium(0) (23.07 mg, 0.02 mmol) in toluene (3 mL) was heated to 120° C. for 45 min under microwave irradiation. The reaction mixture was poured into water and extracted with EtOAc. The organic extracts were dried over anhydrous $Na_2SO_4$, filtered, and evaporated in vacuo. After removal of solvent, the resulting crude material was reconstituted in DMF and purified via preparative HPLC eluting with water (0.05% TFA) and ACN (55-80% gradient, 0.035% TFA). The collected fractions were combined and ACN was removed via rotary evaporation. The resulting aq solution was neutralized with saturated aq $NaHCO_3$ and washed with EtOAc (2×50 mL), dried over anhydrous $Na_2SO_4$, filtered, and the organic phase stripped to dryness via rotary evaporation to give the title compound. [M+H] calc'd for $C_{26}H_{34}FN_5O_6S$, 564; found, 564.

B. 6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one To a solution of tert-butyl 6-((3R,4R)-3-(tert-butoxycarbonylamino)tetrahydro-2H-pyran-4-ylamino)-7-fluoro-4-(3-methylisothiazol-5-yl)-3-oxo-1H-pyrrolo[3,4-c]pyridine-2(3H)-carboxylate (5.5 mg, 9.76 µmol) in DCM (2.0 mL) was added TFA (2.0 mL, 26.0 mmol). The reaction mixture was stirred at RT for 1 h, and concentrated in vacuo. The resulting crude material was reconstituted in DMF and purified via preparative HPLC eluting with water (0.05% TFA) and ACN (55-80% gradient, 0.035% TFA). The collected fractions were combined and the ACN was removed via rotary evaporation. The resulting aq solution was neutralized with saturated aq NaHCO$_3$, washed with EtOAc (2×50 mL), dried over anhydrous Na$_2$SO$_4$, filtered, and the organic phase stripped to dryness via rotary evaporation. The residue was recrystallized from THF/hexane to give a TFA salt of the title compound. [M+H] calc'd for C$_{16}$H$_{18}$FN$_5$O$_2$S, 364; found, 364.

Preparation 53

1: 2-Methyl-5-(tributylstannyl)thiazole

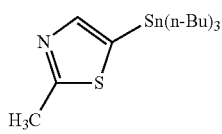

To a cold (−78° C.) solution of 2-methylthiazole (2.80 g, 28.2 mmol) in anhydrous THF (100 mL) was added butyllithium (19.41 mL, 31.1 mmol) dropwise. After stirring for 60 min at −78° C., a solution of tributylchlorostannane (9.14 mL, 33.9 mmol) in anhydrous THF was added to the reaction mixture. The reaction mixture was stirred for 30 min at −78° C. and then allowed to warm to RT over a 2 to 3 h period. Saturated aq NaHCO$_3$ was added and the aqueous phase was extracted with ether (3×200 mL). The combined organic phase was dried over anhydrous Na$_2$SO$_4$, filtered, and evaporated in vacuo. The crude product was purified on a silica gel column eluting with 10-50% EtOAc in Hexane over a 60 min period. The fractions were collected and solvent was removed in vacuo to give the title compound as a yellow oil (72%). $^1$H NMR (500 MHz, DMSO-d$_6$) δ ppm 0.71-0.92 (m, 9 H), 0.96-1.18 (m, 6 H), 1.23-1.38 (m, 6 H), 1.40-1.64 (m, 6 H), 2.69 (s, 3 H), 7.56 (d, J=12.69 Hz, 1 H).

Example 133

6-((3R,4R)-3-Aminotetrahydro-2H-pyran-4-ylamino)-7-fluoro-4-(2-methylthiazol-5-yl)-1H-pyrrolo[3,4-c]pyridin-3(2H)-one

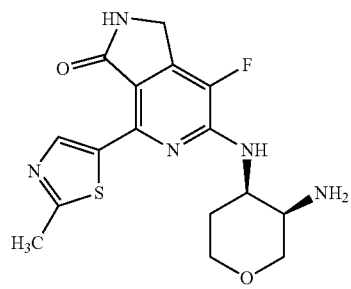 [SMILES: Cc1ncc(-c2nc(N[C@@H]3CCOC[C@@H]3N)c(F)c3c2C(=O)NC3)s1]

A TFA salt of the title compound was prepared in a manner similar to EXAMPLE 132 using 2-methyl-5-(tributylstannyl)thiazole in place of 3-methyl-5-(tributylstannyl)isothiazole. $^1$H NMR (500 MHz, DMSO-d$_6$) δ ppm 1.24 (s, 1 H), 1.73 (d, J=12.69 Hz, 1 H), 1.93-2.03 (m, 1 H), 2.57-2.71 (m, 4 H), 3.38-3.44 (m, 1 H), 3.48-3.55 (m, 1 H), 3.67 (d, J=11.72 Hz, 1 H), 3.82-3.97 (m, 2 H), 4.22 (br s, 1 H), 4.43 (s, 2 H), 7.06 (br s, 1 H), 8.52 (s, 1 H), 9.21-9.34 (m, 1 H). [M+H] calc'd for C$_{16}$H$_{18}$FN$_5$O$_2$S, 364; found, 364.

Example 134

(R)-2-(7-Fluoro-4-(2-methylthiazol-5-yl)-3-oxo-2,3-dihydro-1H-pyrrolo[3,4-c]pyridin-6-ylamino)-4-methylpentanamide

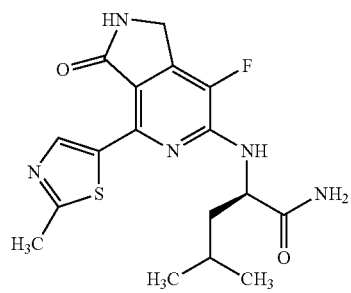 [SMILES: Cc1ncc(-c2nc(N[C@H](CC(C)C)C(N)=O)c(F)c3c2C(=O)NC3)s1]

The title compound was prepared in a manner similar to EXAMPLE 113 using 2-methyl-5-(tributylstannyl)thiazole in place of tributyl(furan-2-yl)stannane. $^1$H NMR (500 MHz, DMSO-d$_6$) δ ppm 0.74-0.98 (m, 6 H), 1.54-1.63 (m, 1 H), 1.64-1.83 (m, 2 H), 2.61-2.68 (m, 3 H), 4.41 (s, 2 H), 4.56 (ddd, J=10.50, 8.30, 4.15 Hz, 1 H), 6.97 (s, 1 H), 7.19 (d, J=7.81 Hz, 1 H), 7.35 (s, 1 H), 8.45 (s, 1 H), 9.22 (s, 1 H). [M+H] calc'd for $C_{17}H_{20}FN_5O_2S$, 378; found, 378.

Example 135

6-((3R,4R)-3-Aminotetrahydro-2H-pyran-4-ylamino)-4-(5-chlorothiophen-2-yl)-7-fluoro-1H-pyrrolo[3,4-c]pyridin-3(2H)-one

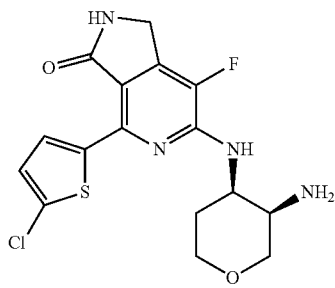 [SMILES: N[C@H]1COCC[C@H]1Nc1nc(-c2ccc(Cl)s2)c2c(c1F)CNC2=O]

To a solution of 6-((3R,4R)-3-aminotetrahydro-2H-pyran-4-ylamino)-7-fluoro-4-(thiophen-2-yl)-1H-pyrrolo[3,4-c]pyridin-3(2H)-one (12 mg, 0.034 mmol) in DCM (3 mL) was added pyridine (8.17 mg, 0.103 mmol) and 1-chloropyrrolidine-2,5-dione (4.60 mg, 0.034 mmol). The reaction mixture was stirred at RT for 3 h. The reaction mixture was subsequently diluted with MeOH (3 mL) and was purified via preparative HPLC eluting with water (0.05% TFA) and ACN (45-70% gradient, 0.035% TFA). The collected fractions were combined and the solvent was removed via rotary evaporation. The resulting product was purified a second time using a gradient eluent of 15-45% ACN in 0.035% TFA (aq). The collected fractions were combined and the solvent was removed via rotary evaporation to yield a TFA salt of the title compound (2 mg, 15%). $^1$H NMR (500 MHz, CD$_3$OD) δ ppm 1.92 (d, J=13.18 Hz, 1 H), 2.14 (dd, J=12.69, 4.88 Hz, 1 H), 3.56-3.66 (m, 2 H), 3.65-3.78 (m, 1 H), 3.90 (d, J=12.20 Hz, 1 H), 4.04-4.19 (m, 3 H), 4.37-4.47 (m, 1 H), 6.99 (d, J=3.91 Hz, 1 H), 8.80 (d, J=3.91 Hz, 1 H). [M+H] calc'd for $C_{16}H_{16}ClFN_4O_2S$, 383; found, 383.

Example 136

6-((3R,4R)-3-Aminotetrahydro-2H-pyran-4-ylamino)-4-(1-cyclopropyl-1H-pyrazol-4-yl)-7-fluoro-1H-pyrrolo[3,4-c]pyridin-3(2H)-one

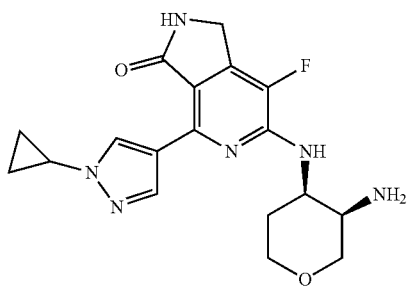 [SMILES: N[C@H]1COCC[C@H]1Nc1nc(-c2cnn(C3CC3)c2)c2c(c1F)CNC2=O]

A 2 mL microwave vial was charged with tert-butyl 6-((3R,4R)-3-(tert-butoxycarbonylamino)tetrahydro-2H-pyran-4-ylamino)-4-chloro-7-fluoro-3-oxo-1H-pyrrolo[3,4-c]pyridine-2(3H)-carboxylate (55 mg, 0.11 mmol), 1-cyclopropyl-4-(4,4,5,5-tetramethyl-1,3,2-dioxaborolan-2-yl)-1H-pyrazole (77 mg, 0.329 mmol), and bis(triphenylphosphine) palladium chloride (15.41 mg, 0.022 mmol) and placed under an inert environment. Dioxane (1.1 mL) was added and the yellow slurry was degassed for 5 min. To the slurry was then added Na$_2$CO$_3$ (220 μL, 0.439 mmol) which caused the reaction slurry to turn orange. The mixture was degassed an additional 3 min. The vessel was capped and the reaction mixture was heated to 80° C. for 4 h. The reaction mixture was subsequently diluted with EtOAc (10 mL) and washed with water (8 mL) followed by brine (8 mL). The organic phase was collected, dried over Na$_2$SO$_4$, and concentrated to an oil, which was diluted with DCM (2 mL) and treated with HCl (4 M in dioxane, 1 mL). The mixture was stirred for 1 h at RT, and then concentrated. The residue was diluted with MeOH (2 mL) and was purified via preparative HPLC to give a TFA salt of the title compound as a white solid. $^1$H NMR (DMSO-d$_6$) δ ppm 1.75 (t, 1 H), 2.03-2.17 (m, 1 H), 3.57-3.67 (m, 1 H), 3.78 (br s, 1 H), 3.82-3.88 (m, 1 H), 3.93-4.02 (m, 2 H), 4.39 (d, J=5.3 Hz, 2 H), 4.45-4.54 (m, 1 H), 4.82 (d, J=5.8 Hz, 2H), 5.15 (dd, J=17.2, 1.5 Hz, 1H), 5.22 (dd, J=10.2, 1.4 Hz, 1 H), 6.04 (dddd, J=16.8, 10.6, 5.8, 5.7 Hz, 1 H), 7.09 (d, J=5.3 Hz, 1 H), 7.93 (d, J=4.3 Hz, 3 H), 8.32 (s, 1 H), 8.40 (s, 1 H), 8.85-9.03 (m, 1 H). [M+H] calc'd for $C_{18}H_{21}FN_6O_2$, 373; found, 373.

TABLE 1, below, lists SYK inhibition data for many of the compounds described in the examples, where larger pIC$_{50}$ values represent higher potency. The compounds were tested in accordance with the assay described on page 59 of the specification.

TABLE 1

SYK Inhibition (pIC$_{50}$) for Example (Ex) Compounds

| Ex | pIC$_{50}$ |
|---|---|
| 1 | 8.1 |
| 2 | 6.9 |
| 3 | 7.6 |
| 4 | 7.8 |
| 5 | 6.2 |
| 6 | 6.3 |
| 7 | 6.0 |
| 8 | 8.1 |
| 9 | 5.1 |
| 10 | <4.7 |
| 11 | 5.9 |
| 12 | 5.7 |
| 13 | 8.7 |
| 14 | 6.9 |
| 15 | 6.0 |
| 16 | 5.5 |
| 17 | 7.4 |
| 18 | 7.1 |
| 19 | 6.6 |
| 20 | 6.7 |
| 21 | 6.3 |
| 22 | 5.7 |
| 23 | 8.7 |
| 24 | 7.6 |
| 25 | 9.0 |
| 26 | 7.5 |
| 27 | 7.4 |
| 28 | 8.6 |
| 29 | 8.5 |
| 30 | 8.4 |
| 31 | 8.6 |
| 32 | 5.4 |
| 33 | 7.3 |
| 34 | 6.5 |
| 35 | 7.3 |
| 36 | 7.6 |

TABLE 1-continued

SYK Inhibition (pIC$_{50}$) for Example (Ex) Compounds

| Ex | pIC$_{50}$ |
|---|---|
| 37 | 6.0 |
| 38 | 6.2 |
| 39 | 5.5 |
| 40 | 6.6 |
| 41 | 5.9 |
| 42 | 6.8 |
| 43 | 5.3 |
| 44 | 6.2 |
| 45 | 6.1 |
| 46 | 5.8 |
| 47 | 8.6 |
| 48 | 6.1 |
| 49 | <4.7 |
| 50 | 8.6 |
| 51 | 7.2 |
| 52 | 7.2 |
| 53 | 5.8 |
| 54 | 6.6 |
| 55 | 7.8 |
| 56 | 5.6 |
| 57 | 7.8 |
| 58 | 5.8 |
| 59 | 7.1 |
| 60 | 7.8 |
| 61 | 7.2 |
| 62 | 8.0 |
| 63 | 8.1 |
| 64 | 8.0 |
| 65 | 8.0 |
| 66 | 6.3 |
| 67 | 7.4 |
| 68 | 7.0 |
| 69 | 6.8 |
| 70 | 8.8 |
| 71 | 8.1 |
| 72 | 7.5 |
| 73 | 8.1 |
| 74 | 8.3 |
| 75 | 9.1 |
| 76 | 9.3 |
| 77 | 7.5 |
| 78 | 8.4 |
| 79 | 7.7 |
| 80 | 5.5 |
| 81 | 8.5 |
| 82 | 9.2 |
| 83 | 6.6 |
| 84 | 7.7 |
| 85 | 8.4 |
| 86 | 5.6 |
| 87 | 7.2 |
| 88 | 8.5 |
| 89 | 8.4 |
| 90 | 8.0 |
| 91 | 6.6 |
| 92 | 7.9 |
| 93 | 8.0 |
| 94 | 8.5 |
| 95 | 5.4 |
| 96 | 6.7 |
| 97 | 6.8 |
| 98 | 5.7 |
| 99 | 8.5 |
| 100 | 6.8 |
| 101 | 7.2 |
| 102 | 8.4 |
| 103 | 6.9 |
| 104 | 8.7 |
| 105 | 9.0 |
| 106 | 8.6 |
| 107 | 6.3 |
| 108 | 8.6 |
| 109 | 8.5 |
| 110 | 7.3 |
| 111 | 8.1 |
| 112 | 8.7 |
| 113 | 6.7 |
| 114 | 6.6 |
| 115 | 6.5 |
| 116 | 8.1 |
| 117 | 7.9 |
| 118 | 7.9 |
| 119 | 7.8 |
| 120 | 6.6 |
| 121 | 5.4 |
| 122 | 6.2 |
| 123 | 8.1 |
| 124 | 7.6 |
| 125 | 8.0 |
| 126 | 8.1 |
| 127 | 8.2 |
| 128 | 7.7 |
| 129 | 8.4 |
| 130 | 5.0 |
| 131 | <4.7 |
| 132 | 8.4 |
| 133 | 7.6 |
| 134 |  |
| 135 |  |
| 136 | 7.5 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

What is claimed is:

1. A method of treating a disease or condition by inhibiting SYK in a subject in need thereof, the method comprising administering to the subject an effective amount of a compound of Formula 1,

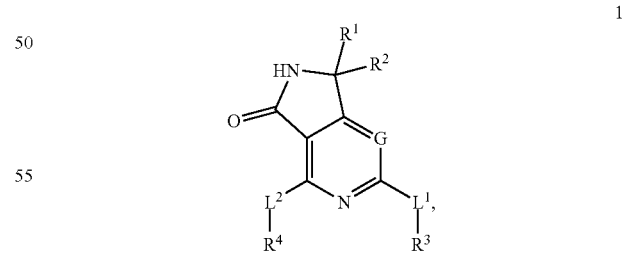

or a pharmaceutically acceptable salt thereof, wherein:
G is C(R$^5$);
L$^1$ and L$^2$ are each independently selected from —NH— and a bond;
R$^1$ and R$^2$ are each independently selected from hydrogen, halo, C$_{1-3}$ alkyl, and C$_{1-3}$ haloalkyl, or R$^1$ and R$^2$, together with the atom to which they are attached, form a C$_{3-6}$ cycloalkyl;

$R^3$ is selected from $C_{2-6}$ alkyl, $C_{3-8}$ cycloalkyl, $C_{2-5}$ heterocyclyl, and $C_{1-9}$ heteroaryl, each optionally substituted with from one to five substituents independently selected from halo, oxo, —$NO_2$, —CN, $R^6$, and $R^7$;

$R^4$ is selected from $C_{3-8}$ cycloalkyl, $C_{2-5}$ heterocyclyl, $C_{6-14}$ aryl, and $C_{1-9}$ heteroaryl, each optionally substituted with from one to five substituents independently selected from halo, oxo, —CN, $R^6$, and $R^7$;

$R^5$ is selected from hydrogen, halo, —CN, $C_{1-4}$ alkyl, $C_{2-4}$ alkenyl, $C_{2-4}$ alkynyl, $C_{2-5}$ heterocyclyl, $C_{1-5}$ heteroaryl, and $R^{10}$, wherein the alkyl, alkenyl, alkynyl moieties are each optionally substituted with from one to five substituents independently selected from halo, —CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with from one to four substituents independently selected from halo, —$NO_2$, —CN, $C_{1-4}$ alkyl, $C_{2-4}$ alkenyl, $C_{2-4}$ alkynyl, $C_{1-4}$ haloalkyl, and $R^{10}$;

each $R^6$ is independently selected from —$OR^8$, —$N(R^8)R^9$, —$NR^8C(O)R^9$, —$C(O)R^8$, —$C(O)OR^8$, —$C(O)N(R^8)R^9$, —$C(O)N(R^8)OR^9$, —$C(O)N(R^8)S(O)_2R^9$, —$N(R^8)S(O)_2R^9$, —$S(O)_nR^8$, and —$S(O)_2N(R^8)R^9$;

each $R^7$ is independently selected from $C_{1-6}$ alkyl, $C_{2-6}$ alkenyl, $C_{2-6}$ alkynyl, $C_{3-6}$ cycloalkyl-$(CH_2)_m$—, $C_{6-14}$ aryl-$(CH_2)_m$—, $C_{2-5}$ heterocyclyl-$(CH_2)_m$—, and $C_{1-9}$ heteroaryl-$(CH_2)_m$—, each optionally substituted with from one to five substituents independently selected from halo, oxo, —$NO_2$, —CN, $C_{1-6}$ alkyl, $C_{1-6}$ haloalkyl, and $R^{10}$;

each $R^8$ and $R^9$ is independently selected from hydrogen or from $C_{1-6}$ alkyl, $C_{2-6}$ alkenyl, $C_{2-6}$ alkynyl, $C_{3-6}$ cycloalkyl-$(CH_2)_m$—, $C_{6-14}$ aryl-$(CH_2)_m$—, $C_{2-5}$ heterocyclyl-$(CH_2)_m$—, and $C_{1-9}$ heteroaryl-$(CH_2)_m$—, each optionally substituted with from one to five substituents independently selected from halo, oxo, —$NO_2$, —CN, $C_{1-6}$ alkyl, $C_{1-6}$ haloalkyl, and $R^{10}$;

each $R^{10}$ is independently selected from —$OR^{11}$, —$N(R^{11})R^{12}$, —$N(R^{11})C(O)R^{12}$, —$C(O)R^{11}$, —$C(O)OR^{11}$, —$C(O)N(R^{11})R^{12}$, —$C(O)N(R^{11})OR^{12}$, —$C(O)N(R^{11})S(O)_2R^{12}$, —$NR^{11}S(O)_2R^{12}$, —$S(O)_nR^{11}$, and —$S(O)_2N(R^{11})R^{12}$;

each $R^{11}$ and $R^{12}$ is independently selected from hydrogen and $C_{1-6}$ alkyl;

each n is independently selected from 0, 1 and 2; and each m is independently selected from 0, 1, 2, 3, and 4;

wherein each of the aforementioned heteroaryl moieties has one to four heteroatoms independently selected from N, O, and S, and each of the aforementioned heterocyclyl moieties is saturated or partially unsaturated and has one or two heteroatoms independently selected from N, O, and S.

2. A method according to claim 1, wherein $L^1$ is —NH—.

3. A method according to claim 1, wherein $L^2$ is a bond.

4. A method according to claim 1, wherein G is $C(R^5)$.

5. A method according to claim 1, wherein $R^1$ and $R^2$ are both hydrogen.

6. A method according to claim 1, wherein $R^3$ is $C_{3-8}$ cycloalkyl, optionally substituted with from one to five substituents independently selected from halo, oxo, —$NO_2$, —CN, $R^6$, and $R^7$.

7. A method according to claim 6, wherein $R^3$ is 2-aminocyclohex-1-yl optionally substituted with from one to four substituents independently selected from halo, oxo, —$NO_2$, —CN, $R^6$, and $R^7$.

8. A method according to claim 1, wherein $R^3$ is $C_{2-5}$ heterocyclyl optionally substituted with from one to five substituents independently selected from halo, oxo, —$NO_2$, —CN, $R^6$, and $R^7$.

9. A method according to claim 8, wherein $R^3$ is 3-aminotetrahydro-2H-pyran-4-yl optionally substituted with from one to four substituents independently selected from halo, oxo, —$NO_2$, —CN, $R^6$, and $R^7$.

10. A method according to claim 1, wherein $R^4$ is $C_{1-9}$ heteroaryl optionally substituted with from one to five substituents independently selected from halo, oxo, —CN, $R^6$, and $R^7$.

11. A method according to claim 10, wherein $R^4$ is a monocyclic $C_{2-4}$ heteroaryl optionally substituted with from one to four substituents independently selected from halo, —CN, $R^6$, and $R^7$.

12. A method according to claim 11, wherein $R^4$ is selected from pyrrolyl, furanyl, thienyl, pyrazolyl, imidazolyl, isoxazolyl, oxazolyl, isothiazolyl, and thiazolyl, each optionally substituted with from one to three substituents independently selected from halo, —CN, $R^6$, and $R^7$.

13. A method according to claim 12, wherein $R^4$ is selected from thienyl, pyrazolyl, isothiazolyl, and thiazolyl, each optionally substituted with from one to three substituents independently selected from halo, —CN, $R^6$, and $R^7$.

14. A method according to claim 13, wherein $R^4$ is pyrazolyl optionally substituted with from one to three substituents independently selected from halo, —CN, $R^6$, and $R^7$.

15. A method according to claim 14, wherein $R^4$ is pyrazol-4-yl optionally substituted with from one to three substituents independently selected from halo, —CN, $R^6$, and $R^7$.

16. A method according to claim 10, wherein $R^4$ is substituted with methyl, ethyl, cyclopropyl or $C_{1-2}$ haloalkyl.

17. A method according to claim 1, wherein $R^5$ is selected from hydrogen and halo.

18. A method according to claim 17, wherein $R^5$ is selected from chloro and fluoro.

19. A method according to claim 1, wherein the compound is selected from the following compounds:

6-((1R,2S)-2-Aminocyclohexylamino)-4-(m-tolylamino)-1H-pyrrolo[3,4-c]pyridin-3(2H)-one;

4-(1H-Indazol-6-ylamino)-6-((1R,2S)-2-aminocyclohexylamino)-1H-pyrrolo[3,4-c]pyridin-3(2H)-one;

6-((1R,2S)-2-Aminocyclohexylamino)-4-(4-fluoro-3-methylphenylamino)-1H-pyrrolo[3,4-c]pyridin-3(2H)-one;

6-((1R,2S)-2-Aminocyclohexylamino)-7-fluoro-4-(m-tolylamino)-1H-pyrrolo[3,4-c]pyridin-3(2H)-one;

6-((1R,2S)-2-Aminocyclohexylamino)-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(1-methyl-1H-pyrazol-4-yl)-1H-pyrrolo[3,4-c]pyridin-3(2H)-one;

6-((1R,2S)-2-Aminocyclohexylamino)-7-chloro-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(pyrazolo[1,5-a]pyridin-3-yl)-1H-pyrrolo[3,4-c]pyridin-3(2H)-one;

6-((1R,2S)-2-Aminocyclohexylamino)-4-(3-(methylsulfonyl)phenylamino)-1H-pyrrolo[3,4-c]pyridin-3(2H)-one;

6-((1R,2S)-2-Aminocyclopentylamino)-4-(3-(methylsulfonyl)phenylamino)-1H-pyrrolo[3,4-c]pyridin-3(2H)-one;

(R)-4-Methyl-2-(4-(3-(methylsulfonyl)phenylamino)-3-oxo-2,3-dihydro-1H-pyrrolo[3,4-c]pyridin-6-ylamino)pentanamide;

(R)-4-Methyl-2-(4-(1-methyl-1H-pyrazol-4-yl)-3-oxo-2,3-dihydro-1H-pyrrolo[3,4-c]pyridin-6-ylamino)pentanamide;

6-((1R,2S)-2-Aminocyclohexylamino)-4-(benzofuran-3-yl)-7-fluoro-1H-pyrrolo[3,4-c]pyridin-3(2H)-one;

6-((1R,2S)-2-aminocyclohexylamino)-7-fluoro-4-(imidazo[1,2-a]pyridin-3-yl)-1H-pyrrolo[3,4-c]pyridin-3(2H)-one;

6-((1R,2S)-2-aminocyclohexylamino)-4-(benzo[b]thiophen-3-yl)-7-fluoro-1H-pyrrolo[3,4-c]pyridin-3(2H)-one;

6-((1S,2R)-2-Aminocyclohexylamino)-7-fluoro-4-(1-methyl-1H-pyrazol-4-yl)-1H-pyrrolo[3,4-c]pyridin-3(2H)-one;

(R)-6-(2-Amino-3-ethoxypropylamino)-4-(m-tolylamino)-1H-pyrrolo[3,4-c]pyridin-3(2H)-one;

(R)-6-(2-Amino-3-ethoxypropylamino)-7-fluoro-4-(m-tolylamino)-1H-pyrrolo[3,4-c]pyridin-3(2H)-one;

6-(2-Amino-3,3,3-trifluoropropylamino)-4-(m-tolylamino)-1H-pyrrolo[3,4-c]pyridin-3(2H)-one;

(R)-4-Methyl-2-(3-oxo-4-(m-tolylamino)-2,3-dihydro-1H-pyrrolo[3,4-c]pyridin-6-ylamino)pentanamide;

6-(cis-4-Aminotetrahydrofuran-3-ylamino)-4-(m-tolylamino)-1H-pyrrolo[3,4-c]pyridin-3(2H)-one;

6-((1R,2S)-2-Aminocyclohexylamino)-4-(1-ethyl-1H-pyrazol-4-yl)-1H-pyrrolo[3,4-c]pyridin-3(2H)-one;

6-((1R,2S)-2-Aminocyclohexylamino)-4-(1-ethyl-1H-pyrazol-4-yl)-7-fluoro-1H-pyrrolo[3,4-c]pyridin-3(2H)-one;

6-((1R,2S)-2-Aminocyclohexylamino)-4-(1-cyclopropyl-1H-pyrazol-4-yl)-1H-pyrrolo[3,4-c]pyridin-3(2H)-one;

6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one;

6-((1R,2S)-2-Aminocyclohexylamino)-4-(1-cyclopropyl-1H-pyrazol-4-yl)-7-fluoro-1H-pyrrolo[3,4-c]pyridin-3(2H)-one;

cis-6-(2-Aminocyclohexylamino)-7-fluoro-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(1-methyl-1H-pyrazol-4-yl)-1H-pyrrolo[3,4-c]pyridin-3(2H)-one;

6-(cis-2-Amino-4,4-difluorocyclopentylamino)-7-fluoro-4-(1-methyl-1H-pyrazol-4-yl)-1H-pyrrolo[3,4-c]pyridin-3(2H)-one;

6-(cis-2-Amino-3,3-difluorocyclohexylamino)-7-fluoro-4-(1-methyl-1H-pyrazol-4-yl)-1H-pyrrolo[3,4-c]pyridin-3(2H)-one;

6-(cis-2-Amino-3,3-difluorocyclohexylamino)-4-(1-(difluoromethyl)-1H-pyrazol-4-yl)-7-fluoro-1H-pyrrolo[3,4-c]pyridin-3(2H)-one;

6-(cis-2-amino-3,3-difluorocyclohexylamino)-4-(1-cyclopropyl-1H-pyrazol-4-yl)-7-fluoro-1H-pyrrolo[3,4-c]pyridin-3(2H)-one;

(R)-2-(7-Fluoro-4-(1-methyl-1H-pyrazol-4-yl)-3-oxo-2,3-dihydro-1H-pyrrolo[3,4-c]pyridin-6-ylamino)-4-methylpentanamide;

(R)-2-(4-(1-(Difluoromethyl)-1H-pyrazol-4-yl)-7-fluoro-3-oxo-2,3-dihydro-1H-pyrrolo[3,4-c]pyridin-6-ylamino)-4-methylpentanamide;

(R)-2-(4-(1-Cyclopropyl-1H-pyrazol-4-yl)-7-fluoro-3-oxo-2,3-dihydro-1H-pyrrolo[3,4-c]pyridin-6-ylamino)-4-methylpentanamide;

(R)-2-(4-(Benzofuran-3-yl)-7-fluoro-3-oxo-2,3-dihydro-1H-pyrrolo[3,4-c]pyridin-6-ylamino)-4-methylpentanamide;

(R)-2-(7-Fluoro-3-oxo-4-(pyrazolo[1,5-a]pyridin-3-yl)-2,3-dihydro-1H-pyrrolo[3,4-c]pyridin-6-ylamino)-4-methylpentanamide;

6-((1R,2S)-2-Aminocyclohexylamino)-7-chloro-4-(m-tolylamino)-1H-pyrrolo[3,4-c]pyridin-3(2H)-one;

6-((1R,2S)-2-Aminocyclohexylamino)-3-oxo-4-(m-tolylamino)-2,3-dihydro-1H-pyrrolo[3,4-c]pyridine-7-carbonitrile;

(R)-6-(2-Amino-3-methoxypropylamino)-4-(m-tolylamino)-1H-pyrrolo[3,4-c]pyridin-3(2H)-one;

(R)-6-(2-Amino-3-methoxypropylamino)-3-oxo-4-(m-tolylamino)-2,3-dihydro-1H-pyrrolo[3,4-c]pyridine-7-carbonitrile;

(R)-6-(2-Amino-3-methoxypropylamino)-7-fluoro-4-(m-tolylamino)-1H-pyrrolo[3,4-c]pyridin-3(2H)-one;

7-Acryloyl-6-((1R,2S)-2-aminocyclohexylamino)-4-(m-tolylamino)-1H-pyrrolo[3,4-c]pyridin-3(2H)-one;

6-((1R,2S)-2-Aminocyclohexylamino)-7-iodo-4-(m-tolylamino)-1H-pyrrolo[3,4-c]pyridin-3(2H)-one;

6-((1R,2S)-2-Aminocyclohexylamino)-7-(1H-pyrazol-4-yl)-4-(m-tolylamino)-1H-pyrrolo[3,4-c]pyridin-3(2H)-one;

6-(cis-2-Amino-3,3-difluorocyclohexylamino)-4-(m-tolylamino)-1H-pyrrolo[3,4-c]pyridin-3(2H)-one;

6-((1R,2S)-2-Aminocyclohexylamino)-7-(1-methyl-1H-pyrazol-5-yl)-4-(m-tolylamino)-1H-pyrrolo[3,4-c]pyridin-3(2H)-one;

6-((3R,4R)-3-Aminotetrahydro-2H-pyran-4-ylamino)-4-(m-tolylamino)-1H-pyrrolo[3,4-c]pyridin-3(2H)-one;

6-((3R,4R)-4-Aminotetrahydro-2H-pyran-3-ylamino)-4-(m-tolylamino)-1H-pyrrolo[3,4-c]pyridin-3(2H)-one;

6-((1R,2S)-2-Aminocyclohexylamino)-7-methyl-4-(m-tolylamino)-1H-pyrrolo[3,4-c]pyridin-3(2H)-one;

6-((3R,4R)-3-Aminotetrahydro-2H-pyran-4-ylamino)-7-fluoro-4-(m-tolylamino)-1H-pyrrolo[3,4-c]pyridin-3(2H)-one;

6-((1R,2S)-2-Aminocyclohexylamino)-7-methyl-4-(1-methyl-1H-pyrazol-4-yl)-1H-pyrrolo[3,4-c]pyridin-3(2H)-one;

(R)-6-(2-Amino-3-methoxypropylamino)-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(pyrazolo[1,5-a]pyridin-3-yl)-1H-pyrrolo[3,4-c]pyridin-3(2H)-one;

6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one;

6-((3R,4R)-3-Aminotetrahydro-2H-pyran-4-ylamino)-4-(benzofuran-3-yl)-7-fluoro-1H-pyrrolo[3,4-c]pyridin-3(2H)-one;

(S)-6-(3-Aminopyrrolidin-1-yl)-7-fluoro-4-(1-methyl-1H-pyrazol-4-yl)-1H-pyrrolo[3,4-c]pyridin-3(2H)-one;

(S)-6-(3-Aminopiperidin-1-yl)-7-fluoro-4-(1-methyl-1H-pyrazol-4-yl)-1H-pyrrolo[3,4-c]pyridin-3(2H)-one;

6-((1R,2S)-2-Aminocyclohexylamino)-7-fluoro-4-(1-isopropyl-1H-pyrazol-4-yl)-1H-pyrrolo[3,4-c]pyridin-3(2H)-one;

7-Fluoro-4,6-bis(1-methyl-1H-pyrazol-4-yl)-1H-pyrrolo[3,4-c]pyridin-3(2H)-one;

6-((1R,2S)-2-Aminocyclohexylamino)-7-bromo-4-(1-methyl-1H-pyrazol-4-yl)-1H-pyrrolo[3,4-c]pyridin-3(2H)-one;

(R)-6-(2-Amino-3-methoxypropylamino)-7-fluoro-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(thiophen-3-yl)-1H-pyrrolo[3,4-c]pyridin-3(2H)-one;

6-((3R,4R)-3-Aminotetrahydro-2H-pyran-4-ylamino)-7-fluoro-4-(4-methylthiophen-2-yl)-1H-pyrrolo[3,4-c]pyridin-3(2H)-one;

6-((1R,2S)-2-Aminocyclohexylamino)-7-fluoro-4-(4-methylthiophen-2-yl)-1H-pyrrolo[3,4-c]pyridin-3(2H)-one;

6-((1R,2S)-2-Aminocyclohexylamino)-7-fluoro-4-(thiophen-3-yl)-1H-pyrrolo[3,4-c]pyridin-3(2H)-one;

(R)-2-(7-Fluoro-4-(1-methyl-1H-pyrazol-4-yl)-3-oxo-2,3-dihydro-1H-pyrrolo[3,4-c]pyridin-6-ylamino)-N,4-dimethylpentanamide;

6-((1R,2S)-2-Aminocyclohexylamino)-7-fluoro-4-(5-methylthiophen-2-yl)-1H-pyrrolo[3,4-c]pyridin-3(2H)-one;

(R)-2-(7-Fluoro-4-(4-methylthiophen-2-yl)-3-oxo-2,3-dihydro-1H-pyrrolo[3,4-c]pyridin-6-ylamino)-4-methylpentanamide;

(R)-2-(7-Fluoro-3-oxo-4-(thiophen-3-yl)-2,3-dihydro-1H-pyrrolo[3,4-c]pyridin-6-ylamino)-4-methylpentanamide;

(R)-2-(7-Fluoro-4-(5-methylthiophen-2-yl)-3-oxo-2,3-dihydro-1H-pyrrolo[3,4-c]pyridin-6-ylamino)-4-methylpentanamide;

6-((1R,2S)-2-Aminocyclohexylamino)-4-(2-aminothiazol-5-yl)-7-fluoro-1H-pyrrolo[3,4-c]pyridin-3(2H)-one;

(R)-2-(7-Fluoro-4-(furan-2-yl)-3-oxo-2,3-dihydro-1H-pyrrolo[3,4-c]pyridin-6-ylamino)-4-methylpentanamide;

(R)-2-(7-Fluoro-4-(furan-3-yl)-3-oxo-2,3-dihydro-1H-pyrrolo[3,4-c]pyridin-6-ylamino)-4-methylpentanamide;

(R)-2-(7-Fluoro-4-(5-methylfuran-2-yl)-3-oxo-2,3-dihydro-1H-pyrrolo[3,4-c]pyridin-6-ylamino)-4-methylpentanamide;

(R)-2-(4-(5-Cyanothiophen-2-yl)-7-fluoro-3-oxo-2,3-dihydro-1H-pyrrolo[3,4-c]pyridin-6-ylamino)-4-methylpentanamide;

(R)-2-(4-(4-Cyanothiophen-2-yl)-7-fluoro-3-oxo-2,3-dihydro-1H-pyrrolo[3,4-c]pyridin-6-ylamino)-4-methylpentanamide;

(R)-2-(7-Fluoro-3-oxo-4-(thiazol-5-yl)-2,3-dihydro-1H-pyrrolo[3,4-c]pyridin-6-ylamino)-4-methylpentanamide;

(R)-2-(7-Fluoro-4-(isothiazol-5-yl)-3-oxo-2,3-dihydro-1H-pyrrolo[3,4-c]pyridin-6-ylamino)-4-methylpentanamide;

6-((1R,2S)-2-Aminocyclohexylamino)-7-fluoro-1,1-dimethyl-4-(1-methyl-1H-pyrazol-4-yl)-1H-pyrrolo[3,4-c]pyridin-3(2H)-one;

((1R,2S)-2-Aminocyclohexylamino)-7-fluoro-4-(1-methyl-1H-pyrazol-3-yl)-1H-pyrrolo[3,4-c]pyridin-3(2H)-one;

6-((1R,2S)-2-Aminocyclohexylamino)-7-fluoro-4-(2-methylthiazol-5-yl)-1H-pyrrolo[3,4-c]pyridin-3(2H)-one;

6-((3R,4R)-3-Aminotetrahydro-2H-pyran-4-ylamino)-7-fluoro-4-(5-methylthiophen-2-yl)-1H-pyrrolo[3,4-c]pyridin-3(2H)-one;

6-((1R,2S)-2-Aminocyclohexylamino)-7-fluoro-1-methyl-4-(1-methyl-1H-pyrazol-4-yl)-1H-pyrrolo[3,4-c]pyridin-3(2H)-one;

(R)-2-(7-Fluoro-3-oxo-4-(thiophen-2-yl)-2,3-dihydro-1H-pyrrolo[3,4-c]pyridin-6-ylamino)-4-methylpentanamide;

6-((3R,4R)-3-Aminotetrahydro-2H-pyran-4-ylamino)-7-fluoro-4-(thiophen-2-yl)-1H-pyrrolo[3,4-c]pyridin-3(2H)-one;

6-((3R,4R)-3-Aminotetrahydro-2H-pyran-4-ylamino)-7-fluoro-4-(thiazol-5-yl)-1H-pyrrolo[3,4-c]pyridin-3(2H)-one;

6-((1R,2S)-2-Aminocyclohexylamino)-7-fluoro-4-(thiophen-2-yl)-1H-pyrrolo[3,4-c]pyridin-3(2H)-one;

6-((3R,4R)-3-Aminotetrahydro-2H-pyran-4-ylamino)-7-fluoro-4-(4-(trifluoromethyl)-1H-imidazol-1-yl)-1H-pyrrolo[3,4-c]pyridin-3(2H)-one;

6-((1R,2S)-2-Aminocyclohexylamino)-7-fluoro-4-(4-methyl-1H-imidazol-1-yl)-1H-pyrrolo[3,4-c]pyridin-3(2H)-one;

6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one;

6-((3R,4R)-3-Aminotetrahydro-2H-pyran-4-ylamino)-7-fluoro-4-(2-methylthiazol-5-yl)-1H-pyrrolo[3,4-c]pyridin-3(2H)-one;

(R)-2-(7-Fluoro-4-(2-methylthiazol-5-yl)-3-oxo-2,3-dihydro-1H-pyrrolo[3,4-c]pyridin-6-ylamino)-4-methylpentanamide;

6-((3R,4R)-3-Aminotetrahydro-2H-pyran-4-ylamino)-4-(5-chlorothiophen-2-yl)-7-fluoro-1H-pyrrolo[3,4-c]pyridin-3(2H)-one;

6-((3R,4R)-3-Aminotetrahydro-2H-pyran-4-ylamino)-4-(1-cyclopropyl-1H-pyrazol-4-yl)-7-fluoro-1H-pyrrolo[3,4-c]pyridin-3(2H)-one;

a stereoisomer of any of the aforementioned compounds; and a pharmaceutically acceptable salt of any of the aforementioned compounds or stereoisomers.

20. A method according to claim 1, wherein the compound is 6-((1R,2S)-2-Aminocyclohexylamino)-7-fluoro-4-(1-methyl-1H-pyrazol-4-yl)-1H-pyrrolo[3,4-c]pyridin-3(2H)-one or a pharmaceutically acceptable salt thereof.

21. A method according to claim 1, wherein the compound is 6-((1S,2R)-2-Aminocyclohexylamino)-7-fluoro-4-(1-methyl-1H-pyrazol-4-yl)-1H-pyrrolo[3,4-c]pyridin-3(2H)-one or a pharmaceutically acceptable salt thereof.

22. A method according to claim 1, wherein the compound is 6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one or a pharmaceutically acceptable salt thereof.

23. A method according to claim 1, wherein the compound is cis-6-(2-Aminocyclohexylamino)-7-fluoro-4-(1-methyl-1H-pyrazol-4-yl)-1H-pyrrolo[3,4-c]pyridin-3(2H)-one or a pharmaceutically acceptable salt thereof.

24. A method according to claim 1, wherein the compound is 6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one or a pharmaceutically acceptable salt thereof.

25. A method according to claim 1, wherein the compound is 6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one or a pharmaceutically acceptable salt thereof.

26. A method of treating a disease or condition by inhibiting SYK in a subject in need thereof, the method comprising administering to the subject an effective amount of a compound of Formula 1,

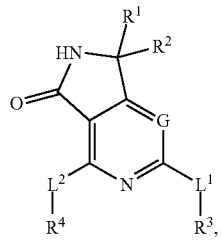

or a pharmaceutically acceptable salt thereof, wherein:
G is $C(R^5)$;
$L^1$ and $L^2$ are each independently selected from -NH- and a bond;
$R^1$ and $R^2$ are each independently selected from hydrogen, halo, $C_{1-3}$ alkyl, and $C_{1-3}$ haloalkyl, or $R^1$ and $R^2$, together with the atom to which they are attached, form a $C_{3-6}$ cycloalkyl;
$R^3$ is selected from $C_{2-6}$ alkyl, $C_{3-8}$ cycloalkyl, $C_{2-5}$ heterocyclyl, and $C_{1-9}$ heteroaryl, each optionally substituted with from one to five substituents independently selected from halo, oxo, -NO$_2$, -CN, $R^6$, and $R^7$;
$R^4$ is selected from $C_{3-8}$ cycloalkyl, $C_{2-5}$ heterocyclyl, $C_{6-14}$ aryl, and $C_{1-9}$ heteroaryl, each optionally substituted with from one to five substituents independently selected from halo, oxo, -CN, $R^6$, and $R^7$;
$R^5$ is selected from hydrogen, halo, -CN, $C_{1-4}$ alkyl, $C_{2-4}$ alkenyl, $C_{2-4}$ alkynyl, $C_{2-5}$ heterocyclyl,
$C_{1-5}$ heteroaryl, and $R^{10}$, wherein the alkyl, alkenyl, alkynyl moieties are each optionally substituted with from one to five substituents independently selected from halo, -CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with from one to four substituents independently selected from halo, -NO$_2$, -CN, $C_{1-4}$ alkyl, $C_{2-4}$ alkenyl, $C_{2-4}$ alkynyl, $C_{1-4}$ haloalkyl, and $R^{10}$;
each $R^6$ is independently selected from -OR$^8$, -N(R$^8$)R$^9$, -NR$^8$C(O)R$^9$, -C(O)R$^8$, -C(O)OR$^8$, -C(O)N(R$^8$)R$^9$, -C(O)N(R$^8$)OR$^9$, -C(O)N(R$^8$)S(O)$_2$R$^9$, -N(R$^8$)S(O)$_2$R$^9$, -S(O)$_n$R$^8$, and -S(O)$_2$N(R$^8$)R$^9$;

each $R^7$ is independently selected from $C_{1-6}$ alkyl, $C_{2-6}$ alkenyl, $C_{2-6}$ alkynyl,
$C_{3-6}$ cycloalkyl-(CH$_2$)$_m$-, $C_{6-14}$ aryl-(CH$_2$)$_m$-, $C_{2-5}$ heterocyclyl-(CH$_2$)$_m$-, and $C_{1-9}$ heteroaryl-(CH$_2$)$_m$-, each optionally substituted with from one to five substituents independently selected from halo, oxo, -NO$_2$, -CN, $C_{1-6}$ alkyl, $C_{1-6}$ haloalkyl, and $R^{10}$;
each $R^8$ and $R^9$ is independently selected from hydrogen or from $C_{1-6}$ alkyl, $C_{2-6}$ alkenyl,
$C_{2-6}$ alkynyl, $C_{3-6}$ cycloalkyl-(CH$_2$)$_m$-, $C_{6-14}$ aryl-(CH$_2$)$_m$-, $C_{2-5}$ heterocyclyl-(CH$_2$)$_m$-, and $C_{1-9}$ heteroaryl-(CH$_2$)$_m$-, each optionally substituted with from one to five substituents independently selected from halo, oxo, -NO$_2$, -CN, $C_{1-6}$ alkyl, $C_{1-6}$ haloalkyl, and $R^{10}$; each $R^{10}$ is independently selected
from -OR$^{11}$, -N(R$^{11}$)R$^{12}$, -N(R$^{11}$)C(O)R$^{12}$, -C(O)OR$^{11}$, -C(O)N(R$^{11}$)R$^{12}$, -C(O) N(R$^{11}$)OR$^{12}$, -C(O)N(R$^{11}$)S(O)$_2$R$^{12}$, -NR$^{11}$S(O)$_n$R$^{11}$, and -S(O)$_2$N(R$^{11}$)R$^{12}$;
each $R^{11}$ and $R^{12}$ is independently selected from hydrogen and $C_{1-6}$ alkyl;
each n is independently selected from 0, 1 and 2; and
each m is independently selected from 0, 1, 2, 3, and 4;
wherein each of the aforementioned heteroaryl moieties has one to four heteroatoms independently selected from N, O, and S, and each of the aforementioned heterocyclyl moieties is saturated or partially unsaturated and has one or two heteroatoms independently selected from N, O, and S;
wherein the disease or condition is selected from allergic rhinitis, allergic asthma, atopic dermatitis, rheumatoid arthritis, multiple sclerosis, systemic lupus erythematosus, psoriasis, immune thrombocytopenic purpura, inflammatory bowel disease, chronic obstructive pulmonary disease, thrombosis, a hematological malignancy, and an epithelial cancer.

27. A method according to claim 26, wherein the hematological malignancy is selected from acute myeloid leukemia, B-cell chronic lymphocytic leukemia, B-cell lymphoma, and T-cell lymphoma.

28. A method according to claim 26, wherein the epithelial cancer is selected from lung cancer, pancreatic cancer, and colon cancer.

29. A method according to claim 26, the method further comprising administering to the subject at least one additional pharmacologically active agent.

30. A method according to claim 29, wherein the additional pharmacologically active agent is a DMARD.

31. A method according to claim 30, wherein the DMARD is methotrexate.

* * * * *